(12) United States Patent
Elder et al.

(10) Patent No.: US 8,912,220 B2
(45) Date of Patent: Dec. 16, 2014

(54) COMPOUNDS AND METHODS OF USE THEREOF

(75) Inventors: Amy Elder, Arlington, MA (US); Geraldine Harriman, Charlestown, RI (US); Silvana Leit, Quebec (CA); Jie Li, Melrose, MA (US); Howard Sard, Arlington, MA (US); Yiliang Zhang, Stoneham, MA (US); Doug Wilson, Ayer, MA (US)

(73) Assignee: Galenea Pharmaceuticals

( * ) Notice: Subject to any disclaimer, the term of this patent is extended or adjusted under 35 U.S.C. 154(b) by 107 days.

(21) Appl. No.: 12/853,782

(22) Filed: Aug. 10, 2010

(65) Prior Publication Data

US 2011/0144090 A1 Jun. 16, 2011

Related U.S. Application Data

(60) Provisional application No. 61/232,772, filed on Aug. 10, 2009.

(51) Int. Cl.

| | |
|---|---|
| *A61K 31/4045* | (2006.01) |
| *C07D 209/14* | (2006.01) |
| *C07D 401/12* | (2006.01) |
| *C07D 403/06* | (2006.01) |
| *C07D 491/04* | (2006.01) |
| *C07D 413/06* | (2006.01) |
| *C07D 209/24* | (2006.01) |
| *C07D 405/04* | (2006.01) |
| *C07D 209/16* | (2006.01) |
| *C07D 403/04* | (2006.01) |
| *C07D 405/12* | (2006.01) |
| *C07D 409/06* | (2006.01) |
| *C07D 487/08* | (2006.01) |
| *C07D 401/04* | (2006.01) |
| *C07D 409/12* | (2006.01) |
| *C07D 401/06* | (2006.01) |
| *C07D 405/06* | (2006.01) |
| *C07D 409/04* | (2006.01) |

(52) U.S. Cl.
CPC ............ *C07D 209/16* (2013.01); *C07D 403/06* (2013.01); *C07D 491/04* (2013.01); *C07D 413/06* (2013.01); *C07D 401/12* (2013.01); *C07D 209/24* (2013.01); *C07D 405/04* (2013.01); *C07D 403/04* (2013.01); *C07D 405/12* (2013.01); *C07D 409/06* (2013.01); *C07D 487/08* (2013.01); *C07D 401/04* (2013.01); *C07D 409/12* (2013.01); *C07D 401/06* (2013.01); *C07D 405/06* (2013.01); *C07D 409/04* (2013.01)
USPC ......... 514/339; 514/415; 546/277.4; 548/504

(58) Field of Classification Search
CPC .. C07D 401/06; C07D 405/06; C07D 409/04; C07D 409/12; C07D 401/04; C07D 487/08; C07D 409/06; C07D 405/12; C07D 403/04; C07D 209/16; C07D 405/04; C07D 209/24; C07D 413/06; C07D 491/04; C07D 403/06

USPC ........................................................ 548/504
See application file for complete search history.

(56) References Cited

U.S. PATENT DOCUMENTS

| 5,002,948 A | 3/1991 | Perregaard et al. |
| 2002/0160999 A1 | 10/2002 | Jacobsen et al. |
| 2005/0153980 A1 | 7/2005 | Schat et al. |
| 2006/0223890 A1 | 10/2006 | Ramakrishna et al. |

FOREIGN PATENT DOCUMENTS

| EP | 1532980 A1 | 5/2005 |
| WO | 90/05721 A1 | 5/1990 |
| WO | 02/078693 A2 | 10/2002 |
| WO | 2004/005607 A1 | 1/2004 |
| WO | 2006/047032 A2 | 5/2006 |
| WO | 2009/102805 A1 | 8/2009 |
| WO | 2009/103710 A1 | 8/2009 |

OTHER PUBLICATIONS

Menta, et al. Document No. 135:92542, retrived from CAPLUS (2001).*
Catrycke, et al. Document No. 131:299301, retrieved from CAPLUS (1999).*
Aubart, et al. Document No. 130:139494, retrieved from CAPLUS (1999).*
Sadanandan, et al. Document 122:187848, retrieved from CAPLUS (1995).*
Sard, et al. Document No. 151:266947, retrieved from (2009).*
International Search Report dated Oct. 14, 2010 issued in related case, international application No. PCT/US10/45053.
2005 Physician's Desk Reference 59th Edition ,Thomson Healthcare, 2004.
Annual Reports in Medicinal Chemistry, Academic Press, Fitzgerald, L., Ennis, M. "5-HT2C Receptor Modulators: Progress in Development of New CNS Medicines" pp. 21-30, vol. 32, 2002.
Berge et al. (1977) "Pharmaceutical Salts", J. Pharm. Sci. 66:1-19.
Blair J B et al: "Effect of Ring Fluorination on the Pharmacology of Hallucinogenic Tryptamines". Journal of Medicinal Chemistry. American Chemical Society. US. vol. 43. Jan. 1, 1992, pp. 2061-2064. XP002538209.
Chiral Liquid Chromatography, W.J. Lough, Ed. Chapman and Hall, New York (1989).
Harrison's Principles of Internal Medicine, Sixteenth Edition, Eds. D.L. Kasper et al. McGraw-Hill Professional, N.Y., NY (2004).
Martin, J., et al, "5-HT2C Receptor Agonists: Pharmacological Characteristics and Therapeutic Potential" J. Pharm. Experimental Ther. 1998, 286, 913.
Supplementary European Serch Report for EP 10 80 6844 dated Jan. 10, 2013.
Troxler F et al: "Abwandlungsprodukte von Psilocybin und Psilocin". Helvetica Chimica Acta. Verlag Helvetica Chimica Acta. Basel. CH. vol. 42. No. 6. Jan. 1, 1959. pp. 2073-2103. XP002082906.

* cited by examiner

*Primary Examiner* — Shawquia Young
(74) *Attorney, Agent, or Firm* — Lando & Anastasi LLP

(57) ABSTRACT

Indole compounds are disclosed. Also disclosed are methods for using the compounds to treat human and animal disease, pharmaceutical compositions of the compounds, and kits including the compounds.

20 Claims, No Drawings

COMPOUNDS AND METHODS OF USE THEREOF

RELATED APPLICATIONS

This application claims priority under 35 U.S.C. §119(e) to U.S. Provisional Application Ser. No. 61/232,772, entitled "COMPOUNDS AND METHODS OF USE THEREOF," filed on Aug. 10, 2009.

BACKGROUND OF THE INVENTION

Serotonin (5-hydroxytryptamine, 5-HT) plays a significant role in influencing a large number of central and peripheral processes. 5-HT-selective pharmacotherapies have been developed to treat a wide variety of medical problems including depression, anxiety, schizophrenia, migraine, emesis, and appetite control (Annual Reports in Medicinal Chemistry, Volume 32, 2002, Academic Press, Fitzgerald, L., Ennis, M. "5-$HT_{2C}$ Receptor Modulators: Progress in Development of New CNS Medicines" pp 21-30). 5-HT exerts its influence through activation of fourteen distinct receptor subtypes in seven separate families (5-$HT_1$, 5-$HT_2$, 5-$HT_3$, 5-$HT_4$, 5-$HT_5$, 5-$HT_6$, 5-$HT_7$).

Each of the seven families may also encompass various subtypes. For example, the 5-$HT_1$ family includes subtypes 5-$HT_{1A}$, 5-$HT_{1B}$, 5-$HT_{1D}$, 5-$HT_{1E}$ and 5-$HT_{1F}$. The 5-$HT_2$ family includes 5-$HT_{2A}$, 5-$HT_{2B}$ and 5-$HT_{2C}$. Lastly, the 5-$HT_3$ family includes 5-$HT_{3A}$ and 5-$HT_{3B}$ while the 5-$HT_5$ family includes 5-$HT_{5A}$. While the 5-HT1, 5-HT2 and 5-HT3 families have been studied most extensively, each family has been linked to various disease indications as discussed below.

Modulation of the 5-HT family of receptors has been shown to play a role in numerous human diseases including obesity, obsessive-compulsive disorder (OCD), sexual dysfunction, epilepsy, schizophrenia, and anxiety disorders (Roth, B., Shapiro, D. "Insights into the Structure and Function of 5-HT2 Family Serotonin Receptors Reveal Novel Strategies for Therapeutic Target Development" *Expert Opin. Ther. Targets* 2001, 5, 685; Martin, J., Bos, M., Jenck, F., Moreau, J-l., Mutel, V., Sleight, A., Wichmann, J., Andrews, J., Berendsen, H., Broekkamp, C., Ruight, G., Kohler, C., van Delft, A. "5-$HT_{2C}$ Receptor Agonists: Pharmacological Characteristics and Therapeutic Potential" *J. Pharm. Experimental Ther.* 1998, 286, 913; Tecott, L., Sun, L., Akana, S., Strack, A., Lowenstein, D., Dallman, M., Julius, D. "Eating Disorder and Epilepsy in Mice Lacking 5-$HT_{2C}$ Serotonin Receptors" *Nature* 1995, 374, 542). A clinical study in 1997 (Sargent, P., Sharpley, A., Williams, C., Cowen, P. "5-$HT_{2C}$-Receptor Activation Decreases Appetite and Body Weight in Obese Subjects" *Psychopharmacology* 1997, 133, 309; Barnes, Nicholas M., Sharp, Trevor "A Review of Central 5-HT Receptors and Their Function" *Neuropharmacology* 1999, 38, 1038). However, a need for potent and selective 5-HT modulators (specifically those associated with 5-$HT_{2A}$, 5-$HT_{2C}$ and 5-$HT_6$) still exists

SUMMARY

Described herein are compounds, pharmaceutical compositions containing the compounds and method of using the compounds to treat a disorder, e.g., a 5-HT related disorder, in a subject. For example a disorder associated with regulation of or expression of 5-$HT_{2A}$, 5-$HT_{2C}$ and 5-$HT_6$.

In one aspect, the invention is directed to a compound selected from the following formula:

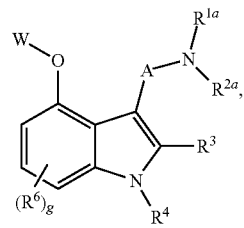

(I)

wherein $R^{1a}$ and $R^{2a}$ are each independently selected from H, optionally substituted $C_{1-8}$ alkyl, optionally substituted aryl, optionally substituted heteroaryl, optionally substituted arylalkyl, optionally substituted heteroaralalkyl, optionally substituted cycloalkyl, optionally substituted heterocyclyl, optionally substituted cycloalkylalkyl, optionally substituted heterocycloalkyl;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or —C(O)$NR^dR^{d'}$;

W is

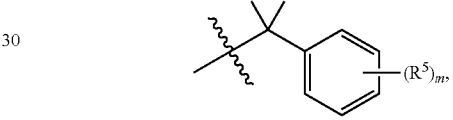

optionally substituted aryl, optionally substituted heteroaryl, optionally substituted aryl$C_2$-$C_6$alkyl, optionally substituted heterocyclyl, optionally substituted cycloalkyl; optionally substituted heteroarylalkyl, optionally substituted cycloalkylalkyl, optionally substituted heterocycloalkyl, optionally substituted arylheteroalkyl, optionally substituted heteroarylheteroalkyl, optionally substituted heterocyclylheteroalkyl, optionally substituted cycloalkylheteroalkyl, -alkyl-O—$C_{0-2}$alkyl-aryl, -alkyl-O—$C_{0-2}$alkyl-heteroaryl, —C(O)$NR^dR^{d'}$, $C_1$ alkyl substituted with —C(O)$NR^dR^{d'}$, or $C_{2-8}$ alkyl substituted with —$NR^dR^{d'}$, —C(O)$NR^dR^{d'}$ or —$OR^d$;

A is optionally substituted $C_{1-4}$ alkylene, optionally substituted cycloalkylene, optionally substituted aryl, optionally substituted heteroaryl, optionally substituted arylene, optionally substituted heteroarylene, or optionally substituted heterocycloalkylene, wherein arylene or heteroarylene are optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —OC(O)$NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —C(O)$NR^dR^{d'}$, and —C(O)$OR^d$, wherein alkylene and cycloalkylene are optionally substituted with 1-3 substituents, each of which is independently selected from the group consisting of halogen, oxo, optionally substituted $C_{1-6}$ alkyl, —S(O)$_{0-2}$alkyl, —OR$^d$ and —NR$^d$R$^{d'}$, aryl, heteroaryl, and $C_3$-$C_8$ cycloalkyl or 4-8 membered heterocyclyl (e.g., wherein two substituents, together with the carbon to which they are attached, form a ring);

R$^4$ is selected from optionally substituted $C_{1-8}$ alkyl, optionally substituted $C_{1-8}$ heteroalkyl, optionally substituted $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ arylalkyl, —S(O)$_2$ heteroarylalkyl, —S(O)$_2$ cycloalkyalkyl, formyl, —OR$^d$, —NR$^d$R$^{d'}$, —C(O)OR$^a$, —C(O)NR$^d$R$^{d'}$, —S(O)$_2$NR$^d$R$^{d'}$, amine-substituted $C_{2-6}$ alkyl, NR$^{d'}$R$^{d''}$-substituted $C_{2-6}$ alkyl, $C_{3-8}$ cycloalkyl, heterocyclyl, cycloalkylalkyl, heterocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and heteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, optionally substituted —C$_1$alkyl-C(O)NR$^e$R$^f$, —C$_2$alkyl-O-aryl, —C$_2$alkyl-O-heteroaryl, —C$_1$alkyl-heterocyclyl, —C$_1$alkyl-cycloalkyl, cyano, nitro, $C_{1-6}$ haloalkyl, $C_{1-6}$ haloalkoxy, —NR$^d$R$^{d'}$, optionally substituted $C_{1-6}$ alkyl-NR$^d$C(O)R$^a$, —C(O)NR$^d$R$^{d'}$, and —C(O)OR$^d$;

R$^5$ is selected from H, halo, and R$^6$;

each R$^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$—C$_{1-4}$alkylaryl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —C$_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

each of R$^7$ and R$^8$ is independently H, optionally substituted $C_{1-8}$ alkyl or fluoro; or R$^7$ and R$^8$ can, together with the carbon to which they are attached, form a ring;

R$^a$, and R$^b$ are each independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocycloalkyl;

R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety;

g is 1, 2 or 3;

m is 0, 1, 2, 3, 4 or 5; and wherein when m is 0, at least one of R$^7$ or R$^8$ is not H.

In some embodiments, R$^{1a}$ and R$^{2a}$ are each independently selected from H, $C_{1-8}$ alkyl, or optionally substituted aryl.

In some embodiments, A is selected from optionally substituted $C_{1-4}$ alkylene, wherein the $C_{1-4}$ alkylene is optionally substituted with 1-3 substituents, each of which is independently selected from the group consisting of halogen, hydroxyl, optionally substituted $C_{1-6}$ alkyl, $C_{1-8}$ alkoxy, —SO$_2$ alkyl, and —NR$^d$R$^{d''}$.

In some embodiments, A is optionally substituted heteroaryl, optionally substituted heteroarylalkyl, optionally substituted aryl. The compound may be optionally substituted heteroaryl, the optionally substituted heteroarylalkyl, or the optionally substituted aryl is substituted with 1-3 substituents, each of which is independently selected from the group consisting of halogen, $C_{3-8}$ cycloalkyl, —OR$^d$, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$ alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted —C$_{1-6}$ alkyl, —NR$^d$C(O)R$^a$, —C(O)NR$^d$R$^{d'}$, and —C(O).

In some embodiments, R$^3$ is selected from H, and optionally substituted $C_{1-8}$ alkyl.

In some embodiments, R$^4$ is selected from optionally substituted $C_{1-8}$ alkyl, aryl, heteroaryl, arylalkyl, heteroarylalkyl, amine-substituted $C_{2-6}$ alkyl, NR$^{d'}$R$^{d''}$-substituted $C_{2-6}$ alkyl, —S(O)$_2$ alkyl, —S(O)$_2$ arylalkyl, —S(O)$_2$ heteroarylalkyl, —S(O)$_2$ aryl, —S(O)$_2$ heteroaryl, —S(O)$_2$ cycloalkyl, —S(O)$_2$ heterocycloalkyl, —S(O)$_2$ heterocycloalkylalkyl, —S(O)$_2$ cycloalkylalkyl, optionally substituted —C$_1$alkyl-C(O)NR$^e$R$^f$, —C$_2$alkyl-O-aryl, —C$_2$alkyl-O-heteroaryl, —C$_1$alkyl-heterocyclyl, and —C$_1$alkyl-cycloalkyl.

In some embodiments, R$^4$ is $C_{1-8}$ alkyl, cycloalkyl, or heterocyclyl optionally substituted with 1-3 substituents selected from halo, alkyl, haloalkyl, heteroalkyl, —OR$^d$, —NR$^d$R$^{d'}$, and wherein aryl or herteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted $C_{2-6}$ alkyl, —NR$^d$C(O)R$^a$, —C(O)NR$^d$R$^{d'}$, and —C(O)OR$^d$.

In some embodiments, R$^4$ is optionally substituted $C_{1-8}$ alkyl.

In some embodiments, W is arylC$_{2-8}$alkyl optionally substituted with —OR$^d$, —NR$^d$R$^{d'}$, or —C(O)NR$^d$R$^{d'}$.

In some embodiments, W is

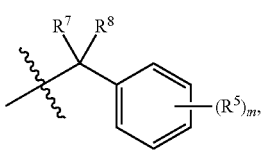

optionally substituted arylC$_2$-C$_6$alkyl, or heteroarylalkyl.

In some embodiments, W is optionally substituted heteroaryl, optionally substituted heteroarylalkyl, or optionally substituted aryl.

In some embodiments, W is optionally substituted heteroarylalkyl.

In some embodiments, W is —(CH$_2$)$_2$—O-phenyl.

In some embodiments, W is

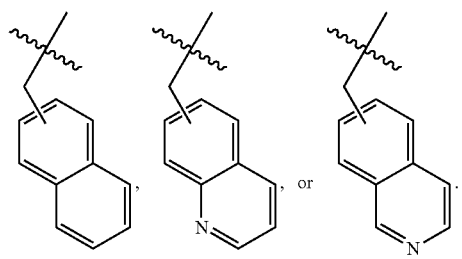

In some embodiments, W is

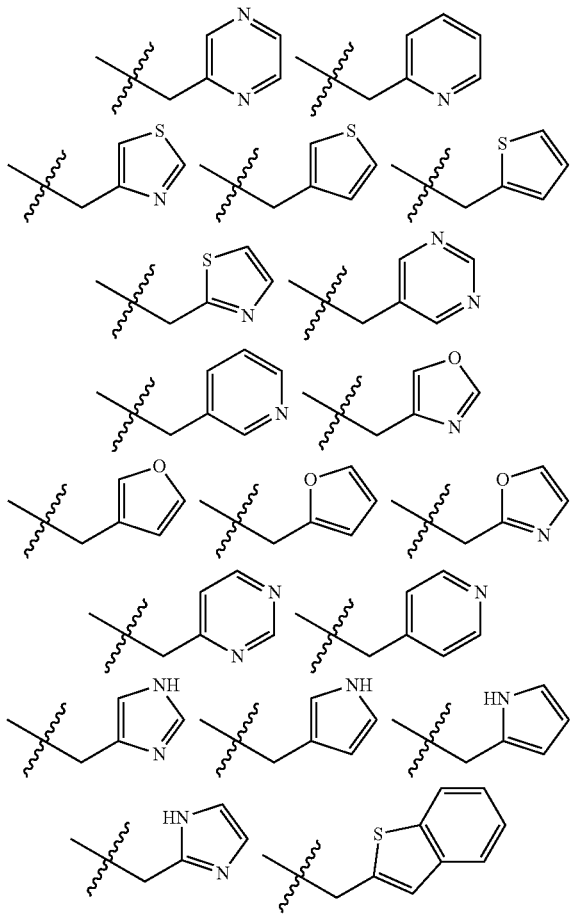

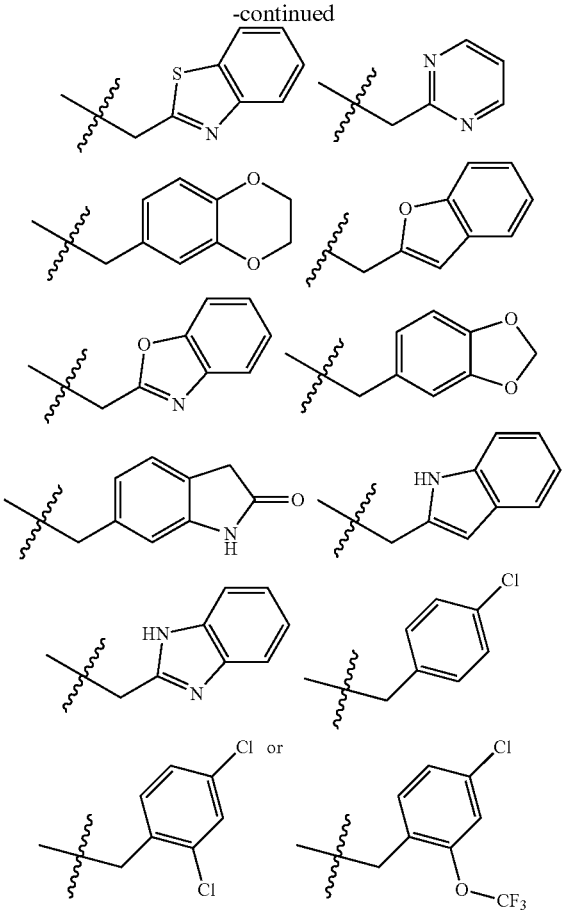

In some embodiments, each R$^5$ is selected from C$_{1-8}$ alkyl, C$_{1-8}$ fluoroalkyl, hydroxyl, C$_{1-8}$ alkoxy, C$_{1-8}$ fluoroalkoxy, nitro, halogen, and —NR$^d$R$^{d'}$.

In some embodiments, each R$^5$ is halo, C$_{1-8}$ alkyl or C$_{1-8}$ haloalkyl.

In some embodiments, each R$^6$ is selected from halogen, C$_{1-8}$ alkyl, hydroxyl, —C$_{1-8}$ fluoroalkyl, C$_{1-8}$ haloalkoxy, and —NR$^d$R$^{d'}$.

In some embodiments, each R$^6$ is halogen.

In some embodiments, each R$^6$ is C$_{1-8}$ alkyl.

In some embodiments, the compound is:

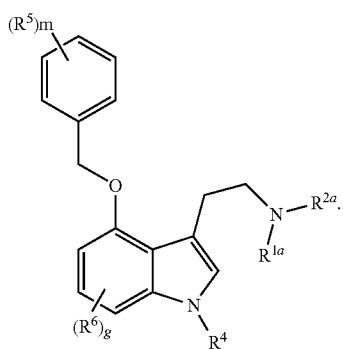

and optionally m=1, and, optionally, g=1.

In some embodiments, the compound is
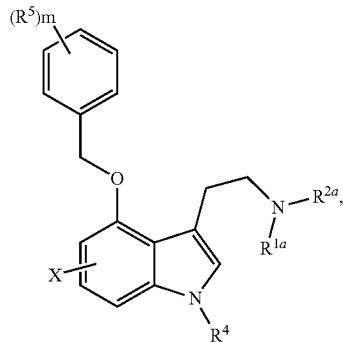
wherein X is a halogen, optionally fluorine.
In some embodiments, the compound selected from
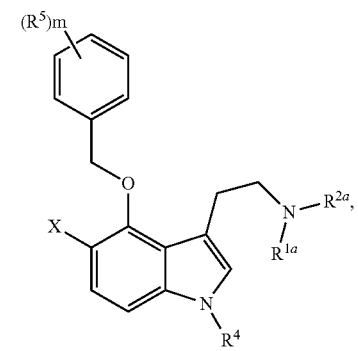
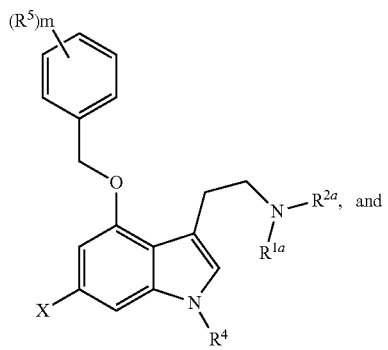
and
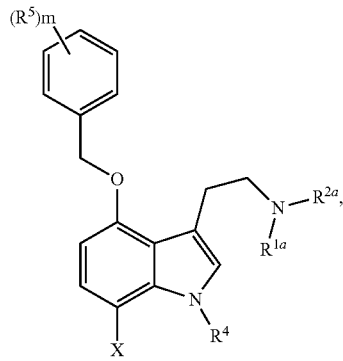
wherein X is a halogen, optionally fluorine. Optionally m=1.
In some embodiments, the compound is:
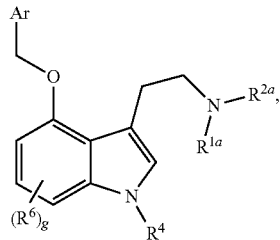
wherein Ar is optionally substituted aryl or optionally substituted heteroaryl.
In some embodiments, the compound is selected from
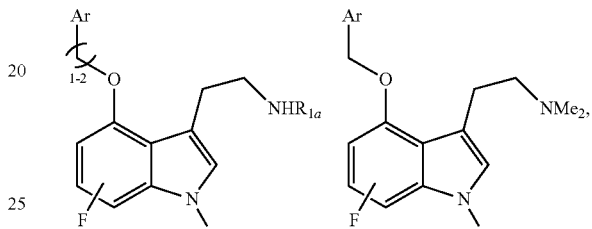
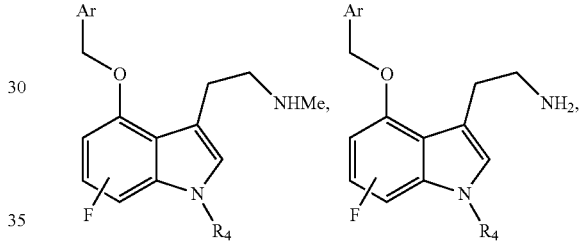
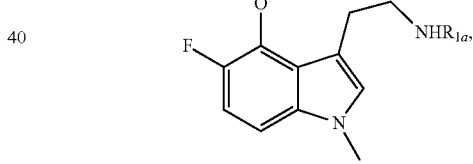
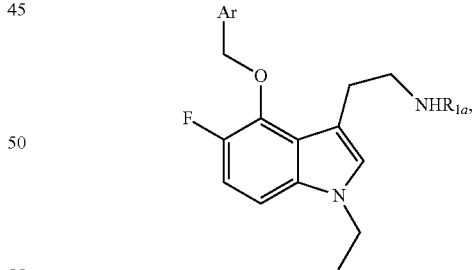
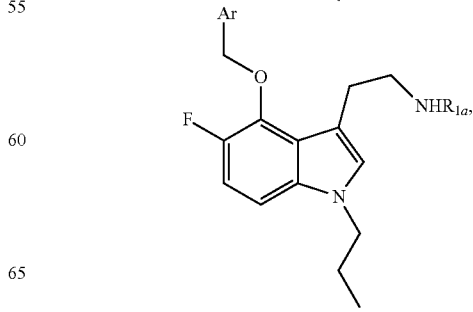

-continued

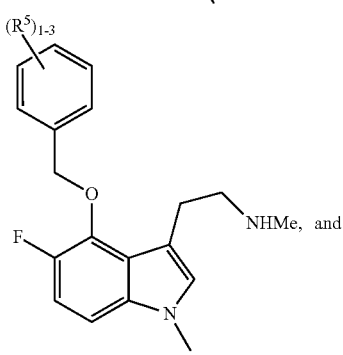

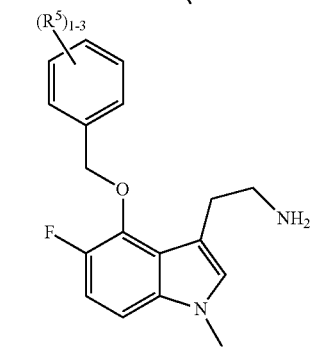

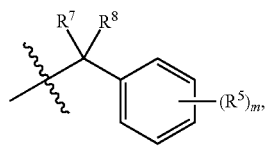

wherein Ar is optionally substituted aryl or optionally substituted heteroaryl.

In some embodiments, W is

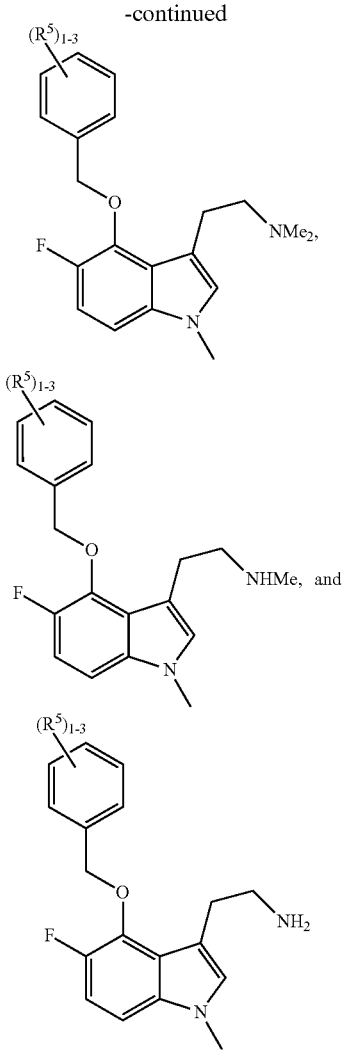

wherein m is 1-3, $R^7$ and $R^8$ are H, and $R^5$ is selected from F, Cl, Br, $CF_3$, methyl, OH, —$OCH_3$, —$OCF_3$, and —$S(O)_{0-2}R^a$.

In some embodiments, the compound is selected from the group consisting of 2-(1-ethyl-6-fluoro-4-(4-fluorobenzyloxy)-1H-indol-3-yl)-N,N-dimethylethanamine,
2-(1-ethyl-6-fluoro-4-(4-methoxybenzyloxy)-1H-indol-3-yl)-N,N-dimethylethanamine,
2-(4-(4-chlorobenzyloxy)-1-ethyl-6-fluoro-1H-indol-3-yl)-N,N-dimethylethanamine,
2-(1-ethyl-6-fluoro-4-(4-(trifluoromethoxy)benzyloxy)-1H-indol-3-yl)-N,N-dimethylethanamine,
2-(1-ethyl-6-fluoro-4-(4-(trifluoromethyl)benzyloxy)-1H-indol-3-yl)-N,N-dimethylethanamine,
2-(1-ethyl-6-fluoro-4-(2-(trifluoromethyl)benzyloxy)-1H-indol-3-yl)-N,N-dimethylethanamine,
2-(1-ethyl-6-fluoro-4-(3-(trifluoromethyl)benzyloxy)-1H-indol-3-yl)-N,N-dimethylethanamine,
2-(3-(2-(dimethylamino)ethyl)-1-ethyl-7-fluoro-1H-indol-4-yloxy)aniline,
2-(1-ethyl-7-fluoro-4-(2-nitrophenoxy)-1H-indol-3-yl)-N,N-dimethylethanamine,
2-(1-ethyl-6-fluoro-4-(5-fluoro-2-methylbenzyloxy)-1H-indol-3-yl)-N,N-dimethylethanamine,
2-(1-ethyl-6-fluoro-4-(pyridin-4-ylmethoxy)-1H-indol-3-yl)-N,N-dimethylethanamine,
2-(1-ethyl-6-fluoro-4-(thiophen-3-ylmethoxy)-1H-indol-3-yl)-N,N-dimethylethanamine,
2-(5-fluoro-1-methyl-4-phenethoxy-1H-indol-3-yl)-N,N-dimethylethanamine,
2-(1-ethyl-6-fluoro-4-phenoxy-1H-indol-3-yl)-N,N-dimethylethanamine,
2-(4-(2-chlorobenzyloxy)-6-fluoro-1-methyl-1H-indol-3-yl)-N-methylethanamine,
2-(4-(4-chlorobenzyloxy)-6-fluoro-1-methyl-1H-indol-3-yl)-N-methylethanamine,
2-(4-(3-chlorobenzyloxy)-6-fluoro-1-methyl-1H-indol-3-yl)-N-methylethanamine,
2-(4-(3-chlorobenzyloxy)-5-fluoro-1-methyl-1H-indol-3-yl)-N-methylethanamine,
2-(4-(4-chlorobenzyloxy)-5-fluoro-1-methyl-1H-indol-3-yl)-N-methylethanamine,
2-(5-fluoro-1-methyl-4-(3-(trifluoromethyl)benzyloxy)-1H-indol-3-yl)-Nmethylethanamine,
2-(5-fluoro-1-methyl-4-(2-methylbenzyloxy)-1H-indol-3-yl)-N-methylethanamine,
2-(4-(2-chlorobenzyloxy)-5-fluoro-1-methyl-1H-indol-3-yl)-N-methylethanamine,
2-(5-fluoro-4-(2-fluorobenzyloxy)-1-methyl-1H-indol-3-yl)-N-methylethanamine,
2-(5-fluoro-4-(4-methoxyphenethoxy)-1-methyl-1H-indol-3-yl)-N-methylethanamine,
2-(5-fluoro-1-methyl-4-phenethoxy-1H-indol-3-yl)-N-methylethanamine,
2-(5-fluoro-1-methyl-4-(4-methylbenzyloxy)-1H-indol-3-yl)-N-methylethanamine,
2-(5-fluoro-4-(4-fluorophenethoxy)-1-methyl-1H-indol-3-yl)-N-methylethanamine,
2-(4-(4-chlorophenethoxy)-5-fluoro-1-methyl-1H-indol-3-yl)-N-methylethanamine,
2-(4-(biphenyl-2-ylmethoxy)-5-fluoro-1-methyl-1H-indol-3-yl)-N-methylethanamine,
2-(5-fluoro-1-methyl-4-(2-(trifluoromethyl)benzyloxy)-1H-indol-3-yl)-N-methylethanamine,
2-(5-fluoro-1-methyl-4-(1-phenylethoxy)-1H-indol-3-yl)-N-methylethanamine,
2-((3-(2-(((2-cyanobenzyl)(methyl)amino)ethyl)-5-fluoro-1-methyl-1H-indol-4-yloxy)methyl)benzonitrile,
2-(5-fluoro-4-(5-fluoro-2-methylbenzyloxy)-1-methyl-1H-indol-3-yl)-N-methylethanamine,
2-(5-fluoro-1-methyl-4-(2-(trifluoromethoxy)benzyloxy)-1H-indol-3-yl)-N-methylethanamine,
2-(5-fluoro-4-(4-fluorobenzyloxy)-1-methyl-1H-indol-3-yl)-N-methylethanamine,
2-(5-fluoro-1-methyl-4-(naphthalen-1-ylmethoxy)-1H-indol-3-yl)-N-methylethanamine,
1-(2-chlorophenyl)-2-(5-fluoro-1-methyl-3-(2-(methylamino)ethyl)-1H-indol-4-yloxy)ethanol,
2-(5-fluoro-1-methyl-4-(4-(methylsulfonyl)benzyloxy)-1H-indol-3-yl)-N-methylethanamine, 2-(5-fluoro-4-(naphthalen-1-ylmethoxy)-1-propyl-1H-indol-3-yl)-N-methylethanamine,
2-(4-(4-chlorobenzyloxy)-5-fluoro-1-propyl-1H-indol-3-yl)-N-methylethanamine,
2-(5-fluoro-1-methyl-4-(quinolin-8-ylmethoxy)-1H-indol-3-yl)-N-methylethanamine,
2-(5-fluoro-1-methyl-4-(2-phenoxyethoxy)-1H-indol-3-yl)-N-methylethanamine,
2-(5-fluoro-4-(4-fluorobenzyloxy)-1-propyl-1H-indol-3-yl)-N-methylethanamine,
2-(5-fluoro-4-(4-methylbenzyloxy)-1-propyl-1H-indol-3-yl)-N-methylethanamine,
2-(5-fluoro-1-methyl-4-(2-methylphenethoxy)-1H-indol-3-yl)-N-methylethanamine,
2-(5-fluoro-4-(4-(methylsulfonyl)benzyloxy)-1-propyl-1H-indol-3-yl)-N-methylethanamine,
2-(4-(2-chlorophenethoxy)-5-fluoro-1-methyl-1H-indol-3-yl)-N-methylethanamine,
2-(4-(2,4-dichlorobenzyloxy)-5-fluoro-1-methyl-1H-indol-3-yl)-N-methylethanamine,
2-(4-(4-chlorobenzyloxy)-5-fluoro-1-propyl-1H-indol-3-yl)ethanamine
2-(4-(4-chloro-3-(trifluoromethoxy)benzyloxy)-5-fluoro-1-methyl-1H-indol-3-yl)-N-methylethanamine, and
2-(5-fluoro-1-methyl-4-(thiophen-2-ylmethoxy)-1H-indol-3-yl)-N,N-dimethylethanamine.

In another aspect, the invention is directed to a compound selected from the following formula:

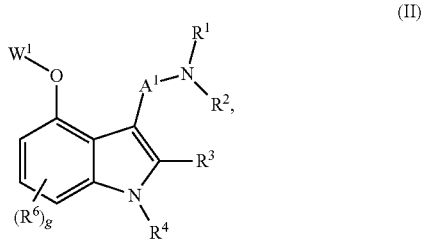

(II)

wherein g is 1, 2 or 3;

$A^1$ is optionally substituted $C_{3-6}$cycloalkylene, optionally substituted heterocyclalkene, optionally substituted aryl, optionally substituted heteroaryl, optionally substituted arylene, optionally substituted heteroarylene, optionally substituted heterocycloalkylene or optionally substituted —C(O)—$C_{1-3}$ alkylene-, wherein arylene or heteroarylene are optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl, —$S(O)_{0-2}$ $C_{1-8}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^dR^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$NR^aS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)OR^d$, wherein cycloalkylene and —C(O)—$C_{1-3}$ alkylene are optionally substituted with 1-3 substituents, each of which are independently selected from the group consisting of halogen, oxo, optionally substituted $C_{1-6}$ alkyl, —$S(O)_{0-2}$ alkyl, —$OR^d$ and —$NR^dR^{d'}$, aryl or heteroaryl, and $C_3$-$C_8$ cycloalkyl or 4-8 membered heterocyclyl. (e.g., wherein two substituents, together with the carbon to which they are attached, form a ring);

$R^1$ and $R^2$ are each independently selected from H, $C_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^1$ is hydrogen, optionally substituted $C_{1-8}$ alkyl, optionally substituted aryl, optionally substituted heteroaryl, optionally substituted arylalkyl, optionally substituted cycloalkyl, optionally substituted heterocyclyl, optionally substituted cycloalkylalkyl, optionally substituted heterocycloalkyl or optionally substituted heteroarylalkyl;

$R^4$ is selected from optionally substituted $C_{1-8}$ alkyl, optionally substituted $C_{1-8}$ heteroalkyl, $C_{2-8}$ alkenyl, $C_{2-8}$ alkynyl, —$S(O)_2$ alkyl, —$S(O)_2$ heteroalkyl, —$S(O)_2$ aryl, —$S(O)_2$ heteroaryl, —$S(O)_2$ cycloalkyl, —$S(O)_2$ heterocyclyl, —$S(O)_2$ heterocycloalkyl, —$S(O)_2$ arylalkyl, —$S(O)_2$ heteroarylalkyl, —$S(O)_2$ cycloalkylalkyl, formyl, —$OR^d$, —$NR^dR^{d'}$, —$C(O)OR^a$, —$C(O)NR^dR^{d'}$, —$S(O)_2NR^dR^{d'}$, $C_{3-8}$ cycloalkyl, heterocyclyl, cycloalkylalkyl, heteocyclylalkyl, aryl, heteroaryl, arylalkyl, and heteroarylalkyl, wherein alkyl, cycloalkyl and heterocyclyl are optionally substituted with 1-3 substituents, halo, alkyl, haloalkyl, heteroalkyl, —$OR^d$, —$NR^dR^{d'}$, and wherein aryl and heteroaryl are optionally substituted with 1-3 substituents, each of which is independently selected from the group consisting of halogen, alkyl, heteroalkyl, cycloalkyl, heterocyclyl, —$OR^d$, —SH, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$-arylalkylaryl, —$S(O)_{0-2}$-heteroarylalkyl, —$OC(O)NR^dR^{d'}$, —$NR^dC(O)NR^dR^{d''}$, —$NR^dC(O)OR^b$, —$OR^d$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$NR^dS(O)_2$-heterocycloalkyl, —$SO_2NR^dR^{d'}$, optionally substituted —$C_1$alkyl-$C(O)NR^eR^f$, —$C_1$alkyl-O-aryl, —$C_1$alkyl-O-heteroaryl, —$C_1$alkyl-heterocyclyl, —$C_1$alkyl-cycloalkyl, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$;

each $R^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^dR^{d''}$, —$NR^dC(O)OR^a$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$alkyl- $NR^dR^{d'}$, optionally substituted $C_{1-6}$ alkyl, $-NR^dC(O)R^a$, $-C(O)NR^dR^{d'}$, and $-C(O)OR^d$; wherein alkyl, aryl, heteroaryl, cycloalkyl and heterocyclyl are optionally substituted;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocycloalkyl; and $R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In another aspect, the invention is directed to a compound selected from the following formula:

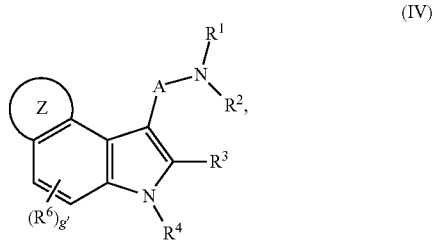

(IV)

wherein g' is 0, 1, 2 or 3;

Z is an optionally substituted heteroaryl or optionally substituted heterocyclyl;

$R^1$ and $R^2$ are each independently selected from H, $C_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, aryl, heteroaryl, $C_{3-8}$ cycloalkyl, $-OR^d$, $C_{1-8}$ haloalkoxy, $-S(O)_{0-2}$ $C_{1-8}$ alkyl, $-S(O)_{0-2}$ aryl, $-S(O)_{0-2}$ heteroaryl, $-S(O)_{0-2}$ arylalkyl, $-S(O)_{0-2}$ heteroarylalkyl), $-S(O)_{0-2}$ cycloalkyl, $-S(O)_{0-2}$ heterocycloalkyl, $-S(O)_{0-2}$ heterocycloalkylalkyl, $-S(O)_{0-2}$ cycloalkylalkyl, $-OC(O)NR^dR^{d'}$, $-NR^dC(O)NR^{d'}R^{d''}$, $-NR^dC(O)OR^b$, $-NR^dS(O)_2$alkyl, $-NR^dS(O)_2$aryl, $-NR^dS(O)_2$heteroaryl, $-NR^dS(O)_2$cycloalkyl, $-NR^dS(O)_2$heterocycloalkyl, $-NR^dS(O)_2$-arylalkyl, $-NR^dS(O)_2$-heteroarylalkyl, $-NR^dS(O)_2$-cycloalkylalkyl, $-NR^dS(O)_2$-heterocycloalkyl, $-SO_2NR^dR^{d'}$, cyano, nitro, $C_{1-6}$ haloalkyl, $C_{1-6}$ haloalkoxy, $-NR^dR^{d'}$, optionally substituted $-C_{1-6}$ alkyl, $-NR^dC(O)R^a$, $-C(O)NR^dR^{d'}$, and $-C(O)OR^d$, wherein alkylene and cycloalkylene are optionally substituted with 1-3 substituents, each of which is independently selected from the group consisting of halogen, oxo, optionally substituted $C_{1-6}$ alkyl, $-S(O)_{0-2}$alkyl, $-OR^d$ and $-NR^dR^{d'}$, aryl or heteroaryl, and $C_3-C_8$ cycloalkyl or 4-8 membered heterocyclyl (e.g., wherein two substituents, together with the carbon to which they are attached, form a ring);

$R^4$ is selected from optionally substituted $C_{1-8}$ alkyl, optionally substituted $C_{1-8}$ heteroalkyl, $C_{2-8}$ alkenyl, $C_{2-8}$ alkynyl, $-S(O)_2$ alkyl, $-S(O)_2$ heteroalkyl, $-S(O)_2$ aryl, $-S(O)_2$ heteroaryl, $-S(O)_2$ cycloalkyl, $-S(O)_2$ heterocyclyl, $-S(O)_2$ heterocycloalkyl, $-S(O)_2$ arylalkyl, $-S(O)_2$ heteroarylalkyl, $-S(O)_2$ cycloalkyalkyl, formyl, $-OR^d$, $-NR^dR^{d'}$, $-C(O)OR^a$, $-C(O)NR^dR^{d'}$, $-S(O)_2NR^dR^{d'}$, $C_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, $-OR^d$, $-NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, $-OR^d$, $-SH$, $C_{1-8}$ haloalkoxy, $-S(O)_{0-2}$ $C_{1-8}$ alkyl, $-S(O)_{0-2}$ aryl, $-S(O)_{0-2}$ heteroaryl, $-S(O)_{0-2}$—$C_{1-4}$alkylaryl, $-S(O)_{0-2}$—$C_{1-4}$alkylheteroaryl, $-OC(O)NR^dR^{d'}$, $-NR^dC(O)NR^{d'}R^{d''}$, $-NR^dC(O)OR^b$, $-OR^d$, $-NR^dS(O)_2$alkyl, $-NR^dS(O)_2$aryl, $-NR^dS(O)_2$heteroaryl, $-NR^dS(O)_2$cycloalkyl, $-NR^dS(O)_2$heterocycloalkyl, $-NR^dS(O)_2$-arylalkyl, $-NR^dS(O)_2$-heteroarylalkyl, $-NR^dS(O)_2$-cycloalkylalkyl, $-NR^aS(O)_2$-heterocycloalkyl, $-SO_2NR^dR^{d'}$, optionally substituted $-C_1$alkyl-$C(O)NR^eR^f$, $-C_1$alkyl-O-aryl, $-C_1$alkyl-O-heteroaryl, $-C_1$alkyl-heterocyclyl, $-C_1$alkyl-cycloalkyl, cyano, nitro, $C_{1-6}$ haloalkyl, $C_{1-6}$ haloalkoxy, $-NR^dR^{d'}$, optionally substituted $C_{1-6}$ alkyl, $-NR^dC(O)R^a$, $-C(O)NR^dR^{d'}$, and $-C(O)OR^d$;

each $R^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, $-SH$, $-OR^d$, $C_{1-8}$ haloalkoxy, $C_{1-8}$ haloalkyl, $-S(O)_{0-2}$ $C_{1-8}$ alkyl, $-S(O)_{0-2}$ aryl, $-S(O)_{0-2}$ heteroaryl, $-S(O)_{0-2}$ arylalkyl, $-S(O)_{0-2}$ heteroarylalkyl, $-S(O)_{0-2}$ cycloalkyl, $-S(O)_{0-2}$ heterocycloalkyl, $-S(O)_{0-2}$ heterocycloalkylalkyl, $-S(O)_{0-2}$ cycloalkylalkyl, $-OC(O)NR^dR^{d'}$, $-NR^dC(O)NR^{d'}R^{d''}$, $-NR^dC(O)OR^a$, $-NR^dS(O)_2$alkyl, $-NR^dS(O)_2$aryl, $-NR^dS(O)_2$heteroaryl, $-NR^dS(O)_2$cycloalkyl, $-NR^dS(O)_2$heterocycloalkyl, $-NR^dS(O)_2$-arylalkyl, $-NR^dS(O)_2$-heteroarylalkyl, $-NR^dS(O)_2$-cycloalkylalkyl, $-NR^aS(O)_2$-heterocycloalkyl, $-SO_2NR^dR^{d'}$, cyano, nitro, $C_{1-6}$ haloalkyl, $C_{1-6}$ haloalkoxy, $-NR^dR^{d'}$, $-C_{1-4}$alkyl-$NR^dR^{d'}$, optionally substituted $C_{1-6}$ alkyl, $-NR^dC(O)R^a$, $-C(O)NR^dR^{d'}$, and $-C(O)OR^d$; wherein alkyl, aryl, heteroaryl, cycloalkyl and heterocyclyl are optionally substituted;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocycloalkyl, or when taken together with the nitrogen atom to which are attached, $R^a$ and $R^b$ form a 4-8 membered heterocyclic moiety; and $R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $R^1$ and $R^2$ are each independently selected from H, $C_{1-8}$ alkyl, and optionally substituted aryl.

In some embodiments, A is selected from optionally substituted $C_{1-4}$ alkylene, wherein the $C_{1-4}$ alkylene is optionally substituted with 1-3 substituents, each of which is independently selected from the group consisting of halogen, hydroxyl, optionally substituted $C_{1-6}$ alkyl, $C_{1-8}$ alkoxy, —$SO_2$ alkyl, —$NR^dR^{d'}$, aryl or heteroaryl, and $C_3$-$C_8$ cycloalkyl or 4-8 membered heterocyclyl (e.g., wherein two substituents, together with the carbon to which they are attached, form a ring)

In some embodiments, $R^3$ is selected from H, halogen, and optionally substituted $C_{1-8}$ alkyl.

In some embodiments, $R^4$ is selected from $C_{1-8}$ alkyl, optionally substituted aryl, optionally substituted heteroaryl, aralalkyl, heteroaralalkyl, —$S(O)_2$ alkyl, —$S(O)_2$ arylalkyl, —$S(O)_2$ heteroarylalkyl, —$S(O)_2$ aryl, —$S(O)_2$ cycloalkyl, —$S(O)_2$ heterocycloalkyl, —$S(O)_2$ heterocycloalkylalkyl, —$S(O)_2$ cycloalkylalkyl, and —$S(O)_2$ heteroaryl.

In some embodiments, $R^4$ is optionally substituted $C_{1-8}$ alkyl.

In some embodiments,

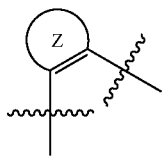 [SMILES: */C=C\*]

is optionally substituted

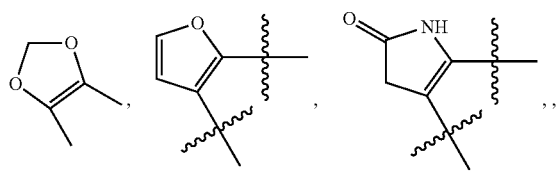

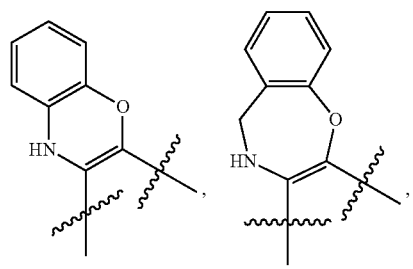

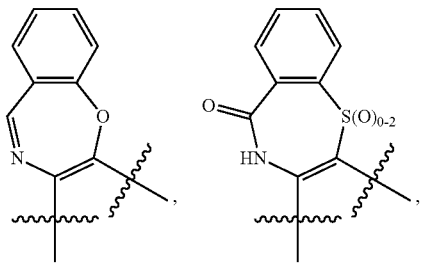

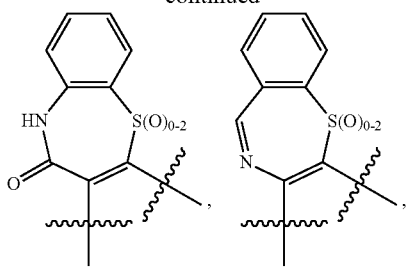

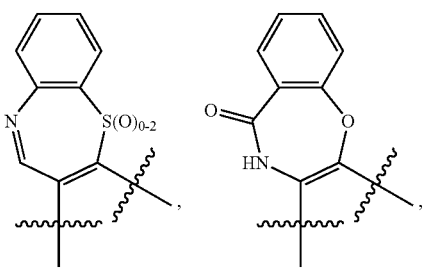

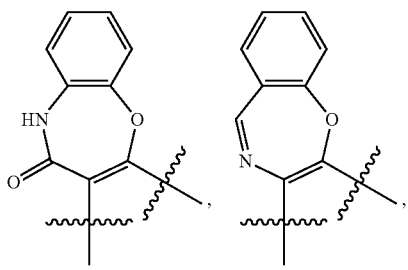

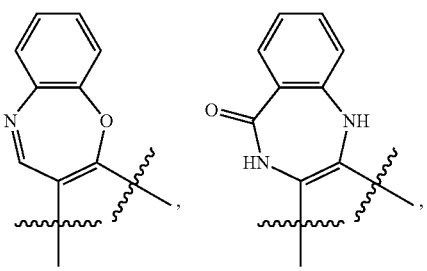

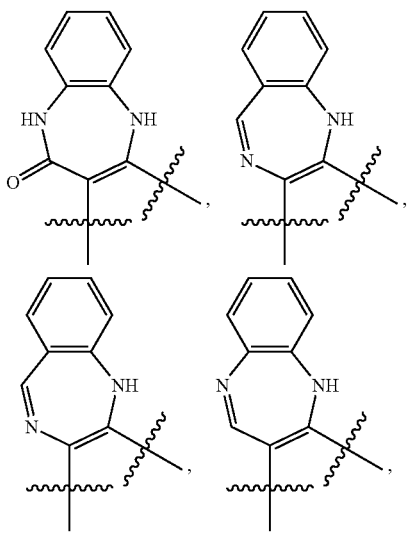

-continued
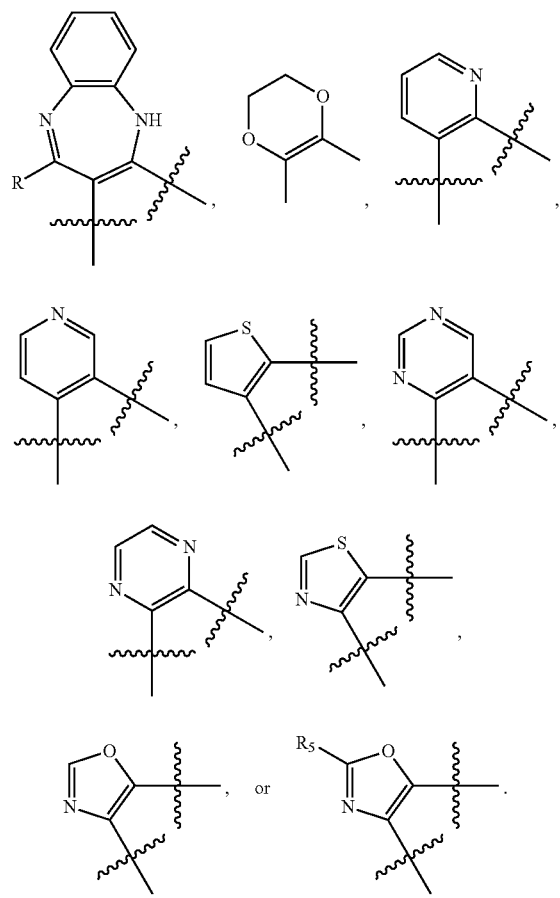
In some embodiments,
In some embodiments, the compound is selected from
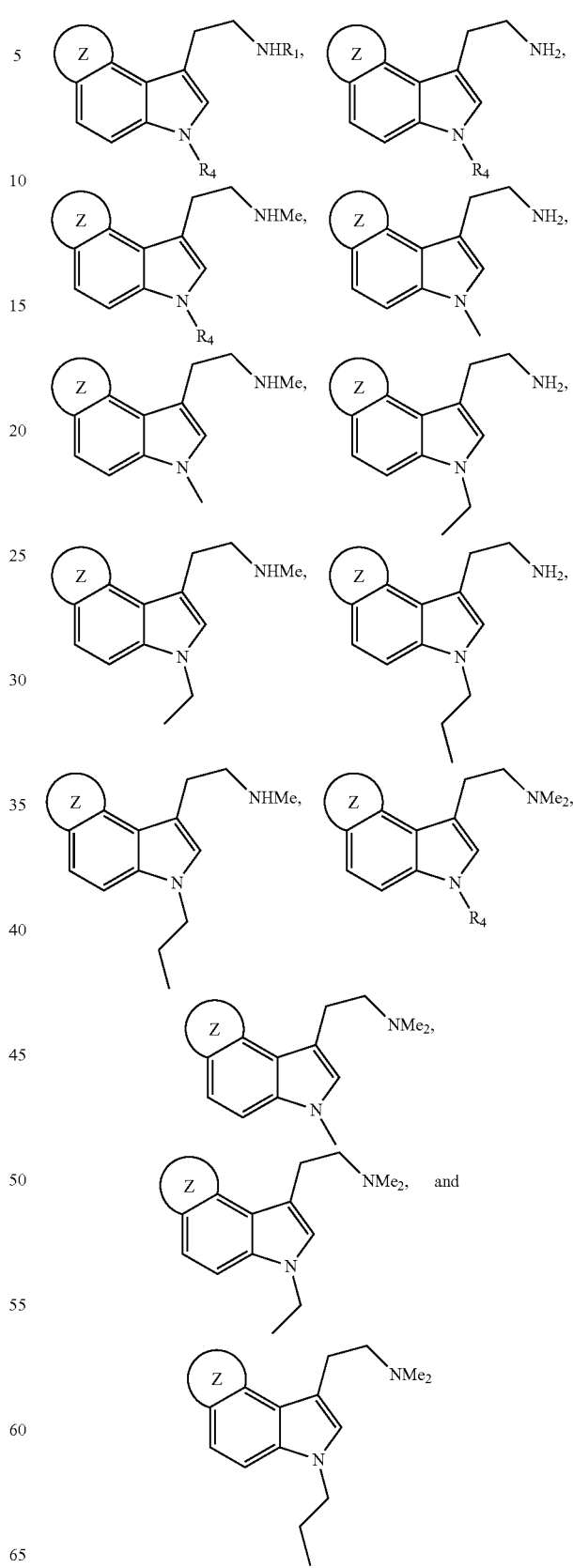

In some embodiments, the compound is 2-(7-propyl-3,7-dihydro-2H-[1,4]dioxino[2,3-e]indol-9-yl) ethanamine.

In another aspect, the invention is directed to a compound selected from the following formula:

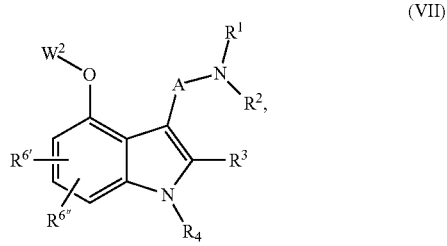

(VII)

wherein $R^1$ and $R^2$ are each independently selected from H, $C_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, optionally substituted aryl, optionally substituted heteroaryl, $C_{3-8}$ cycloalkyl, —OR$^d$, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^{d'}$C(O)NR$^d$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$, wherein alkylene and cycloalkylene are optionally substituted with 1-3 substituents, each of which is independently selected from the group consisting of halogen, oxo, optionally substituted $C_{1-6}$ alkyl, —S(O)$_{0-2}$alkyl, —OR$^d$ and —NR$^dR^{d'}$, aryl or heteroaryl, and $C_3$-$C_8$ cycloalkyl or 4-8 membered heterocyclyl (e.g., wherein two substituents, together with the carbon to which they are attached, form a ring);

$R^4$ is selected from optionally substituted $C_{1-8}$ alkyl, optionally substituted $C_{1-8}$ heteroalkyl, $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ arylalkyl, —S(O)$_2$ heteroarylalkyl, —S(O)$_2$ cycloalkyalkyl, formyl, —OR$^d$, —NR$^d$R$^{d'}$, —C(O)OR$^a$, —C(O)NR$^d$R$^{d'}$, —S(O)$_2$NR$^d$R$^{d'}$, $C_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^dR^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$ aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, optionally substituted —C$_1$alkyl-C(O)NR$^e$R$^f$, —C$_1$alkyl-O-aryl, —C$_1$alkyl-O-heteroaryl, —C$_1$alkyl-heterocyclyl, —C$_1$alkyl-cycloalkyl, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each $R^{6'}$ is independently selected from hydrogen, halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —$C_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$, wherein alkyl, aryl, heteroaryl, cycloalkyl and heterocyclyl are optionally substituted;

$R^{6''}$ is halo, optionally substituted $C_{1-8}$ alkyl, optionally substituted aryl, optionally substituted heteroaryl, heteroalkyl, $C_{3-8}$ cycloalkyl, optionally substituted heterocyclyl, aralalkyl, optionally substituted heteroarylalkyl, optionally substituted cycloalkylalkyl, optionally substituted heterocycloalkyl, —SH, —OR$^d$, $C_{1-8}$ haloalkoxy, $C_{1-8}$ haloalkyl, alkyl-C(O)NR$^e$R$^f$, alkyl-C(O)-heterocyclyl, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, -alkyl-OH, -alkyl-OR$^d$, -alkyl-NH$_2$, -alkyl-NR$^d$R$^{d'}$, -alkynyl-OH, -alkynyl-OR$^d$, -alkenyl-OH, -alkenyl-OR$^d$, -alkynyl-COOR$^d$ and -alkynyl-COOR$^d$, -alkenyl-COOR$^d$ and -alkenyl-COOR$^d$, -alkynyl-CONR$^d$R$^d$, -alkynyl-CO, NR$^d$R$^d$, -alkenyl-CONR$^d$R$^d$ and -alkenyl-CONR$^d$R$^d$, alkynyl-SO$_2$NR$^d$R$^{d'}$, NR$^d$-aryl, NR$^d$- heteroaryl, cyano, nitro, $C_{1-6}$ haloalkyl, $C_{1-6}$ haloalkoxy, $-NR^dR^{d'}$, $-C_{1-4}alkyl-NR^dR^{d'}$, optionally substituted $C_{1-6}$ alkyl, $-NR^dC(O)R^a$, $-C(O)NR^dR^{d'}$, and $-C(O)OR^d$, wherein alkyl, aryl, heteroaryl, cycloalkyl and heterocyclyl are optionally substituted, wherein $R^e$ and $R^f$ are selected from the same groups listed for $R^1$ and $R^2$, respectively;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $R^1$ and $R^2$ are each independently selected from H, optionally substituted $C_{1-8}$ alkyl, and optionally substituted aryl.

In some embodiments, A is $C_{1-4}$ alkylene, wherein the $C_{1-4}$ alkylene is optionally substituted with 1-3 substituents, each of which is independently selected from the group consisting of halogen, hydroxyl, optionally substituted $C_{1-6}$ alkyl, $C_{1-8}$ alkoxy, $-SO_2$ alkyl, and $-NR^dR^{d'}$.

In some embodiments, $R^3$ is selected from H, and optionally substituted $C_{1-8}$ alkyl.

In some embodiments, $R^4$ is selected from optionally substituted $C_{1-8}$ alkyl, aryl, heteroaryl, arylalkyl, heteroarylalkyl, $-S(O)_2$ alkyl, $-S(O)_2$ arylalkyl, $-S(O)_2$ heteroarylalkyl, $-S(O)_2$ aryl, $-S(O)_2$ cycloalkyl, $-S(O)_2$ heterocycloalkyl, $-S(O)_2$ heterocycloalkylalkyl, $-S(O)_2$ cycloalkylalkyl, and $-S(O)_2$ heteroaryl.

In some embodiments, $W^2$ is hydrogen, or $C_{1-8}$ alkyl optionally substituted with $-OR^d$, $-NR^dR^{d'}$, $-C(O)NR^dR^{d'}$.

In some embodiments, $W^2$ is optionally substituted $C_{1-8}$ alkyl.

In some embodiments, $R^{6'}$ is selected from hydrogen, halogen and $C_{1-8}$ alkyl.

In some embodiments, $R^{6''}$ is optionally substituted aryl, optionally substituted heteroaryl, heterocyclyl, cycloalkyl, $-OR^d$, $C_{2-8}$ alkynyl, $-NH$-aryl, $-NH$-heteroaryl, $-NH$-alkyl, $-NR^d$-aryl, $-NR^d$-heteroaryl, $-NR^d$-arylalkyl, $-NR^d$-heteroarylalkyl, $-NR^d$-heterocyclyl, $-NR^d$-heterocyclylalkyl, $-NR^d$-heterocyclyl, $-NR^d$-cyclylalkyl, $-S(O)_{0-2}$ $C_{1-8}$ alkyl, $-S(O)_{0-2}$ aryl, $-S(O)_{0-2}$ heteroaryl, $-S(O)_{0-2}$ arylalkyl, $-S(O)_{0-2}$ heteroarylalkyl, $-S(O)_{0-2}$ cycloalkyl, $-S(O)_{0-2}$ heterocycloalkyl, $-S(O)_{0-2}$ heterocycloalkylalkyl, $-S(O)_{0-2}$ cycloalkylalkyl, $-NR^d$-alkyl, $-C_1alkyl$-aryl, $-C_1alkyl$-heteroaryl, heterocyclyl, $-C_1alkyl$-cycloalkyl, $-C_1alkyl$-$NR^d$-alkyl, aryloxy, and heteroaryloxy.

In some embodiments, $R^{6''}$ is selected from optionally substituted aryl, optionally substituted arylalkyl, optionally substituted heteroarylalkyl, optionally substituted heteroaryl, optionally substituted cycloalkyl, optionally substituted aryloxy, optionally substituted heteroaryloxy, $-NH$-aryl, $C_{1-8}$ alkynoxy, and alkyl-$C(O)NR^eR^f$, wherein $R^e$ and $R^f$ are selected from the same groups listed for $R^1$ and $R^2$, respectively.

In some embodiments, $R^{6''}$ is hydroxyl $C_{2-8}$ alkynyl.

In some embodiments, $R^{6''}$ is $-SO_2aryl$, $-SO_2heteroaryl$, $-C_1alkylCONR^dR^{d'}$, -alkynyl-$OR^d$, -alkyl-$OR^d$, -alkyl-$NR^dR^{d'}$, arylalkyl, heteroarylalkyl, or cycloalkylalkyl.

In some embodiments, the compound is selected from

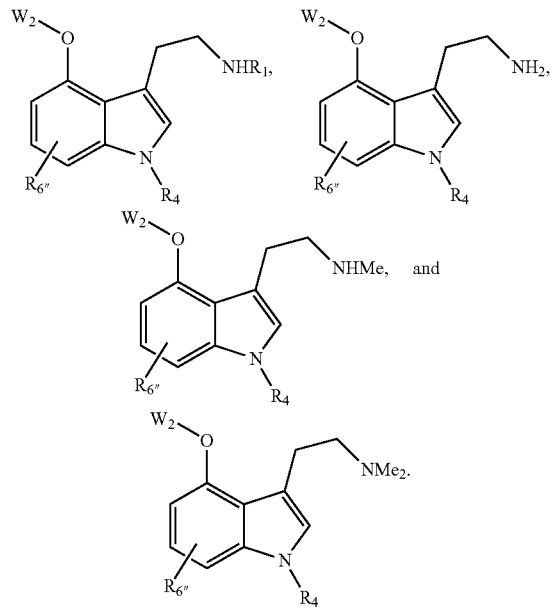

Optionally, R6" is $S(O)_{0-2}$ $C_{1-8}$ alkyl, $-S(O)_{0-2}$ aryl, $-S(O)_{0-2}$ heteroaryl, $-S(O)_{0-2}$ arylalkyl, $-S(O)_{0-2}$ heteroarylalkyl, $-S(O)_{0-2}$ cycloalkyl, $-S(O)_{0-2}$ heterocycloalkyl, $-S(O)_{0-2}$ heterocycloalkylalkyl, or $-S(O)_{0-2}$ cycloalkylalkyl. Optionally, $R^{6''}$ is alkyl-$C(O)NR^eR^f$, wherein $R^e$ and $R^f$ are selected from the same groups listed for $R^1$ and $R^2$, respectively.

In some embodiments, $R^{6''}$ is optionally substituted aryl, heteroaryl, heterocyclyl, cycloalkyl, $-OR^d$, $C_{2-8}$alkynyl, $-NH$-aryl, or $-NH$-heteroaryl.

In some embodiments, the compound is selected from the group consisting of 2-(7-fluoro-4-methoxy-1-methyl-5-phenyl-1H-indol-3-yl)-N,N-dimethylethanamine,
2-(4-methoxy-1-methyl-7-(pyridin-3-yl)-1H-indol-3-yl)-N,N-dimethylethanamine,
2-(4-methoxy-1-methyl-7-phenyl-1H-indol-3-yl)-N,N-dimethylethanamine,
2-(4-methoxy-1-methyl-7-(thiophen-3-yl)-1H-indol-3-yl)-N,N-dimethylethanamine,
2-(4-methoxy-1-methyl-7-(thiophen-2-yl)-1H-indol-3-yl)-N,N-dimethylethanamine,
2-(7-(furan-2-yl)-4-methoxy-1-methyl-1H-indol-3-yl)-N,N-dimethylethanamine,
2-(7-(furan-3-yl)-4-methoxy-1-methyl-1H-indol-3-yl)-N,N-dimethylethanamine,
2-(4-methoxy-1-methyl-7-(1H-pyrrol-2-yl)-1H-indol-3-yl)-N,N-dimethylethanamine,
3-(3-(2-(dimethylamino)ethyl)-4-methoxy-1-methyl-1H-indol-7-yl)prop-2-yn-1-ol,
3-(2-(dimethylamino)ethyl)-4-methoxy-1-methyl-N-phenyl-1H-indol-7-amine,
(E)-methyl 3-(3-(2-(dimethylamino)ethyl)-4-methoxy-1-methyl-1H-indol-7-yl)acrylate,
3-(3-(2-(dimethylamino)ethyl)-1-ethyl-7-fluoro-4-methoxy-1H-indol-5-yl)propan-1-ol,
2-(1-ethyl-4-methoxy-6-phenyl-1H-indol-3-yl)-N,N-dimethylethanamine,
3-(3-(2-(dimethylamino)ethyl)-1-ethyl-7-fluoro-4-methoxy-1H-indol-5-yl)propan-1-amine,
2-(5-(2-(1H-benzo[d]imidazol-2-yl)ethyl)-1-ethyl-7-fluoro-4-methoxy-1H-indol-3-yl)-N,N-dimethylethanamine.

2-(4-methoxy-1-methyl-7-(phenylsulfonyl)-1H-indol-3-yl)-N,N-dimethylethanamine, 2-(7-fluoro-4-methoxy-1-methyl-5-phenyl-1H-indol-3-yl)-N-methylethanamine, 3-(3-(2-(dimethylamino)ethyl)-4-methoxy-1-methyl-1H-indol-7-yl)propan-1-ol, 2-(7-fluoro-4-methoxy-1-methyl-5-phenethyl-1H-indol-3-yl)-N-methylethanamine, and 2-(5-(2-cyclohexylethyl)-7-fluoro-4-methoxy-1-methyl-1H-indol-3-yl)-N-methylethanamine.

In another aspect, the invention is directed to the following formula:

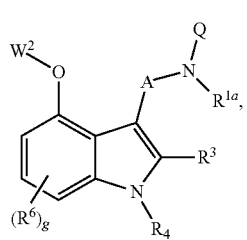

(VIII)

wherein g is 1, 2 or 3;

$R^{1a}$ is selected from H, optionally substituted $C_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl;

Q is selected from aryl, heteroaryl, arylalkyl, heterocycloalkyl, heteroarylalkyl, alkyl-C(O)NR$^e$R$^f$, alkyl-C(O)-heterocyclyl, heterocycloalkyl-alkyl, cycloalkyl, cycloalkylaryl, cycloalkylalkyl, arylheteroalkyl, and heteroarylheteroalkyl, wherein Q is optionally substituted with 1-3 substituents, each of which is independently selected from the group consisting of optionally substituted —$C_{1-6}$heteroalkyl, halogen, $C_{3-8}$ cycloalkyl, —OR$^d$, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —SO$_2$NR$^d$R$^{d'}$, cyano, nitro, $C_{1-6}$ haloalkyl, —NR$^d$R$^{d'}$, aryl, heteroaryl, heterocyclyl, -alkyl-OR$^d$, optionally substituted —$C_{1-6}$ alkyl, —NR$^d$C(O)R$^a$, —C(O)NR$^d$R$^{d'}$, and —C(O), wherein R$^e$ and R$^f$ are selected from the same groups as R$^1$ and R$^2$, respectively;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or C(O)NR$^d$R$^{d'}$;

$W^2$ is hydrogen, optionally substituted $C_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

A is optionally substituted $C_{1-4}$ alkylene, optionally substituted cycloalkylene, optionally substituted arylene, optionally substituted heteroarylene, wherein arylene or heteroarylene are optionally substituted with 1-3 substituents, each of which is independently selected from the group consisting of halogen, optionally substituted aryl, optionally substituted heteroaryl, $C_{3-8}$ cycloalkyl, —OR$^d$, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —OC(O)NR$^d$R$^{d'}$, —NR$^d$C(O)NR$^{d'}$R$^{d''}$, —NR$^d$C(O)OR$^a$, —NR$^d$S(O)$_2$ alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$—$C_{1-4}$alkyl-heteroaryl, —NR$^d$S(O)$_2$—$C_{1-4}$alkyl-cycloalkyl, —NR$^d$S(O)$_2$—$C_{1-4}$ alkyl-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$, wherein alkylene and cycloalkylene are optionally substituted with 1-3 substituents, each of which is independently selected from the group consisting of halogen, oxo, optionally substituted $C_{1-6}$ alkyl, —S(O)$_{0-2}$alkyl, —OR$^d$ and —NR$^d$R$^{d'}$, aryl or heteroaryl, and $C_3$-$C_8$ cycloalkyl or 4-8 membered heterocyclyl (e.g., wherein two substituents, together with the carbon to which they are attached, form a ring);

$R^4$ is selected from optionally substituted $C_{1-8}$ alkyl, optionally substituted $C_{1-8}$ heteroalkyl, $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ arylalkyl, —S(O)$_2$ heteroarylalkyl, —S(O)$_2$ cycloalkylalkyl, formyl, —OR$^d$, —NR$^d$R$^{d'}$, —C(O)OR$^a$, —C(O)NR$^d$R$^{d'}$, —S(O)$_2$NR$^d$R$^{d'}$, $C_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, optionally substituted —$C_1$alkyl-C(O)NR$^e$R$^f$, —$C_1$alkyl-O-aryl, —$C_1$alkyl-O-heteroaryl, —$C_1$alkyl-heterocyclyl, —$C_1$alkyl-cycloalkyl, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each $R^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —$C_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$, and R$^b$ are each independently selected from optionally substituted C$_{1-8}$ alkyl, optionally substituted aryl, optionally substituted heteroaryl, optionally substituted C$_{3-8}$ cycloalkyl, optionally substituted arylalkyl, optionally substituted heteroarylalkyl, optionally substituted cycloalkylalkyl and optionally substituted heterocycloalkyl;

R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In some embodiments, the compound is N-(2-(1-ethyl-7-fluoro-4-methoxy-1H-indol-3-yl)ethyl)aniline or 1-ethyl-7-fluoro-3-(2-(phenylamino)ethyl)-1H-indol-4-ol.

In some embodiments, R$^{1a}$ is selected from H, optionally substituted C$_{1-8}$ alkyl, and optionally substituted aryl.

In some embodiments, A is optionally substituted C$_{1-4}$ alkylene, wherein the C$_{1-4}$ alkylene is optionally substituted with 1-3 substituents, each of which is independently selected from the group consisting of halogen, hydroxyl, optionally substituted C$_{1-6}$ alkyl, C$_{1-8}$ alkoxy, —SO$_2$ alkyl, and —NR$^d$R$^{d'}$.

In some embodiments, R$^3$ is selected from hydrogen, halogen, and optionally substituted C$_{1-8}$ alkyl.

In some embodiments, R$^4$ is selected from optionally substituted C$_{1-8}$ alkyl, aryl, heteroaryl, arylalkyl, heteroarylalkyl, —S(O)$_2$ alkyl, —S(O)$_2$ arylalkyl, —S(O)$_2$ heteroarylalkyl, —S(O)$_2$ aryl, —S(O)$_2$ cycloalkyl, —S(O)$_2$ heterocycloalkyl, —S(O)$_2$ heterocycloalkylalkyl, —S(O)$_2$ cycloalkylalkyl and —S(O)$_2$ heteroaryl.

In some embodiments, W$^2$ is H, or C$_{1-8}$ alkyl optionally substituted with —OR$^d$, —NR$^d$R$^{d'}$, —C(O)NR$^d$R$^{d'}$.

In some embodiments, Q is selected from aryl, heteroaryl, arylalkyl, heterocycloalkyl, heteroarylalkyl, wherein Q is optionally substituted with 1-3 substituents, each of which is independently selected from the group consisting of halogen, C$_{3-8}$ cycloalkyl, —OR$^d$, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^d$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted —C$_{1-6}$ alkyl, —NR$^d$C(O)R$^a$, —C(O)NR$^d$R$^{d'}$, and —C(O).

In some embodiments, Q is optionally substituted aryl, optionally substituted heteroarylalkyl, or optionally substituted arylalkyl.

In some embodiments, Q is optionally substituted arylalkyl or optionally substituted six-membered heteroarylalkyl wherein the substitution is at the ortho or para position.

In some embodiments, R$^6$ is selected from halogen, C$_{1-8}$ alkyl, hydroxyl, —C$_{1-8}$ fluoroalkyl, amino, and —NR$^d$R$^{d'}$.

In some embodiments, the compound is selected from

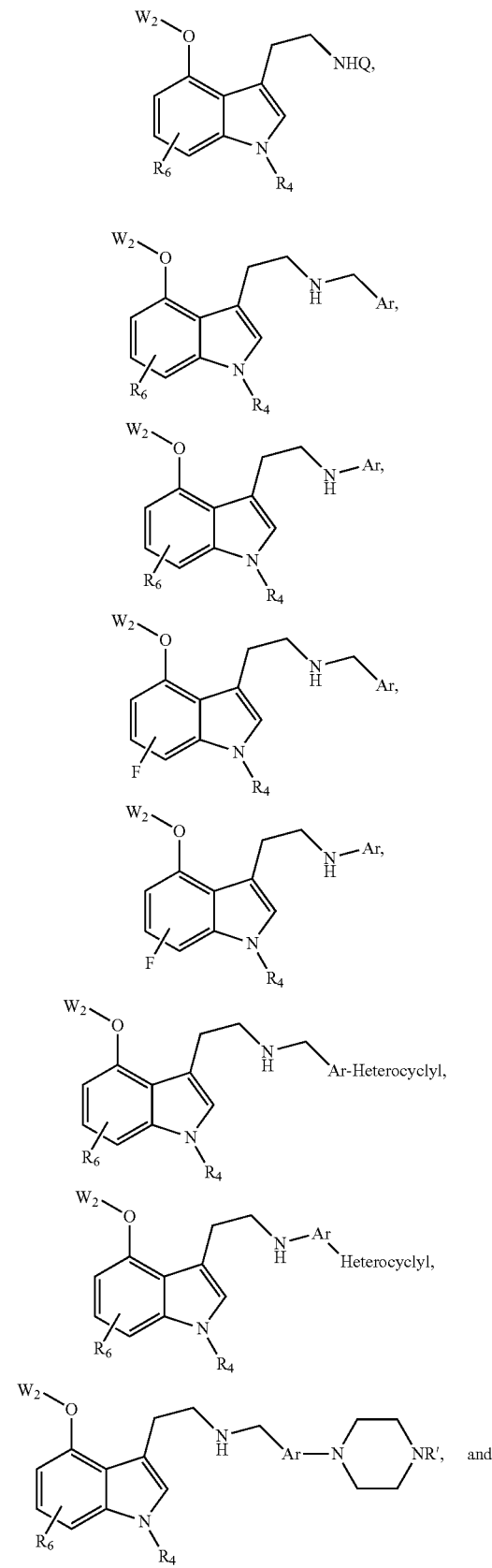

-continued

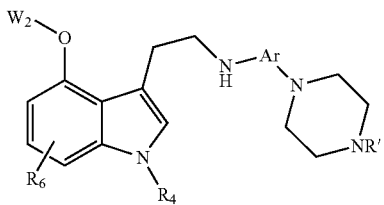

wherein Ar is optionally substituted aryl or optionally substituted heteroaryl, and heterocyclyl is optionally substituted 4-8-member heterocycle. Optionally, Ar or the heterocyclyl is substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)$.

In some embodiments, the compound is selected from
N-(2-(1-ethyl-7-fluoro-4-methoxy-1H-indol-3-yl)ethyl)aniline,
1-ethyl-7-fluoro-3-(2-(phenylamino)ethyl)-1H-indol-4-ol,
N-benzyl-2-(1-ethyl-7-fluoro-4-methoxy-1H-indol-3-yl)ethanamine,
3-(2-(benzylamino)ethyl)-1-ethyl-6-fluoro-1H-indol-4-ol,
2-(4-(benzyloxy)-1-ethyl-6-fluoro-1H-indol-3-yl)-N-(3-(trifluoromethyl)phenethyl)ethanamine,
1-ethyl-6-fluoro-3-(2-(3-(trifluoromethyl)phenethylamino)ethyl)-1H-indol-4-ol,
1-ethyl-6-fluoro-3-(2-(2-phenylpropylamino)ethyl)-1H-indol-4-ol,
N-benzyl-2-(4-(benzyloxy)-1-ethyl-6-fluoro-1H-indol-3-yl)ethanamine,
N-benzyl-2-(4-ethoxy-5-fluoro-1-methyl-1H-indol-3-yl)ethanamine,
N-(2-(4-ethoxy-5-fluoro-1-methyl-1H-indol-3-yl)ethyl)-2,3-dihydro-1H-inden-2-amine,
2-(4-(benzyloxy)-1-ethyl-6-fluoro-1H-indol-3-yl)-N-phenethylethanamine,
N-(2-chlorobenzyl)-2-(4-ethoxy-5-fluoro-1-methyl-1H-indol-3-yl)ethanamine,
N-(benzo[d][1,3]dioxol-5-ylmethyl)-2-(4-ethoxy-5-fluoro-1-methyl-1H-indol-3-yl)ethanamine,
N-(2-(4-ethoxy-5-fluoro-1-methyl-1H-indol-3-yl)ethyl)-2,3-dihydro-1H-inden-1-amine
1-ethyl-6-fluoro-3-(2-(phenethylamino)ethyl)-1H-indol-4-ol,
2-(4-ethoxy-5-fluoro-1-methyl-1H-indol-3-yl)-N-(3-methylbenzyl)ethanamine,
N-benzyl-2-(4-(benzyloxy)-1-ethyl-6-fluoro-1H-indol-3-yl)-N-methylethanamine,
2-(4-ethoxy-5-fluoro-1-methyl-1H-indol-3-yl)-N-(2-(trifluoromethyl)benzyl)ethanamine,
2-(4-ethoxy-5-fluoro-1-methyl-1H-indol-3-yl)-N-(3-(trifluoromethyl)benzyl)ethanamine,
2-(4-ethoxy-5-fluoro-1-methyl-1H-indol-3-yl)-N-phenethylethanamine,
2-(1-ethyl-7-fluoro-4-methoxy-1H-indol-3-yl)-N-phenethylethanamine,
2-(benzo[d][1,3]dioxol-5-yl)-N-(2-(4-ethoxy-5-fluoro-1-methyl-1H-indol-3-yl)ethyl)ethanamine,
N-benzyl-2-(1-ethyl-6-fluoro-4-methoxy-1H-indol-3-yl)ethanamine,
2-(4-ethoxy-5-fluoro-1-methyl-1H-indol-3-yl)-N-(2-(pyridin-2-yl)ethyl)ethanamine,
2-(4-ethoxy-5-fluoro-1-methyl-1H-indol-3-yl)-N-(thiophen-2-ylmethyl)ethanamine,
2-(5-fluoro-4-methoxy-1-methyl-1H-indol-3-yl)-N-(thiophen-2-ylmethyl)ethanamine,
N-benzyl-2-(5-fluoro-4-methoxy-1-methyl-1H-indol-3-yl)ethanamine,
2-(1-ethyl-6-fluoro-4-methoxy-1H-indol-3-yl)-N-(2-(1-ethyl-6-fluoro-4-methoxy-1H-indol-3-yl)ethyl)-N-methylethanamine,
2-(4-(benzyloxy)-1-ethyl-6-fluoro-1H-indol-3-yl)-N-(3-(trifluoromethyl)benzyl)ethanamine,
2-(4-(benzyloxy)-1-ethyl-6-fluoro-1H-indol-3-yl)-N-(3-chlorobenzyl)ethanamine,
2-(1-ethyl-7-fluoro-4-methoxy-1H-indol-3-yl)-N-(1-phenylethyl)ethanamine,
2-(1-ethyl-7-fluoro-4-methoxy-1H-indol-3-yl)-N-(2-methylbenzyl)ethanamine,
N-(2-chlorobenzyl)-2-(1-ethyl-7-fluoro-4-methoxy-1H-indol-3-yl)ethanamine,
N-(3,4-dimethoxybenzyl)-2-(5-fluoro-4-methoxy-1-methyl-1H-indol-3-yl)ethanamine,
3-(2-(benzhydrylamino)ethyl)-1-ethyl-6-fluoro-1H-indol-4-ol,
2-(2-(5-fluoro-4-methoxy-1-methyl-1H-indol-3-yl)ethylamino)-2-phenylethanol,
2-(5-fluoro-4-methoxy-1-methyl-1H-indol-3-yl)-N-(1-phenylethyl)ethanamine,
3-(2-(3-chlorobenzylamino)ethyl)-1-ethyl-6-fluoro-1H-indol-4-ol,
1-ethyl-6-fluoro-3-(2-(3-(trifluoromethyl)benzylamino)ethyl)-1H-indol-4-ol,
N-(2-(5-fluoro-4-methoxy-1-methyl-1H-indol-3-yl)ethyl)-4-phenylbutan-1-amine,
3-(2-(benzylamino)ethyl)-5-fluoro-1-methyl-1H-indol-4-ol,
(S)—N-(2-(5-fluoro-4-methoxy-1-methyl-1H-indol-3-yl)ethyl)-1,2,3,4-tetrahydronaphthalen-1-amine,
(S)—N-(2-(5-fluoro-4-methoxy-1-methyl-1H-indol-3-yl)ethyl)-1,2,3,4-tetrahydronaphthalen-1-amine,
N-(2-(5-fluoro-4-methoxy-1-methyl-1H-indol-3-yl)ethyl)-3-(4-methylpiperazin-1-yl)aniline,
5-fluoro-3-(2-((6-methylpyridin-2-yl)methylamino)ethyl)-1-propyl-1H-indol-4-ol, and
5-fluoro-1-methyl-3-(2-((6-methylpyridin-2-yl)methylamino)ethyl)-1H-indol-4-ol.

In another aspect, the invention is directed to a compound of formula:

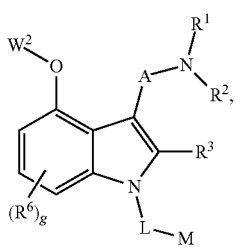

(IX)

wherein

L is a bond, —SO$_2$—, or optionally substituted C$_{1-3}$ alkylene;

M is —C(O)NR$^e$R$^f$, optionally substituted aryl, optionally substituted heteroaryl, optionally substituted arylalkyl, optionally substituted alkyl amido, optionally substituted alkoxy, optionally substituted cycloalkyl, optionally substituted heterocyclyl, optionally substituted cycloalkylalkyl, optionally substituted heterocycloalkyl, optionally substituted heteroarylkyl, optionally substituted aryl alkoxylene, optionally substituted heteroaryl alkoxylene, optionally substituted heterocyclyl alkoxylene, or optionally substituted cycloalkyl alkoxylene wherein R$^e$ and R$^f$ selected from the same groups as R$^1$ and R$^2$, respectively;

R$^1$ and R$^2$ are each independently selected from H, C$_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, R$^1$ and R$^2$ form a 3-8 membered heterocyclic moiety or when taken together with the nitrogen atom to which they are attached R$^1$ or R$^2$ and A form an optionally substituted 4-8 membered heterocyclyl or heteroaryl moiety;

R$^3$ is selected from H, optionally substituted C$_{1-8}$ alkyl, optionally substituted C$_{3-8}$ cycloalkyl, optionally substituted aryl, optionally substituted heteroaryl, optionally substituted heterocyclyl, halogen, or C(O)NR$^d$R$^{d'}$;

W$^2$ is hydrogen, optionally substituted C$_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

A is optionally substituted C$_{1-4}$ alkylene, optionally substituted cycloalkylene, optionally substituted aryl, optionally substituted heteroaryl, optionally substituted arylene, optionally substituted heteroarylene, optionally substituted heterocycloalkylene wherein arylene or heteroarylene are optionally substituted with 1-3 substituents, each of which is independently selected from the group consisting of halogen, C$_{3-8}$ cyclo optionally substituted aryl, optionally substituted heteroaryl, alkyl, —OR$^d$, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^d$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted C$_{1-6}$ alkyl, —NR$^d$C(O)R$^a$, —C(O)NR$^d$R$^{d'}$, and —C(O)OR$^d$, wherein alkylene and cycloalkylene are optionally substituted with 1-3 substituents, each of which is independently selected from the group consisting of halogen, oxo, optionally substituted C$_{1-6}$ alkyl, —S(O)$_{0-2}$alkyl, —OR$^d$ and —NR$^d$R$^{d'}$, aryl or heteroaryl, and C$_3$-C$_8$ cycloalkyl or 4-8 membered heterocyclyl (e.g., wherein two substituents, together with the carbon to which they are attached, form a ring);

each R$^6$ is independently selected from halo, C$_{1-8}$ alkyl, aryl, heteroaryl, heteroalkyl, C$_{3-8}$ cycloalkyl, heterocyclyl, arylalkyl, heteroarylalkyl, cycloalkylalkyl, heterocycloalkyl, —SH, —OR$^d$, C$_{1-8}$ haloalkoxy, C$_{1-8}$ haloalkyl, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^d$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

g is 1, 2, or 3;

R$^a$, and R$^b$ are each independently selected from optionally substituted C$_{1-8}$ alkyl, optionally substituted aryl, optionally substituted heteroaryl, optionally substituted C$_{3-8}$ cycloalkyl, optionally substituted arylalkyl, optionally substituted heteroarylalkyl, optionally substituted cycloalkylalkyl and optionally substituted heterocycloalkyl; and R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In some embodiments, R$^1$ and R$^2$ are each independently selected from H, C$_{1-8}$ alkyl, and optionally substituted aryl.

In some embodiments, A is optionally substituted C$_{1-4}$ alkylene, wherein the C$_{1-4}$ alkylene is optionally substituted with 1-3 substituents, each of which is independently selected from the group consisting of halogen (e.g., fluorine), hydroxyl, optionally substituted C$_{1-6}$ alkyl, C$_{1-8}$ alkoxy, —SO$_2$ alkyl, and —NR$^d$R$^{d'}$.

In some embodiments, R$^3$ is selected from H, and optionally substituted C$_{1-8}$ alkyl.

In some embodiments, L is a bond, or optionally substituted C$_{1-3}$ alkylene.

In some embodiments, L is a bond.

In some embodiments, L is SO$_2$.

In some embodiments, M is optionally substituted with 1-3 substituents, each of which is independently selected from the group consisting of halogen, C$_{3-8}$ cycloalkyl, —OR$^d$, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —OC(O)NR$^d$R$^{d'}$, —NR$^d$C(O)NR$^d$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted —C$_{1-6}$ alkyl, —NR$^d$C(O)R$^a$, —C(O)NR$^d$R$^{d'}$, and —C(O)OR$^d$.

In some embodiments, M is arylalkyl or heteroarylalkyl optionally substituted on the alkyl moiety.

In some embodiments, M is optionally substituted heteroarylalkyl.

In some embodiments, M is optionally substituted alkyl amido.

In some embodiments, M is optionally substituted alkoxy.

In some embodiments, M is optionally substituted arylalkoxylene, optionally substituted heteroarylalkoxylene, optionally substituted cycloalkylalkoxylene, or optionally substituted heterocycloalkylalkoxylene.

In some embodiments, $W^2$ is $C_{1-8}$ alkyl optionally substituted with $-OR^d$, $-NR^dR^{d'}$, $-C(O)NR^dR^{d'}$.

In some embodiments, each $R^6$ is selected from halogen, optionally substituted $C_{1-8}$ alkyl, hydroxyl, $-C_{1-8}$ fluoroalkyl, $C_{1-8}$ haloalkoxy, and $-NR^dR^{d'}$.

In some embodiments, the compound is selected from:
2-(6-fluoro-4-methoxy-1-(phenylsulfonyl)-1H-indol-3-yl)-N,N-dimethylethanamine,
2-(1-benzyl-4-(benzyloxy)-7-fluoro-1H-indol-3-yl)-N,N-dimethylethanamine,
2-(6-fluoro-4-methoxy-1-(pyrimidin-2-yl)-1H-indol-3-yl)-N,N-dimethylethanamine,
2-(4-(benzyloxy)-7-fluoro-1-(4-methoxybenzyl)-1H-indol-3-yl)-N,N-dimethylethanamine,
3-(2-(dimethylamino)ethyl)-7-fluoro-1-(4-methoxybenzyl)-1H-indol-4-ol,
2-(4-(benzyloxy)-7-fluoro-1-(pyridin-2-ylmethyl)-1H-indol-3-yl)-N,N-dimethylethanamine,
3-(2-(dimethylamino)ethyl)-7-fluoro-1-(pyridin-2-ylmethyl)-1H-indol-4-ol,
2-(4-(benzyloxy)-7-fluoro-1-(naphthalen-2-ylmethyl)-1H-indol-3-yl)-N,N-dimethylethanamine,
3-(2-(dimethylamino)ethyl)-7-fluoro-1-(naphthalen-2-ylmethyl)-1H-indol-4-ol,
2-(4-(benzyloxy)-7-fluoro-1-(thiophen-2-ylmethyl)-1H-indol-3-yl)-N,N-dimethylethanamine,
and
1-benzyl-3-(2-(dimethylamino)ethyl)-7-fluoro-1H-indol-4-ol.

In some embodiments, M is $C(O)NR^eR^f$,

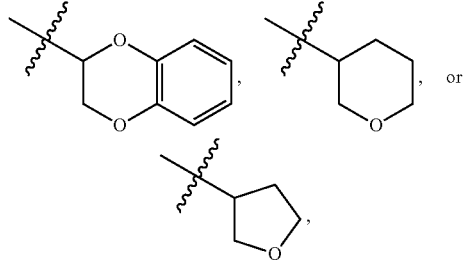

wherein $R^e$ and $R^f$ selected from the same groups as $R^1$ and $R^2$, respectively. Optionally, L is $-CH_2-$.

In some embodiments, M is $-C(O)NR^eR^f$, aryl, heteroaryl, arylalkoxylene, or heteroarylalkoxylene, wherein $R^e$ and $R^f$ selected from the same groups as $R^1$ and $R^2$, respectively.

In some embodiments, M is heterocyclyl and L is optionally substituted $C_1$alkyl.

In some embodiments, L is $C_1$-alkyl and M is $-C(O)NR^eR^f$, aryl, heteroaryl, or heterocyclyl.

In some embodiments, L is $C_2$-$C_4$-alkyl and M is $-O$-aryl, $-NR^e$-aryl, $-O$-heteroaryl, or $-NR^e$-heteroaryl.

In some embodiments, L is $C_2$-$C_4$-alkyl and M is optionally substituted aryl alkoxylene, optionally substituted heteroaryl alkoxylene.

In some embodiments, the compound is selected from

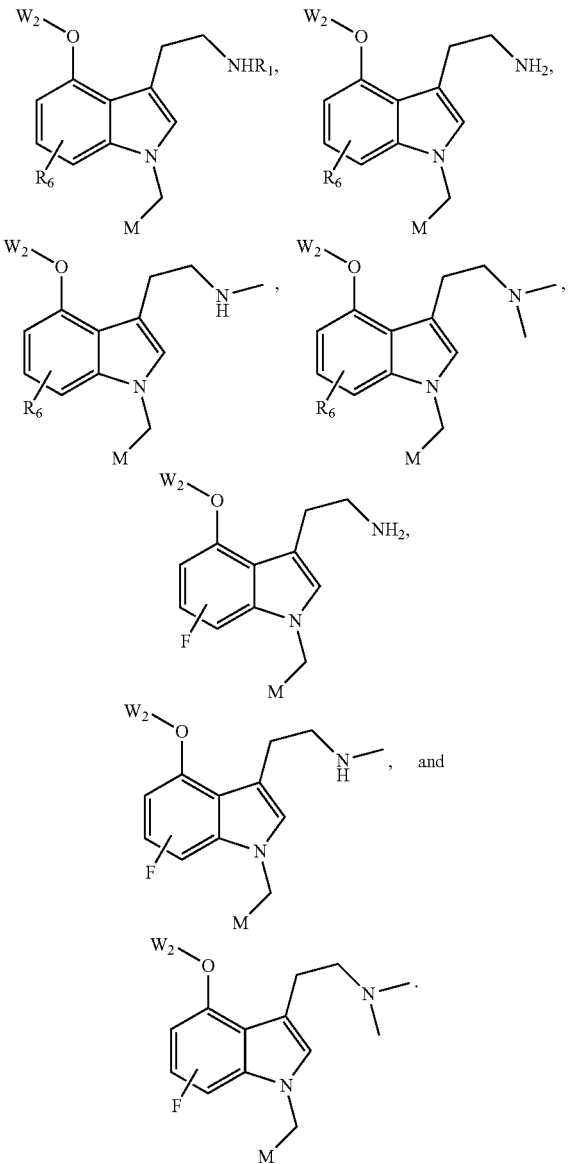

In another aspect, the invention is directed to a compound of formula:

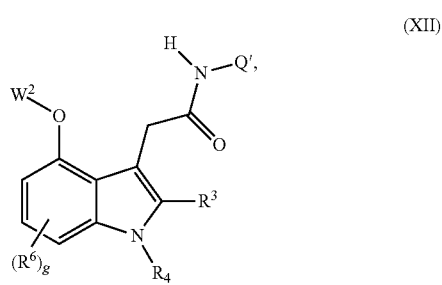

(XII)

wherein
g is 1, 2 or 3;
R³ is selected from H, optionally substituted C₁₋₈ alkyl, optionally substituted C₃₋₈ cycloalkyl, optionally substituted aryl, optionally substituted heteroaryl, optionally substituted heterocyclyl, halogen, or C(O)NR$^d$R$^{d'}$;

W² is hydrogen, optionally substituted C₁₋₈ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

Q' is selected from is aryl, heteroaryl, arylalkyl, heterocloalkyl or heteroarylalkyl, wherein Q' is optionally substituted with 1-3 substituents, each of which is independently selected from the group consisting of halogen, C₃₋₈ cycloalkyl, —OR$^d$, C₁₋₈ haloalkoxy, —S(O)₀₋₂ C₁₋₈ alkyl, —S(O)₀₋₂ aryl, —S(O)₀₋₂ heteroaryl, —S(O)₀₋₂ arylalkyl, —S(O)₀₋₂ heteroarylalkyl), —S(O)₀₋₂ cycloalkyl, —S(O)₀₋₂ heterocycloalkyl, —S(O)₀₋₂ heterocycloalkylalkyl, —S(O)₀₋₂ cycloalkylalkyl, —OC(O)NR$^d$R$^{d'}$, —NR$^d$C(O)NR$^d$R$^{d''}$, —NR$^d$C(O)OR$^b$, —NR$^d$S(O)₂alkyl, —NR$^d$S(O)₂aryl, —NR$^d$S(O)₂heteroaryl, —NR$^d$S(O)₂cycloalkyl, —NR$^d$S(O)₂heterocycloalkyl, —NR$^d$S(O)₂-arylalkyl, —NR$^d$S(O)₂-heteroarylalkyl, —NR$^d$S(O)₂-cycloalkylalkyl, —NR$^d$S(O)₂-heterocycloalkyl, —SO₂NR$^d$R$^{d'}$, cyano, nitro, C₁₋₆ haloalkyl, C₁₋₆ haloalkoxy, —NR$^d$R$^{d'}$, optionally substituted —C₁₋₆ alkyl, —NR$^d$C(O)R$^a$, —C(O)NR$^d$R$^{d'}$, and —C(O);

R⁴ is selected from optionally substituted C₁₋₈ alkyl, C₁₋₈ heteroalkyl, C₂₋₈ alkenyl, C₂₋₈ alkynyl, —S(O)₂ alkyl, —S(O)₂ heteroalkyl, —S(O)₂ aryl, —S(O)₂ heteroaryl, —S(O)₂ cycloalkyl, —S(O)₂ heterocyclyl, —S(O)₂ heterocycloalkyl, —S(O)₂ arylalkyl, —S(O)₂ heteroarylalkyl, —S(O)₂ cycloalkyalkyl, formyl, —OR$^d$, —NR$^d$R$^{d'}$, —C(O)OR$^a$, —C(O)NR$^d$R$^{d'}$, —S(O)₂NR$^d$R$^{d'}$, C₃₋₈ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, C₁₋₈ haloalkoxy, —S(O)₀₋₂ C₁₋₈ alkyl, —S(O)₀₋₂ aryl, —S(O)₀₋₂ heteroaryl, —S(O)₀₋₂-arylalkyl, —S(O)₀₋₂-heteroarylalkyl, —OC(O)NR$^d$R$^{d'}$, —NR$^d$C(O)NR$^d$R$^{d''}$, —NR$^d$C(O)OR$^b$, —OR$^d$, —NR$^d$S(O)₂alkyl, —NR$^d$S(O)₂aryl, —NR$^d$S(O)₂heteroaryl, —NR$^d$S(O)₂cycloalkyl, —NR$^d$S(O)₂heterocycloalkyl, —NR$^d$S(O)₂-arylalkyl, —NR$^d$S(O)₂-heteroarylalkyl, —NR$^d$S(O)₂-cycloalkylalkyl, —NR$^d$S(O)₂-heterocycloalkyl, —SO₂NR$^d$R$^{d'}$, optionally substituted —C₁alkyl-C(O)NR$^e$R$^f$, —C₁alkyl-O-aryl, —C₁alkyl-O-heteroaryl, —C₁alkyl-heterocyclyl, —C₁alkyl-cycloalkyl, cyano, nitro, C₁₋₆ haloalkyl, C₁₋₆ haloalkoxy, —NR$^d$R$^{d'}$, optionally substituted C₁₋₆ alkyl, —NR$^d$C(O)R$^a$, —C(O)NR$^d$R$^{d'}$, and —C(O)OR$^d$;

each R⁶ is independently selected from halo, C₁₋₈ alkyl, aryl, heteroaryl, heteroalkyl, C₃₋₈ cycloalkyl, heterocyclyl, arylalkyl, heteroarylalkyl, cycloalkylalkyl, heterocycloalkyl, —SH, —OR$^d$, C₁₋₈ haloalkoxy, C₁₋₈ haloalkyl, —S(O)₀₋₂ C₁₋₈ alkyl, —S(O)₀₋₂ aryl, —S(O)₀₋₂ heteroaryl, —S(O)₀₋₂ arylalkyl, —S(O)₀₋₂ heteroarylalkyl, —S(O)₀₋₂ cycloalkyl, —S(O)₀₋₂ heterocycloalkyl, —S(O)₀₋₂ heterocycloalkylalkyl, —S(O)₀₋₂ cycloalkylalkyl, —OC(O)NR$^d$R$^{d'}$, —NR$^d$C(O)NR$^d$R$^{d''}$, —NR$^d$C(O)OR$^a$, —NR$^d$S(O)₂alkyl, —NR$^d$S(O)₂aryl, —NR$^d$S(O)₂heteroaryl, —NR$^d$S(O)₂cycloalkyl, —NR$^d$S(O)₂heterocycloalkyl, —NR$^d$S(O)₂-arylalkyl, —NR$^d$S(O)₂-heteroarylalkyl, —NR$^d$S(O)₂-cycloalkylalkyl, —NR$^d$S(O)₂-heterocycloalkyl, —SO₂NR$^d$R$^{d'}$, cyano, nitro, C₁₋₆ haloalkyl, C₁₋₆ haloalkoxy, —NR$^d$R$^{d'}$, —C₁₋₄alkyl-NR$^d$R$^{d'}$, optionally substituted C₁₋₆ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$, and R$^b$ are each independently selected from optionally substituted C₁₋₈ alkyl, optionally substituted aryl, optionally substituted heteroaryl, optionally substituted C₃₋₈ cycloalkyl, optionally substituted arylalkyl, optionally substituted heteroarylalkyl, optionally substituted cycloalkylalkyl and optionally substituted heterocycloalkyl;

R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In another aspect, the invention is directed to a compound of formula:

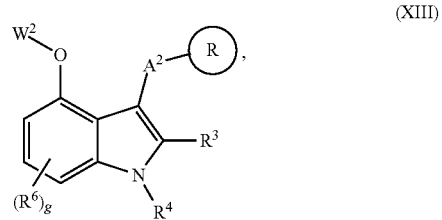

(XIII)

wherein
g is 1, 2 or 3;

is an optionally substituted N-containing heterocyclyl or optionally substituted N-containing heteroaryl;
A² is a bond or and optionally substituted C₁₋₄ alkylene;
R³ is selected from H, optionally substituted C₁₋₈ alkyl, optionally substituted C₃₋₈ cycloalkyl, optionally substituted aryl, optionally substituted heteroaryl, optionally substituted heterocyclyl, halogen, or C(O)NR$^d$R$^{d'}$;

W² is hydrogen, optionally substituted C₁₋₈ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

R⁴ is selected from optionally substituted C₁₋₈ alkyl, optionally substituted C₁₋₈ heteroalkyl, C₂₋₈ alkenyl, C₂₋₈ alkynyl, —S(O)₂ alkyl, —S(O)₂ heteroalkyl, —S(O)₂ aryl, —S(O)₂ heteroaryl, —S(O)₂ cycloalkyl, —S(O)₂ heterocyclyl, —S(O)₂ heterocycloalkyl, —S(O)₂ arylalkyl, —S(O)₂ heteroarylalkyl, —S(O)₂ cycloalkyalkyl, formyl, —OR$^d$, —NR$^d$R$^{d'}$, —C(O)OR$^a$, —C(O)NR$^d$R$^{d'}$, —S(O)₂NR$^d$R$^{d'}$, C₃₋₈ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$ aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^a$S(O)$_2$-heterocycloalkyl, —SO$_2$NR$^d$R$^{d'}$, optionally substituted —C$_1$alkyl-C(O)NR$^e$R$^f$, —C$_1$alkyl-O-aryl, —C$_1$alkyl-O-heteroaryl, —C$_1$alkyl-heterocyclyl, —C$_1$alkyl-cycloalkyl, cyano, nitro, C$_{1-6}$ haloalkyl, C$_{1-6}$ haloalkoxy, —NR$^d$R$^{d'}$, optionally substituted C$_{1-6}$ alkyl, —NR$^d$C(O)R$^a$, —C(O)NR$^d$R$^{d'}$, and —C(O)OR$^d$;

each R$^6$ is independently selected from halo, C$_{1-8}$ alkyl, aryl, heteroaryl, heteroalkyl, C$_{3-8}$ cycloalkyl, heterocyclyl, arylalkyl, heteroarylalkyl, cycloalkylalkyl, heterocycloalkyl, —SH, —OR$^d$, C$_{1-8}$ haloalkoxy, C$_{1-8}$ haloalkyl, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^a$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$ and R$^b$ are each independently selected from optionally substituted C$_{1-8}$ alkyl, optionally substituted aryl, optionally substituted heteroaryl, optionally substituted C$_{3-8}$ cycloalkyl, optionally substituted arylalkyl, optionally substituted heteroarylalkyl, optionally substituted cycloalkylalkyl and optionally substituted heterocycloalkyl, or when taken together with the nitrogen atom to which they are attached, R$^a$ and R$^b$ form a 4-8 membered heterocyclic moiety;

R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In some embodiments, A$^2$ is optionally substituted C$_{1-4}$ alkylene.

In some embodiments, R$^3$ is selected from H, and optionally substituted C$_{1-8}$ alkyl.

In some embodiments, R$^4$ is selected from optionally substituted C$_{1-8}$ alkyl, aryl, heteroaryl, arylalkyl, heteroarylalkyl, —S(O)$_2$ alkyl, —S(O)$_2$ arylalkyl, —S(O)$_2$ heteroarylalkyl, —S(O)$_2$ aryl, —S(O)$_2$ heteroaryl, —S(O)$_2$ cycloalkyl, —S(O)$_2$ heterocycloalkyl, —S(O)$_2$ heterocycloalkylalkyl, and —S(O)$_2$ cycloalkylalkyl.

In some embodiments, W$^2$ is C$_{1-8}$ alkyl optionally substituted with —OR$^d$, —NR$^d$R$^{d'}$, —C(O)NR$^d$R$^{d'}$.

In some embodiments, g is 1.

In some embodiments, each R$^6$ is selected from halogen, optionally substituted C$_{1-8}$ alkyl, hydroxyl, —C$_{1-8}$ fluoroalkyl, C$_{1-8}$ haloalkoxy, and —NR$^d$R$^{d'}$.

In some embodiments, the compound is selected from

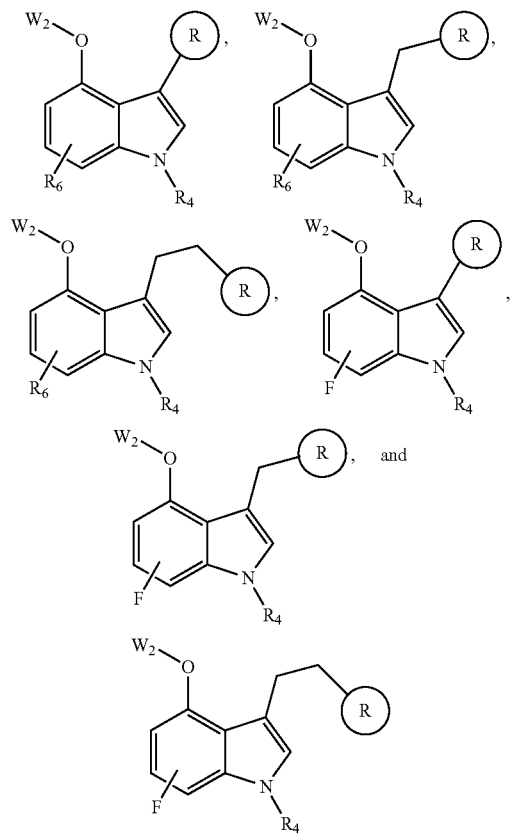

wherein

is an optionally substituted N-containing heterocyclyl or optionally substituted N-containing heteroaryl.

In some embodiments,

is 3-14 membered (e.g., 4-14 membered, or 5-8 membered) heteroaryl or heterocyclyl.

In some embodiments,

is an N-containing heterocyclyl optionally substituted with 1-3 substituents independently selected from the group consisting of aryl, heteroaryl, alkyl, arylalkyl, and heteroarylalkyl.

In some embodiments,  is optionally substituted:

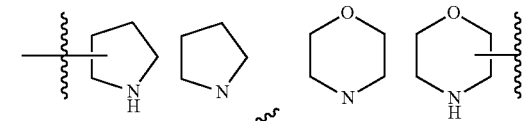

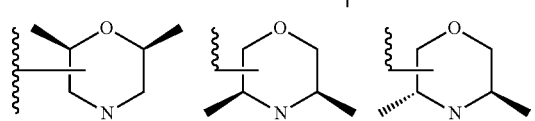

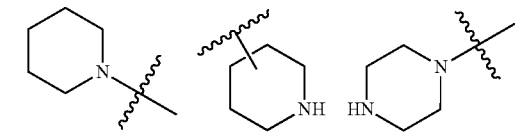

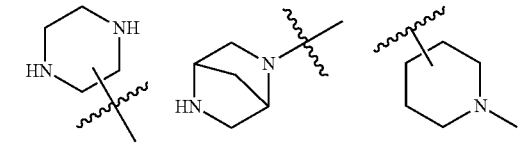

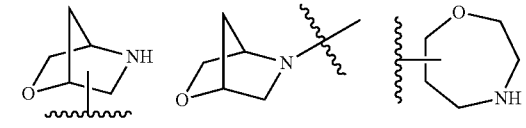

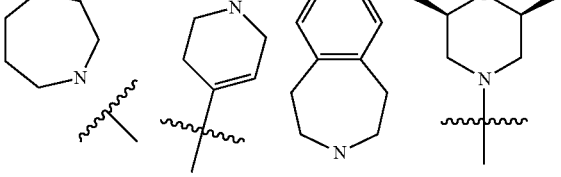

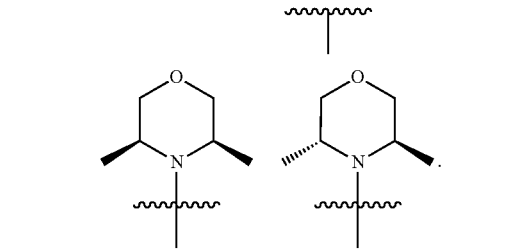

In some embodiments,

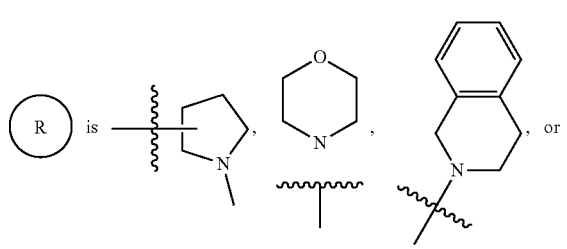

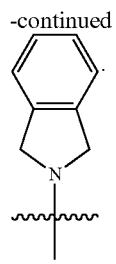

In some embodiments,

 is an optionally substituted

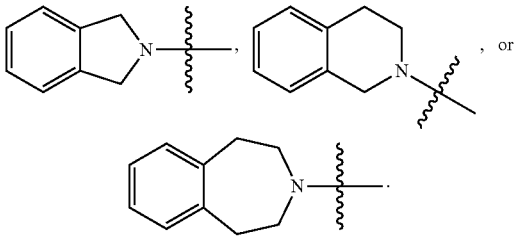

Sometimes,

 is optionally substituted with 1-3 substituents independently selected from the group consisting of halogen, alkyl, and haloalkyl.

In some embodiments, the compound is

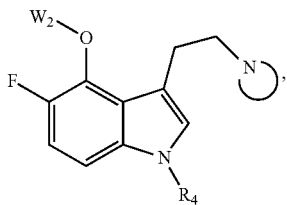

wherein

is a heterocycle.

In some embodiments, the compound is selected from 4-(2-(7-fluoro-4-methoxy-1-methyl-1H-indol-3-yl)ethyl)morpholine,
1-ethyl-6-fluoro-3-(2-morpholinoethyl)-1H-indol-4-ol,
1-ethyl-6-fluoro-3-(2-(pyrrolidin-1-yl)ethyl)-1H-indol-4-ol, 7-fluoro-4-methoxy-1-methyl-3-(2-(pyrrolidin-1-yl)ethyl)-1H-indole,
4-(benzyloxy)-1-ethyl-6-fluoro-3-(1,2,3,6-tetrahydropyridin-4-yl)-1H-indole,
3-(2-(1,4-oxazepan-4-yl)ethyl)-1-ethyl-6-fluoro-1H-indol-4-ol,
3-(2-((2S,6R)-2,6-dimethylmorpholino)ethyl)-1-ethyl-6-fluoro-1H-indol-4-ol,
3-(2-(3,3-difluoropyrrolidin-1-yl)ethyl)-1-ethyl-6-fluoro-1H-indol-4-ol,
1-ethyl-6-fluoro-3-(piperidin-3-yl)-1H-indol-4-ol,
1-ethyl-6-fluoro-3-(1-methylpiperidin-3-yl)-1H-indol-4-ol,
1-ethyl-6-fluoro-3-(2-(piperazin-1-yl)ethyl)-1H-indol-4-ol,
4-(benzyloxy)-1-ethyl-6-fluoro-3-(2-(isoindolin-2-yl)ethyl)-1H-indole,
1-ethyl-6-fluoro-3-(2-(isoindolin-2-yl)ethyl)-1H-indol-4-ol,
4-(2-(4-ethoxy-5-fluoro-1-methyl-1H-indol-3-yl)ethyl)morpholine,
(1-(2-(4-ethoxy-5-fluoro-1-methyl-1H-indol-3-yl)ethyl)pyrrolidin-2-yl)methanol,
4-ethoxy-5-fluoro-1-methyl-3-(2-(pyrrolidin-1-yl)ethyl)-1H-indole,
5-fluoro-4-methoxy-1-methyl-3-(2-(piperazin-1-yl)ethyl)-1H-indole,
3-(2-((1S,4S)-5-benzyl-2,5-diazabicyclo[2.2.1]heptan-2-yl)ethyl)-1-ethyl-6-fluoro-1H-indol-4-ol,
5-fluoro-4-methoxy-1-methyl-3-(2-(4-phenylpiperazin-1-yl)ethyl)-1H-indole,
3-(2-(4-(3-chlorophenyl)piperazin-1-yl)ethyl)-5-fluoro-4-methoxy-1-methyl-1H-indole,
2-(2-(5-fluoro-4-methoxy-1-methyl-1H-indol-3-yl)ethyl)-1,2,3,4-tetrahydroisoquinoline,
8-chloro-3-(2-(5-fluoro-4-methoxy-1-methyl-1H-indol-3-yl)ethyl)-1-methyl-2,3,4,5-tetrahydro-1H-benzo[d]azepine, and
1-(2-(5-fluoro-4-methoxy-1-methyl-1H-indol-3-yl)ethyl)pyrrolidine-2-carboxamide.

In another aspect, the invention is directed to compounds of formula:

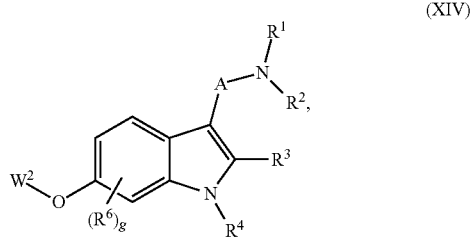

(XIV)

wherein g is 1, 2 or 3;

$R^1$ and $R^2$ are each independently selected from H, $C_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or $—C(O)NR^dR^{d'}$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, optionally substituted aryl, optionally substituted heteroaryl, $C_{3-8}$ cycloalkyl, $—OR^d$, $C_{1-8}$ haloalkoxy, $—S(O)_{0-2}$ $C_{1-8}$ alkyl, $—S(O)_{0-2}$ aryl, $—S(O)_{0-2}$ heteroaryl, $—S(O)_{0-2}$ arylalkyl, $—S(O)_{0-2}$ heteroarylalkyl), $—S(O)_{0-2}$ cycloalkyl, $—S(O)_{0-2}$ heterocycloalkyl, $—S(O)_{0-2}$ heterocycloalkylalkyl, $—S(O)_{0-2}$ cycloalkylalkyl, $—OC(O)NR^dR^{d'}$, $—NR^dC(O)NR^{d'}R^{d''}$, $—NR^dC(O)OR^b$, $—NR^dS(O)_2$alkyl, $—NR^dS(O)_2$aryl, $—NR^dS(O)_2$heteroaryl, $—NR^dS(O)_2$cycloalkyl, $—NR^dS(O)_2$heterocycloalkyl, $—NR^dS(O)_2$-arylalkyl, $—NR^dS(O)_2$-heteroarylalkyl, $—NR^dS(O)_2$-cycloalkylalkyl, $—NR^dS(O)_2$-heterocycloalkyl, $—SO_2NR^dR^{d'}$, cyano, nitro, $C_{1-6}$ haloalkyl, $C_{1-6}$ haloalkoxy, $—NR^dR^{d'}$, optionally substituted $C_{1-6}$ alkyl, $—NR^dC(O)R^a$, $—C(O)NR^dR^{d'}$, and $—C(O)OR^d$, wherein alkylene and cycloalkylene are optionally substituted with 1-3 substituents, each of which is independently selected from the group consisting of halogen, oxo, optionally substituted $C_{1-6}$ alkyl, $—S(O)_{0-2}$alkyl, $—OR^d$ and $—NR^dR^{d'}$, aryl or heteroaryl, and $C_3$-$C_8$ cycloalkyl or 4-8 membered heterocyclyl (e.g., wherein two substituents, together with the carbon to which they are attached, form a ring);

$R^4$ is selected from optionally substituted $C_{1-8}$ alkyl, optionally substituted $C_{1-8}$ heteroalkyl, $C_{2-8}$ alkenyl, $C_{2-8}$ alkynyl, $—S(O)_2$ alkyl, $—S(O)_2$ heteroalkyl, $—S(O)_2$ aryl, $—S(O)_2$ heteroaryl, $—S(O)_2$ cycloalkyl, $—S(O)_2$ heterocyclyl, $—S(O)_2$ heterocycloalkyl, $—S(O)_2$ arylalkyl, $—S(O)_2$ heteroarylalkyl, $—S(O)_2$ cycloalkyalkyl, formyl, $—OR^d$, $—NR^dR^{d'}$, $—C(O)OR^a$, $—C(O)NR^dR^{d'}$, $—S(O)_2NR^dR^{d'}$, $C_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, $—OR^d$, $—NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, $—OR^d$, $—SH$, $C_{1-8}$ haloalkoxy, $—S(O)_{0-2}$ $C_{1-8}$ alkyl, $—S(O)_{0-2}$ aryl, $—S(O)_{0-2}$ heteroaryl, $—S(O)_{0-2}$-arylalkyl, $—S(O)_{0-2}$-heteroarylalkyl, $—OC(O)NR^dR^{d'}$, $—NR^dC(O)NR^{d'}R^{d''}$, $—NR^dC(O)OR^b$, $—OR^d$, $—NR^dS(O)_2$alkyl, $—NR^dS(O)_2$aryl, $—NR^dS(O)_2$heteroaryl, $—NR^dS(O)_2$cycloalkyl, $—NR^dS(O)_2$heterocycloalkyl, $—NR^dS(O)_2$-arylalkyl, $—NR^dS(O)_2$-heteroarylalkyl, $—NR^dS(O)_2$-cycloalkylalkyl, $—NR^dS(O)_2$-heterocycloalkyl, $—SO_2NR^dR^{d'}$, optionally substituted $—C_1$alkyl-$C(O)NR^eR^f$, $—C_1$alkyl-O-aryl, $—C_1$alkyl-O-heteroaryl, $—C_1$alkyl-heterocyclyl, $—C_1$alkyl-cycloalkyl, cyano, nitro, $C_{1-6}$ haloalkyl, $C_{1-6}$ haloalkoxy, $—NR^dR^{d'}$, optionally substituted $C_{1-6}$ alkyl, $—NR^dC(O)R^a$, $—C(O)NR^dR^{d'}$, and $—C(O)OR^d$;

each $R^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —OR$^d$, C$_{1-8}$ haloalkoxy, C$_{1-8}$ haloalkyl, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^a$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$ and R$^b$ are each independently selected from optionally substituted C$_{1-8}$ alkyl, optionally substituted aryl, optionally substituted heteroaryl, optionally substituted C$_{3-8}$ cycloalkyl, optionally substituted arylalkyl, optionally substituted heteroarylalkyl, optionally substituted cycloalkylalkyl and optionally substituted heterocycloalkyl;

R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In another aspect, the invention is directed to compounds of formula:

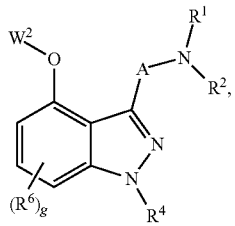

(XV)

wherein g is 1, 2 or 3;

R$^1$ and R$^2$ are each independently selected from H, C$_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, R$^1$ and R$^2$ form a 3-8 membered heterocyclic moiety or when taken together with the nitrogen atom to which they are attached R$^1$ or R$^2$ and A form an optionally substituted 4-8 membered heterocyclyl or heteroaryl moiety;

W$^2$ is hydrogen, optionally substituted C$_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

A is optionally substituted C$_{1-4}$ alkylene, optionally substituted cycloalkylene, optionally substituted arylene, optionally substituted heteroarylene, wherein arylene or heteroarylene are optionally substituted with 1-3 substituents, each of which is independently selected from the group consisting of halogen, optionally substituted aryl, optionally substituted heteroaryl, C$_{3-8}$ cycloalkyl, —OR$^d$, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl), —OC(O)NR$^d$R$^{d'}$, —NR$^d$C(O)NR$^{d'}$R$^{d''}$, —NR$^d$C(O)OR$^a$, —NR$^d$S(O)$_2$ alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$—C$_{1-4}$alkyl-heteroaryl, —NR$^d$S(O)$_2$—C$_{1-4}$alkyl-cycloalkyl, —NR$^d$S(O)$_2$—C$_{1-4}$alkyl-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted —C$_{1-6}$ alkyl, —NR$^d$C(O)R$^a$, —C(O)NR$^d$R$^{d'}$, and —C(O)OR$^d$, wherein alkylene and cycloalkylene are optionally substituted with 1-3 substituents, each of which is independently selected from the group consisting of halogen, oxo, optionally substituted C$_{1-6}$ alkyl, —S(O)$_{0-2}$alkyl, —OR$^d$ and —NR$^d$R$^{d'}$, aryl or heteroaryl, and C$_3$-C$_8$ cycloalkyl or 4-8 membered heterocyclyl (e.g., wherein two substituents, together with the carbon to which they are attached, form a ring);

R$^4$ is selected from optionally substituted C$_{1-8}$ alkyl, optionally substituted C$_{1-8}$ heteroalkyl, C$_{2-8}$ alkenyl, C$_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ arylalkyl, —S(O)$_2$ heteroarylalkyl, —S(O)$_2$ cycloalkylalkyl, formyl, —OR$^d$, —NR$^d$R$^{d'}$, —C(O)OR$^a$, —C(O)NR$^d$R$^{d'}$, —S(O)$_2$NR$^d$R$^{d'}$, C$_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and heteroaryl are optionally substituted with 1-3 substituents, each of which is independently selected from the group consisting of halogen, alkyl, heteroalkyl, cycloalkyl, heterocyclyl, —OR$^d$, —SH, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$ aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, optionally substituted —C$_1$alkyl-C(O)NR$^e$R$^f$, —C$_1$alkyl-O-aryl, —C$_1$alkyl-O-heteroaryl, —C$_1$alkyl-heterocyclyl, —C$_1$alkyl-cycloalkyl, cyano, nitro, C$_{1-6}$ haloalkyl, C$_{1-6}$ haloalkoxy, —NR$^d$R$^{d'}$, optionally substituted C$_{1-6}$ alkyl, —NR$^d$C(O)R$^a$, —C(O)NR$^d$R$^{d'}$, and —C(O)OR$^d$;

each R$^6$ is independently selected from halo, C$_{1-8}$ alkyl, aryl, heteroaryl, heteroalkyl, C$_{3-8}$ cycloalkyl, heterocyclyl, arylalkyl, heteroarylalkyl, cycloalkylalkyl, heterocycloalkyl, —SH, —OR$^d$, C$_{1-8}$ haloalkoxy, C$_{1-8}$ haloalkyl, —S(O)$_{0-2}$ C$_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^a$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$ and R$^b$ are each independently selected from optionally substituted C$_{1-8}$ alkyl, optionally substituted aryl, optionally substituted heteroaryl, optionally substituted C$_{3-8}$ cycloalkyl, optionally substituted arylalkyl, optionally substituted heteroarylalkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In another aspect, the invention is directed to compounds of formula:

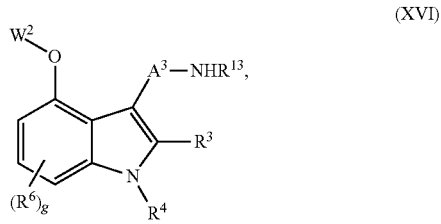

(XVI)

wherein g is 1, 2 or 3;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —C(O)NR$^d$R$^{d'}$;

$A^3$ is $C_{2-8}$-optionally substituted branched alkylene or cylcoalkyl, wherein alkylene may form a $C_3$-$C_8$ cycloalkyl or 4-8 membered heterocyclyl;

$R^4$ is selected from optionally substituted $C_{1-8}$ alkyl, optionally substituted $C_{1-8}$ heteroalkyl, $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ arylalkyl, —S(O)$_2$ heteroarylalkyl, —S(O)$_2$ cycloalkyalkyl, formyl, —OR$^d$, $C_{1-8}$ aryloxy, $C_{1-8}$ heteroaryloxy, —NR$^d$R$^{d'}$, $C_{1-8}$ alkylamino, di($C_{1-8}$ alkyl)amino, —C(O)OR$^a$, —C(O)NR$^d$R$^{d'}$, —S(O)$_2$NR$^d$R$^{d'}$, $C_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$ aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^d$S(O)$_2$-heterocycloalkyl, —SO$_2$NR$^d$R$^{d'}$, optionally substituted —C$_1$alkyl-C(O)NR$^e$R$^f$, —C$_1$alkyl-O-aryl, —C$_1$alkyl-O-heteroaryl, —C$_1$alkyl-heterocyclyl, —C$_1$alkyl-cycloalkyl, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each $R^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-arylalkyl, —NR$^d$S(O)$_2$-heteroarylalkyl, —NR$^d$S(O)$_2$-cycloalkylalkyl, —NR$^a$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —C$_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

$R^{13}$ is selected from hydrogen and methyl; and $R^a$ and $R^b$ are each independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $A^3$ is 1-methylethylene.

In some embodiments, $A^3$ is

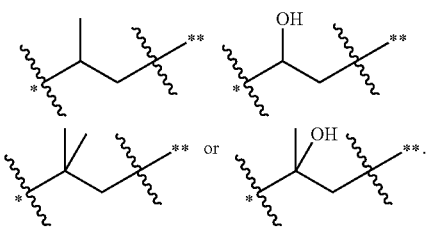

In some embodiments, $R^3$ is selected from H, and optionally substituted $C_{1-8}$ alkyl.

In some embodiments, $R^4$ is selected from optionally substituted $C_{1-8}$ alkyl, aryl, heteroaryl, arylalkyl, heteroarylalkyl, —S(O)$_2$ alkyl, —S(O)$_2$ arylalkyl, —S(O)$_2$ heteroarylalkyl, —S(O)$_2$ aryl, —S(O)$_2$ heteroaryl, —S(O)$_2$ cycloalkyl, —S(O)$_2$ heterocycloalkyl, —S(O)$_2$ heterocycloalkylalkyl, and —S(O)$_2$ cycloalkylalkyl.

In some embodiments, $W^2$ is $C_{1-8}$ alkyl optionally substituted with —OR$^d$, —NR$^d$R$^{d'}$, —C(O)NR$^d$R$^{d'}$.

In some embodiments, g is 1.

In some embodiments, each $R^6$ is selected from halogen, $C_{1-8}$ alkyl, hydroxyl, —C$_{1-8}$ fluoroalkyl, $C_{1-8}$ haloalkoxy, and —NR$^d$R$^{d'}$.

In some embodiments, the compounds is 2-(7-fluoro-4-methoxy-1-methyl-1H-indol-3-yl)propan-1-amine.

In some embodiments, the compound is selected from

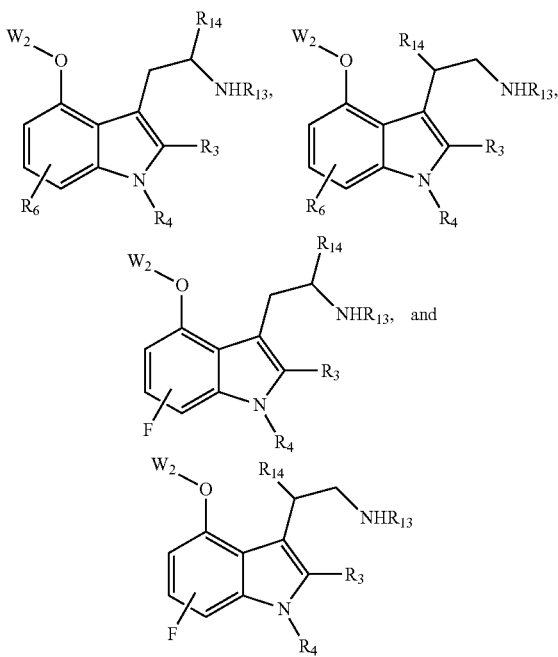

wherein R$_{14}$ is optionally substituted aryl, heteroaryl, alkyl, cycloalkyl, or heterocyclyl. Optionally, R$_{14}$ and —NHR$_{13}$ together form a 4-8 member heteroalkyl or heteroaryl ring.

In another aspect, the invention is directed to compound of formulae I, II, IV, VII, VIII, IX, XII, XIII, XIV, XV or XVI wherein the compound comprises a Positron Emission Tomography (PET) isotope. In some embodiments, the isotope is $^{11}$C or $^{19}$F.

In another aspect, the invention is directed to compound of formulae I, II, IV, VII, VIII, IX, XII, XIII, XIV, XV or XVI wherein the compound is enantiomerically enriched for a selected stereoisomer or enantiomer.

In another aspect, the invention is directed to a pharmaceutical composition comprising a compound of formulae I, II, IV, VII, VIII, IX, XII, XIII, XIV, XV or XVI. In some embodiments, the pharmaceutical composition further comprises a Positron Emission Tomography (PET) isotope. In some embodiments, the isotope is $^{11}$C or $^{19}$F.

In another aspect, the invention is directed to a method for the treatment of obesity in a subject, the method comprising administering to the subject a compound of formulae I, II, IV, VII, VIII, IX, XII, XIII, XIV, XV or XVI, such that obesity is treated in the subject.

In another aspect, the invention is directed to a method for the treatment of Obsessive Compulsive Disorder (OCD) in a subject, the method comprising administering to the subject a compound of formulae I, II, IV, VII, VIII, IX, XII, XIII, XIV, XV or XVI, such that OCD is treated in the subject.

In another aspect, the invention is directed to a method for suppressing appetite in a subject, the method comprising administering to the subject a compound of formulae I, II, IV, VII, VIII, IX, XII, XIII, XIV, XV or XVI, such that appetite is suppressed in the subject.

In another aspect, the invention is directed to a method for the treatment of schizophrenia or psychosis in a subject, the method comprising administering to the subject a compound of formulae I, II, IV, VII, VIII, IX, XII, XIII, XIV, XV or XVI, such that schizophrenia or psychosis is treated in the subject.

In another aspect, the invention is directed to a method for the treatment of anxiety or depression in a subject, the method comprising administering to the subject a compound of formulae I, II, IV, VII, VIII, IX, XII, XIII, XIV, XV or XVI, such that anxiety or depression is treated in the subject.

In another aspect, the invention is directed to a method for the treatment of diabetes in a subject, the method comprising administering to the subject a compound of formulae I, II, IV, VII, VIII, IX, XII, XIII, XIV, XV or XVI, such that diabetes is treated in the subject.

In another aspect, the invention is directed to a method for the treatment of attention deficit hyperactivity disorder (ADHD) in a subject, the method comprising administering to the subject a compound of formulae I, II, IV, VII, VIII, IX, XII, XIII, XIV, XV or XVI, such that ADHD is treated in the subject.

In another aspect, the invention is directed to a method of modulating (e.g., inhibit or activate) a serotonin receptor (e.g., a 5-HT receptor), the method comprising contacting a serotonin receptor with a compound of formulae I, II, IV, VII, VIII, IX, XII, XIII, XIV, XV or XVI. In some embodiments, the receptor is a 5-HT$_{2A}$, 5-HT$_{2C}$, and/or 5-HT$_6$ receptor.

In one aspect, the invention is directed to a compound selected from the following formula:

(I)

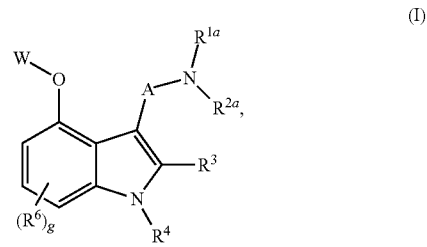

wherein

R$^{1a}$ and R$^{2a}$ are each independently selected from H, optionally substituted C$_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl;

R$^3$ is selected from H, optionally substituted C$_{1-8}$ alkyl, optionally substituted C$_{3-8}$ cycloalkyl, optionally substituted aryl, optionally substituted heteroaryl, optionally substituted heterocyclyl, halogen, or C(O)NR$^d$R$^{d'}$;

W is

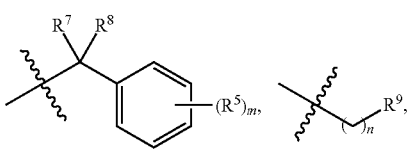

optionally substituted aryl, optionally substituted heteroaryl, optionally substituted heterocyclyl, optionally substituted cycloalkyl; optionally substituted heteroaralkyl, optionally substituted cycloalkylalkyl, optionally substituted heterocycloalkyl, —C(O)NR$^d$R$^{d'}$, C$_1$ alkyl substituted with —C(O)NR$^d$R$^{d'}$ or C$_{2-8}$ alkyl substituted with —NR$^d$R$^{d'}$, —C(O)NR$^d$R$^{d'}$ or —OR$^d$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$, wherein alkylene and cycloalkylene are optionally substituted with 1-3 substituents, each of which is independently selected from the group consisting of halogen, oxo, optionally substituted $C_{1-6}$ alkyl, —$S(O)_{0-2}$alkyl, —$OR^d$ and —$NR^dR^{d'}$;

$R^4$ is selected from $C_{1-8}$ alkyl, $C_{1-8}$ heteroalkyl, $C_{2-8}$ alkenyl, $C_{2-8}$ alkynyl, —$S(O)_2$ alkyl, —$S(O)_2$ heteroalkyl, —$S(O)_2$ aryl, —$S(O)_2$ heteroaryl, —$S(O)_2$ cycloalkyl, —$S(O)_2$ heterocyclyl, —$S(O)_2$ heterocycloalkyl, —$S(O)_2$ aralkyl, —$S(O)_2$ heteroaralkyl, —$S(O)_2$ cycloalkyalkyl, formyl, —$OR^d$, —$NR^dR^{d'}$, —$C(O)OR^a$, —$C(O)NR^dR^{d'}$, —$S(O)_2NR^dR^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —$OR^d$, —$NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, —$OR^d$, —SH, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$-aralkyl, —$S(O)_{0-2}$-heteroaralkyl, —$OC(O)NR^dR^{d'}$, —$NR^dC(O)NR^{d'}R^{d''}$, —$NR^dC(O)OR^b$, —$OR^d$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$;

$R^5$ is selected from H and $R^6$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^a$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$—$C_{1-4}$alkylaryl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$alkyl-$NR^dR^{d'}$, optionally substituted $C_{1-6}$ alkyl, —$NR^dC(O)R^a$, —$C(O)NR^dR^{d'}$, and —$C(O)OR^d$; wherein alkyl, aryl, heteroaryl, cycloalkyl and heterocyclyl are optionally substituted;

each of $R^7$ and $R^8$ is independently H, optionally substituted $C_{1-8}$ alkyl or fluoro; or $R^7$ and $R^8$ can, together with the carbon to which they are attached, form a ring;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety;

g is 1, 2 or 3;

m is 0, 1, 2, 3, 4 or 5; and n is 2, 3, or 4; and wherein when m is 0, at least one of $R^7$ or $R^8$ is not H.

In some embodiments, n is 2.

In some embodiments, $R^{1a}$ and $R^{2a}$ are each independently selected from H, $C_{1-8}$ alkyl, or optionally substituted aryl.

In some embodiments, $R^{1a}$ and $R^{2a}$ are each independently selected from H or $C_{1-8}$ alkyl.

In some embodiments, $R^{1a}$ and $R^{2a}$ are H.

In some embodiments, $R^{1a}$ and $R^{2a}$ are each optionally substituted $C_{1-8}$ alkyl (e.g., methyl).

In some embodiments, $R^{1a}$ is H and $R^{2a}$ is optionally substituted $C_{1-8}$ alkyl (e.g., methyl)

In some embodiments, $R^{1a}$ is optionally substituted $C_{1-8}$ alkyl and $R^{2a}$ is H.

In some embodiments, A is selected from optionally substituted $C_{1-4}$ alkylene, wherein the $C_{1-4}$ alkylene is optionally substituted with 1-3 substituents, each of which is independently selected from the group consisting of halogen (e.g., fluorine), hydroxyl, optionally substituted $C_{1-6}$ alkyl, $C_{1-8}$ alkoxy, —$SO_2$ alkyl, and —$NR^dR^{d''}$.

In some embodiments, A is selected from optionally substituted $C_{1-4}$ alkylene, wherein the $C_{1-4}$ alkylene is optionally substituted with —$SO_2$ alkyl (e.g., methylsulfone).

In some embodiments, A is optionally substituted $C_{1-4}$ alkylene, wherein the $C_{1-4}$ alkylene is optionally substituted with hydroxyl

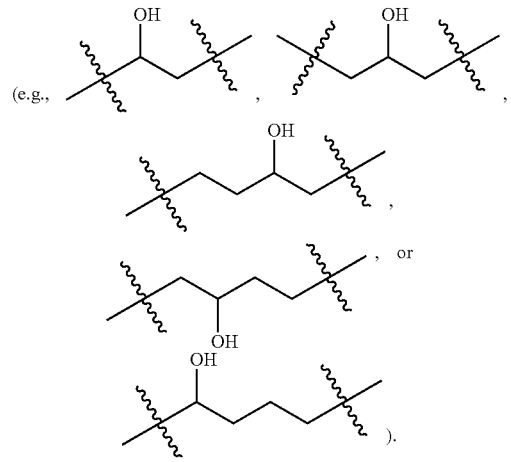

(e.g.,

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine).

In some embodiments, A is optionally substituted $C_{1-4}$ alkylene, wherein the $C_{1-4}$ alkylene is optionally substituted with 1-3 substituents, each of which is independently selected from the group consisting of optionally substituted $C_{1-6}$ alkyl (e.g., methyl, ethyl, i-propyl, —$C_{1-2}$ alkyl-OH, —$C_{1-2}$ alkyl-CF$_3$, —$C_{1-2}$ alkyl-CHF$_2$, —$C_{1-2}$ alkyl-CH$_2$F, —$C_{1-2}$ alkyl-NR$^d$R$^{d'}$).

In some embodiments, A is optionally substituted $C_{1-4}$ alkylene (e.g., methylene, ethylene, propylene or butylene).

In some embodiments, A is optionally substituted ethylene (e.g., 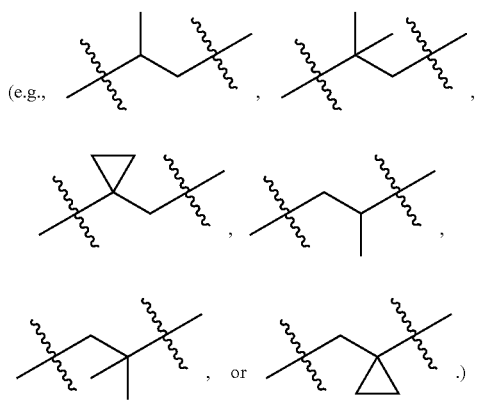.)

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-OR$^d$, —$C_{1-4}$ alkyl-NR$^d$R$^{d'}$, or $C_{1-4}$ alkyl-C(O)NR$^d$R$^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, —S(O)$_2$ alkyl, —S(O)$_2$ aralkyl, —S(O)$_2$ heteroaralkyl, —S(O)$_2$ aryl, —S(O)$_2$ heteroaryl, —S(O)$_2$ cycloalkyl, —S(O)$_2$ heterocycloalkyl, —S(O)$_2$ heterocycloalkylalkyl, and —S(O)$_2$ cycloalkylalkyl.

In some embodiments, $R^4$ is $C_{1-8}$ alkyl (e.g., methyl or ethyl).

In some embodiments, $R^4$ is $C_{1-8}$ alkyl, optionally substituted with 1-3 fluorine substituents (e.g., —CF$_3$, —C$_1$ alkyl-CF$_3$, —C$_1$ alkyl-CHF$_2$, —C$_1$ alkyl-CH$_2$F).

In some embodiments, W is $C_{2-8}$ alkyl optionally substituted with —OR$^d$, —NR$^d$R$^{d'}$, or —C(O)NR$^d$R$^{d'}$.

In some embodiments, W is

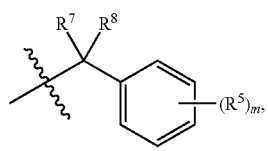

or optionally substituted aryl.

In some embodiments, W is

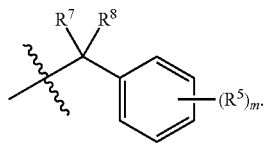

In some embodiments, W is

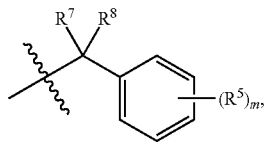

wherein m is 1-3 and $R^5$ is selected from F, Cl, Br, CF$_3$, methyl, OH, OCF$_3$, or S(O)$_{0-2}$R$^a$.

In some embodiments, W is

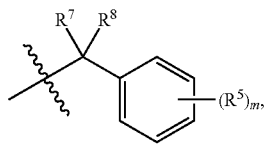

wherein m is 1-3, $R^7$ and $R^8$ are H and $R^5$ is selected from F, Cl, Br, CF$_3$, methyl, OH, —OCH$_3$, —OCF$_3$, S(O)$_{0-2}$R$^a$.

In some embodiments, W is optionally substituted heteroaryl (e.g., pyridine, thiophene, furan, isoxazole, oxazole, pyrimidine, pyrazine or thiazole).

In some embodiments, W is optionally substituted heteroaralkyl (e.g., C$_1$ alkyl-heteroaryl).

In some embodiments, W is optionally substituted aryl (e.g., monocyclic aryl).

In some embodiments, W is optionally substituted monocyclic aryl (e.g., phenyl).

In some embodiments, W is optionally substituted phenyl (e.g., aniline, halophenyl, alkoxyphenyl, alkylphenyl, benzoic acid, benzamide or nitrophenyl).

In some embodiments, W is

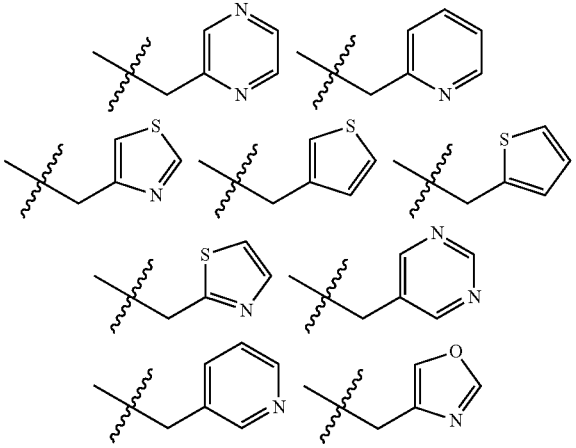

-continued

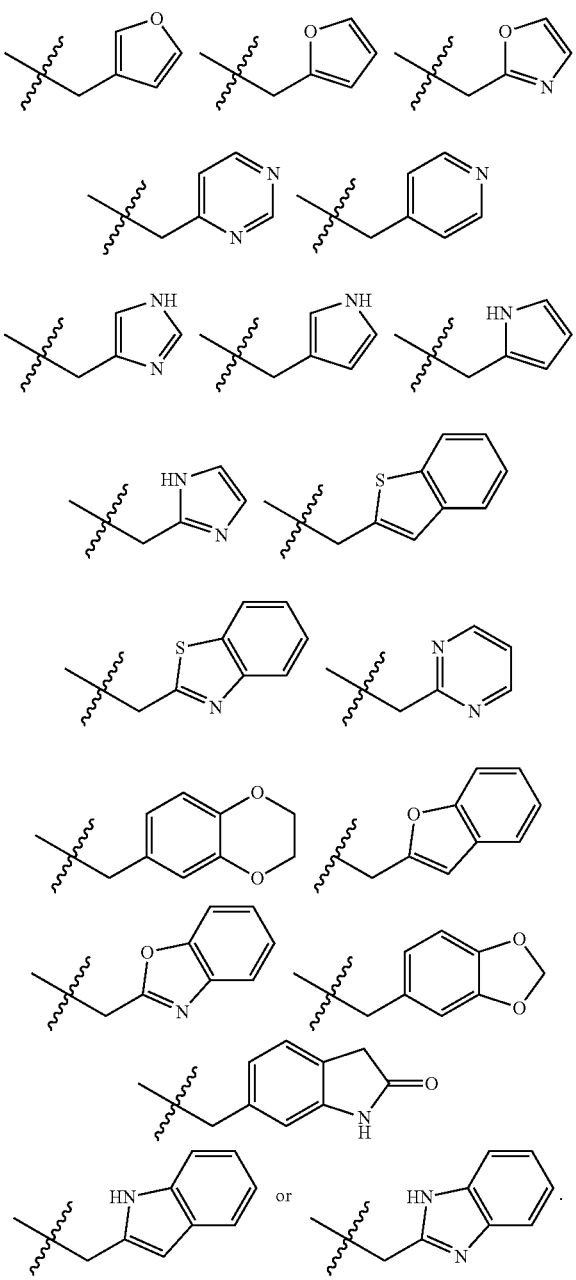

In some embodiments, m is 0.
In some embodiments, m is 1.
In some embodiments, m is 2.
In some embodiments, each $R^5$ is selected from $C_{1-8}$ alkyl, $C_{1-8}$ fluoroalkyl, hydroxyl, $C_{1-8}$ alkoxy, $C_{1-8}$ fluoroalkoxy, nitro, halogen, and $-NR^dR^{d'}$.
In some embodiments, each $R^5$ is selected from H, $C_{1-8}$ alkyl, $C_{1-8}$ alkoxy, $C_{1-8}$ fluoroalkyl, halogen, hydroxyl, $C_{1-8}$ fluoroalkoxy, nitro and amino
In some embodiments, each $R^5$ is selected from H, $C_{1-8}$ alkyl, $C_{1-8}$ fluoroalkyl, $C_{1-8}$ fluoroalkoxy, amino, nitro and halogen.
In some embodiments, each $R^5$ is $C_{1-8}$ alkyl (e.g., methyl).
In some embodiments, each $R^5$ is $C_{1-8}$ fluoroalkyl (e.g., trifluoromethyl).

In some embodiments, each $R^5$ is $C_{1-8}$ fluoroalkoxy (e.g., trifluoromethoxy).
In some embodiments, each $R^5$ is halogen (e.g., chlorine or fluorine).
In some embodiments, each $R^5$ is H.
In some embodiments, g is 1.
In some embodiments, g is 2.
In some embodiments, each $R^6$ is selected from halogen, $C_{1-8}$ alkyl, hydroxyl, $-C_{1-8}$ fluoroalkyl, $C_{1-8}$ haloalkoxy, and $-NR^dR^{d'}$.
In some embodiments, each $R^6$ is selected from halogen, hydroxyl, $-C_{1-8}$ fluoroalkyl, $-C_{1-8}$ fluoroalkoxy, $-NR^dR^{d'}$, $-C_{1-4}$ alkyl-$NR^dR^{d'}$, aryl, heteroaryl, and $C_{1-8}$ alkyl.
In some embodiments, each $R^6$ is halogen (e.g., fluorine or chlorine).
In some embodiments, each $R^6$ is $C_{1-8}$ alkyl (e.g., methyl).
In some embodiments, each $R^6$ is $C_{1-8}$ fluoroalkyl (e.g., $CF_3$).
In some embodiments, each $R^6$ is $C_{1-8}$ fluoroalkoxy (e.g., $-OCF_3$).
In some embodiments, each $R^6$ is aryl (e.g., phenyl).
In some embodiments, each $R^6$ is heteroaryl (e.g., pyridine).
In some embodiments, each $R^6$ is heterocyclyl further substituted with aryl.
In some embodiments, each $R^6$ is heterocyclyl further substituted with heteroaryl.
In some embodiments, a compound of Formula I is enantiomerically enriched (e.g., having an ee >60%, >70%, >80%, >90%, >95%, >97%, >98% or >99%).
In some embodiments, the compound is selected from the following formulas:

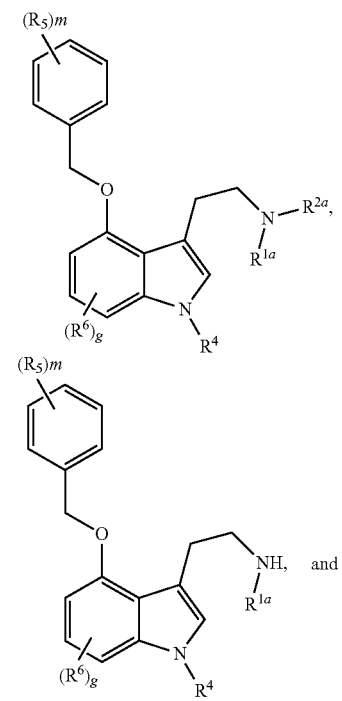

-continued

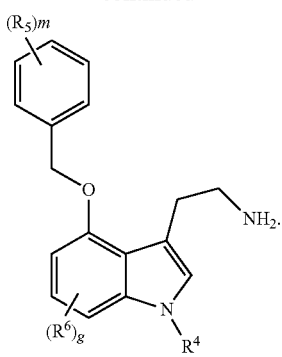

In some embodiments, the compound is selected from the following formulas:

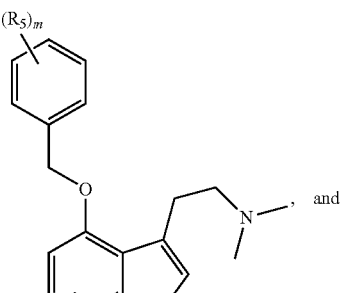

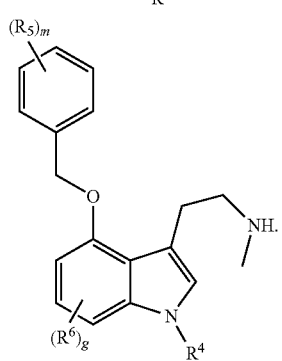

In some embodiments, the compound is selected from the following formulas:

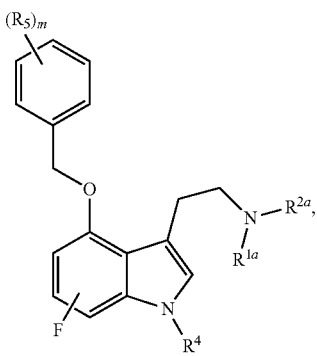

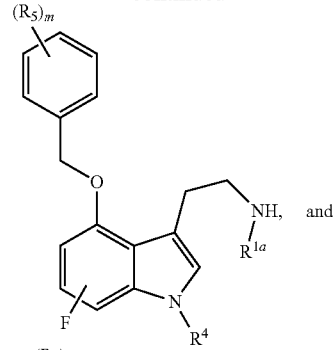

In another aspect, the invention is directed to a compound selected from the following formula:

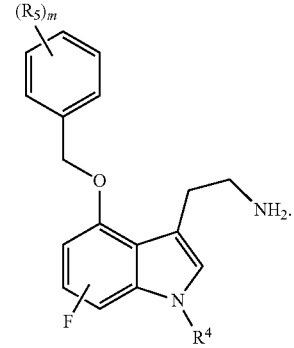

(II)

wherein
g is 1, 2 or 3;
$A^1$ is optionally substituted $C_{3-6}$cycloalkylene, optionally substituted heterocyclylene, optionally substituted arylene, optionally substituted heteroarylene, optionally substituted heterocycloalkylene or optionally substituted —C(O)—$C_{1-3}$ alkylene-, wherein arylene or heteroarylene are optionally substituted with 1-3 substituents, each of which is independently selected from the group consisting of halogen, $C_{3-8}$ cycloalkyl, —OR$^d$, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl, —S(O)$_{0-2}$ $C_{1-8}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^a$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted —$C_{1-6}$ alkyl, —NR$^d$C(O)R$^a$, —C(O)NR$^d$R$^{d'}$, and —C(O)OR$^d$, wherein cycloalkylene and —C(O)—$C_{1-3}$ alkylene are optionally substituted with 1-3 substituents, each of which is independently selected from the group consisting of halogen, oxo, optionally substituted $C_{1-6}$ alkyl, $C_{1-8}$ alkoxy, —S(O)$_{0-2}$alkyl, —OR$^d$ and —NR$^d$R$^{d'}$;

$R^1$ and $R^2$ are each independently selected from H, $C_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or C(O)NR$^d$R$^{d'}$;

$W^1$ is hydrogen, optionally substituted $C_{1-8}$ alkyl, optionally substituted aryl, optionally substituted heteroaryl, optionally substituted aralkyl, optionally substituted cycloalkyl, optionally substituted heterocyclyl, optionally substituted cycloalkylalkyl, optionally substituted heterocycloalkyl or optionally substituted heteroaralkyl;

$R^4$ is selected from $C_{1-8}$ alkyl, $C_{1-8}$ heteroalkyl, $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ aralkyl, —S(O)$_2$ heteroaralkyl, —S(O)$_2$ cycloalkylalkyl, formyl, —OR$^d$, —NR$^d$R$^{d'}$, —C(O)OR$^a$, —C(O)NR$^d$R$^{d'}$, —S(O)$_2$NR$^d$R$^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and heteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-aralkylaryl, —S(O)$_{0-2}$-heteroaralkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^a$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —C$_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl; and $R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $R^3$ is selected from H, and optionally substituted $C_{1-8}$ alkyl.

In some embodiments, $R^3$ is optionally substituted $C_{1-8}$ alkyl (e.g., —C$_{1-4}$alkyl-OR$^d$, —C$_{1-4}$alkyl-NR$^d$R$^{d'}$, or —C$_{1-4}$alkyl-C(O)NR$^d$R$^{d'}$).

In some embodiments, $A^1$ is optionally substituted aryl.

In some embodiments, $A^1$ is optionally substituted heteroaryl.

In some embodiments, $A^1$ is aryl (e.g. phenyl).

In some embodiments, $W^1$ is hydrogen, optionally substituted $C_{1-8}$ alkyl, optionally substituted aryl, optionally substituted heteroaryl, optionally substituted aralkyl, or optionally substituted heteroaralkyl In some embodiments, $W^1$ is H, optionally substituted $C_{1-8}$ alkyl., arylalkyl, or heteroaralkyl.

In some embodiments, $W^1$ is optionally substituted $C_{1-8}$ alkyl (e.g., —CF$_3$, —CH$_2$CF$_3$, or —CF$_2$CF$_3$)

In some embodiments, $W^1$ is $C_{1-8}$ alkyl. (e.g., methyl or ethyl).

In some embodiments, $W^1$ is arylalkyl (e.g. benzyl).

In some embodiments, a compound of Formula II is enantiomerically enriched (e.g., having an ee >60%, >70%, >80%, >90%, >95%, >97%, >98% or >99%).

In another aspect, the invention is directed to a compound selected from the following formula:

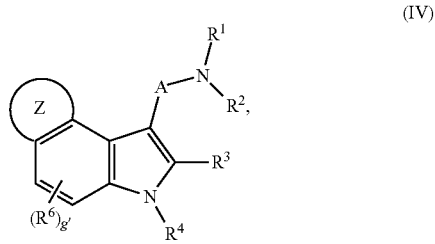

(IV)

wherein g' is 0, 1, 2 or 3;

Z is an optionally substituted heteroaryl or optionally substituted heterocyclyl;

$R^1$ and $R^2$ are each independently selected from H, $C_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or C(O)NR$^d$R$^{d'}$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)OR^d$, wherein alkylene and cycloalkylene are optionally substituted with 1-3 substituents, each of which is independently selected from the group consisting of halogen, oxo, optionally substituted $C_{1-6}$ alkyl, —$S(O)_{0-2}$alkyl, —$OR^d$ and —$NR^dR^{d'}$;

$R^4$ is selected from $C_{1-8}$ alkyl, $C_{1-8}$ heteroalkyl, $C_{2-8}$ alkenyl, $C_{2-8}$ alkynyl, —$S(O)_2$ alkyl, —$S(O)_2$ heteroalkyl, —$S(O)_2$ aryl, —$S(O)_2$ heteroaryl, —$S(O)_2$ cycloalkyl, —$S(O)_2$ heterocyclyl, —$S(O)_2$ heterocycloalkyl, —$S(O)_2$ aralkyl, —$S(O)_2$ heteroaralkyl, —$S(O)_2$ cycloalkyalkyl, formyl, —$OR^d$, —$NR^dR^{d'}$, —$C(O)OR^a$, —$C(O)NR^dR^{d'}$, —$S(O)_2NR^dR^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —$OR^d$, —$NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, —$OR^d$, —SH, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$—$C_{1-4}$alkylaryl, —$S(O)_{0-2}$—$C_{1-4}$alkylheteroaryl, —$OC(O)NR^dR^{d'}$, —$NR^dC(O)NR^{d'}R^{d''}$, —$NR^dC(O)OR^b$, —$OR^d$, —$NR^dS(O)_2$ alkyl, —$NR^dS(O)_2$aryl, —$NR^dS(O)_2$heteroaryl, —$NR^dS(O)_2$ cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^a$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$alkyl-$NR^dR^{d'}$, optionally substituted $C_{1-6}$ alkyl, —$NR^dC(O)R^a$, —$C(O)NR^dR^{d'}$, and —$C(O)OR^d$; wherein alkyl, aryl, heteroaryl, cycloalkyl and heterocyclyl are optionally substituted;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl, or when taken together with the nitrogen atom to which they are attached, $R^a$ and $R^b$ form a 4-8 membered heterocyclic moiety; and $R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $R^1$ and $R^2$ are each independently selected from H, $C_{1-8}$ alkyl, and optionally substituted aryl.

In some embodiments, $R^1$ and $R^2$ are each independently selected from H and $C_{1-8}$ alkyl.

In some embodiments, $R^1$ and $R^2$ are H.

In some embodiments, $R^1$ and $R^2$ are each optionally substituted $C_{1-8}$ alkyl (e.g., methyl).

In some embodiments, $R^1$ is H and $R^2$ is optionally substituted $C_{1-8}$ alkyl (e.g., methyl)

In some embodiments, $R^1$ is optionally substituted $C_{1-8}$ alkyl and $R^2$ is H.

In some embodiments, A is selected from optionally substituted $C_{1-4}$ alkylene, wherein the $C_{1-4}$ alkylene is optionally substituted with 1-3 substituents, each of which is independently selected from the group consisting of halogen (e.g., fluorine), hydroxyl, optionally substituted $C_{1-6}$ alkyl, $C_{1-8}$ alkoxy, —$SO_2$ alkyl, and —$NR^dR^{d'}$.

In some embodiments, A is optionally substituted $C_{1-4}$ alkylene, wherein the $C_{1-4}$ alkylene is optionally substituted with —$SO_2$ alkyl (e.g., methylsulfone).

In some embodiments, A is optionally substituted $C_{1-4}$ alkylene, wherein the $C_{1-4}$ alkylene is optionally substituted with hydroxyl (e.g., 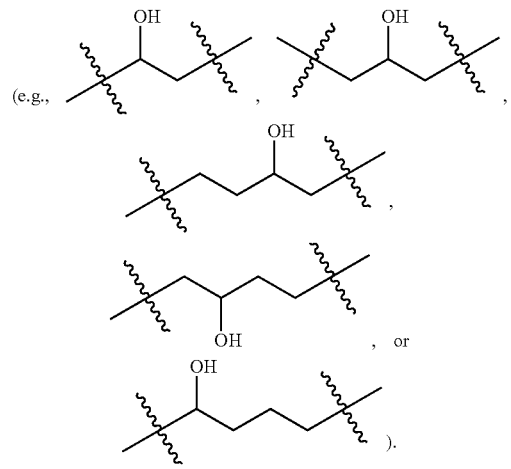 ).

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine).

In some embodiments, A is optionally substituted $C_{1-4}$ alkylene, wherein the $C_{1-4}$ alkylene is optionally substituted with 1-3 substituents, each of which is independently selected from the group consisting of optionally substituted $C_{1-6}$ alkyl (e.g., methyl, ethyl, i-propyl, —$C_{1-2}$ alkyl-OH, —$C_{1-2}$ alkyl-$CF_3$, —$C_{1-2}$ alkyl-$CHF_2$, —$C_{1-2}$ alkyl-$CH_2F$, —$C_{1-2}$ alkyl-$NR^dR^{d'}$).

In some embodiments, A is optionally substituted $C_{1-4}$ alkylene (e.g., methylene, ethylene, propylene or butylene).

In some embodiments, A is optionally substituted ethylene (e.g., 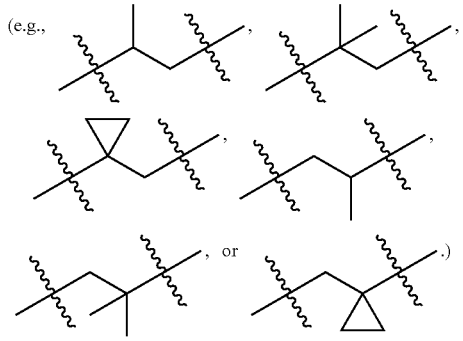)

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-$OR^d$, —$C_{1-4}$ alkyl-$NR^dR^{d'}$, or —$C_{1-4}$ alkyl-$C(O)NR^dR^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, —$S(O)_2$ alkyl, —$S(O)_2$ aralkyl, —$S(O)_2$ heteroaralkyl, —$S(O)_2$ aryl, —$S(O)_2$ cycloalkyl, —$S(O)_2$ heterocycloalkyl, —$S(O)_2$ heterocycloalkylalkyl, —$S(O)_2$ cycloalkylalkyl, and —$S(O)_2$ heteroaryl.

In some embodiments, $R^4$ is selected from $C_{1-8}$ alkyl (e.g., methyl or ethyl).

In some embodiments, $R^4$ is $C_{1-8}$ alkyl, optionally substituted with 1-3 fluorine substituents (e.g., —$C_1$ alkyl-$CF_3$, —$CF_3$, —$C_1$-alkyl-$CHF_2$, or —$C_1$alkyl-$CH_2F$).

In some embodiments,

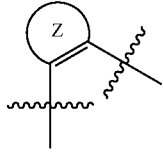 [SMILES: */C=C\*]

is optionally substituted heteroaryl.

In some embodiments,

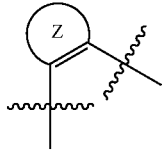 [SMILES: */C=C\*]

is 5-14 membered heteroaryl.

In some embodiments,

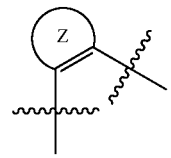 [SMILES: */C=C\*]

is optionally substituted heterocycyl.

In some embodiments,

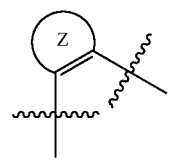 [SMILES: */C=C\*]

is 5-14 membered heterocyclyl.

In some embodiments,

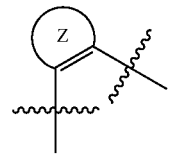 [SMILES: */C=C\*]

is optionally substituted

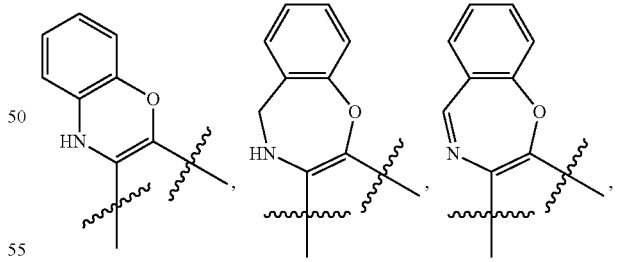

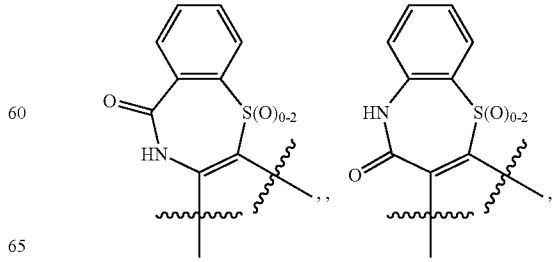

-continued
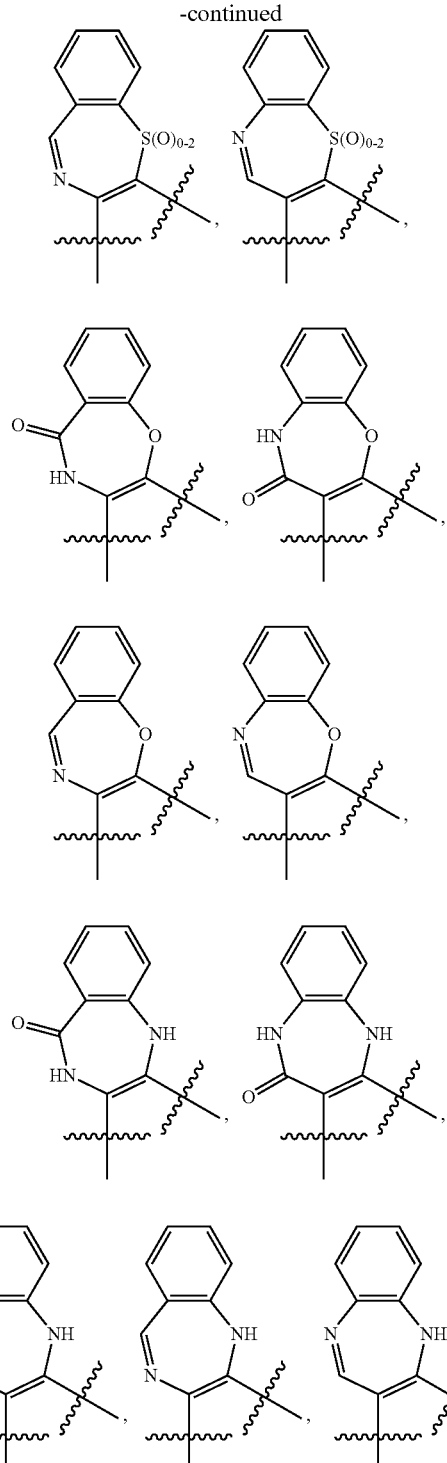
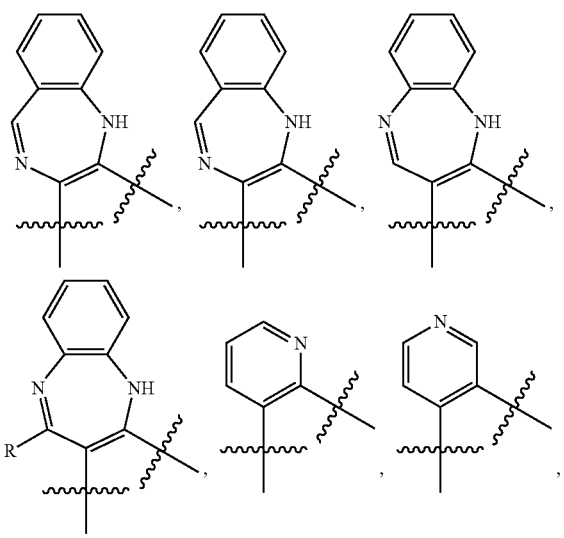
-continued
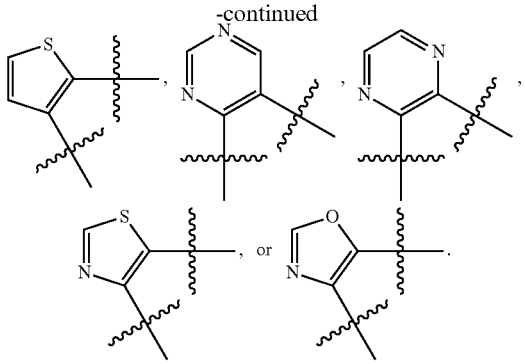
In some embodiments,
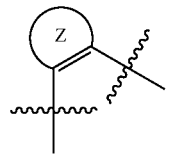 [SMILES: */C=C\*]
is optionally substituted on a carbon and/or nitrogen.
The compound according to claim xx, wherein
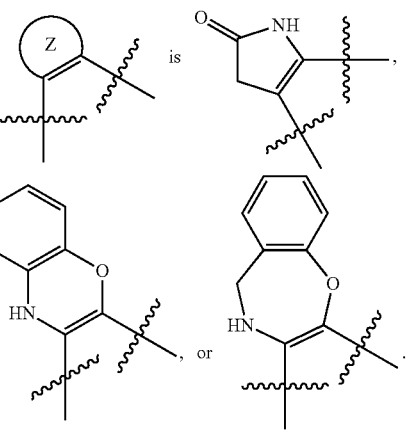
In some embodiments, a compound of Formula IV is enantiomerically enriched (e.g., having an ee >60%, >70%, >80%, >90%, >95%, >97%, >98% or >99%).
In another aspect, the invention is directed to a compound selected from the following formula:
(VII)
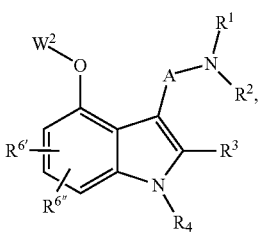

wherein $R^1$ and $R^2$ are each independently selected from H, $C_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —$C(O)NR^dR^{d'}$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$, wherein alkylene and cycloalkylene are optionally substituted with 1-3 substituents, each of which is independently selected from the group consisting of halogen, oxo, optionally substituted $C_{1-6}$ alkyl, —$S(O)_{0-2}$alkyl, —$OR^d$ and —$NR^dR^{d'}$;

$R^4$ is selected from $C_{1-8}$ alkyl, $C_{1-8}$ heteroalkyl, $C_{2-8}$ alkenyl, $C_{2-8}$ alkynyl, —$S(O)_2$ alkyl, —$S(O)_2$ heteroalkyl, —$S(O)_2$ aryl, —$S(O)_2$ heteroaryl, —$S(O)_2$ cycloalkyl, —$S(O)_2$ heterocyclyl, —$S(O)_2$ heterocycloalkyl, —$S(O)_2$ aralkyl, —$S(O)_2$ heteroaralkyl, —$S(O)_2$ cycloalkyalkyl, formyl, —$OR^d$, —$NR^dR^{d'}$, —$C(O)OR^a$, —$C(O)NR^dR^{d'}$, —$S(O)_2NR^dR^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —$OR^d$, —$NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, —$OR^d$, —SH, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$-aralkyl, —$S(O)_{0-2}$-heteroaralkyl, —$OC(O)NR^dR^{d'}$, —$NR^dC(O)NR^{d'}R^{d''}$, —$NR^dC(O)OR^b$, —$OR^d$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$;

each $R^{6'}$ is independently selected from hydrogen, halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$ alkyl-$NR^dR^{d'}$, optionally substituted $C_{1-6}$ alkyl, —$NR^dC(O)R^a$, —$C(O)NR^dR^{d'}$, and —$C(O)OR^d$, wherein alkyl, aryl, heteroaryl, cycloalkyl and heterocyclyl are optionally substituted;

$R^{6''}$ is optionally substituted aryl, heteroaryl, heterocyclyl, cycloalkyl, —$OR^d$, $C_{2-8}$ alkynyl, —NH-aryl, —NH-heteroaryl, —NH-alkyl, —$NR^d$-aryl, —$NR^d$-heteroaryl, —$NR^d$-arylalkyl, —$NR^d$-heteroarylalkyl, —$NR^d$-heterocyclyl, —$NR^d$-heterocyclylalkyl, —$NR^d$-heterocyclyl, —$NR^d$-cyclylalkyl, —$NR^d$-alkyl, —$C_1$alkyl-aryl, —$C_1$alkyl-heteroaryl, heterocyclyl, —$C_1$alkyl-cycloalkyl, —$C_1$alkyl-$NR^d$-alkyl, aryloxy, and heteroaryloxy; and $R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, the compound is selected from:

2-(7-fluoro-4-methoxy-1-methyl-5-phenyl-1H-indol-3-yl)-N,N-dimethylethanamine, 2-(4-methoxy-1-methyl-7-(pyridin-3-yl)-1H-indol-3-yl)-N,N-dimethylethanamine, 2-(4-methoxy-1-methyl-7-phenyl-1H-indol-3-yl)-N,N-dimethylethanamine, 2-(4-methoxy-1-methyl-7-(thiophen-3-yl)-1H-indol-3-yl)-N,N-dimethylethanamine, 2-(4-methoxy-1-methyl-7-(thiophen-2-yl)-1H-indol-3-yl)-N,N-dimethylethanamine, 2-(7-(furan-2-yl)-4-methoxy-1-methyl-1H-indol-3-yl)-N,N-dimethylethanamine, 2-(7-(furan-3-yl)-4-methoxy-1-methyl-1H-indol-3-yl)-N,N-dimethylethanamine, 2-(4-methoxy-1-methyl-7-(1H-pyrrol-2-yl)-1H-indol-3-yl)-N,N-dimethylethanamine, 3-(3-(2-(dimethylamino)ethyl)-4-methoxy-1-methyl-1H-indol-7-yl)prop-2-yn-1-ol, and 3-(2-(dimethylamino)ethyl)-4-methoxy-1-methyl-N-phenyl-1H-indol-7-amine.

In some embodiments, $R^1$ and $R^2$ are each independently selected from H, $C_{1-8}$ alkyl, and optionally substituted aryl.

In some embodiments, $R^1$ and $R^2$ are each independently selected from H and $C_{1-8}$ alkyl.

In some embodiments, $R^1$ and $R^2$ are H.

In some embodiments, $R^1$ and $R^2$ are each optionally substituted $C_{1-8}$ alkyl (e.g., methyl).

In some embodiments, $R^1$ is H and $R^2$ is optionally substituted $C_{1-8}$ alkyl (e.g., methyl)

In some embodiments, $R^1$ is optionally substituted $C_{1-8}$ alkyl and $R^2$ is H.

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine), hydroxyl, optionally substituted $C_{1-6}$ alkyl, $C_{1-8}$ alkoxy, —$SO_2$ alkyl, and —$NR^dR^{d'}$.

In some embodiments, A is optionally substituted $C_{1-4}$ alkylene, wherein the $C_{1-4}$ alkylene is optionally substituted with —$SO_2$ alkyl (e.g., methylsulfone).

In some embodiments, A is optionally substituted $C_{1-4}$ alkylene, wherein the $C_{1-4}$ alkylene is optionally substituted with hydroxyl (e.g., 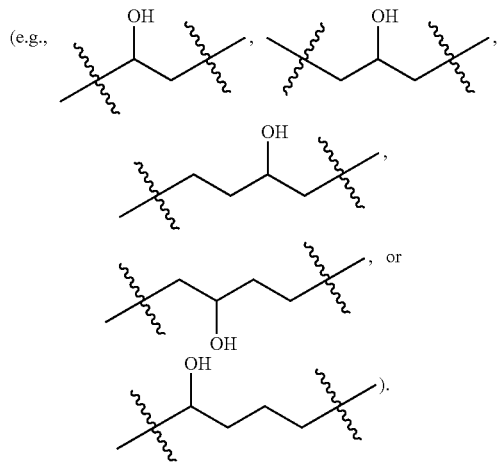 ).

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine).

In some embodiments, A optionally substituted $C_{1-4}$ alkylene, wherein the $C_{1-4}$ alkylene is optionally substituted with 1-3 substituents, each of which is independently selected from the group consisting of optionally substituted $C_{1-6}$ alkyl (e.g., methyl, ethyl, i-propyl, —$C_{1-2}$ alkyl-OH, —$C_{1-2}$ alkyl-$CF_3$, —$C_{1-2}$ alkyl-$CHF_2$, —$C_{1-2}$ alkyl-$CH_2F$, —$C_{1-2}$ alkyl-$NR^dR^{d'}$).

In some embodiments, A is optionally substituted $C_{1-4}$ alkylene (e.g., methylene, ethylene, propylene or butylene).

In some embodiments, A is optionally substituted ethylene (e.g., 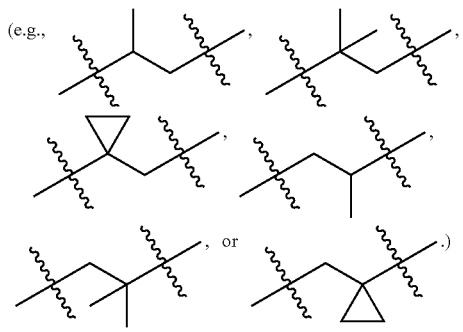 .)

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-$OR^d$, —$C_{1-4}$ alkyl-$NR^dR^{d'}$, or —$C_{1-4}$ alkyl-$C(O)NR^dR^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, —$S(O)_2$ alkyl, —$S(O)_2$ aralkyl, —$S(O)_2$ heteroaralkyl, —$S(O)_2$ aryl, —$S(O)_2$ cycloalkyl, —$S(O)_2$ heterocycloalkyl, —$S(O)_2$ heterocycloalkylalkyl, —$S(O)_2$ cycloalkylalkyl, and —$S(O)_2$ heteroaryl.

In some embodiments, $R^4$ is selected from $C_{1-8}$ alkyl (e.g., methyl or ethyl).

In some embodiments, $R^4$ is selected from $C_{1-8}$ alkyl, optionally substituted with 1-3 fluorine substituents (e.g., —$C_1$alkyl-$CF_3$, —$CF_3$, —$C_1$-alkyl-$CHF_2$, and —$C_1$-alkyl-$CH_2F$).

In some embodiments, $W^2$ is $C_{1-8}$ alkyl optionally substituted with —$OR^d$, —$NR^dR^{d'}$, —$C(O)NR^dR^{d'}$.

In some embodiments, $W^2$ is $C_{2-8}$ alkyl optionally substituted with —$OR^d$, —$NR^dR^{d'}$, —$C(O)NR^dR^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., —$CF_3$, —$CF_2CF_3$, or —$CH_2CF_3$).

In some embodiments, $W^2$ is $C_{1-8}$ alkyl (e.g. methyl or ethyl).

In some embodiments, $W^2$ is optionally substituted aralkyl (e.g., benzyl). In some embodiments, $R^{6'}$ is selected from hydrogen, halogen, $C_{1-8}$ alkyl, $C_{1-8}$ fluoroalkyl, $C_{1-8}$ haloalkoxy, cycloalkyl, and $C_{1-8}$ fluoroalkoxy.

In some embodiments, $R^{6'}$ is $C_{1-8}$ fluoroalkoxy (e.g., —$OCF_3$).

In some embodiments, $R^{6'}$ is selected from hydrogen, halogen and $C_{1-8}$ alkyl.

In some embodiments, $R^{6'}$ is selected from hydrogen and halogen.

In some embodiments, $R^{6'}$ is hydrogen.

In some embodiments, $R^{6'}$ is halogen (e.g., fluorine).

In some embodiments, $R^{6''}$ is selected from optionally substituted aryl, optionally substituted heteroaryl, optionally substituted aryloxy, optionally substituted heteroaryloxy, —NH-aryl and $C_{1-8}$ alkynoxy.

In some embodiments, $R^{6''}$ is selected from optionally substituted aryl, optionally substituted heteroaryl, —NH-aryl, hydroxyl, and $C_{2-8}$ alkynyl.

In some embodiments, $R^{6''}$ is optionally substituted aryl (e.g., monocyclic aryl)

In some embodiments, $R^{6''}$ is optionally substituted monocyclic aryl (e.g., phenyl).

In some embodiments, $R^{6''}$ is optionally substituted heteroaryl (e.g., monocyclic heteroaryl).

In some embodiments, $R^{6''}$ is optionally substituted monocyclic heteroaryl (e.g., 2-pyridyl, 3-pyridyl, 4-pyridyl, 3-thionyl, 2-thionyl, 2-furanyl, 3-furanyl or 2-pyrollyl).

In some embodiments, $R^{6''}$ is —NH-aryl (e.g., NHphenyl).

In some embodiments, R$^{6''}$ is hydroxyl C$_{2-8}$ alkynyl

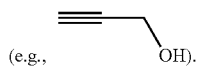

(e.g., ).

In some embodiments, a compound of Formula VII is enantiomerically enriched (e.g., having an ee >60%, >70%, >80%, >90%, >95%, >97%, >98% or >99%).

In another aspect, the invention is directed to a compound selected from the following formula:

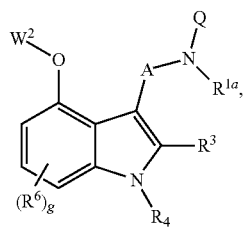

(VIII)

wherein
g is 1, 2 or 3;
R$^{1a}$ is selected from H, optionally substituted C$_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl;
Q is selected from is aryl, heteroaryl, aralkyl, heterocycloalkyl or heteroaralkyl, wherein Q is optionally substituted with 1-3 substituents, each of which is independently selected from the group consisting of halogen, C$_{3-8}$ cycloalkyl, —OR$^d$, C$_{1-8}$ haloalkoxy, —S(O)$_{0-2}$C$_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted —C$_{1-6}$ alkyl, —NR$^d$C(O)R$^a$, —C(O)NR$^d$R$^{d'}$, and —C(O);
R$^3$ is selected from H, optionally substituted C$_{1-8}$ alkyl, optionally substituted C$_{3-8}$ cycloalkyl, optionally substituted aryl, optionally substituted heteroaryl, optionally substituted heterocyclyl, halogen, or C(O)NR$^d$R$^{d'}$;
W$^2$ is hydrogen, optionally substituted C$_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —C(O)NR$^d$R$^{d'}$;
A is optionally substituted C$_{1-4}$ alkylene, optionally substituted cycloalkylene, optionally substituted arylene, optionally substituted heteroarylene, wherein arylene or heteroarylene are optionally substituted with 1-3 substituents, each of which is independently selected from the group consisting of halogen, C$_{3-8}$ cycloalkyl, —OR$^d$, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl), —OC(O) NR$^d$R$^{d'}$, —NR$^d$C(O)NR$^{d'}$R$^{d''}$, —NR$^d$C(O)OR$^a$, —NR$^d$S (O)$_2$ alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$—C$_{1-4}$alkyl-heteroaryl, —NR$^d$S(O)$_2$—C$_{1-4}$alkyl-cycloalkyl, —NR$^d$S(O)$_2$—C$_{1-4}$alkyl-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted C$_{1-6}$ alkyl, —NR$^d$C(O)R$^a$, —C(O)NR$^d$R$^{d'}$, and —C(O)OR$^d$, wherein alkylene and cycloalkylene are optionally substituted with 1-3 substituents, each of which is independently selected from the group consisting of fluorine, oxo, optionally substituted C$_{1-6}$ alkyl, —S(O)$_{0-2}$alkyl, —OR$^d$ and —NR$^d$R$^{d'}$;
R$^4$ is selected from C$_{1-8}$ alkyl, C$_{1-8}$ heteroalkyl, C$_{2-8}$ alkenyl, C$_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ aralkyl, —S(O)$_2$ heteroaralkyl, —S(O)$_2$ cycloalkyalkyl, formyl, —OR$^d$, —NR$^d$R$^{d'}$, —C(O)OR$^a$, —C(O)NR$^d$R$^{d'}$, —S(O)$_2$NR$^d$R$^{d'}$, C$_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$-aralkyl, —S(O)$_{0-2}$-heteroaralkyl, —OC(O)NR$^d$R$^{d'}$, —NR$^d$C(O) NR$^d$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted C$_{1-6}$ alkyl, —NR$^d$C(O)R$^a$, —C(O)NR$^d$R$^{d'}$, and —C(O)OR$^d$;
each R$^6$ is independently selected from halo, C$_{1-8}$ alkyl, aryl, heteroaryl, heteroalkyl, C$_{3-8}$ cycloalkyl, heterocyclyl, aralkyl, heteroaralkyl, cycloalkylalkyl, heterocycloalkyl, —SH, —OR$^d$, C$_{1-8}$ haloalkoxy, C$_{1-8}$ haloalkyl, —S(O)$_{0-2}$ C$_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C (O)NR$^{d'}$R$^{d''}$, —NR$^d$C(O)OR$^a$, —NR$^d$S(O)$_2$alkyl, —NR$^d$S (O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^d$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;
R$^a$, and R$^b$ are each independently selected from optionally substituted C$_{1-8}$ alkyl, optionally substituted aryl, optionally substituted heteroaryl, optionally substituted C$_{3-8}$ cycloalkyl, optionally substituted aralkyl, optionally substituted heteroaralkyl, optionally substituted cycloalkylalkyl and optionally substituted heterocycloalkyl;
R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In some embodiments, the compound is N-(2-(1-ethyl-7-fluoro-4-methoxy-1H-indol-3-yl)ethyl)aniline.

In some embodiments, $R^{1a}$ is selected from H, $C_{1-8}$ alkyl, and optionally substituted aryl.

In some embodiments, $R^{1a}$ is selected from H and $C_{1-8}$ alkyl.

In some embodiments, $R^{1a}$ is H.

In some embodiments, $R^{1a}$ is optionally substituted $C_{1-8}$ alkyl (e.g., methyl).

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine), hydroxyl, optionally substituted $C_{1-6}$ alkyl, $C_{1-8}$ alkoxy, $-SO_2$ alkyl, and $-NR^d R^{d'}$.

In some embodiments, A is optionally substituted $C_{1-4}$ alkylene, wherein the $C_{1-4}$ alkylene is optionally substituted with $-SO_2$ alkyl (e.g., methylsulfone).

In some embodiments, A is optionally substituted $C_{1-4}$ alkylene, wherein the $C_{1-4}$ alkylene is optionally substituted with hydroxyl

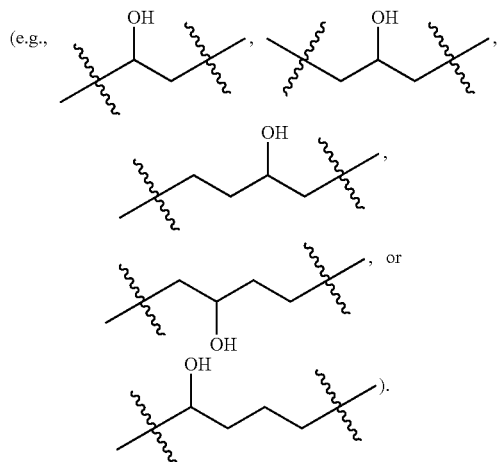

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine).

In some embodiments, A is optionally substituted $C_{1-4}$ alkylene, wherein the $C_{1-4}$ alkylene is optionally substituted with 1-3 substituents, each of which is independently selected from the group consisting of optionally substituted $C_{1-6}$ alkyl (e.g., methyl, ethyl, i-propyl, $-C_{1-2}$ alkyl-OH, $-C_{1-2}$ alkyl-$CF_3$, $-C_{1-2}$ alkyl-$CHF_2$, $-C_{1-2}$ alkyl-$CH_2F$, $-C_{1-2}$ alkyl-$NR^d R^{d'}$).

In some embodiments, A is optionally substituted $C_{1-4}$ alkylene (e.g., methylene, ethylene, propylene or butylene).

In some embodiments, A is optionally substituted ethylene

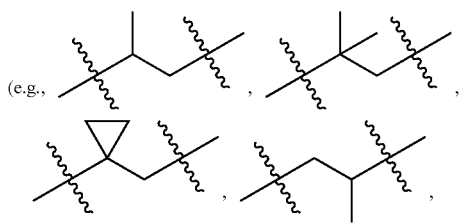

In some embodiments, $R^3$ is selected from H, and optionally substituted $C_{1-8}$ alkyl.

In some embodiments, $R^3$ is $C_{1-8}$ alkyl (e.g., $-C_{1-4}$ alkyl-$OR^d$, $-C_{1-4}$ alkyl-$NR^d R^{d'}$, or $-C_{1-4}$ alkyl-$C(O)NR^d R^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, $-S(O)_2$ alkyl, $-S(O)_2$ aralkyl, $-S(O)_2$ heteroaralkyl, $-S(O)_2$ aryl, $-S(O)_2$ cycloalkyl, $-S(O)_2$ heterocycloalkyl, $-S(O)_2$ heterocycloalkylalkyl, $-S(O)_2$ cycloalkylalkyl and $-S(O)_2$ heteroaryl.

In some embodiments, $R^4$ is selected from $C_{1-8}$ alkyl (e.g., methyl or ethyl).

In some embodiments, $R^4$ is selected from $C_{1-8}$ alkyl, optionally substituted with 1-3 fluorine substituents (e.g., $-C_1$-alkyl-$CF_3$, $-C_1$-alkyl-$CH_2F$, $-C_1$-alkyl-$CHF_2$, $-CF_3$).

In some embodiments, $W^2$ is $C_{1-8}$ alkyl optionally substituted with $-OR^d$, $-NR^d R^{d'}$, $-C(O)NR^d R^{d'}$.

In some embodiments, $W^2$ is $C_{2-8}$ alkyl optionally substituted with $-OR^d$, $-NR^d R^{d'}$, $-C(O)NR^d R^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., $-CF_3$, $-CF_2 CF_3$, or $-CH_2 CF_3$).

In some embodiments, $W^2$ is $C_{1-8}$ alkyl (e.g. methyl or ethyl).

In some embodiments, $W^2$ is optionally substituted aralkyl (e.g., benzyl). In some embodiments, $W^2$ is $C_{1-8}$ alkyl (e.g., methyl).

In some embodiments, Q is optionally substituted aryl or optionally substituted heteroaryl.

In some embodiments, Q is optionally substituted aryl (e.g., monocyclic aryl).

In some embodiments, Q is optionally substituted monocyclic aryl (e.g., phenyl).

In some embodiments, Q is optionally substituted arylalkyl.

In some embodiments, Q is optionally substituted heteroarylalkyl.

In some embodiments, Q is arylalkyl (e.g. benzyl).

In some embodiments, each $R^6$ is selected from halogen, $C_{1-8}$ alkyl, hydroxyl, $-C_{1-8}$ fluoroalkyl, amino, and $-NR^d R^{d'}$.

In some embodiments, each $R^6$ is selected from halogen, hydroxyl, $-C_{1-8}$ fluoroalkyl, $-C_{1-8}$ fluoroalkoxy, $-NR^d R^{d'}$, $-C_{1-4}$ alkyl-$NR^d R^{d'}$, aryl, heteroaryl, and $C_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., $CF_3$).

In some embodiments, each $R^6$ is $C_{1-8}$ fluoroalkoxy (e.g., $-OCF_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, a compound of Formula VIII is enantiomerically enriched (e.g., having an ee >60%, >70%, >80%, >90%, >95%, >97%, >98% or >99%).

In another aspect, the invention is directed to a compound selected from formula:

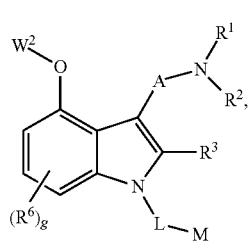

(IX)

L is a bond, —SO$_2$—, or optionally substituted C$_{1-3}$ alkylene;

M is optionally substituted C$_{1-8}$ alkyl, optionally substituted aryl, optionally substituted heteroaryl, optionally substituted aralkyl, optionally substituted cycloalkyl, optionally substituted heterocyclyl, optionally substituted cycloalkylalkyl, optionally substituted heterocycloalkyl or optionally substituted heteroaralkyl;

$R^1$ and $R^2$ are each independently selected from H, C$_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted C$_{1-8}$ alkyl, optionally substituted C$_{3-8}$ cycloalkyl, optionally substituted aryl, optionally substituted heteroaryl, optionally substituted heterocyclyl, halogen, or C(O)NR$^d$R$^{d'}$;

W$^2$ is hydrogen, optionally substituted C$_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —C(O)NR$^d$R$^{d'}$;

A is optionally substituted C$_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, C$_{3-8}$ cycloalkyl, —OR$^d$, C$_{1-8}$ haloalkoxy, —S(O)$_{0-2}$ C$_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl), —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^b$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^a$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, optionally substituted C$_{1-6}$ alkyl, —NR$^d$C(O)R$^a$, —C(O)NR$^d$R$^{d'}$, and —C(O)OR$^d$, wherein alkylene and cycloalkylene are optionally substituted with 1-3 substituents, each of which is independently selected from the group consisting of halogen, oxo, optionally substituted C$_{1-6}$ alkyl, —S(O)$_{0-2}$alkyl, —OR$^d$ and —NR$^d$R$^{d'}$;

each $R^6$ is independently selected from halo, C$_{1-8}$ alkyl, aryl, heteroaryl, heteroalkyl, C$_{3-8}$ cycloalkyl, heterocyclyl, aralkyl, heteroaralkyl, cycloalkylalkyl, heterocycloalkyl, —SH, —OR$^d$, C$_{1-8}$ haloalkoxy, C$_{1-8}$ haloalkyl, —S(O)$_{0-2}$ C$_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^a$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

$R^a$, and $R^b$ are each independently selected from optionally substituted C$_{1-8}$ alkyl, optionally substituted aryl, optionally substituted heteroaryl, optionally substituted C$_{3-8}$ cycloalkyl, optionally substituted aralkyl, optionally substituted heteroaralkyl, optionally substituted cycloalkylalkyl and optionally substituted heterocycloalkyl; and $R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety;

with the proviso that when W$^2$ is H, and L is SO$_2$, then M is not unsubstituted methyl or ethyl In some embodiments, $R^1$ and $R^2$ are each independently selected from H, C$_{1-8}$ alkyl, and optionally substituted aryl.

In some embodiments, $R^1$ and $R^2$ are each independently selected from H and C$_{1-8}$ alkyl.

In some embodiments, $R^1$ and $R^2$ are H.

In some embodiments, $R^1$ and $R^2$ are each optionally substituted C$_{1-8}$ alkyl (e.g., methyl).

In some embodiments, $R^1$ is H and $R^2$ is optionally substituted C$_{1-8}$ alkyl (e.g., methyl)

In some embodiments, $R^1$ is optionally substituted C$_{1-8}$ alkyl and $R^2$ is H.

In some embodiments, A is optionally substituted C$_{1-4}$ alkylene, wherein the C$_{1-4}$ alkylene is optionally substituted with 1-3 substituents, each of which is independently selected from the group consisting of halogen (e.g., fluorine), hydroxyl, optionally substituted C$_{1-6}$ alkyl, C$_{1-8}$ alkoxy, —SO$_2$ alkyl, and —NR$^d$R$^{d'}$.

In some embodiments, A is optionally substituted C$_{1-4}$ alkylene, wherein the C$_{1-4}$ alkylene is optionally substituted with —SO$_2$ alkyl (e.g., methylsulfone).

In some embodiments, A is optionally substituted C$_{1-4}$ alkylene, wherein the C$_{1-4}$ alkylene is optionally substituted with hydroxyl

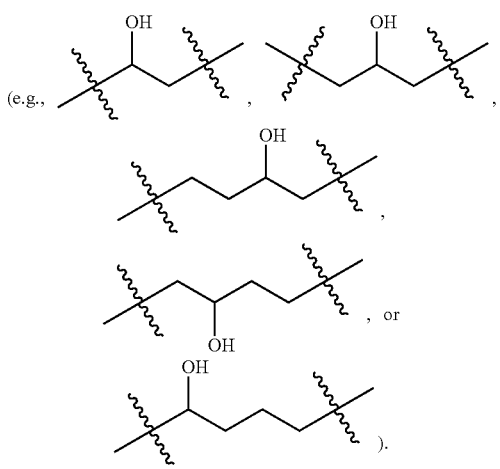

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine).

In some embodiments, A is optionally substituted $C_{1-4}$ alkylene, wherein the $C_{1-4}$ alkylene is optionally substituted with 1-3 substituents, each of which is independently selected from the group consisting of optionally substituted $C_{1-6}$ alkyl (e.g., methyl, ethyl, i-propyl, —$C_{1-2}$ alkyl-OH, —$C_{1-2}$ alkyl-$CF_3$, —$C_{1-2}$ alkyl-$CHF_2$, —$C_{1-2}$ alkyl-$CH_2F$, —$C_{1-2}$ alkyl-$NR^dR^{d'}$).

In some embodiments, A is optionally substituted $C_{1-4}$ alkylene (e.g., methylene, ethylene, propylene or butylene).

In some embodiments, A is optionally substituted ethylene

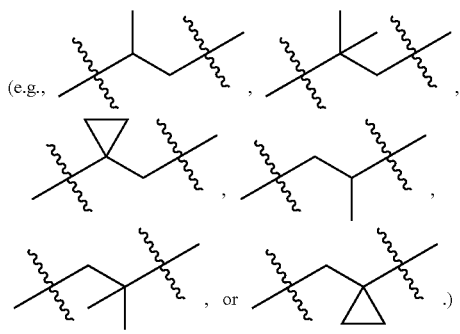

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-$OR^d$, —$C_{1-4}$ alkyl-$NR^dR^{d'}$, or —$C_{1-4}$ alkyl-$C(O)NR^dR^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, L is a bond.

In some embodiments, L is $SO_2$.

In some embodiments, M is optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl), —$OC(O)NR^dR^{d'}$, —$NR^dC(O)NR^dR^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^aS(O)_2$-cycloalkylalkyl, —$NR^aS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)OR^d$.

In some embodiments, M is aralkyl or heteroaralkyl optionally substituted on the alkyl moiety.

In some embodiments, M is optionally substituted aryl (e.g., monocyclic aryl).

In some embodiments, M is optionally substituted monocyclic aryl (e.g., phenyl).

In some embodiments, M is optionally substituted heteroaryl (e.g., N-containing heteroaryl).

In some embodiments, M is N-containing heteroaryl (e.g., 2-pyrimidyl).

In some embodiments, M is optionally substituted aralkyl (e.g., monocyclic or bicyclic aralkyl).

In some embodiments, M is optionally substituted monocyclic aralkyl (e.g., benzyl or methylanisole).

In some embodiments, M is optionally substituted bicyclic aralkyl (e.g., methylnaphthyl).

In some embodiments, M is optionally substituted heteroaralkyl (e.g., N-containing heteroaralkyl or S-containing heteroaralkyl).

In some embodiments, M is optionally substituted N-containing heteroaralkyl (e.g., methylpyridyl).

In some embodiments, M is optionally substituted S-containing heteroaralkyl (e.g., methylthionyl).

In some embodiments, $W^2$ is $C_{1-8}$ alkyl optionally substituted with —$OR^d$, —$NR^dR^{d'}$, —$C(O)NR^dR^{d'}$.

In some embodiments, $W^2$ is $C_{2-8}$ alkyl optionally substituted with —$OR^d$, —$NR^dR^{d'}$, —$C(O)NR^dR^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., —$CF_3$, —$CF_2CF_3$, or —$CH_2CF_3$).

In some embodiments, $W^2$ is $C_{1-8}$ alkyl (e.g. methyl or ethyl).

In some embodiments, $W^2$ is optionally substituted aralkyl (e.g., benzyl).

In some embodiments, each $R^6$ is selected from halogen, $C_{1-8}$ alkyl, hydroxyl, —$C_{1-8}$ fluoroalkyl, $C_{1-8}$ haloalkoxy, and —$NR^dR^{d'}$.

In some embodiments, each $R^6$ is selected from halogen, hydroxyl, —$C_{1-8}$ fluoroalkyl, —$C_{1-8}$ fluoroalkoxy, —$NR^dR^{d'}$, —$C_{1-4}$ alkyl-$NR^dR^{d'}$, aryl, heteroaryl, and $C_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., $CF_3$).

In some embodiments, each $R^6$ is $C_{1-8}$ fluoroalkoxy (e.g., —$OCF_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, a compound of Formula IX is enantiomerically enriched (e.g., having an ee >60%, >70%, >80%, >90%, >95%, >97%, >98% or >99%).

In some embodiments, the compound is selected from:
2-(6-fluoro-4-methoxy-1-(phenylsulfonyl)-1H-indol-3-yl)-N,N-dimethylethanamine,
2-(1-benzyl-4-(benzyloxy)-7-fluoro-1H-indol-3-yl)-N,N-dimethylethanamine,
2-(6-fluoro-4-methoxy-1-(pyrimidin-2-yl)-1H-indol-3-yl)-N,N-dimethylethanamine,
2-(4-(benzyloxy)-7-fluoro-1-(4-methoxybenzyl)-1H-indol-3-yl)-N,N-dimethylethanamine,
3-(2-(dimethylamino)ethyl)-7-fluoro-1-(4-methoxybenzyl)-1H-indol-4-ol,
2-(4-(benzyloxy)-7-fluoro-1-(pyridin-2-ylmethyl)-1H-indol-3-yl)-N,N-dimethylethanamine,
3-(2-(dimethylamino)ethyl)-7-fluoro-1-(pyridin-2-ylmethyl)-1H-indol-4-ol,
2-(4-(benzyloxy)-7-fluoro-1-(naphthalen-2-ylmethyl)-1H-indol-3-yl)-N,N-dimethylethanamine,
3-(2-(dimethylamino)ethyl)-7-fluoro-1-(naphthalen-2-ylmethyl)-1H-indol-4-ol,
2-(4-(benzyloxy)-7-fluoro-1-(thiophen-2-ylmethyl)-1H-indol-3-yl)-N,N-dimethylethanamine, and
1-benzyl-3-(2-(dimethylamino)ethyl)-7-fluoro-1H-indol-4-ol.

In another aspect, the invention is directed to a compound selected from formula:

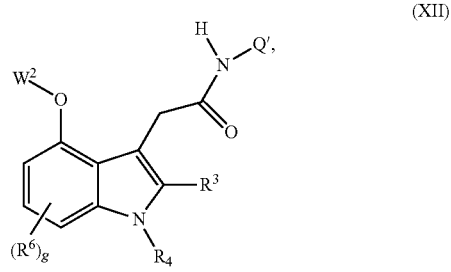

(XII)

g is 1, 2 or 3;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —$C(O)NR^dR^{d'}$;

Q' is selected from is aryl, heteroaryl, aralkyl, heterocycloalkyl or heteroaralkyl, wherein Q' is optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)$;

$R^4$ is selected from $C_{1-8}$ alkyl, $C_{1-8}$ heteroalkyl, $C_{2-8}$ alkenyl, $C_{2-8}$ alkynyl, —$S(O)_2$ alkyl, —$S(O)_2$ heteroalkyl, —$S(O)_2$ aryl, —$S(O)_2$ heteroaryl, —$S(O)_2$ cycloalkyl, —$S(O)_2$ heterocyclyl, —$S(O)_2$ heterocycloalkyl, —$S(O)_2$ aralkyl, —$S(O)_2$ heteroaralkyl, —$S(O)_2$ cycloalkyalkyl, formyl, —$OR^d$, —$NR^dR^{d'}$, —$C(O)OR^a$, —$C(O)NR^dR^{d'}$, —$S(O)_2NR^dR^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —$OR^d$, —$NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, —$OR^d$, —$SH$, $C_{1-8}$ haloalkoxy, —$S(O)_{0-2}C_{1-8}$ alkyl, —$S(O)_{0-2}$ aryl, —$S(O)_{0-2}$ heteroaryl, —$S(O)_{0-2}$-aralkyl, —$S(O)_{0-2}$-heteroaralkyl, —$OC(O)NR^dR^{d'}$, —$NR^dC(O)NR^dR^{d''}$, —$NR^dC(O)OR^b$, —$OR^d$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^aS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —$SH$, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^a$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^aS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$alkyl-$NR^dR^{d'}$, optionally substituted $C_{1-6}$ alkyl, —$NR^dC(O)R^a$, —$C(O)NR^dR^{d'}$, and —$C(O)OR^d$; wherein alkyl, aryl, heteroaryl, cycloalkyl and heterocyclyl are optionally substituted;

$R^a$, and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-$OR^d$, —$C_{1-4}$ alkyl-$NR^dR^{d'}$, or —$C_{1-4}$ alkyl-$C(O)NR^dR^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, —$S(O)_2$ alkyl, —$S(O)_2$ aralkyl, —$S(O)_2$ heteroaralkyl, —$S(O)_2$ aryl, —$S(O)_2$ heteroaryl, —$S(O)_2$ cycloalkyl, —$S(O)_2$ heterocycloalkyl, —$S(O)_2$ heterocycloalkylalkyl, and —$S(O)_2$ cycloalkylalkyl.

In some embodiments, $R^4$ is selected from $C_{1-8}$ alkyl (e.g., methyl or ethyl).

In some embodiments, $R^4$ is selected from $C_{1-8}$ alkyl, optionally substituted with 1-3 fluorine substituents (e.g., —CF$_3$, —C$_1$-alkyl-CF$_3$, —C$_1$-alkyl-CHF$_2$, —C$_1$-alkyl-CH$_2$F).

In some embodiments, $W^2$ is $C_{1-8}$ alkyl optionally substituted with —OR$^d$, —NR$^d$R$^{d'}$, —C(O)NR$^d$R$^{d'}$.

In some embodiments, $W^2$ is $C_{2-8}$ alkyl optionally substituted with —OR$^d$, —NR$^d$R$^{d'}$, —C(O)NR$^d$R$^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., —CF$_3$, —CF$_2$CF$_3$, or —CH$_2$CF$_3$).

In some embodiments, $W^2$ is $C_{1-8}$ alkyl (e.g. methyl or ethyl).

In some embodiments, $W^2$ is optionally substituted aralkyl (e.g., benzyl).

In some embodiments, g is 1.

In some embodiments, g is 2.

In some embodiments, each $R^6$ is selected from halogen, $C_{1-8}$ alkyl, hydroxyl, —$C_{1-8}$ fluoroalkyl, $C_{1-8}$ haloalkoxy, and —NR$^d$R$^{d'}$.

In some embodiments, each $R^6$ is selected from halogen, hydroxyl, —$C_{1-8}$ fluoroalkyl, —$C_{1-8}$ fluoroalkoxy, —NR$^d$R$^{d'}$, —$C_{1-4}$ alkyl-NR$^d$R$^{d'}$, aryl, heteroaryl, and $C_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., CF$_3$).

In some embodiments, each $R^6$ is $C_{1-8}$ fluoroalkoxy (e.g., —OCF$_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, a compound of Formula XII is enantiomerically enriched (e.g., having an ee >60%, >70%, >80%, >90%, >95%, >97%, >98% or >99%).

In some embodiments, Q' is optionally substituted aryl (e.g., monocyclic aryl).

In some embodiments, Q' is optionally substituted monocyclic aryl (e.g., phenyl).

In some embodiments, the compound is 2-(5-bromo-1-ethyl-7-fluoro-4-methoxy-1H-indol-3-yl)-N-phenylacetamide.

In some aspects, the invention is directed to a compound selected from formula:

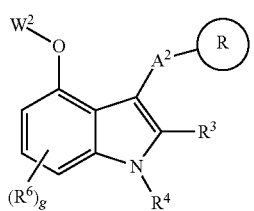

(XIII)

g is 1, 2 or 3;

is an optionally substituted N-containing heterocyclyl or optionally substituted N-containing heteroaryl;

$A^2$ is a bond or and optionally substituted $C_{1-4}$ alkylene;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or C(O)NR$^d$R$^{d'}$;

$W^2$ is hydrogen, optionally substituted $C_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —C(O)NR$^d$R$^{d'}$;

$R^4$ is selected from $C_{1-8}$ alkyl, $C_{1-8}$ heteroalkyl, $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ aralkyl, —S(O)$_2$ heteroaralkyl, —S(O)$_2$ cycloalkylalkyl, formyl, —OR$^d$, —NR$^d$R$^{d'}$, —C(O)OR$^a$, —C(O)NR$^d$R$^{d'}$, —S(O)$_2$NR$^d$R$^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-aralkyl, —S(O)$_{0-2}$-heteroaralkyl, —OC(O)NR$^d$R$^{d'}$, —NR$^d$C(O)NR$^d$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^d$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^a$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —$C_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

$R^a$ and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl, or when taken together with the nitrogen atom to which they are attached, $R^a$ and $R^b$ form a 4-8 membered heterocyclic moiety;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $A^2$ is optionally substituted $C_{1-4}$ alkylene (e.g., methylene or ethylene).

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-$OR^d$, —$C_{1-4}$ alkyl-$NR^dR^{d'}$, or —$C_{1-4}$ alkyl-$C(O)NR^dR^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, —$S(O)_2$ alkyl, —$S(O)_2$ aralkyl, —$S(O)_2$ heteroaralkyl, —$S(O)_2$ aryl, —$S(O)_2$ heteroaryl, —$S(O)_2$ cycloalkyl, —$S(O)_2$ heterocycloalkyl, —$S(O)_2$ heterocycloalkylalkyl, and —$S(O)_2$ cycloalkylalkyl.

In some embodiments, $R^4$ is selected from $C_{1-8}$ alkyl (e.g., methyl or ethyl).

In some embodiments, $R^4$ is selected from $C_{1-8}$ alkyl, optionally substituted with 1-3 fluorine substituents (e.g., —$CF_3$, —$C_1$-alkyl-$CF_3$, —$C_1$-alkyl-$CHF_2$, —$C_1$-alkyl-$CH_2F$).

In some embodiments, $W^2$ is $C_{1-8}$ alkyl optionally substituted with —$OR^d$, —$NR^dR^{d'}$, —$C(O)NR^dR^{d'}$.

In some embodiments, $W^2$ is $C_{2-8}$ alkyl optionally substituted with —$OR^d$, —$NR^dR^{d'}$, —$C(O)NR^dR^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., —$CF_3$, —$CF_2CF_3$, or —$CH_2CF_3$).

In some embodiments, $W^2$ is $C_{1-8}$ alkyl (e.g. methyl or ethyl).

In some embodiments, $W^2$ is optionally substituted aralkyl (e.g., benzyl).

In some embodiments, g is 1.

In some embodiments, g is 2.

In some embodiments, each $R^6$ is selected from halogen, $C_{1-8}$ alkyl, hydroxyl, —$C_{1-8}$ fluoroalkyl, $C_{1-8}$ haloalkoxy, and —$NR^dR^{d'}$.

In some embodiments, each $R^6$ is selected from halogen, hydroxyl, —$C_{1-8}$ fluoroalkyl, —$C_{1-8}$ fluoroalkoxy, —$NR^dR^{d'}$, —$C_{1-4}$ alkyl-$NR^dR^{d'}$, aryl, heteroaryl, and $C_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., $CF_3$).

In some embodiments, each $R^6$ is $C_{1-8}$ fluoroalkoxy (e.g., —$OCF_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, a compound of Formula XIII is enantiomerically enriched (e.g., having an ee >60%, >70%, >80%, >90%, >95%, >97%, >98% or >99%).

In some embodiments,

is 3-14 membered (e.g., 4-14 membered, or 5-8 membered) heteroaryl or heterocyclyl.

In some embodiments,

is optionally substituted:

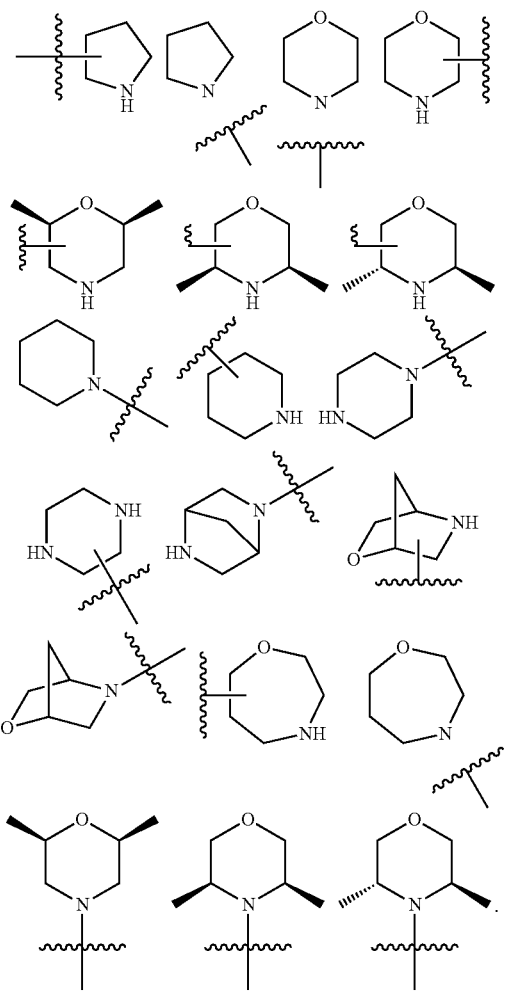

In some embodiments,

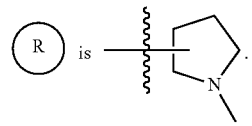

In some embodiments,

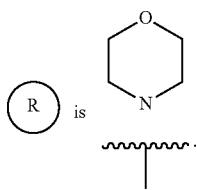

In some embodiments,

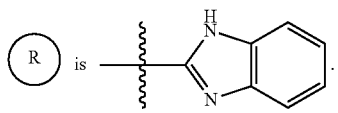

In some embodiments,

is optionally substituted on a carbon and/or nitrogen.

In some embodiments, the compound is selected from:
3-(benzo[d]oxazol-2-ylmethyl)-1-ethyl-6-fluoro-1H-indol-4-ol,
4-(2-(7-fluoro-4-methoxy-1-methyl-1H-indol-3-yl)ethyl) morpholine,
3-((1H-benzo[d]imidazol-2-yl) methyl)-1-ethyl-6-fluoro-1H-indol-4-ol,
1-ethyl-6-fluoro-3-(2-morpholinoethyl)-1H-indol-4-ol,
1-ethyl-6-fluoro-3-(2-(pyrrolidin-1-yl)ethyl)-1H-indol-4-ol, and
7-fluoro-4-methoxy-1-methyl-3-(2-(pyrrolidin-1-yl)ethyl)-1H-indole.

In another aspect, the invention is directed to a compound selected from formula:

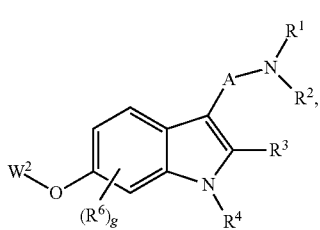

(XIV)

g is 1, 2 or 3;

$R^1$ and $R^2$ are each independently selected from H, $C_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or $—C(O)NR^dR^{d'}$;

A is optionally substituted $C_{1-4}$ alkylene, optionally substituted cycloalkylene, optionally substituted arylene, optionally substituted heteroarylene, optionally substituted heterocycloalkylene wherein arylene or heteroarylene are optionally substituted with 1-3 substituents, each of which is independently selected from the group consisting of halogen, $C_{3-8}$ cycloalkyl, $—OR^d$, $C_{1-8}$ haloalkoxy, $—S(O)_{0-2}$ $C_{1-8}$ alkyl, $—S(O)_{0-2}$ aryl, $—S(O)_{0-2}$ heteroaryl, $—S(O)_{0-2}$ aralkyl, $—S(O)_{0-2}$ heteroaralkyl), $—S(O)_{0-2}$ cycloalkyl, $—S(O)_{0-2}$ heterocycloalkyl, $—S(O)_{0-2}$ heterocycloalkylalkyl, $—S(O)_{0-2}$ cycloalkylalkyl, $—OC(O)NR^dR^{d'}$, $—NR^dC(O)NR^{d'}R^{d''}$, $—NR^dC(O)OR^b$, $—NR^dS(O)_2$alkyl, $—NR^dS(O)_2$aryl, $—NR^dS(O)_2$heteroaryl, $—NR^dS(O)_2$cycloalkyl, $—NR^dS(O)_2$heterocycloalkyl, $—NR^dS(O)_2$-aralkyl, $—NR^dS(O)_2$-heteroaralkyl, $—NR^dS(O)_2$-cycloalkylalkyl, $—NR^dS(O)_2$-heterocycloalkyl, $—SO_2NR^dR^{d'}$, cyano, nitro, $C_{1-6}$ haloalkyl, $C_{1-6}$ haloalkoxy, $—NR^dR^{d'}$, optionally substituted $C_{1-6}$ alkyl, $—NR^dC(O)R^a$, $—C(O)NR^dR^{d'}$, and $—C(O)OR^d$, wherein alkylene and cycloalkylene are optionally substituted with 1-3 substituents, each of which is independently selected from the group consisting of halogen, oxo, optionally substituted $C_{1-6}$ alkyl, $—S(O)_{0-2}$alkyl, $—OR^d$ and $—NR^dR^{d'}$;

$R^4$ is selected from $C_{1-8}$ alkyl, $C_{1-8}$ heteroalkyl, $C_{2-8}$ alkenyl, $C_{2-8}$ alkynyl, $—S(O)_2$ alkyl, $—S(O)_2$ heteroalkyl, $—S(O)_2$ aryl, $—S(O)_2$ heteroaryl, $—S(O)_2$ cycloalkyl, $—S(O)_2$ heterocyclyl, $—S(O)_2$ heterocycloalkyl, $—S(O)_2$ aralkyl, $—S(O)_2$ heteroaralkyl, $—S(O)_2$ cycloalkyalkyl, formyl, $—OR^d$, $—NR^dR^{d'}$, $—C(O)OR^a$, $—C(O)NR^dR^{d'}$, $—S(O)_2NR^dR^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, $—OR^d$, $—NR^dR^{d'}$, and wherein aryl and herteroaryl are optionally substituted with 1-3 substituents, each of which is independently selected from the group consisting of halogen, alkyl, heteroalkyl, cycloalkyl, heterocyclyl, $—OR^d$, $—SH$, $C_{1-8}$ haloalkoxy, $—S(O)_{0-2}$ $C_{1-8}$ alkyl, $—S(O)_{0-2}$ aryl, $—S(O)_{0-2}$ heteroaryl, $—S(O)_{0-2}$-aralkyl, $—S(O)_{0-2}$-heteroaralkyl, $—OC(O)NR^dR^{d'}$, $—NR^dC(O)NR^{d'}R^{d''}$, $—NR^dC(O)OR^b$, $—OR^d$, $—NR^dS(O)_2$alkyl, $—NR^dS(O)_2$aryl, $—NR^dS(O)_2$heteroaryl, $—NR^dS(O)_2$cycloalkyl, $—NR^dS(O)_2$ heterocycloalkyl, $—NR^dS(O)_2$-aralkyl, $—NR^dS(O)_2$-heteroaralkyl, $—NR^dS(O)_2$-cycloalkylalkyl, $—NR^dS(O)_2$-heterocycloalkyl, $—SO_2NR^dR^{d'}$, cyano, nitro, $C_{1-6}$ haloalkyl, $C_{1-6}$ haloalkoxy, $—NR^dR^{d'}$, optionally substituted $C_{1-6}$ alkyl, $—NR^dC(O)R^a$, $—C(O)NR^dR^{d'}$, and $—C(O)OR^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, $—SH$, $—OR^d$, $C_{1-8}$ haloalkoxy, $C_{1-8}$ haloalkyl, $—S(O)_{0-2}$ $C_{1-8}$ alkyl, $—S(O)_{0-2}$ aryl, $—S(O)_{0-2}$ heteroaryl, $—S(O)_{0-2}$ aralkyl, $—S(O)_{0-2}$ heteroaralkyl, $—S(O)_{0-2}$ cycloalkyl, $—S(O)_{0-2}$ heterocycloalkyl, $—S(O)_{0-2}$ heterocycloalkylalkyl, $—S(O)_{0-2}$ cycloalkylalkyl, $—OC(O)NR^dR^{d'}$, $—NR^dC(O)NR^{d'}R^{d''}$, $—NR^dC(O)OR^a$, $—NR^dS(O)_2$alkyl, $—NR^dS(O)_2$aryl, $—NR^dS(O)_2$heteroaryl, $—NR^dS(O)_2$cycloalkyl, $—NR^dS(O)_2$heterocycloalkyl, $—NR^dS(O)_2$-aralkyl, $—NR^dS(O)_2$-heteroaralkyl, $—NR^dS(O)_2$-cycloalkylalkyl, —NR$^a$S(O)$_2$-heterocycloalkyl, —SO$_2$NR$^d$R$^{d'}$, cyano, nitro, C$_{1-6}$ haloalkyl, C$_{1-6}$ haloalkoxy, —NR$^d$R$^{d'}$, —C$_{1-4}$alkyl-NR$^d$R$^{d'}$, optionally substituted C$_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$ and R$^b$ are each independently selected from optionally substituted C$_{1-8}$ alkyl, optionally substituted aryl, optionally substituted heteroaryl, optionally substituted C$_{3-8}$ cycloalkyl, optionally substituted aralkyl, optionally substituted heteroaralkyl, optionally substituted cycloalkylalkyl and optionally substituted heterocycloalkyl;

R$^d$, R$^{d'}$, and R$^{d''}$ are each independently selected from H and R$^a$, or when taken together with the atom to which they are attached two of R$^d$, R$^{d'}$ and R$^{d''}$ form a 4-8 membered heterocyclic moiety.

In some embodiments, R$^1$ and R$^2$ are each independently selected from H, C$_{1-8}$ alkyl, and optionally substituted aryl.

In some embodiments, R$^1$ and R$^2$ are each independently selected from H and C$_{1-8}$ alkyl.

In some embodiments, R$^1$ and R$^2$ are H.

In some embodiments, R$^1$ and R$^2$ are each optionally substituted C$_{1-8}$ alkyl (e.g., methyl).

In some embodiments, R$^1$ is H and R$^2$ is optionally substituted C$_{1-8}$ alkyl (e.g., methyl)

In some embodiments, R$^1$ is optionally substituted C$_{1-8}$ alkyl and R$^2$ is H.

In some embodiments, A is optionally substituted C$_{1-4}$ alkylene, wherein the C$_{1-4}$ alkylene is optionally substituted with 1-3 substituents, each of which is independently selected from the group consisting of halogen (e.g., fluorine), hydroxyl, optionally substituted C$_{1-6}$ alkyl, C$_{1-8}$ alkoxy, —SO$_2$ alkyl, and —NR$^d$R$^{d'}$.

In some embodiments, A is optionally substituted C$_{1-4}$ alkylene, wherein the C$_{1-4}$ alkylene is optionally substituted with —SO$_2$ alkyl (e.g., methylsulfone).

In some embodiments, A is optionally substituted C$_{1-4}$ alkylene, wherein the C$_{1-4}$ alkylene is optionally substituted with hydroxyl (e.g., [structures shown]).

In some embodiments, A is optionally substituted C$_{1-4}$ alkylene, wherein the C$_{1-4}$ alkylene is optionally substituted with 1-3 substituents, each of which is independently selected from the group consisting of halogen (e.g., fluorine).

In some embodiments, A is optionally substituted C$_{1-4}$ alkylene, wherein the C$_{1-4}$ alkylene is optionally substituted with 1-3 substituents, each of which is independently selected from the group consisting of optionally substituted C$_{1-6}$ alkyl (e.g., methyl, ethyl, i-propyl, —C$_{1-2}$ alkyl-OH, —C$_{1-2}$ alkyl-CF$_3$, —C$_{1-2}$ alkyl-CHF$_2$, —C$_{1-2}$ alkyl-CH$_2$F, —C$_{1-2}$ alkyl-NR$^d$R$^{d'}$).

In some embodiments, A is optionally substituted C$_{1-4}$ alkylene (e.g., methylene, ethylene, propylene or butylene).

In some embodiments, A is selected from optionally substituted ethylene (e.g., [structures shown], or [structure shown].)

In some embodiments, R$^3$ is selected from H, and optionally substituted C$_{1-8}$ alkyl.

In some embodiments, R$^3$ is optionally substituted C$_{1-8}$ alkyl (e.g., —C$_{1-4}$ alkyl-OR$^d$, —C$_{1-4}$ alkyl-NR$^d$R$^{d'}$, or —C$_{1-4}$ alkyl-C(O)NR$^d$R$^{d'}$).

In some embodiments, R$^3$ is H.

In some embodiments, R$^3$ is halogen (e.g., fluorine).

In some embodiments, R$^3$ is optionally substituted aryl.

In some embodiments, R$^3$ is optionally substituted heteroaryl.

In some embodiments, R$^4$ is selected from C$_{1-8}$ alkyl, aryl, heteroaryl, aralkyl, heteroaralkyl, —S(O)$_2$ alkyl, —S(O)$_2$ aralkyl, —S(O)$_2$ heteroaralkyl, —S(O)$_2$ aryl, —S(O)$_2$ heteroaryl, —S(O)$_2$ cycloalkyl, —S(O)$_2$ heterocycloalkyl, —S(O)$_2$ heterocycloalkylalkyl, and —S(O)$_2$ cycloalkylalkyl.

In some embodiments, R$^4$ is selected from C$_{1-8}$ alkyl (e.g., methyl or ethyl).

In some embodiments, R$^4$ is selected from C$_{1-8}$ alkyl, optionally substituted with 1-3 fluorine substituents (e.g., —CF$_3$, —C$_1$-alkyl-CF$_3$, —C$_1$-alkyl-CHF$_2$, —C$_1$-alkyl-CH$_2$F).

In some embodiments, W$^2$ is C$_{1-8}$ alkyl optionally substituted with —OR$^d$, —NR$^d$R$^{d'}$, —C(O)NR$^d$R$^{d'}$.

In some embodiments, W$^2$ is C$_{2-8}$ alkyl optionally substituted with —OR$^d$, —NR$^d$R$^{d'}$, —C(O)NR$^d$R$^{d'}$.

In some embodiments, W$^2$ is H.

In some embodiments, W$^2$ is optionally substituted C$_{1-8}$ alkyl.

In some embodiments, W$^2$ is optionally substituted C$_{1-8}$ alkyl (e.g., —CF$_3$, —CF$_2$CF$_3$, or —CH$_2$CF$_3$).

In some embodiments, W$^2$ is C$_{1-8}$ alkyl (e.g. methyl or ethyl).

In some embodiments, W$^2$ is optionally substituted aralkyl (e.g., benzyl).

In some embodiments, g is 1.

In some embodiments, g is 2.

In some embodiments, each R$^6$ is selected from halogen, C$_{1-8}$ alkyl, hydroxyl, —C$_{1-8}$ fluoroalkyl, C$_{1-8}$ haloalkoxy, and —NR$^d$R$^{d'}$.

In some embodiments, each R$^6$ is selected from halogen, hydroxyl, —C$_{1-8}$ fluoroalkyl, —C$_{1-8}$ fluoroalkoxy, —NR$^d$R$^{d'}$, —C$_{1-4}$ alkyl-NR$^d$R$^{d'}$, aryl, heteroaryl, and C$_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., $CF_3$).

In some embodiments, each $R^6$ is $C_{1-8}$ fluoroalkoxy (e.g., —$OCF_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, a compound of Formula XIV is enantiomerically enriched (e.g., having an ee >60%, >70%, >80%, >90%, >95%, >97%, >98% or >99%).

In some embodiments, the compound is 2-(6-(benzyloxy)-5-fluoro-1H-indol-3-yl)-N,N-dimethylethanamine.

In another aspect, the invention is directed to a compound selected from formula:

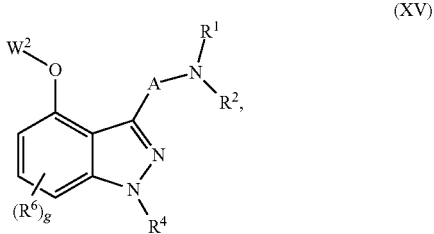

(XV)

wherein g is 1, 2 or 3;

$R^1$ and $R^2$ are each independently selected from H, $C_{1-8}$ alkyl, optionally substituted aryl, optionally substituted heteroaryl, optionally substituted aralkyl, optionally substituted heteroaralkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;

$W^2$ is hydrogen, optionally substituted $C_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —C(O)$NR^dR^{d'}$;

A is optionally substituted $C_{1-4}$ alkylene, optionally substituted cycloalkylene, optionally substituted arylene, optionally substituted heteroarylene, wherein arylene or heteroarylene are optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl), —OC(O)$NR^dR^{d'}$, —$NR^dC(O)NR^{d'}R^{d''}$, —$NR^dC(O)OR^a$, —$NR^dS(O)_2$ alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$—$C_{1-4}$alkyl-heteroaryl, —$NR^dS(O)_2$—$C_{1-4}$alkyl-cycloalkyl, —$NR^dS(O)_2$—$C_{1-4}$alkyl-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)OR^d$, wherein alkylene and cycloalkylene are optionally substituted with 1-3 substituents, each of which is independently selected from the group consisting of fluorine, oxo, optionally substituted $C_{1-6}$ alkyl, —$S(O)_{0-2}$alkyl, —$OR^d$ and —$NR^dR^{d'}$;

$R^4$ is selected from $C_{1-8}$ alkyl, $C_{1-8}$ heteroalkyl, $C_{2-8}$ alkenyl, $C_{2-8}$ alkynyl, —$S(O)_2$ alkyl, —$S(O)_2$ heteroalkyl, —$S(O)_2$ aryl, —$S(O)_2$ heteroaryl, —$S(O)_2$ cycloalkyl, —$S(O)_2$ heterocyclyl, —$S(O)_2$ heterocycloalkyl, —$S(O)_2$ aralkyl, —$S(O)_2$ heteroaralkyl, —$S(O)_2$ cycloalkyalkyl, formyl, —$OR^d$, —$NR^dR^{d'}$, —$C(O)OR^a$, —$C(O)NR^dR^{d'}$, —$S(O)_2NR^dR^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —$OR^d$, —$NR^dR^{d'}$, and wherein aryl and heteroaryl are optionally substituted with 1-3 substituents, each of which is independently selected from the group consisting of halogen, alkyl, heteroalkyl, cycloalkyl, heterocyclyl, —$OR^d$, —SH, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$-aralkyl, —$S(O)_{0-2}$-heteroaralkyl, —OC(O)$NR^dR^{d'}$, —$NR^dC(O)NR^{d'}R^{d''}$, —$NR^dC(O)OR^b$, —$OR^d$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted $C_{1-6}$ alkyl, —$NR^dC(O)R^a$, —$C(O)NR^dR^{d'}$, and —$C(O)OR^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ aralkyl, —$S(O)_{0-2}$ heteroaralkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —OC(O)$NR^dR^{d'}$, —$NR^dC(O)NR^{d'}R^{d''}$, —$NR^dC(O)OR^a$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-aralkyl, —$NR^dS(O)_2$-heteroaralkyl, —$NR^dS(O)_2$-cycloalkylalkyl, —$NR^aS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$alkyl-$NR^dR^{d'}$, optionally substituted $C_{1-6}$ alkyl, —$NR^dC(O)R^a$, —$C(O)NR^dR^{d'}$, and —$C(O)OR^d$; wherein alkyl, aryl, heteroaryl, cycloalkyl and heterocyclyl are optionally substituted;

$R^a$ and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $R^1$ and $R^2$ are each independently selected from H, $C_{1-8}$ alkyl, and optionally substituted aryl.

In some embodiments, $R^1$ and $R^2$ are each independently selected from H and $C_{1-8}$ alkyl.

In some embodiments, $R^1$ and $R^2$ are H.

In some embodiments, $R^1$ and $R^2$ are each optionally substituted $C_{1-8}$ alkyl (e.g., methyl).

In some embodiments, $R^1$ is H and $R^2$ is optionally substituted $C_{1-8}$ alkyl (e.g., methyl)

In some embodiments, $R^1$ is optionally substituted $C_{1-8}$ alkyl and $R^2$ is H.

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine), hydroxyl, optionally substituted $C_{1-6}$ alkyl, $C_{1-8}$ alkoxy, $-SO_2$ alkyl, and $-NR^d R^{d'}$.

In some embodiments, A is optionally substituted $C_{1-4}$ alkylene, wherein the $C_{1-4}$ alkylene is optionally substituted with $-SO_2$ alkyl (e.g., methylsulfone).

In some embodiments, A is optionally substituted $C_{1-4}$ alkylene, wherein the $C_{1-4}$ alkylene is optionally substituted with hydroxyl (e.g.,

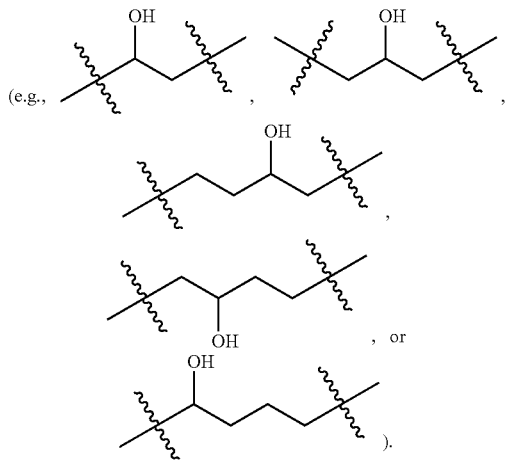

),

In some embodiments, A is optionally substituted $C_{1-4}$ alkylene, wherein the $C_{1-4}$ alkylene is optionally substituted with 1-3 substituents, each of which is independently selected from the group consisting of halogen (e.g., fluorine).

In some embodiments, A is optionally substituted $C_{1-4}$ alkylene, wherein the $C_{1-4}$ alkylene is optionally substituted with 1-3 substituents, each of which is independently selected from the group consisting of optionally substituted $C_{1-6}$ alkyl (e.g., methyl, ethyl, i-propyl, $-C_{1-2}$ alkyl-OH, $-C_{1-2}$ alkyl-$CF_3$, $-C_{1-2}$ alkyl-$CHF_2$, $-C_{1-2}$ alkyl-$CH_2F$, $-C_{1-2}$ alkyl-$NR^d R^{d'}$).

In some embodiments, A is optionally substituted $C_{1-4}$ alkylene (e.g., methylene, ethylene, propylene or butylene).

In some embodiments, A is optionally substituted ethylene (e.g.,

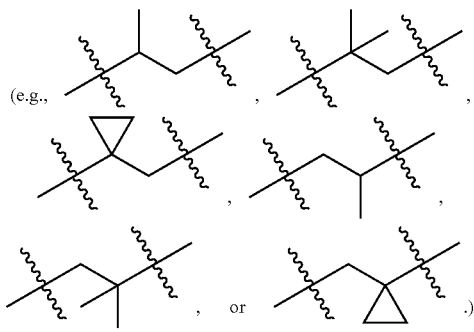

.)

In some embodiments, $R^4$ is selected from $C_{1-8}$ alkyl, aryl, heteroaryl, aralkyl, heteroaralkyl, $-S(O)_2$ alkyl, $-S(O)_2$ aralkyl, $-S(O)_2$ heteroaralkyl, $-S(O)_2$ aryl, $-S(O)_2$ heteroaryl, $-S(O)_2$ cycloalkyl, $-S(O)_2$ heterocycloalkyl, $-S(O)_2$ heterocycloalkylalkyl, and $-S(O)_2$ cycloalkylalkyl.

In some embodiments, $R^4$ is selected from $C_{1-8}$ alkyl (e.g., methyl or ethyl).

In some embodiments, $R^4$ is selected from $C_{1-8}$ alkyl, optionally substituted with 1-3 fluorine substituents (e.g., $-CF_3$, $-C_1$ alkyl-$CF_3$, $-C_1$ alkyl-$CHF_2$, $-C_1$ alkyl-$CH_2F$).

In some embodiments, $W^2$ is $C_{1-8}$ alkyl optionally substituted with $-OR^d$, $-NR^d R^{d'}$, $-C(O)NR^d R^{d'}$.

In some embodiments, $W^2$ is $C_{2-8}$ alkyl optionally substituted with $-OR^d$, $-NR^d R^{d'}$, $-C(O)NR^d R^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., $-CF_3$, $-CF_2CF_3$, or $-CH_2CF_3$).

In some embodiments, $W^2$ is $C_{1-8}$ alkyl (e.g. methyl or ethyl).

In some embodiments, $W^2$ is optionally substituted aralkyl (e.g., benzyl).

In some embodiments, g is 1.

In some embodiments, g is 2.

In some embodiments, each $R^6$ is selected from halogen, $C_{1-8}$ alkyl, hydroxyl, $-C_{1-8}$ fluoroalkyl, $C_{1-8}$ haloalkoxy, and $-NR^d R^{d'}$.

In some embodiments, each $R^6$ is selected from halogen, hydroxyl, $-C_{1-8}$ fluoroalkyl, $-C_{1-8}$ fluoroalkoxy, $-NR^d R^{d'}$, $-C_{1-4}$ alkyl-$NR^d R^{d'}$, aryl, heteroaryl, and $C_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., $CF_3$).

In some embodiments, each $R^6$ is $C_{1-8}$ fluoroalkoxy (e.g., $-OCF_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, a compound of Formula XV is enantiomerically enriched (e.g., having an ee >60%, >70%, >80%, >90%, >95%, >97%, >98% or >99%).

In some embodiments, the compound is of the following formula:

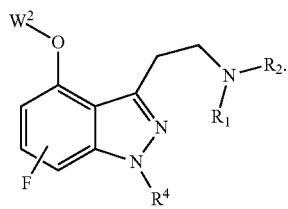

In another aspect, the invention is directed to a compound selected from formula:

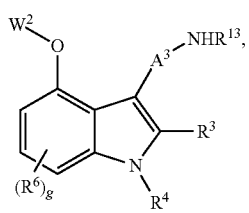

formula (XVI)

wherein g is 1, 2 or 3;

$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, or $C(O)NR^dR^{d'}$;

$W^2$ is hydrogen, optionally substituted $C_{1-8}$ alkyl, optionally substituted aryl, optionally substituted aralkyl, optionally substituted heteroaryl, optionally substituted heterocyclyl, optionally substituted heteroaralkyl, optionally substituted cycloalkyl, optionally substituted cycloalkylalkyl, optionally substituted heterocycloalkyl, or —C(O)NR$^d$R$^{d'}$;

$A^3$ is $C_{2-8}$ branched alkylene;

$R^4$ is selected from $C_{1-8}$ alkyl, $C_{1-8}$ heteroalkyl, $C_{2-8}$ alkenyl, $C_{2-8}$ alkynyl, —S(O)$_2$ alkyl, —S(O)$_2$ heteroalkyl, —S(O)$_2$ aryl, —S(O)$_2$ heteroaryl, —S(O)$_2$ cycloalkyl, —S(O)$_2$ heterocyclyl, —S(O)$_2$ heterocycloalkyl, —S(O)$_2$ aralkyl, —S(O)$_2$ heteroaralkyl, —S(O)$_2$ cycloalkylalkyl, formyl, —OR$^d$, $C_{1-8}$ aryloxy, $C_{1-8}$ heteroaryloxy, —NR$^d$R$^{d'}$, $C_{1-8}$ alkylamino, di($C_{1-8}$ alkyl)amino, —C(O)OR$^a$, —C(O)NR$^d$R$^{d'}$, —S(O)$_2$NR$^d$R$^{d'}$, $C_{3-8}$ cycloalkyl, heterocyclyl, cycloalkylalkyl, heteocyclylalkyl, aryl, heteroaryl, aralkyl, and heteroaralkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and heteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-aralkyl, —S(O)$_{0-2}$-heteroaralkyl, —OC(O)NR$^d$R$^{d'}$, —NR$^d$C(O)NR$^d$R$^{d''}$, —NR$^d$C(O)OR$^b$, —OR$^d$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^d$S(O)$_2$-heteroaralkyl, —NR$^d$S(O)$_2$-cycloalkylalkyl, —NR$^d$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each $R^6$ is independently selected from halo, $C_{1-8}$ alkyl, aryl, heteroaryl, heteroalkyl, $C_{3-8}$ cycloalkyl, heterocyclyl, aralkyl, heteroaralkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ aralkyl, —S(O)$_{0-2}$ heteroaralkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^d$R$^{d''}$, —NR$^d$C(O)OR$^a$, —NR$^d$S(O)$_2$alkyl, —NR$^d$S(O)$_2$aryl, —NR$^d$S(O)$_2$heteroaryl, —NR$^d$S(O)$_2$cycloalkyl, —NR$^d$S(O)$_2$heterocycloalkyl, —NR$^d$S(O)$_2$-aralkyl, —NR$^a$S(O)$_2$-heteroaralkyl, —NR$^d$S(O)$_2$-cycloalkylalkyl, —NR$^a$S(O)$_2$-heterocycloalkyl, —SO$_2$NR$^d$R$^{d'}$, cyano, nitro, $C_{1-6}$ haloalkyl, $C_{1-6}$ haloalkoxy, —NR$^d$R$^{d'}$, —$C_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

$R^{13}$ is selected from hydrogen and methyl; and $R^a$ and $R^b$ are each independently selected from optionally substituted $C_{1-8}$ alkyl, optionally substituted aryl, optionally substituted heteroaryl, optionally substituted $C_{3-8}$ cycloalkyl, optionally substituted aralkyl, optionally substituted heteroaralkyl, optionally substituted cycloalkylalkyl and optionally substituted heterocycloalkyl;

$R^d$, $R^{d'}$, and $R^{d''}$ are each independently selected from H and $R^a$, or when taken together with the atom to which they are attached two of $R^d$, $R^{d'}$ and $R^{d''}$ form a 4-8 membered heterocyclic moiety.

In some embodiments, $A^3$ is 1-methylethylene.

In some embodiments, $A^3$ is

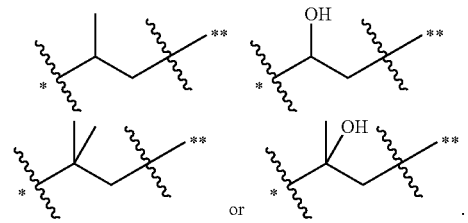

In some embodiments, $R^3$ is selected from H, and optionally substituted $C_{1-8}$ alkyl.

In some embodiments, $R^3$ is $C_{1-8}$ alkyl (e.g., —$C_{1-4}$ alkyl-OR$^d$, —$C_{1-4}$ alkyl-NR$^d$R$^{d'}$, or —$C_{1-4}$ alkyl-C(O)NR$^d$R$^{d'}$).

In some embodiments, $R^3$ is H.

In some embodiments, $R^3$ is halogen (e.g., fluorine).

In some embodiments, $R^3$ is optionally substituted aryl.

In some embodiments, $R^3$ is optionally substituted heteroaryl.

In some embodiments, $R^4$ is selected from $C_{1-8}$ alkyl, aryl, heteroaryl, aralkyl, heteroaralkyl, —S(O)$_2$ alkyl, —S(O)$_2$ aralkyl, —S(O)$_2$ heteroaralkyl, —S(O)$_2$ aryl, —S(O)$_2$ heteroaryl, —S(O)$_2$ cycloalkyl, —S(O)$_2$ heterocycloalkyl, —S(O)$_2$ heterocycloalkylalkyl, and —S(O)$_2$ cycloalkylalkyl.

In some embodiments, $R^4$ is selected from $C_{1-8}$ alkyl (e.g., methyl or ethyl).

In some embodiments, $R^4$ is selected from $C_{1-8}$ alkyl, optionally substituted with 1-3 fluorine substituents (e.g., —CF$_3$, —C$_1$-alkyl-CF$_3$, —C$_1$-alkyl-CHF$_2$, —C$_1$-alkyl-CH$_2$F).

In some embodiments, $W^2$ is $C_{1-8}$ alkyl optionally substituted with —OR$^d$, —NR$^d$R$^{d'}$, —C(O)NR$^d$R$^{d'}$.

In some embodiments, $W^2$ is $C_{2-8}$ alkyl optionally substituted with —OR$^d$, —NR$^d$R$^{d'}$, —C(O)NR$^d$R$^{d'}$.

In some embodiments, $W^2$ is H.

In some embodiments, $W^2$ is optionally substituted $C_{1-8}$ alkyl.

In some embodiments, $W^2$ is optionally substituted $C_{1-8}$ alkyl (e.g., —CF$_3$, —CF$_2$CF$_3$, or —CH$_2$CF$_3$).

In some embodiments, $W^2$ is $C_{1-8}$ alkyl (e.g. methyl or ethyl).

In some embodiments, $W^2$ is optionally substituted aralkyl (e.g., benzyl).

In some embodiments, g is 1.

In some embodiments, g is 2.

In some embodiments, each $R^6$ is selected from halogen, $C_{1-8}$ alkyl, hydroxyl, —$C_{1-8}$ fluoroalkyl, $C_{1-8}$ haloalkoxy, and —NR$^d$R$^{d'}$.

In some embodiments, each $R^6$ is selected from halogen, hydroxyl, —$C_{1-8}$ fluoroalkyl, —$C_{1-8}$ fluoroalkoxy, —$NR^{d}R^{d'}$, —$C_{1-4}$ alkyl-$NR^{d}R^{d'}$, aryl, heteroaryl, and $C_{1-8}$ alkyl.

In some embodiments, each $R^6$ is halogen (e.g., fluorine or chlorine).

In some embodiments, each $R^6$ is $C_{1-8}$ alkyl (e.g., methyl).

In some embodiments, each $R^6$ is $C_{1-8}$ fluoroalkyl (e.g., $CF_3$).

In some embodiments, each $R^6$ is $C_{1-8}$ fluoroalkoxy (e.g., —$OCF_3$).

In some embodiments, each $R^6$ is aryl (e.g., phenyl).

In some embodiments, each $R^6$ is heteroaryl (e.g., pyridine).

In some embodiments, each $R^6$ is heterocyclyl further substituted with aryl.

In some embodiments, each $R^6$ is heterocyclyl further substituted with heteroaryl.

In some embodiments, the compounds is 2-(7-fluoro-4-methoxy-1-methyl-1H-indol-3-yl)propan-1-amine.

In some embodiments, a compound of Formula XVI is enantiomerically enriched (e.g., having an ee >60%, >70%, >80%, >90%, >95%, >97%, >98% or >99%).

In one aspect, the invention features a pharmaceutical composition comprising a compound of formulae I, II, IV, VII, VIII, IX, XII, XIII, XIV, XV or XVI.

In one aspect, the invention features a dosage form comprising a compound of formulae I, II, IV, VII, VIII, IX, XII, XIII, XIV, XV or XVI. In some embodiments, the dosage form is an oral dosage form.

In one aspect, the invention features a method for the treatment of obesity in a subject, the method comprising administering to the subject a compound as described herein, such that obesity is treated.

In one aspect, the invention features a method for the treatment of Obsessive Compulsive Disorder (OCD) in a subject, the method comprising administering to the subject a compound as described herein, such that OCD is treated.

In one aspect, the invention features a method for suppressing appetite in a subject, the method comprising administering to the subject a compound as described herein, such that appetite is suppressed in the subject.

In one aspect, the invention features a method for the treatment of obesity in a subject, the method comprising administering to the subject a compound as described herein, such that obesity is treated.

In one aspect, the invention features a method for the treatment of schizophrenia or psychosis in a subject, the method comprising administering to the subject a compound as described herein, such that schizophrenia or psychosis is treated.

In one aspect, the invention features a method for the treatment of anxiety or depression in a subject, the method comprising administering to the subject a compound as described herein, such that anxiety or depression is treated in the subject.

In one aspect, the invention features a method for the treatment of diabetes in a subject, the method comprising administering to the subject a compound as described herein, such that diabetes is treated in the subject.

In one aspect, the invention features a method for the treatment of attention deficit hyperactivity disorder (ADHD) in a subject, the method comprising administering to the subject a compound as described herein, such that ADHD is treated in the subject.

In one aspect, the invention features a method for the treatment of suicidal behavior in a subject, the method comprising administering to the subject a compound as described herein, such that suicidal behavior is treated in the subject.

In one aspect, the invention features a method for the treatment of migraine in a subject, the method comprising administering to the subject a compound as described herein, such that migraine is treated in the subject.

In one aspect, the invention features a method for enhancing cognition (e.g., treating cognitive deficiency) in a subject, the method comprising administering to the subject a compound as described herein, such that cognition is enhanced in the subject.

In one aspect, the invention features a method for treating bipolar disorder in a subject, the method comprising administering to the subject a compound as described herein, such that bipolar disorder is treated in the subject.

In one aspect, the invention features a method for the treatment of a central nervous system disorder in a subject, the method comprising administering to the subject a compound as described herein, such that the central nervous system disorder is treated. In some embodiments, the central nervous system disorder is selected from the group consisting of epilepsy, Alzheimer's disease, sexual dysfunction, addiction, anorexia nervosa, Tourette's syndrome, and trichotillomania.

In one aspect, the invention features a method for the treatment of acral lick dermatitis (ALD) in a canine subject, the method comprising administering to the subject a compound as described herein, such that acral lick dermatitis is treated.

In one aspect, the invention features a method of modulating (e.g., inhibit or activate) a serotonin receptor (e.g., a 5-HT receptor), the method comprising contacting a serotonin receptor with a compound of formulae I, II, IV, VII, VIII, IX, XII, XIII, XIV, XV or XVI. In some embodiments, the invention features a method of inhibiting a 5-HT receptor. In some embodiments, the invention features a method of activating a 5-HT receptor. In some embodiments, the invention features a method of modulating (e.g., inhibiting or activating) a 5-$HT_{2A}$ receptor. In some embodiments, the invention features a method of modulating (e.g., inhibiting or activating) a 5-$HT_{2C}$ receptor. In some embodiments, the invention features a method of modulating (e.g., inhibiting or activating) a 5-$HT_6$ receptor. In some embodiments, the compound is selective towards a 5-$HT_{2A}$ receptor. In some embodiments, the compound is selective toward a 5-$HT_{2C}$ receptor. In some embodiments, the compound is selective toward a 5-$HT_6$ receptor.

DETAILED DESCRIPTION

1. Definitions

Before further description of the present invention, and in order that the invention may be more readily understood, certain terms are first defined and collected here for convenience.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "alkenyl" refers to a straight or branched hydrocarbon chain containing 2-12 carbon atoms (unless otherwise noted) and having one or more double bonds. Examples of alkenyl groups include, but are not limited to, alyl, propenyl, 2-butenyl, 3-hexenyl and 3-octenyl groups. One of the double bond carbons may optionally be the point of attachment of the alkenyl substituent.

The term "alkenylene" refers to a divalent alkenyl, e.g. —CH═CH—, —CH$_2$—CH═CH—, and —CH═CH—CH$_2$—.

The term "alkynyl" refers to a straight or branched hydrocarbon chain containing 2-12 carbon atoms (unless otherwise noted) and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkynylene" refers to a divalent alkynyl, e.g. —CH≡CH—, —CH$_2$—CH≡CH—, and —CH≡CH—CH$_2$—.

The terms "alkoxyl" or "alkoxy" as used herein refers to an alkyl group, as defined below, having an oxygen radical attached thereto. Representative alkoxy groups include methoxy, ethoxy, propyloxy, tert-butoxy and the like. The term "alkoxyalkyl" refers to an alkyl in which one or more hydrogen atoms are replaced by an alkoxy group.

An "ether" is two hydrocarbons covalently linked by an oxygen.

The term "alkyl" refers to the radical of saturated aliphatic groups, including straight-chain alkyl groups, and branched-chain alkyl groups. In preferred embodiments, a straight chain or branched chain alkyl has 12 or fewer carbon atoms in its backbone (unless otherwise noted) e.g., from 1-12, 1-8, 1-6, or 1-4. Exemplary alkyl moieties include methyl, ethyl, propyl (e.g., n-propyl or isopropyl), butyl (e.g., n-butyl, isobutyl or t-butyl), pentyl (e.g., n-pentyl, isopentyl or pentan-3-yl), hexyl and hepty.

The term "alkylene" refers to a divalent alkyl, e.g., —CH$_2$—, —CH$_2$CH$_2$—, and —CH$_2$CH$_2$CH$_2$—.

The term "alkoxylene" refers to an alkylene wherein a CH$_2$ is substituted with an oxygen. For example, an alkoxylene aryl refers to a group with an alkylene attached to an aryl group through an oxygen, an optionally substituted alkoxylene heteroaryl refers to a group with an alkylene attached to an heteroaryl group through an oxygen.

The term "amino" refers to —NH$_2$.

The terms "alkylamino" and "dialkylamino" refer to —NH(alkyl) and —N(alkyl)$_2$ radicals respectively.

The term "aralkylamino" refers to a —NH(aralkyl) radical. The term alkylaminoalkyl refers to a (alkyl)NH-alkyl-radical; the term dialkylaminoalkyl refers to a (alkyl)$_2$N-alkyl-radical.

The term "amido" refers to a —NHC(O)— or C(O)NH$_2$ substituent.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent. Examples of aryl moieties include, but are not limited to, phenyl, naphthyl and the like. The term "arylalkyl" refers to alkyl substituted with an aryl. Exemplary aralkyls include but are not limited to benzyl, 1-phenylethyl, 2-phenylethyl, 3-phenylpropyl, 9-fluorenyl, benzhydryl, phenethyl, and trityl groups. The term "arylalkenyl" refers to an alkenyl substituted with an aryl. The term "arylalkynyl" refers to an alkynyl substituted with an aryl. Terms such as "arylC$_2$-C$_6$alkyl" are to be read as a further limitation on the size of the alkyl group. The term "arylalkoxy" refers to an alkoxysubstituted with aryl. The term "arylenyl" refers to a divalent aryl (i.e., —Ar—).

The terms "cycloalkyl" or "cyclyl" as employed herein include saturated and partially unsaturated cyclic hydrocarbon groups having 3 to 12 carbons, preferably 3 to 8 carbons, and more preferably 3 to 6 carbons, wherein the cycloalkyl group may be optionally substituted. Exemplary cyclyl groups include, without limitation, cyclopropyl, cyclobutyl, cyclopentyl, cyclopentenyl, cyclohexyl, cyclohexenyl, cycloheptyl, and cyclooctyl. Cyclyl moieties also include both bridged and fused ring systems. Cyclyl groups also include those that are fused to additional ring systems, which may be saturated or unsaturated. A cyclyl group may thus be a bicyclic group in which one ring is saturated or partially unsaturated and the other is fully unsaturated (e.g., indanyl).

The term "cyclylalkyl" as used herein, refers to an alkyl group substituted with a cyclyl group. Cyclylalkyl includes groups in which more than one hydrogen atom of an alkyl group has been replaced by a cyclyl group.

The term "cycloalkylalkyl" as used herein, refers to an alkyl group substituted with a cycloalkyl group.

The term "halo" or "halogen" refers to any radical of fluorine, chlorine, bromine or iodine.

The term "haloalkyl" refers to an alkyl group that may have any number of hydrogens available on the group replaced with a halogen atom. Representative haloalkyl groups include but are not limited to: —CH$_2$Cl, —CH$_2$ClCF$_3$, —CHBr$_2$, —CF$_3$, —CH$_2$F, —CHF$_2$, and —CH$_2$CF$_3$. The term "fluoroalkyl" refers to an alkyl group that may have any number of hydrogens available on the group replaced with a fluorine atom. Representative fluoroalkyl groups include but are not limited to: —CH$_2$F, —CH$_2$FCF$_3$, —CHF$_2$ or —CF$_3$. The term "haloalkoxy" refers to an alkoxy group that may have any number of hydrogen atoms available on the alkyl group replaced with a halogen atom. Representative haloalkoxy groups include but are not limited to: —OCH$_2$Cl, —OCH$_2$ClCF$_3$, —OCHBr$_2$, —OCHF$_2$ or —OCF$_3$. The term "fluoroalkoxy" refers to an alkoxy group that may have any number of hydrogens available on the group replaced with a fluorine atom. Representative fluoroalkoxy groups include but are not limited to: —OCH$_2$F, —OCH$_2$FCF$_3$, —OCHF$_2$ or —OCF$_3$.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, oxazolyl and the like. The term "heteroarylalkyl" or the term "heteroaralkyl" refers to an alkyl substituted with a heteroaryl. The term "heteroarylalkenyl" refers to an alkenyl substituted with a heteroaryl. The term "heteroarylalkynyl" refers to an alkynyl substituted with a heteroaryl. The term "heteroarylalkoxy" refers to an alkoxy substituted with heteroaryl.

The term "heteroaryl" refers to a group having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. When a heteroaryl is substituted by a hydroxy group, it also includes its corresponding tautomer. The term "heteroaryl," as used herein, also includes groups in which a heteroaromatic ring is fused to one or more aryl rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group," or "heteroaromatic," any of which terms include rings that are optionally substituted. A ring nitrogen atom of a heteroaryl may be oxidized to form the corresponding N-oxide compound. A nonlimiting example of such a heteroaryl having an oxidized ring nitrogen atom is N-oxopyridyl.

The term "heteroarylalkyl" refers to an alkyl group substituted by a heteroaryl. Heteroarylalkyl includes groups in which more than one hydrogen atom has been replaced by a heteroaryl group.

As used herein, the terms "heterocycle," "heterocyclyl" and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2/y-pyrrolyl), NH (as in pyrrolidinyl), or $NR^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydropyranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiomorpholinyl. A heterocyclyl group may be mono-, bi-, tri-, or polycyclic, preferably mono-, bi-, or tricyclic, more preferably mono- or bicyclic. Additionally, a heterocyclic ring also includes groups in which the heterocyclyl ring is fused to one or more aryl, heteroaryl or cyclyl rings. A ring nitrogen atom of a heterocyclic ring also may be oxidized to form the corresponding N-hydroxy compound.

The term "heterocyclylalkyl" refers to an alkyl group substituted by a heterocyclyl. Heterocyclylalkyl includes groups in which more than one hydrogen atom has been replaced by a heterocyclyl group.

In the case of arylalkyl, heteroarylalkyl, cyclylalkyl, heterocyclylalkyl etc. The terms "hetaralkyl" and "heteroaralkyl", as used herein, refers to an alkyl group substituted with a heteroaryl group. Examplary heteroaralkyl groups include but are not limited to methylpyridyl or methylpyrimidyl.

The term "heterocyclyl" or "heterocyclylalkyl" refers to a nonaromatic 5-8 membered monocyclic, 5-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and include both bridged and fused ring systems. The term "heterocyclylalkyl" refers to an alkyl substituted with a heterocyclyl.

The term "heterocyclylalkyl", as used herein, refers to an alkyl group substituted with a heterocycle group.

The term "heteroalkyl," as used herein, refers to a saturate or unsaturated, straight or branched chain aliphatic group, wherein one or more of the carbon atoms in the chain are independently replaced by a heteroatom. Exemplary heteroatoms include O, S, and N.

Aralkyl, heteroalkyl, etc groups described as optionally substituted, it is intended that either or both aryl, alkyl or heteroraryl and alkyl may be independent optionally substituted or unsubstituted.

The term "hydroxyalkyl" refers to an alkyl in which one or more hydrogen atoms are replaced by a hydroxy group.

The term "oxo" refers to an oxygen atom (=O), which forms a carbonyl when attached to carbon, an N-oxide when attached to nitrogen, and a sulfoxide or sulfone when attached to sulfur.

The term "thioalkyl" as used herein refers to an —S(alkyl) group, where the point of attachment is through the sulfur atom and the alkyl group is as defined above.

The term "thiono" refers to a sulfur atom (=S), which forms a thioketone when attached to carbon.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

The term "substituent" refers to a group "substituted" on a moiety described herein. Any atom on any substituent can be substituted. Substituents can include any substituents described herein. Examplary substituents include, without limitation, alkyl (e.g., C1, C2, C3, C4, C5, C6, C7, C8, C9, C10, C11, $C_{1-2}$ straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkyl amino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

As used herein, the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

As used herein, the term "optionally substituted" means substituted or unsubstituted.

The term "administration" or "administering" includes routes of introducing the compound(s) of the invention to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, a compound described herein can be coated with or disposed in a selected material to protect it from natural conditions which may detrimentally affect its ability to perform its intended function. A compound or composition described herein can be administered alone, or in conjunction with either another agent as described above or with a pharmaceutically-acceptable carrier, or both. A compound or composition described herein can be administered prior to the administration of the other agent, simultaneously with the agent, or after the administration of the agent. Furthermore, a compound described herein can also be administered in a pro-drug form which is converted into its active metabolite, or more active metabolite in vivo.

The language "biological activities" of a compound described herein includes all activities elicited by a compound described herein in a responsive subject or cell. It includes genomic and non-genomic activities elicited by these compounds.

The term "chiral" refers to molecules which have the property of non-superimposability of the mirror image partner, while the term "achiral" refers to molecules which are superimposable on their mirror image partner. With respect to the nomenclature of a chiral center, terms "R" and "S" configuration are as defined by the IUPAC Recommendations. As to the use of the terms, diastereomer, racemate, epimer and enantiomer will be used in their normal context to describe the stereochemistry of preparations.

The term "diastereomers" refers to stereoisomers with two or more centers of dissymmetry and whose molecules are not mirror images of one another.

An "effective amount" or "an amount effective" refers to an amount of the compound or composition which is effective, upon single or multiple dose administrations to a subject and for periods of time necessary, in treating a cell, or curing, alleviating, relieving or improving a symptom of a disorder, e.g., a disorder described herein. An effective amount of a compound described herein may vary according to factors such as the disease state, age, and weight of the subject, and the ability of a compound described herein to elicit a desired response in the subject. Dosage regimens may be adjusted to provide the optimum therapeutic response. An effective amount is also one in which any toxic or detrimental effects (e.g., side effects) of a compound described herein are outweighed by the therapeutically beneficial effects. The term "effective amount" includes an amount effective, at dosages and for periods of time necessary, to achieve the desired result, e.g., suppress appetite in a subject and/or treat a disorder described herein such as a serotonin receptor related disorder. Exemplary disorders include obesity; a disorder wherein appetite suppression is desirable; a disorder in which treating weight gain is desirable; a disorder in which cognitive enhancement is desirable; depressive disorders (e.g., depression, atypical depression, major depressive disorder, dysthymic disorder, and substance-induced mood disorder); bipolar disorders (e.g., bipolar I disorder, bipolar II disorder, and cyclothymic disorder); anxiety disorders (e.g., panic attack, agoraphobia, panic disorder, specific phobia, social phobia, obsessive compulsive disorder, posttraumatic stress disorder, acute stress disorder, generalized anxiety disorder, separation anxiety disorder, and substance-induced anxiety disorder); mood episodes (e.g., major depressive episode, manic episode, mixed episode, and hypomanic episode); adjustment disorders (e.g., adjustment disorder with anxiety and/or depressed mood); intellectual deficit disorders (e.g., dementia, Alzheimer's disease, and memory deficit); eating disorders (e.g., hyperphagia, bulimia or anorexia nervosa); schizophrenia (e.g., paranoid type, disorganized type, catatonic type, and undifferentiated type); schizophreniform disorder, schizoaffective disorder, delusional disorder, other psychotic disorders (e.g., substance-induced psychotic disorder, L-DOPA-induced psychosis, psychosis associated with Alzheimer's dementia, psychosis associated with Parkinson's disease, psychosis associated with Lewy body disease); sleep disorders (e.g., sleep apnea); suicidal behaviors; sexual dysfunction; migraine; cephalic pain or other pain; raised intracranial pressure; epilepsy; personality disorders; age-related behavioral disorders; behavioral disorders associated with dementia; organic mental disorders; mental disorders in childhood; aggressivity; age-related memory disorders; chronic fatigue syndrome; addiction (e.g., drug and alcohol addiction); premenstrual tension; damage of the central nervous system such as by trauma, stroke, neurodegenerative diseases or toxic or infective CNS diseases such as encephalitis or meningitis; cardiovascular disorders (e.g., thrombosis); hypertension; hyperlipidemia; arterial constriction; osteoarthritis; gall bladder disease; gout; gastrointestinal disorders (e.g., dysfunction of gastrointestinal motility); diabetes mellitus (e.g., Type 2 diabetes mellitus) and diabetes insipidus; cancer; infertility; early mortality; spinal cord injuries; Tourette's syndrome; trichotillomania; other central nervous system disorders; attention deficit hyperactivity disorder (ADHD); canine veterinary diseases (e.g., acral lick dermatitis); and combinations of these disorders that may be present in a mammal.

An effective amount of a compound described herein may vary according to factors such as the disease state, age, and weight of the subject, and the ability of a compound described herein to elicit a desired response in the subject. Dosage regimens may be adjusted to provide the optimum therapeutic response. An effective amount is also one in which any toxic or detrimental effects (e.g., side effects) of a compound described herein are outweighed by the therapeutically beneficial effects.

A therapeutically effective amount of a compound described herein (i.e., an effective dosage) may range from about 0.001 to 50 mg/kg body weight, preferably about 0.01 to 40 mg/kg body weight, more preferably about 0.1 to 35 mg/kg body weight, still more preferably about 1 to 30 mg/kg, and even more preferably about 10 to 30 mg/kg. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound described herein can include a single treatment or, preferably, can include a series of treatments. In one example, a subject is treated with a compound described herein in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound described herein used for treatment may increase or decrease over the course of a particular treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

The term "heteroatom" as used herein means an atom of any element other than carbon or hydrogen. Preferred heteroatoms are nitrogen, oxygen, sulfur, phosphorus and silicon. A heteroatom may be present in any oxidation state (e.g., any oxidized form of nitrogen, sulfur, phosphorus or silicon) and any charged state (e.g., the quaternized form of any basic nitrogen), and includes a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "enantiomers" refers to two stereoisomers of a compound which are non-superimpos able mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space. For example, isomers include cis- and trans-isomers, E- and Z-isomers, R- and S-enantiomers, diastereomers, (D)-isomers, (L)-isomers, racemic mixtures thereof, and other mixtures thereof.

The language "improved biological properties" refers to any activity inherent in a compound described herein that enhances its effectiveness in vivo. In a preferred embodiment, this term refers to any qualitative or quantitative improved therapeutic property of a compound described herein, such as reduced off-target effects.

The term "modulate" refers to an increase or decrease, e.g., in the activity of a serotonin receptor in response to exposure to a compound described herein, e.g., the stimulation of serotonin receptor activity of at least a sub-population of cells in an animal such that a desired end result is achieved, e.g., a therapeutic result. In some embodiments, a compound as described herein is an inhibitor of a serotonin receptor described herein.

As used herein, the term "partially unsaturated" refers to a moiety that includes at least one double or triple bond between atoms. The term "partially unsaturated" encompasses rings, e.g., having one or more sites of unsaturation, but that are not completely unsaturated so as to be aryl or heteroaryl.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, the term "treat" or "treating" is defined as applying or administering a compound or composition, alone or in combination with a second compound or composition, to a subject, e.g., a patient, or applying or administering the compound or composition to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "Positron Emission Tomography isotope," "PET isotope," and "PET tracer" may be used interchangeably to describe one or more isotopes that are known to be detectable using positron emission tomography. Such isotopes may include any positron-creating radioisotope that can be incorporated into a compound, thus allowing imaging of the delivery, metabolism, etc., of a compound of the invention. Exemplary isotopes include $^{11}C$, $^{13}N$, $^{15}O$, and $^{18}F$. The compounds and methods of the invention are intended to broadly include the substitution of one or more natural isotopes in the compounds with PET isotopes.

The language "a prophylactically effective amount" of a compound refers to an amount of a compound described herein any formula herein or otherwise described herein which is effective, upon single or multiple dose administration to the patient, in preventing or treating a disease or condition.

The language "reduced off-target effects" is intended to include a reduction in any undesired side effect elicited by a compound described herein when administered in vivo. In some embodiments, a compound described herein has little to no cardio and/or pulmonary toxicity (e.g., when administered to a subject). In some embodiments, a compound described herein has little to no hallucinogenic activity (e.g., when administered to a subject).

The term "selective" means a greater activity against a first target (e.g., a 5-HT receptor subtype) relative to a second target (e.g., a second 5-HT receptor subtype). In some embodiments a compound has a selectivity of at least 1.25-fold, at least 1.5 fold, at least 2-fold, at least 3-fold, at least 4-fold, at least 5-fold, at least 6-fold, at least 10-fold or at least 100-fold greater towards a first target relative to a second target. In some embodiments, a compound described herein is selective towards the $5\text{-HT}_{2A}$ receptor relative to one or more other 5-HT receptor subtypes such as $5\text{-HT}_{2C}$ and/or $5\text{-HT}_{6}$. In some embodiments, a compound described herein is selective towards the $5\text{-HT}_{2C}$ receptor relative to one or more other 5-HT receptor subtypes such as $5\text{-HT}_{2A}$ and/or $5\text{-HT}_{6}$. In some embodiments, a compound described herein is selective towards the $5\text{-HT}_{6}$ receptor relative to one or more other 5-HT receptor subtypes such as $5\text{-HT}_{2A}$ and/or $5\text{-HT}_{2C}$.

The term "subject" includes organisms which are capable of suffering from a serotonin-receptor-related disorder or who could otherwise benefit from the administration of a compound described herein of the invention, such as human and non-human animals. Preferred humans include human patients suffering from or prone to suffering from a serotonin-related disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The phrases "systemic administration," "administered systemically", "peripheral administration" and "administered peripherally" as used herein mean the administration of a compound described herein(s), drug or other material, such that it enters the patient's system and, thus, is subject to metabolism and other like processes, for example, subcutaneous administration.

2. Compounds of the Invention

The compounds described herein (e.g., a compound of formula I, II, IV, VII, VIII, IX, XII, XIII, XIV, XV, or XVI) can be used for a variety of therapeutic purposes, including the modulation of a 5-HT receptor and can be used, for example to inhibit or activate a 5-HT receptor in a subject. For example $5\text{-HT}_{2A}$, $5\text{-HT}_{2C}$ and/or $5\text{-HT}_{6}$.

Exemplary compounds include compounds of formulae I, II, IV, VII, VIII, IX, XII, XIII, XIV, XV, and XVI as shown below. The substituents as provided in compounds I, II, IV, VII, VIII, IX, XII, XIII, XIV, XV, and XVI are as defined above. Exemplary compounds also include the tables and Examples disclosed herein.

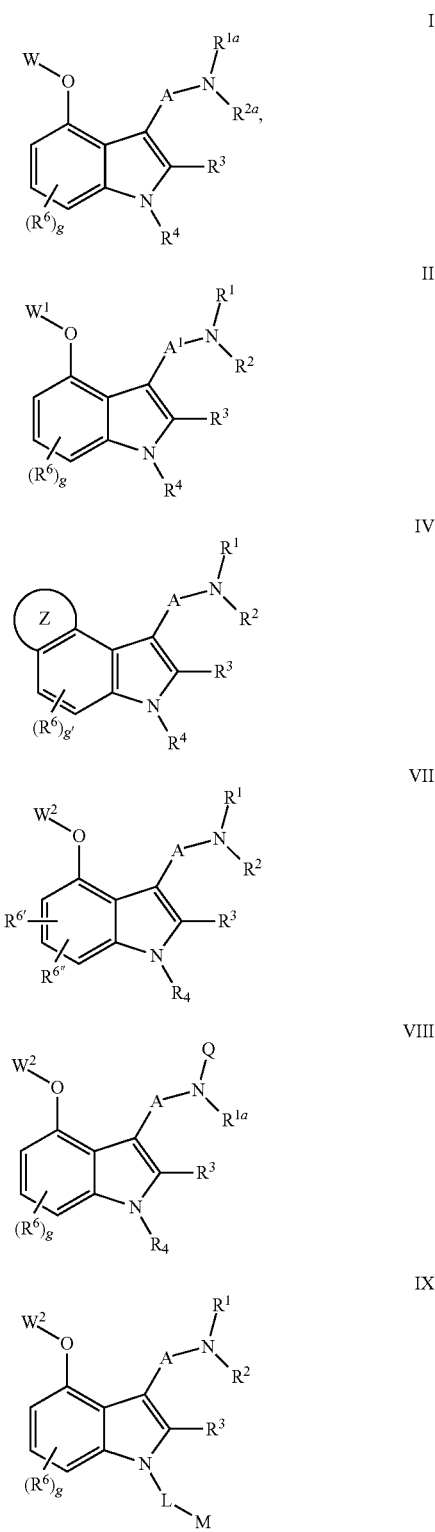

XII
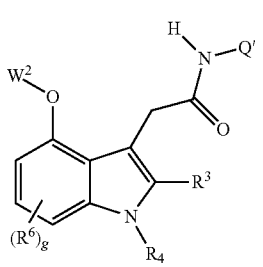

XIII
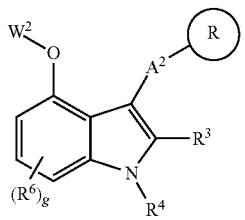

XIV
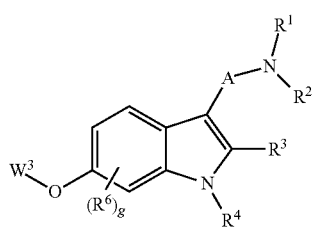

XV
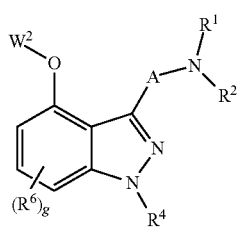

XVI
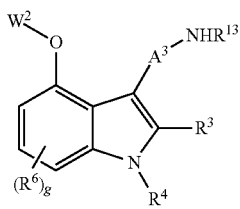

The compounds of the invention can be prepared by a variety of methods, including those known in the art or apparent to the skilled artisan in light of the present specification. For example, N-unsubstituted indoles can be N-alkylated, for example, with an alkyl halide, using a base such as sodium hydride, to give N-alkylated indoles. 4-substituted indoles can be hydrogenated using, for example, palladium hydroxide on carbon as catalyst in the presence of hydrogen gas, to give 4-hydroxyindoles. 4-hydroxyindoles can be O-alkylated, for example, with an alkyl halide, using a base such as sodium hydride, to give 4-O-alkoxy-N-substituted indoles. N-unsubstituted indoles can be prepared starting from 3-fluoro-2-benzyloxy benzaldehyde via cyclization of a intermediate styrylazide to the ester, followed by hydrolysis, with for example, sodium hydroxide, decarboxylation using as example a copper catalyst and 2-phenylpyridine, oxamidation with oxalyl chloride followed by a secondary amine, and then reduction.

The present invention includes compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

In the compounds of the present invention, any atom not specifically designated as a particular isotope is meant to represent any stable isotope of that atom unless otherwise stated (e.g., hydrogen, $H^2$ or deuterium and $H^3$ or tritium). The formulas described herein may or may not indicate whether atoms at certain positions are isotopically enriched. When a structural formula is silent with respect to whether a particular position is isotopically enriched, it is to be understood that the isotopes at that particular position are present in natural abundance or, that the particular position is isotopically enriched with one or more naturally occurring stable isotopes. For example, the formula —$CH_2$— represents the following possible structures: —$CH_2$—, —CHD- or —$CD_2$-.

The variable "D" is defined as deuterium.

The terms "compound" or "compounds," when referring to a compound of this invention or a compound described herein, refers to a collection of molecules having an identical chemical structure, except that there may be isotopic variation among the constituent atoms of the molecules. Thus, it will be clear to those of skill in the art that a compound represented by a particular chemical structure containing indicated hydrogen atoms will contain lesser amounts of isotopologues having deuterium atoms at one or more of the designated hydrogen positions in that structure. Alternatively, a compound represented by a particular chemical structure containing indicated deuterium atoms will contain lesser amounts of isotopologues having hydrogen atoms at one or more of the designated deuterium positions in that structure. The relative amount of such isotopologues in a compound of this invention will depend on a number of factors including isotopic purity of deuterated reagents used to make the compound and the efficiency of incorporation of deuterium in the various synthetic steps used to prepare the compound. The relative amount of such isotopologues in total will be less than 55% of the compound. In other embodiments, the relative amount of such isotopologues in total will be less than 50%, less than 45%, less than 40%, less than 35%, less than 35%, less than 15%, less than 10%, less than 5%, less than 1% or less than 0.5% of the compound.

The term "isotopologue" refers to a species that differs from a specific compound of this invention only in the isotopic composition thereof. Isotopologues can differ in the level of isotopic enrichment at one or more positions and/or in the position(s) of isotopic enrichment.

The compounds of this invention may contain one or more asymmetric centers and thus occur as racemates and racemic mixtures, single enantiomers, individual diastereomers and diastereomeric mixtures. Described herein are enantiomerically enriched compounds (e.g., a compound resolved to an enantiomeric excess of 60%, 70%, 80%, 85%, 90%, 95%, 99% or greater). All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts. For example a compound can be resolved to an enantiomeric excess (e.g., 60%, 70%, 80%, 85%, 90%, 95%, 99% or greater) via formation of diastereomeric salts, e.g. with a chiral base, e.g., (+) or (−) □-methylbenzylamine, or via high performance liquid chromatography using a chiral column. In some embodiments a product is purified directly on a chiral column to provide enantiomerically enriched compound.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

3. Uses of the Compounds of the Invention

As described herein below, it has now surprisingly been found that the compounds of the invention have serotonin receptor activity, and can be used to treat or prevent conditions associated with serotonin receptor activity. In some embodiments, a compound described herein has agonist activity against a 5-HT receptor with an $EC_{50}$ of ≤10 µM.

Thus, in one embodiment, the invention provides methods for treating a subject for a serotonin-receptor-related disorder (i.e., a 5-HT receptor related disorder), or preventing a serotonin-receptor-related disorder (i.e., a 5-HT receptor related disorder), by administering to the subject an effective amount of a compound described herein, such that the serotonin-receptor-related disorder is treated or prevented.

Fourteen distinct 5-HT receptor subtypes exist in seven separate families. There is particular interest in the three receptor subtypes of the 5-HT$_2$ family, e.g., 5-HT$_{2A}$, 5-HT$_{2C}$, and/or 5-HT$_6$. In some embodiments, a compound described herein is selective for a particular subtype (e.g., 5-HT$_{2A}$, 5-HT$_{2C}$ or 5-HT$_6$). For example, a compound described herein, when administered in vitro or in vivo, has an activity of at least 1.25-fold higher against 5-HT$_{2A}$ over another subtype such as 5-HT$_{2C}$ or 5-HT$_6$ (e.g., at least 1.25-fold, at least 1.5 fold, at least 2-fold, at least 3-fold, at least 4-fold, at least 5-fold, at least 6-fold, at least 10-fold or at least 100-fold). In another example, a compound described herein, when administered in vitro or in vivo, has an activity of at least 1.25-fold higher against 5-HT$_{2C}$ over another subtype such as 5-HT$_{2A}$ or 5-HT$_6$ (e.g., at least 1.25-fold, at least 1.5 fold, at least 2-fold, at least 3-fold, at least 4-fold, at least 5-fold, at least 6-fold, at least 10-fold or at least 100-fold). In another example, a compound described herein, when administered in vitro or in vivo, has an activity of at least 1.25-fold higher against 5-HT$_6$ over another subtype such as 5-HT$_{2A}$ or 5-HT$_{2C}$ (e.g., at least 1.25-fold, at least 1.5 fold, at least 2-fold, at least 3-fold, at least 4-fold, at least 5-fold, at least 6-fold, at least 10-fold or at least 100-fold). In some embodiments a compound described herein has agonist activity against 5-HT$_{2A}$ with an $EC_{50}$ of ≤10 µM. In some embodiments, a compound described herein has agonist activity against 5-HT$_{2C}$ with an $EC_{50}$ of ≤10 µM. In some embodiments, a compound described herein has agonist activity against 5-HT$_6$ with an $EC_{50}$ of ≤10 µM.

Thus, a compound described herein may be used in the treatment or prevention of disorders such as obesity; a disorder wherein appetite suppression is desirable; a disorder in which treating weight gain is desirable; a disorder in which cognitive enhancement is desirable; depressive disorders (e.g., depression, atypical depression, major depressive disorder, dysthymic disorder, and substance-induced mood disorder); bipolar disorders (e.g., bipolar I disorder, bipolar II disorder, and cyclothymic disorder); anxiety disorders (e.g., panic attack, agoraphobia, panic disorder, specific phobia, social phobia, obsessive compulsive disorder, posttraumatic stress disorder, acute stress disorder, generalized anxiety disorder, separation anxiety disorder, and substance-induced anxiety disorder); mood episodes (e.g., major depressive episode, manic episode, mixed episode, and hypomanic episode); adjustment disorders (e.g., adjustment disorder with anxiety and/or depressed mood); intellectual deficit disorders (e.g., dementia, Alzheimer's disease, and memory deficit); eating disorders (e.g., hyperphagia, bulimia or anorexia nervosa); schizophrenia (e.g., paranoid type, disorganized type, catatonic type, and undifferentiated type); schizophreniform disorder, schizoaffective disorder, delusional disorder, other psychotic disorders (e.g., substance-induced psychotic disorder, L-DOPA-induced psychosis, psychosis associated with Alzheimer's dementia, psychosis associated with Parkinson's disease, psychosis associated with Lewy body disease); sleep disorders (e.g., sleep apnea); suicidal behaviors; sexual dysfunction; migraine; cephalic pain or other pain; raised intracranial pressure; epilepsy; personality disorders; age-related behavioral disorders; behavioral disorders associated with dementia; organic mental disorders; mental disorders in childhood; aggressivity; age-related memory disorders; chronic fatigue syndrome; addiction (e.g., drug and alcohol addiction); premenstrual tension; damage of the central nervous system such as by trauma, stroke, neurodegenerative diseases or toxic or infective CNS diseases such as encephalitis or meningitis; cardiovascular disorders (e.g., thrombosis); hypertension; hyperlipidemia; arterial constriction; osteoarthritis; gall bladder disease; gout; gastrointestinal disorders (e.g., dysfunction of gastrointestinal motility); diabetes mellitus (e.g., Type 2 diabetes mellitus) and diabetes insipidus; cancer; infertility; early mortality; spinal cord injuries; Tourette's syndrome; trichotillomania; other central nervous system disorders; attention deficit hyperactivity disorder (ADHD); canine veterinary diseases (e.g., acral lick dermatitis); and combinations of these disorders that may be present in a mammal. A compound described herein may also be used to suppress appetite in a subject, to enhance cognition (e.g., treating cognitive deficiency) in a subject, or treat weight gain in a subject.

In one embodiment, a method of treating a subject suffering from or susceptible to a serotonin-receptor-related disorder includes administering to a subject in need thereof a therapeutically effective amount of a compound described herein, to thereby treat the subject suffering from or susceptible to a serotonin-receptor-related disorder.

A further aspect relates to a method of treating a subject suffering from or susceptible to obesity, including administering to the subject an effective amount of a compound described herein to thereby treat the subject suffering from or susceptible to obesity.

A further aspect relates to a method of suppressing appetite in a subject, including administering to the subject an effective amount of a compound described herein to thereby suppress appetite in the subject.

A further aspect relates to treating weight gain in a subject (e.g., weight gain associated with treatment with another medication), including administering to the subject an effective amount of a compound described herein to thereby treat weight gain in the subject.

A further aspect relates to enhancing cognition in a subject, including administering to the subject an effective amount of a compound described herein to thereby enhance cognition in the subject.

A further aspect relates to treating suicidal behavior in a subject, including administering to the subject an effective amount of a compound described herein to thereby treat suicidal behavior in the subject.

A further aspect relates to a method of treating a subject suffering from or susceptible to Obsessive Compulsive Disorder (OCD), including administering to the subject an effective amount of a compound described herein to thereby treat the subject suffering from or susceptible to OCD.

A further aspect relates to a method of treating a subject suffering from or susceptible to schizophrenia or psychosis, including administering to the subject an effective amount of a compound described herein to thereby treat the subject suffering from or susceptible to schizophrenia or psychosis.

A further aspect relates to a method of treating a subject suffering from or susceptible to anxiety or depression, including administering to the subject an effective amount of a compound described herein to thereby treat the subject suffering from or susceptible to anxiety or depression.

A further aspect relates to a method of treating a subject suffering from or susceptible to migraine, including administering to the subject an effective amount of a compound described herein to thereby treat the subject suffering from or susceptible to migraine.

In certain embodiments, the methods of the invention include administering to a subject a therapeutically effective amount of a compound described herein in combination with another pharmaceutically active compound. Examples of pharmaceutically active compounds include compounds known to treat serotonin-related diseases. Other pharmaceutically active compounds that may be used can be found in *Harrison's Principles of Internal Medicine*, Sixteenth Edition, Eds. D. L. Kasper et al. McGraw-Hill Professional, N.Y., NY (2004); and the 2005 Physician's Desk Reference 59th Edition, Thomson Healthcare, 2004, the complete contents of which are expressly incorporated herein by reference. A compound described herein and a pharmaceutically active compound may be administered to the subject in the same pharmaceutical composition or in different pharmaceutical compositions (at the same time or at different times).

Determination of a therapeutically effective or a prophylactically effective amount of a compound described herein, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific serotonin-receptor-related disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of a compound described herein with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired.

Compounds determined to be effective for the prevention or treatment of serotonin-receptor-related disorders in animals, e.g., dogs, chickens, and rodents, may also be useful in treatment of serotonin-receptor-related disorders in humans. Those skilled in the art of treating serotonin-receptor-related disorders in humans will know, based upon the data obtained in animal studies, the dosage and route of administration of the compound to humans. In general, the dosage and route of administration in humans is expected to be similar to that in animals.

The identification of those patients who are in need of prophylactic treatment for serotonin-receptor-related disorders is well within the ability and knowledge of one skilled in the art. Certain of the methods for identification of patients which are at risk of developing serotonin-receptor-related disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

In another aspect, a compound described herein is packaged in a therapeutically effective amount with a pharmaceutically acceptable carrier or diluent. The composition may be formulated for treating a subject suffering from or susceptible to a serotonin-receptor-related disorder, and packaged with instructions to treat a subject suffering from or susceptible to a serotonin-receptor-related disorder.

In another aspect, the invention provides methods for stimulating or increasing serotonin receptor activity. In one embodiment, a method of increasing serotonin receptor activity (or a serotonin receptor related activity) according to the invention includes contacting cells with a compound capable of increasing serotonin receptor activity. The contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a serotonin-receptor-related disorder in a subject include administering an effective amount of a compound described herein (e.g., a compound of any of the formulae herein capable of increasing serotonin receptor activity) to the subject. The administration may be by any route of administering known in the pharmaceutical arts. The subject may have a serotonin-receptor-related disorder, may be at risk of developing a serotonin-receptor-related disorder, or may need prophylactic treatment prior to anticipated or unanticipated exposure to a conditions capable of increasing susceptibility to a serotonin-receptor-related disorder.

In one aspect, a method of monitoring the progress of a subject being treated with a serotonin receptor active compound described herein includes determining the pre-treatment status of the serotonin-receptor-related disorder, administering a therapeutically effective amount of a compound described herein to the subject, and determining the status of the serotonin-receptor-related disorder after an initial period of treatment, wherein the modulation (e.g., improvement) of the status indicates efficacy of the treatment.

In one aspect, methods of selecting a subject suffering from or susceptible to a serotonin-receptor-related disorder for treatment with a compound described herein comprise determining the pre-treatment status of the serotonin-receptor-related disorder, administering a therapeutically effective amount of a compound described herein to the subject, and determining the status (of the serotonin-receptor-related disorder after an initial period of treatment with the compound, wherein the modulation (e.g., improvement) of the status is an indication that the serotonin-receptor-related disorder is likely to have a favorable clinical response to treatment with a compound described herein.

The subject may be at risk of a serotonin-receptor-related disorder, may be exhibiting symptoms of a serotonin-receptor-related disorder, may be susceptible to a serotonin-receptor-related disorder and/or may have been diagnosed with a serotonin-receptor-related disorder.

The initial period of treatment may be the time in which it takes to establish a stable and/or therapeutically effective blood serum level of the compound, or the time in which it take for the subject to clear a substantial portion of the compound, or any period of time selected by the subject or healthcare professional that is relevant to the treatment.

If the modulation of the status indicates that the subject may have a favorable clinical response to the treatment, the subject may be treated with the compound. For example, the subject can be administered therapeutically effective dose or doses of the compound.

Kits of the invention include kits for treating a serotonin-receptor-related disorder in a subject. The invention also includes kits for assessing the efficacy of a treatment for a serotonin-receptor-related disorder in a subject, monitoring the progress of a subject being treated for a serotonin-receptor-related disorder, selecting a subject with a serotonin-receptor-related disorder for treatment according to the invention, and/or treating a subject suffering from or susceptible to a serotonin-receptor-related disorder. The kit may include a compound described herein, for example, a compound of any of formula described herein, pharmaceutically acceptable esters, salts, and prodrugs thereof, and instructions for use. The instructions for use may include information on dosage, method of delivery, storage of the kit, etc. The kits may also include reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of a treatment for a serotonin-receptor-related disorder may be packaged with a kit for monitoring the progress of a subject being treated for a serotonin-receptor-related disorder according to the invention.

Certain of the present methods can be performed on cells in culture, e.g. in vitro or ex vivo, or on cells present in an animal subject, e.g., in vivo. A compound described herein can be initially tested in vitro using cells that express a serotonin receptor (see, e.g., the Examples, infra).

Alternatively, the effects of a compound described herein can be characterized in vivo using animals models.

4. Pharmaceutical Compositions

The invention also provides a pharmaceutical composition, comprising an effective amount of a compound described herein (e.g., a compound capable of treating or preventing a condition as described herein, e.g., a compound of any formula herein or otherwise described herein) and a pharmaceutically acceptable carrier.

In an embodiment, a compound described herein is administered to the subject using a pharmaceutically-acceptable formulation, e.g., a pharmaceutically-acceptable formulation that provides sustained delivery of a compound described herein to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to a compound described herein, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound described herein(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound described herein(s) with the carrier and, optionally, one or more accessory ingredients. In general, the formulations are prepared by uniformly and intimately bringing into association a compound described herein with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound described herein(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of a compound described herein include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to a compound described herein may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compounds described herein with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound described herein include powders, sprays, ointments, pastes, creams, lotions, gels, solutions, patches and inhalants. A compound described herein may be mixed under sterile conditions with a pharmaceutically-acceptable carrier, and with any preservatives, buffers, or propellants which may be required.

The ointments, pastes, creams and gels may contain, in addition to a compound described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A compound described herein can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound described herein to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compounds described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of one or more compounds described herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When a compound described herein is administered as a pharmaceutical, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, a compound described herein, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of a compound described herein is the maximum that a patient can tolerate and not develop serious side effects. Preferably, the compound of the present invention is administered at a concentration or amount of about 0.001 mg to about 100 mg per kilogram of body weight, about 0.01-about 50 mg/kg or about 10 mg-about 30 mg/kg of body weight. Ranges intermediate to the above-recited values are also intended to be part of the invention.

The invention is further illustrated by the following examples which are intended to illustrate but not limit the scope of the invention.

EXAMPLES

Chemical Synthesis

General.

All exemplified target compounds are fully analyzed and characterized (mp, TLC, LCMS, $^1$H-NMR) prior to submission for biological evaluation. Thin-layer chromatography was carried out on Merck Si 250F plates. Visualization was accomplished with ultraviolet exposure or with phosphomolybdic acid. Flash chromatography and Isco (CombiFlash) was carried out on silica gel (60□M). MS were carried out on a Agilent 1100 and 1200 series HPLC-Mass Spectrometer. $^1$H and $^{13}$C NMR spectra were recorded at 300 and 75 MHz, respectively, on a Jeol Eclipse 300 Spectrometer or $^1$H NMR spectra were recorded at 400 MHz on a Avance III 400 Ultra shield-plus TM digital Spectrometer or 300 MHz Varian. NMR assignments are based on a combination of the $^1$H, $^{13}$C, $^1$H COSY, HMBC and HMQC spectra. Coupling constants are given in hertz (Hz). Anhydrous methylene chloride, tetrahydrofuran, and dimethylformamide are Aldrich Sure/Seal™, and other materials are reagent grade.

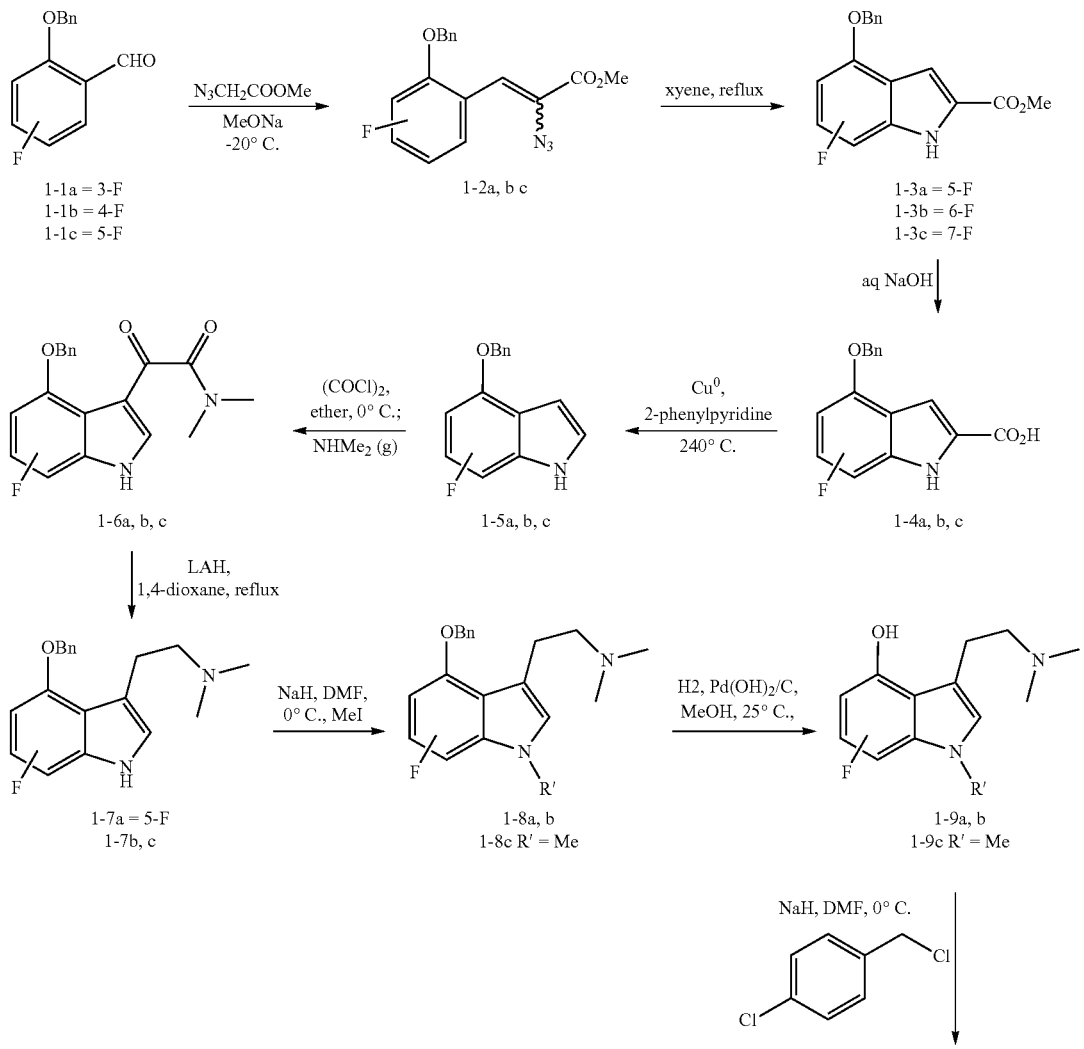

Scheme 1

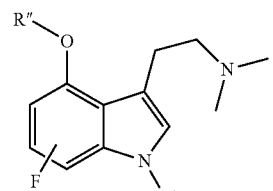

1-10a, c
Example 1 = 1-10b
(R' = Et, R'' = p-ClPh—CH2—)

Example 1

2-(4-(4-chlorobenzyloxy)-1-ethyl-6-fluoro-1H-indol-3-yl)-N,N-dimethylethanamine (1-10b)

Synthesis of 2-(4-Benzyloxy-5-fluoro-1H-indol-3-yl)-N,N-dimethylethanamine (1-7a)

Step 1 and 2: Methyl 4-benzyloxy-5-fluoro-1H-indole-2-carboxylate (1-3a)

In a pre-dried 3-neck roundbottom flask was added anhydrous MeOH (100 mL), followed by Na metal (5.52 g, 0.24 mol) portionwisely at 0° C. The resulting solution was cooled in a dry ice/acetone bath to −20° C. A solution of 1-1a (prepared according to U.S. Pat. No. 5,330,992 or from commercial sources) (18.4 g, 0.08 mol) and methyl azidoacetate (27.6 g, 0.24 mol) in dry MeOH (50 mL) was added dropwise over 60 min. After stirring for 1 h, the reaction was warmed to room temperature and stirring continued for 1.5 h. The heterogeneous mixture was then poured onto ice, and the precipitate was collected by filtration. The yellow solid (1-2a) was immediately dissolved in p-xylenes (400 mL) and the solution was washed with brine, followed by drying over $Na_2SO_4$. After filtration the resulting solution was heated at reflux until TLC indicated the reaction was complete (about 1 h). The solvent was distilled under reduced pressure to precipitate the product as white crystals (6.73 g). An additional 1.36 g of product (1-3a) was obtained by chromatography of the residue on silica gel, eluting with EtOAc/hexanes (overall yield 35%). $^1$H NMR (300 MHz, $CDCl_3$-d) δ (ppm) 3.94 (s, 3H), 5.33 (s, 2H), 6.98-7.03 (m, 1H), 7.10 (dd, 1H, J=11.8, 8.8), 7.29-7.41 (m, 4H), 7.48-7.50 (m, 2H), 8.81 (br, 1H). APCI [M+1]: 300.2.

Step 3: 4-(Benzyloxy)-5-fluoro-1H-indole-2-carboxylic acid (1-4a)

Compound 1-3a was added to a solution of aqueous 2 N NaOH. The suspension was stirred at 80-90° C. until the reaction mixture became clear and was then held at reflux for 1-2 h. The solution was cooled and acidified with aqueous 3 N HCl, then the resulting precipitate was collected by filtration, washed with water, and dried under vacuum over $P_2O_5$ to provide the product (1-4a) in 99% yield. $^1$H NMR ($CDCl_3$-d, 300 MHz) δ (ppm) 5.31 (s, 2H), 7.06-7.18 (m, 3H), 7.30-7.42 (m, 3H), 7.47-7.50 (m, 2H), 11.93 (bs, 1H).

Step 4: 4-Benzyloxy-5-fluoro-1H-indole (1-5a)

Compound 1-4a (6.28 g, 0.022 mol), copper powder (7.05 g, 0.11 mol) and 2-phenylpyridine (50 mL) were heated at reflux (230-240° C.) under a stream of nitrogen for 10 min, by which time TLC analysis showed complete reaction. The reaction mixture was cooled, filtered through Celite, and the filter cake was washed with EtOAc. The filtrate and EtOAc washings were combined, diluted with water, and extracted three times with EtOAc. The organic extract was washed with 1 N HCl, $H_2O$ and brine, dried with $NaSO_4$, and concentrated. The resulting residue was purified by column chromatography on silica gel eluting with EtOAc/hexanes to give the product as a greenish solid (1-5a) in 62% yield, 3.32 g. $^1$H NMR (300 MHz, $CDCl_3$-d) δ (ppm) 5.31 (s, 2H), 6.62-6.64 (m, 1H), 6.93-7.03 (m, 2H), 7.15 (dd, 1H, J=3.0, 2.5), 7.31-7.40 (m, 3H), 7.49-7.52 (m, 2H), 8.12 (br, 1H). APCI [M+1]: 242.1.

Step 5: 2-(4-Benzyloxy-5-fluoro-1H-indol-3-yl)-N,N-dimethyl-2-oxoacetamide (1-6a)

A solution of oxalyl chloride (0.78 mL, 8.963 mmol) in anhydrous ether (20 mL) was added dropwise over 20 min to a 0° C. solution of 1-5a (1.44 g, 5.975 mmol) in anhydrous ether (20 mL). The reaction mixture was stirred at room temperature for 5 h, cooled to −20° C., and treated with a stream of dimethyl amine gas. The reaction was diluted with EtOAc, washed with water and brine, and dried over $Na_2SO_4$. After concentration, the resulting residue was recrystallized from EtOAc to provide the product (1-6a) as white crystals in 87% yield, 1.58 g. $^1$H NMR (300 MHz, $CDCl_3$-d) δ (ppm) 2.92 (s, 3H), 2.94 (s, 3H), 5.17 (s, 2H), 6.91-7.00 (m, 2H), 7.29-7.37 (m, 3H), 7.58-7.61 (m, 2H), 7.70-7.72 (m, 1H), 10.02 (br, 1H). APCI [M+1]: 341.2.

Step 6: 2-(4-Benzyloxy-5-fluoro-1H-indol-3-yl)-N,N-dimethylethanamine (1-7a)

A solution of 1-6a (2.26 g, 6.647 mmol) in dry 1,4-dioxane (30 mL) was added dropwise to a slurry of $LiAlH_4$ (2.52 g, 66.47 mmol) in dry 1,4-dioxane (40 mL) at reflux. The mixture was held at reflux for 1 h. The mixture was then cooled, quenched with ice-water (mixed with NaOH), filtered through Celite, and the filter cake was washed with EtOAc. The filtrate and EtOAc washings were combined and extracted three times with EtOAc. The organic layer was washed with 1 N NaOH and brine, dried over $Na_2SO_4$ and concentrated. The resulting residue was purified by column chromatography on silica gel with $CH_2Cl_2$ (100%) to 5% $NH_4OH$ in $CH_2Cl_2$ as eluent to give the product (1-7a) as a brown oil in 80% yield, 1.67 g. $^1$H NMR (300 MHz, $CDCl_3$-d) δ (ppm) 2.14 (s, 6H). 2.52-2.57 (m, 2H), 2.91-2.97 (m, 2H), 5.25 (s, 2H), 6.92-6.98 (m, 3H), 7.31-7.40 (m, 3H), 7.49-7.52 (m, 2H), 7.97 (br, 1H). APCI [M+1]: 313.1.

Synthesis of 3-(2-Dimethylaminoethyl)-7-fluoro-1-methyl-1H-indol-4-ol (1-9c)

Step 1 to 6: 2-(4-Benzyloxy-7-fluoro-1H-indol-3-yl)-N,N-dimethylethanamine (1-7c)

Following the procedures (step 1-6) used to prepare compound 1-7a, compound 1-1c was used as starting material to obtain compound 1-7c.

Step 7: 4-Benzyloxy-3-(2-dimethylaminoethyl)-7-fluoro-1-methyl-1H-indole (1-8c)

At 0° C., NaH (2 eq) was added to a solution of 1 eq of compound 1-7c in DMF. After 30 min, a solution of 0.1 M methyl iodide in DMF was added slowly over 30 min, and then the reaction mixture was allowed to warm to 25° C. and stirred at that temperature for 1 h. After standard workup, the brown oil residue was purified by column chromatography, eluting with $CH_2Cl_2$/2% $NH_4OH$. A brown oil (1-8c) was obtained in 84% yield. $^1$H NMR ($CDCl_3$-d, 300 MHz) δ (ppm) 2.13 (s, 6H), 2.50-2.56 (m, 2H), 2.95-3.01 (m, 2H), 3.89 (d, 3H, J=1.9), 5.13 (s, 2H), 6.29 (dd, 1H, J=8.5, 2.8), 6.67 (dd, 1H, J=8.5, 12.1), 6.69 (s, 1H), 7.29-7.40 (m, 3H), 7.45-7.48 (m, 2H). APCI [M+1]: 327.2.

Step 8: 3-(2-Dimethylaminoethyl)-7-fluoro-1-methyl-1H-indol-4-ol (1-9c)

A mixture of 1-8c and $Pd(OH)_2$/C in MeOH was hydrogenated at ambient pressure for 2 h at 25° C., then the mixture was filtered through a plug of Celite and washed with EtOAc. The crude product was purified by column chromatography eluting with $CH_2Cl_2$/2% $NH_4OH$ to give a white solid (1-9c) in 88% yield. $^1$H NMR ($CDCl_3$-d, 300 MHz) ppm 2.35 (s, 6H), 2.63-2.67 (m, 2H), 2.86-2.89 (m, 2H), 3.87 (d, 3H, J=2.2), 6.33 (dd, 1H, J=8.2, 3.3), 6.61 (s, 1H), 6.69 (dd, 1H, J=8.5, 12.4). APCI [M+1]: 237.2.

Synthesis of 2-(4-(4-chlorobenzyloxy)-1-ethyl-6-fluoro-1H-indol-3-yl)-N,N-dimethylethanamine (1-10b, Example 1)

Step 1 to 6: 2-(4-Benzyloxy-6-fluoro-1H-indol-3-yl)-N,N-dimethylethanamine (1-7b)

Following the procedures (step 1-6, scheme 1) used to prepare compound 1-7a, compound 1-1b was used as starting material to obtain compound 1-7b.

Step 7-8: 3-(2-(dimethylamino)ethyl)-1-ethyl-6-fluoro-1H-indol-4-ol (1-9b)

Following the procedures (step 7-8 scheme 1) used to prepare compound 1-9c, compound 1-7b was used as starting material to obtain compound 1-9b.

Step 9: 2-(4-(4-chlorobenzyloxy)-1-ethyl-6-fluoro-1H-indol-3-yl)-N,N-dimethylethanamine (1-10b)

Following the procedure (step 7, scheme 1) used to prepare compound 1-8c, compound 1-9b and 1-chloro-4-(chloromethyl)benzene were used as starting material to obtain compound 1-10b.

1H NMR ($CDCl_3$-d) δ (ppm): 12.14 (br. s, 1H), 7.41-7.46 (m, 4H), 6.92 (s, 1H), 6.65 (dd, J1=2.0 Hz, J2=7.8 Hz, 1H), 6.38 (dd, J1=2.0 Hz, J2=5.2 Hz, 1H), 5.06 (s, 2H), 4.00 (q, J=7.2 Hz, 2H), 3.22-3.26 (m, 2H), 3.06-3.10 (m, 2H), 2.41 (s, 6H), 1.39 (t, J=3.2 Hz, 3H).

The compounds in table I were made according to processes described in scheme 1.

TABLE I

| Structure | name | Ex. number | ID number | NMR | MS | Procedure of scheme |
|---|---|---|---|---|---|---|
| (structure shown) | 2-(4-(4-chloro-benzyloxy)-1-ethyl-6-fluoro-1H-indol-3-yl)-N,N-dimethyl-ethanamine | 1 | 1-10b | 1H NMR ($CDCl_3$-d) δ (ppm) 12.14 (br.s, 1 H), 7.41-7.46 (m, 4 H), 6.92 (s, 1 H), 6.65 (dd, J1 = 2.0 Hz, J2 = 7.8 Hz, 1 H), 6.38 (dd, J1 = 2.0 Hz, J2 = 5.2 Hz, 1 H), 5.06 (s, 2 H), 4.00 (q, J = 7.2 Hz, 2 H), 3.22-3.26 (m, 2 H), 3.06-3.10 (m, 2 H), 2.41 (s, 6 H), 1.39 (t, J = 3.2 Hz, 3 H) | calc 374.1, found 375.1 [MH]+ | 1 |

TABLE I-continued

| Structure | name | Ex. number | ID number | NMR | MS | Procedure of scheme |
|---|---|---|---|---|---|---|
| | 2-(1-ethyl-6-fluoro-4-(4-(trifluoromethoxy)benzyloxy)-1H-indol-3-yl)-N,N-dimethyl-ethanamine | 2 | 1-11b | 1H NMR (CDCl$_3$-d) δ (ppm) 11.97 (br.s, 1 H), 7.56 (d, J = 8.8 Hz, 2 H), 7.32 (d, J = 8.0 Hz, 2 H), 6.95 (s, 1 H), 6.66 (dd, J1 = 2.0 Hz, J2 = 7.8 Hz, 1 H), 6.40 (dd, J1 = 2.0 Hz, J2 = 9.8 Hz, 1 H), 5.10 (s, 2 H), 4.01 (q, J = 7.2 Hz, 2 H), 3.22-3.26 (m, 2 H), 3.08-3.12 (m, 2 H), 2.39 (d, J = 4.4 Hz, 6 H), 1.40 (t, J = 7.2 Hz, 3 H) | calc 424.2 found 425.1 [MH]+ | 1 |
| 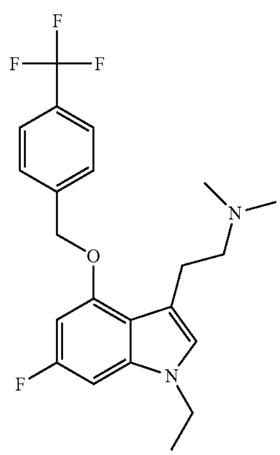 [SMILES: CCn1cc(CCN(C)C)c2c(OCc3ccc(C(F)(F)F)cc3)cc(F)cc21] | 2-(1-ethyl-6-fluoro-4-(4-(trifluoromethyl)benzyloxy)-1H-indol-3-yl)-N,N-dimethyl-ethanamine | 3 | 1-12b | 1H NMR (CDCl$_3$-d) δ (ppm) 12.28 (br.s, 1 H), 7.72 (s, 2 H), 7.65 (s, 2 H), 6.98 (br.s, 1 H), 6.66 (d, J = 9.6 Hz, 1 H), 6.38 (d, J = 9.2 Hz, 1 H), 5.19 (s, 2 H), 4.02 (s, 2 H), 3.30 (s, 2 H), 3.12 (s, 2 H), 2.44 (br.s, 6 H), 1.41 (s, 3 H) | calc 408.2, found 409.1 [MH]+ | 1 |
| 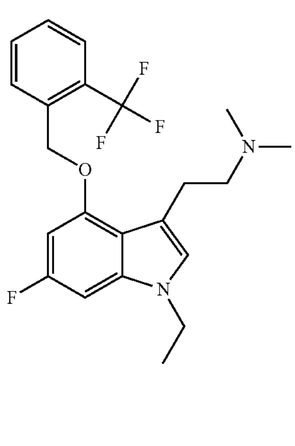 [SMILES: CCn1cc(CCN(C)C)c2c(OCc3ccccc3C(F)(F)F)cc(F)cc21] | 2-(1-ethyl-6-fluoro-4-(2-(trifluoromethyl)benzyloxy)-1H-indol-3-yl)-N,N-dimethyl-ethanamine | 4 | 1-13b | 1H NMR (CDCl$_3$-d) δ (ppm) 7.77 (d, J = 8.0 Hz, 1 H), 7.64-7.71 (m, 2 H), 7.53 (t, J = 7.2 Hz, 1 H), 6.92 (s, 1 H), 6.66 (dd, J1 = 1.6 Hz, J2 = 2.3 Hz, 1 H), 6.39 (dd, J1 = 1.6 Hz, J2 = 9.7 Hz, 1 H), 5.28 (s, 2 H), 4.01 (q, J = 7.2 Hz, 2 H), 3.19-3.23 (m, 2 H), 3.01-3.05 (m, 2 H), 2.34 (s, 6 H), 1.40 (t, J = 7.2 Hz, 3 H) | calc 408.2, found 409.1 [MH]+ | 1 |

TABLE I-continued

| Structure | name | Ex. number | ID number | NMR | MS | Procedure of scheme |
|---|---|---|---|---|---|---|
| 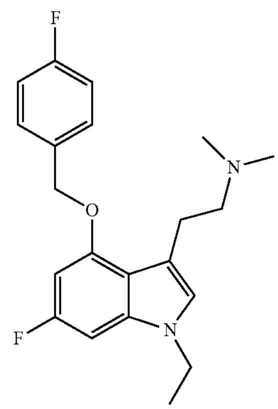 [SMILES: CCn1cc(CCN(C)C)c2c(OCc3ccc(F)cc3)cc(F)cc21] | 2-(1-ethyl-6-fluoro-4-(4-fluorobenzyloxy)-1H-indol-3-yl)-N,N-dimethyl-ethanamine | 5 | 1-14b | 1H NMR (CDCl₃-d) ⊓ppm: 11.93 (br.s, 1 H), 7.51 (s, 2 H), 7.17 (t, J = 7.6 Hz, 2 H), 6.97 (s, 1 H), 6.68 (d, J = 9.2 Hz, 1 H), 6.43 (d, J = 9.6 Hz, 1 H), 5.08 (s, 2 H), 4.03 (d, J = 6.4 Hz, 2 H), 3.26 (s, 2 H), 3.12 (s, 2 H), 2.43 (s, 6 H), 1.42 (t, J = 6.4 Hz, 3 H) | calc 358.2, found 359.1 [MH]+ | 1 |
| 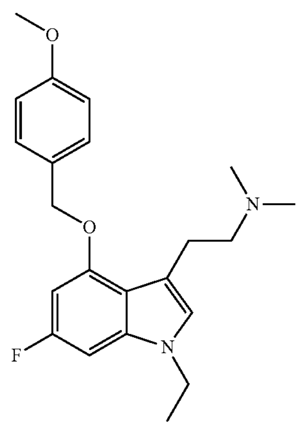 [SMILES: CCn1cc(CCN(C)C)c2c(OCc3ccc(OC)cc3)cc(F)cc21] | 2-(1-ethyl-6-fluoro-4-(4-methoxy-benzyloxy)-1H-indol-3-yl)-N,N-dimethyl-ethanamine | 6 | 1-15b | 1H NMR (CDCl₃-d) δ (ppm) 7.41 (d, J = 8.8 Hz, 2 H), 6.95 (d, J = 8.8 Hz, 2 H), 6.87 (s, 1 H), 6.63 (dd, J1 = 2.4 Hz, J2 = 7.6 Hz, 1 H), 6.41 (dd, J1 = 2.0 Hz, J2 = 9.7 Hz, 1 H), 5.01 (s, 2 H), 4.00 (q, J = 7.2 Hz, 2 H), 3.83 (s, 3 H), 3.13-3.17 (m, 2 H), 2.95-2.99 (m, 2 H), 2.27 (s, 6 H), 1.40 (t, J = 7.6 Hz, 3 H) | calc 370.2, found 371.1 [MH]+ | 1 |
| 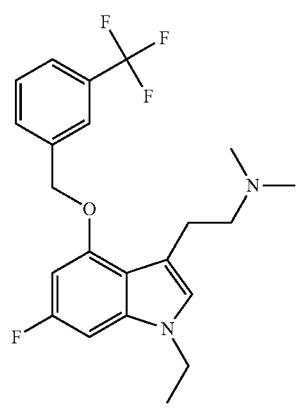 [SMILES: CCn1cc(CCN(C)C)c2c(OCc3cccc(C(F)(F)F)c3)cc(F)cc21] | 2-(1-ethyl-6-fluoro-4-(3-(trifluoro-methyl)benzyloxy)-1H-indol-3-yl)-N,N-dimethyl-ethanamine | 7 | 1-16b | 1H NMR (CDCl₃-d) δ (ppm) 7.76 (s, 1 H), 7.58-7.72 (m, 3 H), 6.92 (s, 1 H), 6.66 (dd, J1 = 2.4 Hz, J2 = 7.6 Hz, 1 H), 6.39 (dd, J1 = 2.0 Hz, J2 = 9.1 Hz, 1 H), 5.17 (s, 2 H), 4.01 (q, J = 7.2 Hz, 2 H), 3.18-3.23 (m, 2 H), 2.961-3.00 (m, 2 H), 2.33 (s, 6 H), 1.41 (t, J = 7.2 Hz, 3 H) | calc 408.2, found 409.1 [MH]+ | 1 |
| 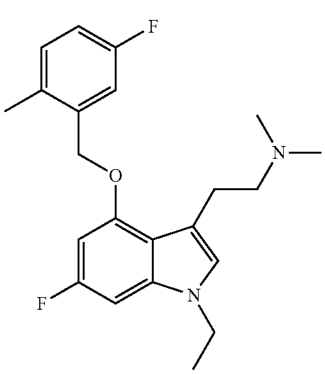 | 2-(1-ethyl-6-fluoro-4-(5-fluoro-2-methyl-benzyloxy)-1H-indol-3-yl)-N,N-dimethyl-ethanamine | 8 | 1-17b | 1H NMR (CDCl₃-d) δ (ppm) 7.17-7.21 (m, 2 H), 6.95-7.00 (m, 1 H), 6.84 (s, 1 H), 6.64 (dd, J1 = 2.0 Hz, J2 = 7.8 Hz, 1 H), 6.37 (dd, J1 = 2.0 Hz, J2 = 9.8 Hz, 1 H), 5.07 (s ,2 H), 4.01 (t, J = 7.2 Hz, 2 H), 3.04-3.08 (m, 2 H), 2.72-2.77 (m, 2 H), 2.37 (d, J = 7.6 Hz, 3 H), 2.20 (s, 6 H), 1.41 (t, J = 7.6 Hz, 3 H) | calc 372.2, found 373.1 [MH]+ | 1 |

TABLE I-continued

| Structure | name | Ex. number | ID number | NMR | MS | Procedure of scheme |
|---|---|---|---|---|---|---|
| 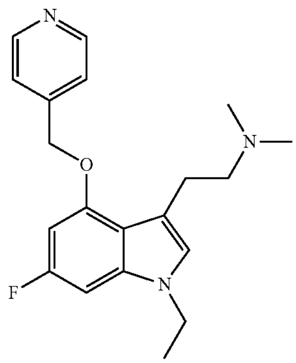 [SMILES: CCn1cc(CCN(C)C)c2c(OCc3ccncc3)cc(F)cc21] | 2-(1-ethyl-6-fluoro-4-(pyridin-4-ylmethoxy)-1H-indol-3-yl)-N,N-dimethyl-ethanamine | 9 | 1-18b | $^1$H NMR (CDCl$_3$) δ (ppm) 8.63 (dd, J = 4.5, 1.5 Hz, 2 H), 7.42 (d, J = 5.9 Hz, 2 H), 6.81 (s, 1 H), 6.62 (dd, J = 9.6, 1.9 Hz, 1 H), 6.25 (dd, J = 11.5, 1.9 Hz, 1H), 5.19 (s, 2 H), 4.01 (q, J = 7.3 Hz, 2 H), 3.10-3.01 (m, 2 H), 2.65-2.55 (m, 2 H), 2.22 (s, 6 H), 1.41 (t, J = 7.3 Hz, 3 H), | Calc 341.2, found [MH]+ 342.4 | 1 |
| 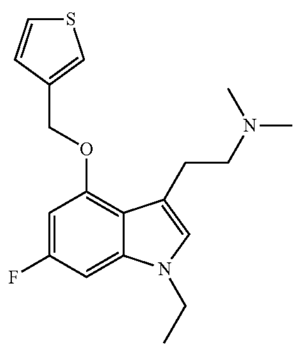 [SMILES: CCn1cc(CCN(C)C)c2c(OCc3ccsc3)cc(F)cc21] | 2-(1-ethyl-6-fluoro-4-(thiophen-3-ylmethoxy)-1H-indol-3-yl)-N,N-dimethyl-ethanamine | 10 | 1-19b | $^1$H-NMR (400 MHz, CDCl$_3$): δ (ppm) 7.39 (d, J = 2.0 Hz, 1 H), 7.35-7.33 (m, 1 H), 7.19 (d, J = 5.2 Hz, 1 H), 6.77 (s, 1 H), 6.59 (dd, J = 8.0, 1.6 Hz, 1 H), 6.34 (dd, J = 10.0, 1.6 Hz, 1 H), 5.14 (s, 2 H), 4.01 (q, J = 2 H), 2.98 (t, J = 7.6 Hz, 2 H), 2.59-2.55 (m, 2 H), 2.17 (s, 6 H), 1.39 (t, J = 7.2 Hz, 3 H). | calc 346.2, found 347.1 [MH]+ | 1 |
| 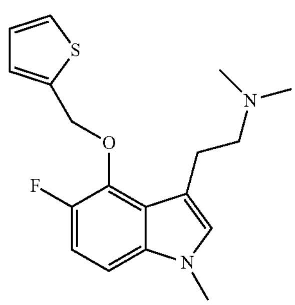 [SMILES: CN(C)CCc1cn(C)c2ccc(F)c(OCc3cccs3)c12] | 2-(5-fluoro-1-methyl-4-(thiophen-2-ylmethoxy)-1H-indol-3-yl)-N,N-dimethyl-ethanamine | 11 | 1-20a | 1H NMR (300 MHz, MeOD-d6) δ (ppm) 7.44-7.35 (m, 1 H), 7.12 (d, J = 2.9 Hz, 1 H), 7.04-6.89 (m, 4 H), 5.41 (s, 2 H), 3.69 (s, 3 H), 2.98-2.87 (m, 2 H), 2.69-2.58 (m, 2 H), 2.24 (s, 6 H) | calc 332.14, found 333.1 [MH]+ | 1 |

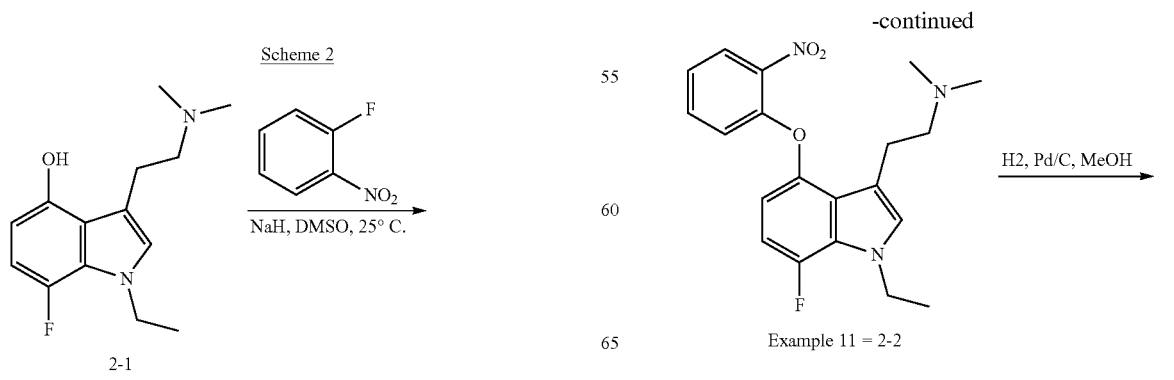

Scheme 2

Example 11 = 2-2

-continued

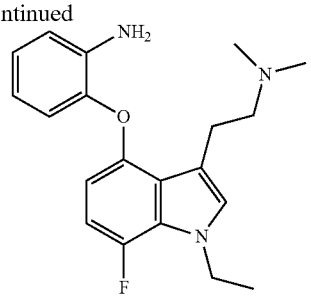

Example 12 = 2-3

Example 11

2-(1-ethyl-7-fluoro-4-(2-nitrophenoxy)-1H-indol-3-yl)-N,N-dimethylethanamine (2-2)

Following the procedure (step 7, scheme 1) used to prepare compound 1-8c, compound 2-1 (prepared according to step 1-8, scheme 1) in DMSO and 1-fluoro-2-nitrobenzene were used as starting material to obtain compound 2-2.

Example 12

2-(3-(2-(dimethylamino)ethyl)-1-ethyl-7-fluoro-1H-indol-4-yloxy)aniline (2-3)

Following the procedure (step 8, scheme 1) used to prepare compound 1-9c, compound 2-2 was used as starting material, using Pd/C (10%) as source of Pd to obtain compound 2-3.

The compounds in table 2 were made according to processes described in scheme 2.

TABLE 2

| Structure | name | Ex. number | ID number | NMR | MS | Procedure of scheme |
|---|---|---|---|---|---|---|
| 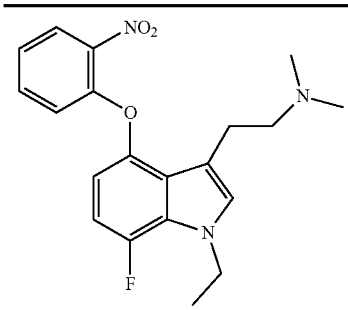 | 2-(1-ethyl-7-fluoro-4-(2-nitrophenoxy)-1H-indol-3-yl)-N,N-dimethylethanamine | 11 | 2-2 | 1H NMR (CDCl$_3$-d) δ(ppm): 8.07 (dd, J1 = 1.6 Hz, J2 = 6.3 Hz, 1H), 7.59-7.64(m, 2H), 7.29 (dd, J1 = 2.0 Hz, J2 = 7.8 Hz, 1H), 6.90-6.95(m, 2H), 6.54(dd, J1 = 3.2 Hz, J2 = 6.1 Hz, 1H), 4.28(q, J = 7.2 Hz, 2H), 2.68(t, J = 7.2 Hz, 2H), 2.37(t, J = 7.2 Hz, 2H), 2.03(d, J = 7.6 Hz, 6H), 1.37(t, J = 4.8 Hz, 3H) | calc 371.2 found 372.0 [MH]+ | 2 |
| 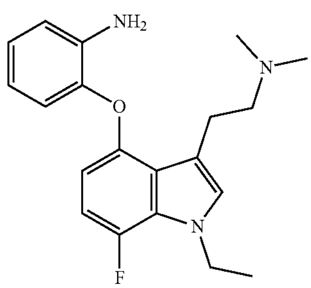 [SMILES: CCn1cc(CCN(C)C)c2c(Oc3ccccc3N)ccc(F)c21] | 2-(3-(2-(dimethylamino)ethyl)-1-ethyl-7-fluoro-1H-indol-4-yloxy)aniline | 12 | 2-3 | 1H NMR (CDCl$_3$-d) δ(ppm) 6.92-6.96(m, 1H), 6.87(s, 1H), 6.82(dd, J1 = 1.2 Hz, J2 = 6.5 Hz, 1H), 6.78(dd, J1 = 1.6 Hz, J2 = 6.6 Hz, 1H), 6.65-6.72(m, 2H), 6.29(dd, J1 = 3.2 Hz, J2 = 6.1 Hz, 1H), 4.41 (br.s, 2H), 4.27(q, J = 7.6 Hz, 2H), 3.02(t, J = 7.6 Hz, 2H), 2.70(dd, J1 = 3.6 Hz, J2 = 4.1 Hz, 2H), 2.30(s, 6H), 1.45(t, J = 7.2 Hz, 3H) | Calc 341.2, found 342.0 [MH]+ | 2 |

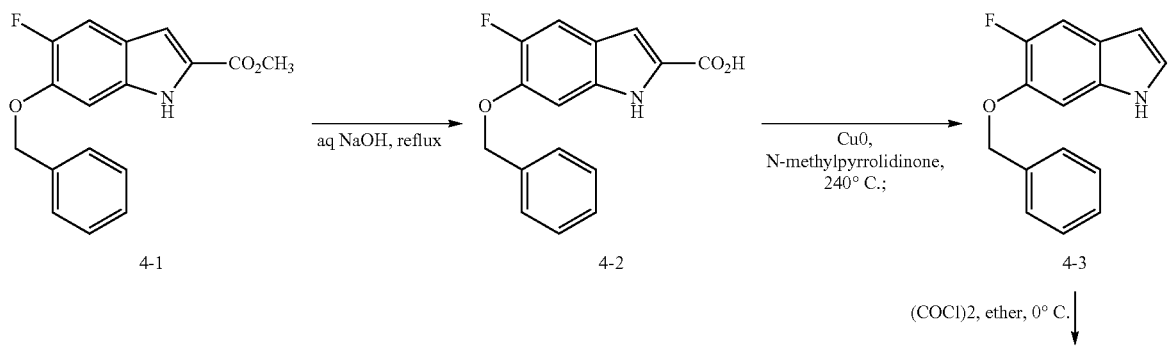

Scheme 4

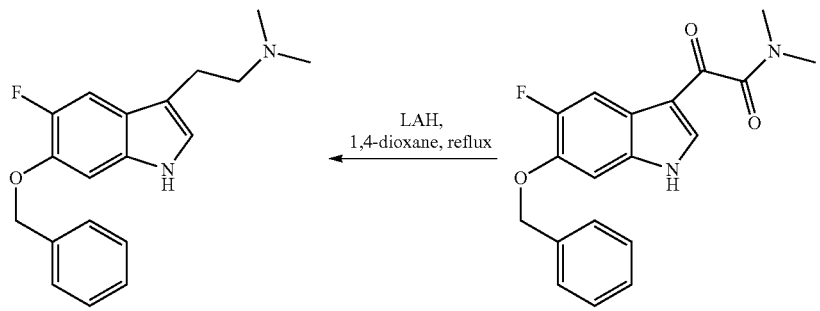

Example 14: 4-5 → 4-4 (LAH, 1,4-dioxane, reflux)

Example 14

2-(6-(benzyloxy)-5-fluoro-1H-indol-3-yl)-N,N-dimethylethanamine (4-5)

Step 1: 6-Benzyloxy-5-fluoro-1H-indole-2-carboxylic acid (4-2)

A suspension of compound 4-1, prepared according to WO2005/123716, (3.09 g, 10.3 mmol) in 150 mL of 2 M NaOH solution was heated at reflux for 4 h. The clear solution was cooled to 0° C., and acidified by 3 M HCl to pH~1, as white precipitate appeared. The suspension was filtered and washed with water, and then dried under vacuum (75° C.) overnight. Compound 4-2 was obtained as a white solid (2.89 g, 98%). $^1$H NMR (DMSO-$d_6$, 300 MHz) ☐ 5.19 (s, 2H), 7.01 (d, 1H, J=1.6), 7.09 (d, 1H, J=8.0), 7.32-7.52 (m, 6H), 11.70 (bs, 1H). APCI [M−1]: 284.

Step 2: 6-Benzyloxy-5-fluoro-1H-indole (4-3)

A mixture of compound 4-2 (2.58 g, 9.07 mmol) and copper (2.97 g, 45.1 mmol) in 80 mL of 1-methylpyrrolidin-2-one was heated at reflux overnight under nitrogen. After cooling to room temperature, the mixture was filtered through Celite and washed with EtOAc. The filtrate was partitioned between water and EtOAc (2×150 mL). The combined organic phase was washed with water and brine, and then dried over anhydrous $Na_2SO_4$. The black residue was purified by column chromatography (hexanes/EtOAc 2% to 12%) to give compound 4-3 (1.31 g, 60%) as a white solid. $^1$H NMR (CDCl$_3$, 300 MHz) ☐ 5.16 (s, 2H), 6.94-6.98 (m, 1H), 6.96 (d, 1H, J=7.1), 7.10-7.14 (m, 1H), 7.29-7.42 (m, 4H), 7.44-7.50 (m, 2H), 8.01 (bs, 1H). APCI [M−1]: 240.

Step 3: 2-(6-Benzyloxy-5-fluoro-1H-indol-3-yl)-N,N-dimethyl-2-oxoacetamide (4-4)

Following the procedure used to prepare compound 1-6a (step 5, scheme 1), compound 4-3 gave compound 4-4 in 82% yield as a white solid. $^1$H NMR (CDCl$_3$, 300 MHz) ☐ 3.06 (s, 3H), 3.08 (s, 3H), 5.14 (s, 2H), 6.94 (d, 1H, J=6.9), 7.32-7.47 (m, 5H), 7.82 (d, 1H, J=3.0), 8.05 (d, 1H, J=11.3), 8.96 (bs, 1H). APCI [M+1]: 386.2.

Step 4: 2-(6-Benzyloxy-5-fluoro-1H-indol-3-yl)-N,N-dimethylethanamine (4-5)

Following the procedure used to prepare compound 1-7a (step 6 scheme 1), compound 4-4 gave compound 4-5 in 77% yield as a brown oil.

The compound in table 4 was made according to processes described in scheme 4.

TABLE 4

| Structure | name | Ex. number | ID number | NMR | MS | Procedure of scheme |
|---|---|---|---|---|---|---|
| 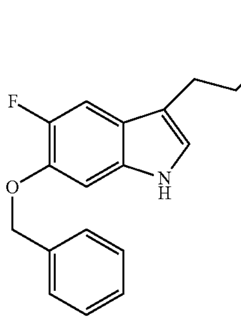 | 2-(6-(benzyloxy)-5-fluoro-1H-indol-3-yl)-N,N-dimethylethanamine | 14 | 4-5 | $^1$H NMR (DMSO-$d_6$) (HCl salt) δ (ppm) 10.89 (s, 1H), 7.33-7.50 (m, 7H), 7.17 (m, 1H), 7.10 (d, J = 7.4 Hz, 1H), 3.24-3.30 (m, 2H), 2.99-3.07 (m, 2H), 2.82 (s, 6H). | calc 312.2, found 313.1 [MH]$^+$ | 4 |

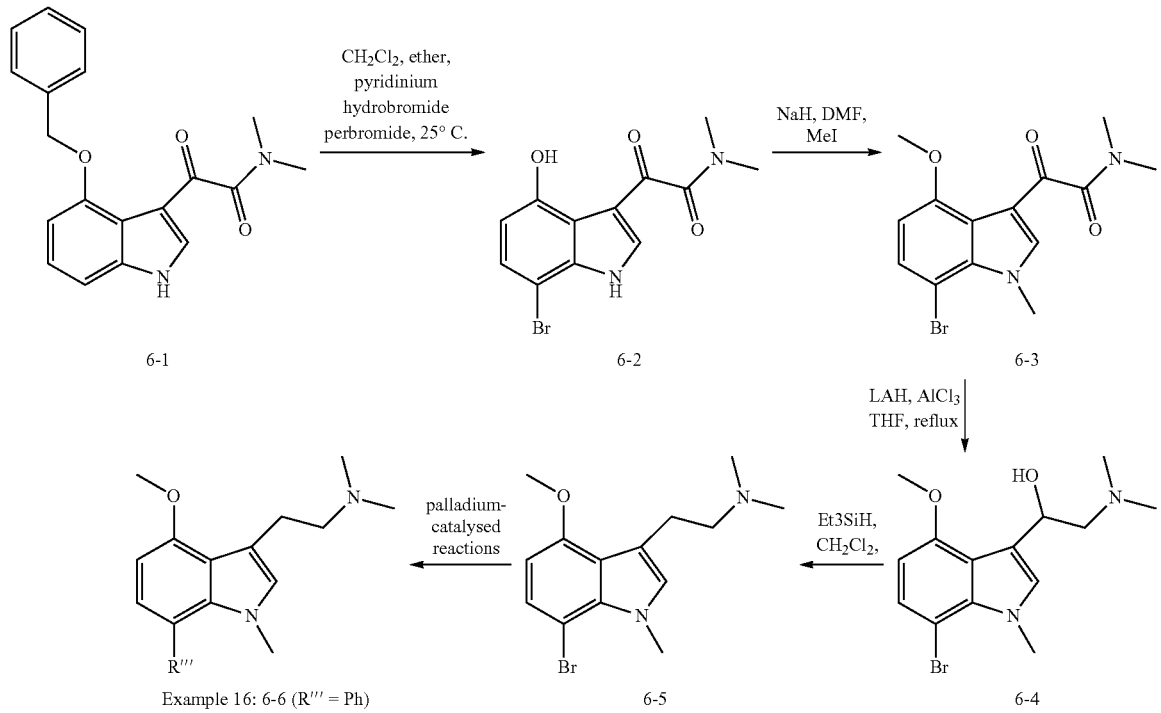

Scheme 6

Example 16: 6-6 (R''' = Ph)

Example 16

2-(4-methoxy-1-methyl-7-phenyl-1H-indol-3-yl)-N,N-dimethylethanamine (6-6)

Step 1: 2-(7-Bromo-4-hydroxy-1H-indol-3-yl)-N,N-dimethyl-2-oxoacetamide (6-2)

To a solution of compound 6-1, prepared according to *Helv. Chim. Acta*, 1959, 42, 1557 (3.22 g, 10 mmol) in CH$_2$Cl$_2$ (90 mL) and ether (75 mL) was added pyridinium hydrobromide perbromide and the reaction mixture was stirred overnight at 25° C. Solvent was removed under reduced pressure and the crude material was purified by column chromatography (elution with ethyl acetate/hexanes) to give compound 6-2 (2.04 g, 65%) as a yellow solid. $^1$H NMR (CD$_3$OD, 300 MHz) δ (ppm) 3.07 (s, 3H), 3.11 (s, 3H), 6.57 (d, 1H, J=8.5), 7.30 (d, 1H, J=8.5), 7.98 (s, 1H). APCI [M+1]: 311, 3.

Step 2: 2-(7-Bromo-4-methoxy-1-methyl-1H-indol-3-yl)-N,N-dimethyl-2-oxoacetamide (6-3)

To a solution of compound 6-2 (1.28 g, 4.12 mmol) in DMF at 0° C. was added NaH (660 mg, 16.5 mmol) and the reaction mixture was stirred for 10 min. To this reaction mixture, methyl iodide (3.5 g, 24.7 mmol) was added slowly and the reaction was monitored by MS. After 2 h, the reaction was quenched by adding water and EtOAc and washed with water, dried, and concentrated. The crude product was purified by column chromatography (1% NH$_4$OH/1% MeOH/EtOAc) to obtain compound 6-3 (1.30 g, 92%) as a white solid. $^1$H NMR (CDCl$_3$, 300 MHz) δ (ppm) 3.07 (s, 3H), 3.09 (s, 3H), 3.88 (s, 3H), 4.19 (s, 3H), 6.51 (d, 1H, J=8.5), 7.32 (d, 1H, J=8.5), 7.79 (s, 1H). APCI [M+1]: 339, 341.

Step 3: 1-(7-Bromo-4-methoxy-1-methyl-1H-indol-3-yl)-2-(dimethylamino)ethanol (6-4)

To a slurry of LiAlH$_4$ (419 mg, 11.03 mmol) in anhydrous THF at 0° C. under a nitrogen atmosphere was added AlCl$_3$ (488 mg, 3.67 mmol) and the reaction mixture was stirred for 10 min. To this slurry was then added compound 6-3 (500 mg, 1.47 mmol) and stirring continued for 30 min by which time MS showed no starting material. The reaction was quenched by adding water, extracted by ether, dried, and concentrated. The crude material was purified by column chromatography to give compound 6-4 (480 mg, 90%) as a white solid. $^1$H NMR (CDCl$_3$, 300 MHz) δ (ppm) 2.42 (s, 6H), 2.58 (dd, 1H, J=12.4, 9.6), 2.71 (dd, 1H, J=12.4, 3.3), 3.89 (s, 3H), 4.08 (s, 3H), 5.28 (dd, 1H, J=9.2, 3.0), 6.33 (d, 1H, J=8.5), 6.97 (s, 1H), 7.20 (d, 1H, J=8.3). APCI [M+1]: 309, 311, 327, 329.

Step 4: 2-(7-Bromo-4-methoxy-1-methyl-1H-indol-3-yl)-N,N-dimethylethanamine (Compound 6-5)

To a solution of compound 6-4 (430 mg, 1.31 mmol) in anhydrous CH$_2$Cl$_2$ (20 mL) at 0° C. was added Et$_3$SiH (1.52 g, 13.1 mmol) and the reaction mixture was stirred for 10 min. To this mixture was added CF$_3$CO$_2$H (1.2 g, 10.5 mmol) and stirring continued for 30 min. The reaction was quenched by adding sodium bicarbonate and it was extracted with CH$_2$Cl$_2$ and washed by water and brine. The organic layer was dried over sodium sulfate and concentrated. The crude material was purified by column chromatography (2% NH$_4$OH in CH$_2$Cl$_2$) to get compound 6-5 (76 mg, 12%) as an off-white solid. $^1$H NMR (CDCl$_3$, 300 MHz) δ (ppm) 2.31 (s, 6H), 2.51-2.57 (m, 2H), 2.95-3.02 (m, 2H), 3.87 (s, 3H), 4.06 (s, 3H), 6.30 (d, 1H, J=8.3), 6.67 (s, 1H), 7.17 (d, 1H, J=8.5). APCI [M+1]: 311.2, 313.2.

General Procedure for Preparation of 6-6, 6-7, 6-8, 6-9, 6-10, 6-13 and 6-14:

To a clean dry sealed tube containing palladium catalyst (4% mol) of (tetrakis-(triphenylphosphine) palladium (0) or dichlorobis(triphenylphosphine) palladium (II)) was added arylboronic acid (1.1 eq) (or pinacol boronate esters) and potassium(sodium) carbonate (2 eq). The tube was sealed and the air displaced with nitrogen before the addition of dry degassed 1,4-dioxane (5 mL) followed by compound 6-5 (1.0 eq). The mixture was heated at 150° C. either in a microwave for 10 to 30 min or in an oil bath for 16 h. The reaction was cooled to room temperature, filtered, evaporated to dryness and purified by column chromatography using $CH_2Cl_2$/$NH_4OH$ (2-5%) as the eluent. The products were further purified by reverse phase chromatography (C-18) using gradient MeOH/$H_2O$ (0.1% TFA) as the eluent. Appropriate fractions were combined, neutralized, evaporated to dryness and the products were identified by $^1H$ NMR, MS and HPLC.

Step 5: 2-(4-Methoxy-1-methyl-7-phenyl-1H-indol-3-yl)-N,N-dimethylethanamine hydrochloride (6-6)

Prepared using phenylboronic acid, potassium carbonate and tetrakis-(triphenylphosphine) palladium (0) in an oil bath heating for 16 h and the compound was converted to hydrochloride salt. Obtained a light blue solid, mp 285-287° C.

Example 17

2-[4-Methoxy-1-methyl-7-(thiophen-2-yl)-1H-indol-3-yl]-N,N-dimethylethanamine (6-7)

Prepared using thiophen-2-ylboronic acid, sodium carbonate and dichloro-bis(triphenylphosphine) palladium (II) in a microwave heating for 30 min Obtained off-white solid, mp 131-133° C.

Example 18

2-[7-(Furan-2-yl)-4-methoxy-1-methyl-1H-indol-3-yl]-N,N-dimethylethanamine (6-8)

Prepared using furan-2-ylboronic acid, sodium carbonate and dichloro-bis(triphenylphosphine) palladium (II) in a microwave heating for 10 min Obtained off-white solid, mp 90-93° C.

Example 19

2-[7-(Furan-3-yl)-4-methoxy-1-methyl-1H-indol-3-yl]-N,N-dimethylethanamine (6-9)

Prepared using pinacol furan-3-ylboronate ester, sodium carbonate and dichloro-bis(triphenylphosphine) palladium (II) in a microwave heating for 30 min. Obtained white solid, mp 80-81° C.

Example 20

2-[4-Methoxy-1-methyl-7-(1H-pyrrol-2-yl)-1H-indol-3-yl]-N,N-dimethylethanamine (6-10)

Prepared using N-Boc-pyrrol-2-ylboronic acid, sodium carbonate and dichloro-bis(triphenylphosphine) palladium (II) in a microwave heating for 30 min. The Boc group was cleaved by TFA during reverse phase chromatography. Obtained a gray solid, mp 203-206° C.

Example 23

2-[4-Methoxy-1-methyl-7-(thiophen-3-yl)-1H-indol-3-yl]-N,N-dimethylethanamine (6-13)

Prepared according to the general coupling method in using thiophen-3-ylboronic acid, sodium carbonate and dichlorobis(triphenylphosphine) palladium (II) in a microwave heating for 60 min Obtained brown solid, mp 120-122° C.

Example 24

2-(4-Methoxy-1-methyl-7-(pyridin-3-yl)-1H-indol-3-yl)-N,N-dimethylethanamine (6-14)

Prepared according to the general coupling method in using pinacol pyridine-3-ylboronate ester, potassium carbonate, copper(I) iodide and tetrakis-(triphenylphosphine) palladium (0) in an oil bath heating for 4 h. Obtained a yellow solid, mp 227-230° C.

Example 21

3-[3-(2-Dimethylaminoethyl)-4-methoxy-1-methyl-1H-indol-7-yl]prop-2-yn-1-ol (6-11)

In a clean dry sealed tube, copper iodide (4 mg, 10% mol) was added to a mixture of dichlorobis(triphenylphosphine) palladium (II) (17 mg, 10% mol), compound 6-5 (62 mg, 0.2 mmol) and propargyl alcohol (35 □L, 0.6 mmol) in dry triethylamine (3 mL) under nitrogen. The mixture was heated at 150° C. in a microwave for 2 h. The reaction was cooled to room temperature, filtered, evaporated to dryness and purified by column chromatography using $CH_2Cl_2$/$NH_4OH$ as the eluent, giving a brown solid (30 mg, 53%), mp 101-104° C.

Example 22

3-(2-dimethylaminoethyl)-4-methoxy-1-methyl-N-phenyl-1H-indol-7-amine (6-12)

In a clean dry sealed tube, sodium tert-butylate (20 mg, 0.2 mmol) was added to a mixture of tris(dibenzylideneacetone) dipalladium(0) (18 mg, 20% mol), 2.2'-bis(diphenylphosphino)-1,1'-binaphthyl (26 mg, 40%), compound 6-5 (31 mg, 0.1 mmol) and aniline (14 mg, 0.15 mmol) in dry toluene (3 mL) under nitrogen. The mixture was heated at 120° C. in an oil bath for 16 h. The reaction was cooled to room temperature, filtered, evaporated to dryness and purified by column chromatography using $CH_2Cl_2$/$NH_4OH$ as the eluent, giving red solid, mp 158-160° C.

The compounds in table 6 were made according to processes described in scheme 6.

TABLE 6

| Structure | name | Ex. number | ID number | NMR | MS | Procedure of scheme |
|---|---|---|---|---|---|---|
| 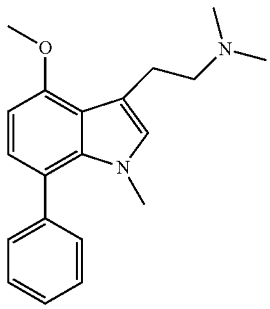 [SMILES: COc1ccc(-c2ccccc2)c2c1c(CCN(C)C)cn2C] | 2-(4-methoxy-1-methyl-7-phenyl-1H-indol-3-yl)-N,N-dimethylethanamine | 16 | 6-6 | $^1$H NMR (DMSO-d$_6$) (HCl salt) δ (ppm) 10.14 (bs, 1H), 7.33-7.46 (m, 5H), 7.04 (s, 1H), 6.83 (d, J = 7.7 Hz, 1H), 6.58 (d, J = 8.0 Hz, 1H), 3.92 (s, 3H), 3.22-3.29 (m, 2H), 3.18 (s, 3H), 3.13-3.19 (m, 2H), 2.83 (s, 6H). | calc 308.2, found 309.2 [MH]$^+$ | 6 |
| 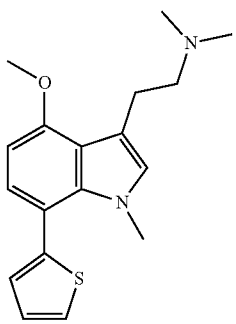 [SMILES: COc1ccc(-c2cccs2)c2c1c(CCN(C)C)cn2C] | 2-(4-methoxy-1-methyl-7-(thiophen-2-yl)-1H-indol-3-yl)-N,N-dimethylethanamine | 17 | 6-7 | $^1$H NMR (CDCl$_3$) δ (ppm) 7.32 (dd, J = 1.1, 5.0 Hz, 1H), 7.05 (dd, J = 3.3, 5.2 Hz, 1H), 7.04 (d, J = 8.2 Hz, 1H), 7.00 (dd, J = 1.1, 3.4 Hz, 1H), 6.67 (s, 1H), 6.47 (d, J = 8.0 Hz, 1H), 3.93 (s, 3H), 3.33 (s, 3H), 3.02-3.08 (m, 2H), 2.60-2.66 (m, 2H), 2.36 (s, 6H). | calc 314.2, found 315.2 [MH]$^+$ | 6 |
| 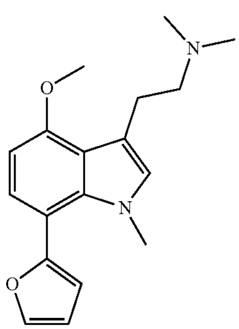 [SMILES: COc1ccc(-c2ccco2)c2c1c(CCN(C)C)cn2C] | 2-(7-(furan-2-yl)-4-methoxy-1-methyl-1H-indol-3-yl)-N,N-dimethylethanamine | 18 | 6-8 | $^1$H NMR (CDCl$_3$) δ (ppm) 7.51 (s, 1H), 7.06 (d, J = 8.0 Hz, 1H), 6.68 (s, 1H), 6.46-6.51 (m, 1H), 6.45 (d, J = 8.0 Hz, 1H), 6.36 (d, J = 2.7 Hz, 1H), 3.93 (s, 3H), 3.36 (s, 3H), 3.00-3.06 (m, 2H), 2.57-2.63 (m, 2H), 2.34 (s, 6H). | calc 298.2, found 299.2 [MH]$^+$ | 6 |
| 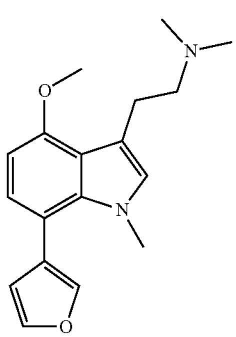 [SMILES: COc1ccc(-c2ccoc2)c2c1c(CCN(C)C)cn2C] | 2-(7-(furan-3-yl)-4-methoxy-1-methyl-1H-indol-3-yl)-N,N-dimethylethanamine | 19 | 6-9 | $^1$H NMR (CDCl$_3$) δ (ppm) 7.40-7.51 (m, 2H), 6.91 (d, J = 8.0 Hz, 1H), 6.67 (s, 1H), 6.51 (s, 1H), 6.45 (d, J = 7.7 Hz, 1H), 3.92 (s, 3H), 3.46 (s, 3H), 3.01-3.07 (m, 2H), 2.58-2.64 (m, 2H), 2.34 (s, 6H). | calc 298.2, found 299.2 [MH]$^+$ | 6 |

TABLE 6-continued

| Structure | name | Ex. number | ID number | NMR | MS | Procedure of scheme |
|---|---|---|---|---|---|---|
| 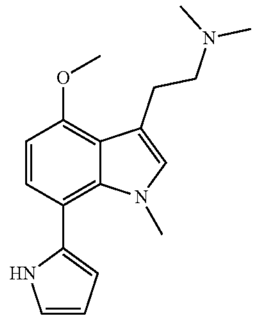 [SMILES: COc1ccc(-c2ccc[nH]2)c2c1c(CCN(C)C)cn2C] | 2-(4-methoxy-1-methyl-7-(1H-pyrrol-2-yl)-1H-indol-3-yl)-N,N-dimethylethanamine | 20 | 6-10 | $^1$H NMR (DMSO-d$_6$) (HCl salt) δ (ppm) 11.03 (bs, 1H), 7.02 (s, 1H), 6.92 (d, J = 8.0 Hz, 1H), 6.54 (m, 1H), 6.54 (d, J = 7.7 Hz, 1H), 6.07-6.11 (m, 1H), 6.59-6.63 (m, 1H), 3.90 (s, 3H), 3.23 (s, 3H), 3.10-3.29 (m, 4H), 2.81-2.87 (m, 6H). | calc 297.2, found 298.2 [MH]$^+$ | 6 |
| 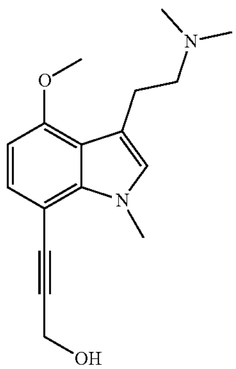 [SMILES: COc1ccc(C#CCO)c2c1c(CCN(C)C)cn2C] | 3-(3-(2-(dimethylamino)ethyl)-4-methoxy-1-methyl-1H-indol-7-yl)prop-2-yn-1-ol | 21 | 6-11 | $^1$H NMR (CDCl$_3$) δ (ppm) 7.20 (d, J = 8.0 Hz, 1H), 6.64 (s, 1H), 6.38 (d, J = 8.2 Hz, 1H), 4.53 (s, 2H), 4.04 (s, 3H), 3.90 (s, 3H), 2.96-3.02 (m, 2H), 2.53-2.59 (m, 2H), 2.32 (s, 6H). | calc 286.2, found 287.2 [MH]$^+$ | 6 |
| 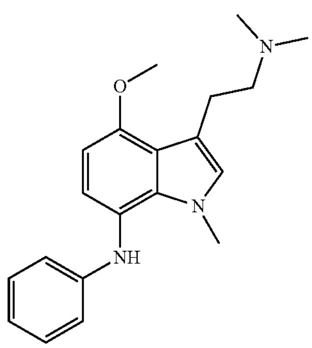 [SMILES: COc1ccc(Nc2ccccc2)c2c1c(CCN(C)C)cn2C] | 3-(2-dimethylamino)ethyl)-4-methoxy-1-methyl-N-phenyl-1H-indol-7-amine | 22 | 6-12 | $^1$H NMR (CDCl$_3$) δ (ppm) 7.13 (dd, J = 7.4, 8.5 Hz, 2H), 6.85 (d, J = 8.2 Hz, 1H), 6.72 (tt, J = 1.1, 7.4 Hz, 1H), 6.63 (s, 1H), 6.54 (dd, J = 1.1, 7.7 Hz, 2H), 6.40 (d, J = 8.0 Hz, 1H), 3.91 (s, 3H), 3.75 (s, 3H), 3.00-3.06 (m, 2H), 2.57-2.63 (m, 2H), 2.34 (s, 6H). | calc 323.2, found 324.2 [MH]$^+$ | 6 |
| 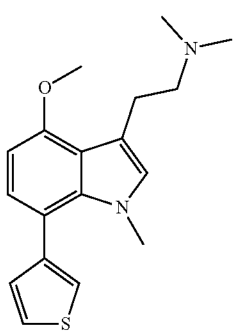 [SMILES: COc1ccc(-c2ccsc2)c2c1c(CCN(C)C)cn2C] | 2-(4-methoxy-1-methyl-7-(thiophen-3-yl)-1H-indol-3-yl)-N,N-dimethylethanamine | 23 | 6-13 | $^1$H NMR (CDCl$_3$) δ (ppm) 7.33 (dd, J = 3.0, 5.0 Hz, 1H), 7.20 (dd, J = 1.1, 2.9 Hz, 1H), 7.13 (dd, J = 1.1, 5.0 Hz, 1H), 6.93 (d, J = 8.0 Hz, 1H), 6.66 (s, 1H), 6.47 (d, J = 8.0 Hz, 1H), 3.93 (s, 3H), 3.27 (s, 3H), 3.02-3.08 (m, 2H), 2.59-2.65 (m, 2H), 2.35 (s, 6H). | calc 314.1, found 315.1 [MH]$^+$ | 6 |

TABLE 6-continued

| Structure | name | Ex. number | ID number | NMR | MS | Procedure of scheme |
|---|---|---|---|---|---|---|
| 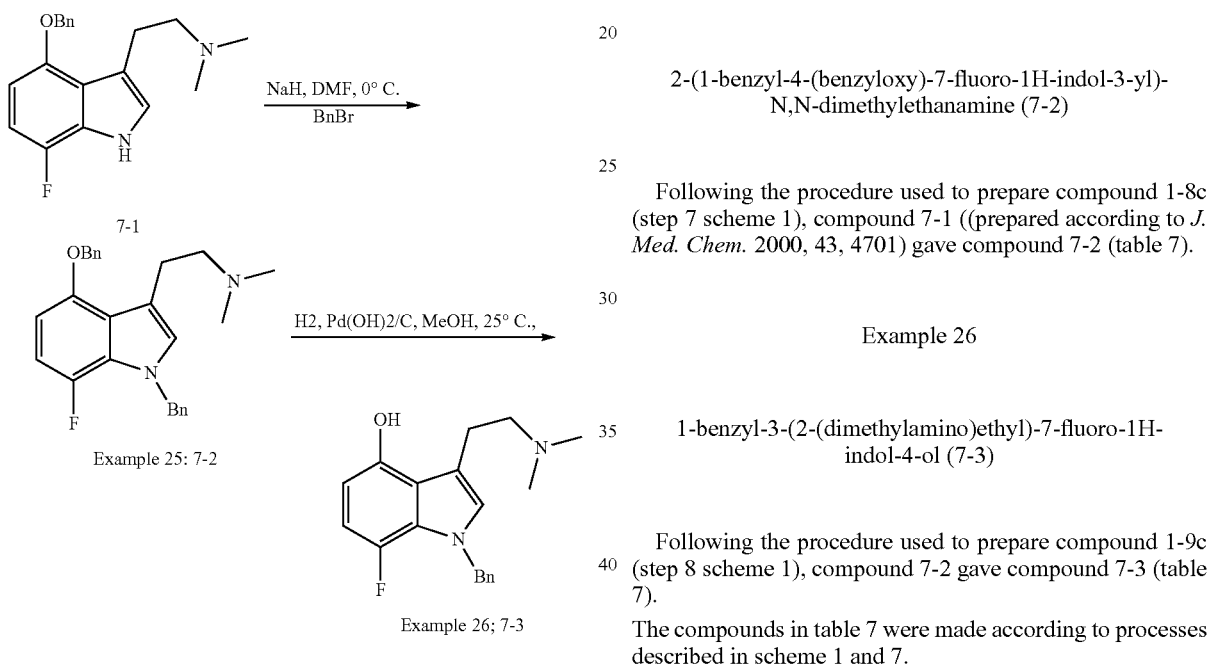 | 2-(4-methoxy-1-methyl-7-(pyridin-3-yl)-1H-indol-3-yl)-N,N-dimethylethanamine | 24 | 6-14 | $^1$H NMR (DMSO-$d_6$) (HCl salt) δ (ppm) 10.58 (bs, 1H), 8.91 (s, 1H), 8.83 (d, J = 5.5 Hz, 1H), 8.37 (d, J = 8.3 Hz, 1H), 7.91 (dd, J = 5.5, 8.3 Hz, 1H), 7.12 (s, 1H), 6.98 (d, J = 8.0 Hz, 1H), 6.68 (d, J = 8.0 Hz, 1H), 3.95 (s, 3H), 3.26 (s, 3H), 3.17-3.24 (bs, 4H), 2.82 (d, J = 5.0 Hz, 6H). | calc 309.2, found 310.2 [MH]$^+$ | 6 |

Scheme 7

Example 25: 7-2

Example 26; 7-3

Example 25

2-(1-benzyl-4-(benzyloxy)-7-fluoro-1H-indol-3-yl)-N,N-dimethylethanamine (7-2)

Following the procedure used to prepare compound 1-8c (step 7 scheme 1), compound 7-1 ((prepared according to *J. Med. Chem.* 2000, 43, 4701) gave compound 7-2 (table 7).

Example 26

1-benzyl-3-(2-(dimethylamino)ethyl)-7-fluoro-1H-indol-4-ol (7-3)

Following the procedure used to prepare compound 1-9c (step 8 scheme 1), compound 7-2 gave compound 7-3 (table 7).

The compounds in table 7 were made according to processes described in scheme 1 and 7.

TABLE 7

| Structure | name | Ex. number | ID number | NMR | MS | Procedure of scheme |
|---|---|---|---|---|---|---|
| 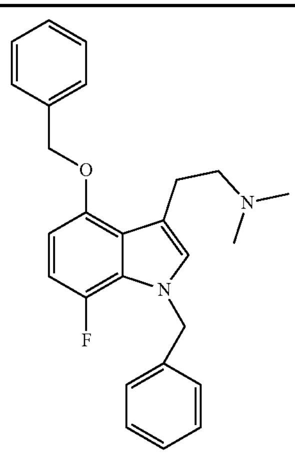 | 2-(1-benzyl-4-(benzyloxy)-7-fluoro-1H-indol-3-yl)-N,N-dimethylethanamine | 25 | 7-2 | $^1$H NMR (CDCl$_3$) (HCl salt) δ (ppm) 12.10 (bs, 1H), 7.40-7.50 (m, 5H), 7.26-7.30 (m, 3H), 7.11-7.14 (m, 2H), 6.93 (s, 1H), 6.77 (dd, J = 12.1, 8.3 Hz, 1H), 6.43 (dd, J = 8.5, 2.8 Hz, 1H), 5.36 (s, 2H), 5.03 (s, 2H), 3.16-3.22 (m, 2H), 3.00-3.07 (m, 2H), 2.23 (s, 3H), 2.22 (s, 3H) | calc 402.5, found 403.3 [MH]$^+$ | 7 Step 1 |

TABLE 7-continued

| Structure | name | Ex. number | ID number | NMR | MS | Procedure of scheme |
|---|---|---|---|---|---|---|
| 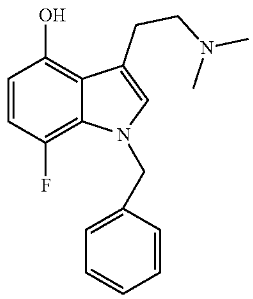 [SMILES: CN(C)CCc1cn(Cc2ccccc2)c2c(F)ccc(O)c12] | 1-benzyl-3-(2-(dimethylamino)ethyl)-7-fluoro-1H-indol-4-ol | 26 | 7-3 | $^1$H NMR (DMSO-d$_6$) (HCl salt) δ (ppm) 10.04 (bs, 1H), 9.70 (bs, 1H), 7.21-7.33 (m, 4H), 7.09-7.12 (m, 2H), 6.66 (dd, J = 12.4, 8.2 Hz, 1H), 6.27 (dd, J = 8.5, 3.3 Hz, 1H), 5.38 (s, 2H), 3.28-3.32 (m, 2H), 3.14-3.19 (m, 2H), 2.80 (s, 6H) | calc 312.3, found 313.2 [MH]$^+$ | 7 |
| 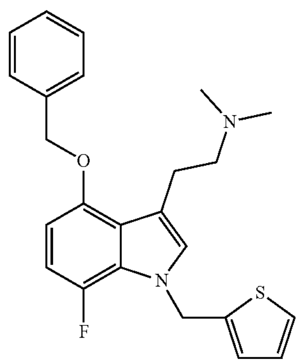 [SMILES: CN(C)CCc1cn(Cc2cccs2)c2c(F)ccc(OCc3ccccc3)c12] | 2-(4-(benzyloxy)-7-fluoro-1-(thiophen-2-ylmethyl)-1H-indol-3-yl)-N,N-dimethylethanamine | 27 | 7-4 | $^1$H NMR (CDCl$_3$) (HCl salt) δ (ppm) 12.06 (bs, 1H), 7.41-7.49 (m, 5H), 7.20 (dd, J = 5.0, 1.1 Hz, 1H), 6.95-6.97 (m, 2H), 6.92 (dd, J = 5.0, 3.6 Hz, 2H), 6.80 (dd, J = 12.1, 8.5 Hz, 1H), 6.44 (dd, J = 8.5, 2.8 Hz, 1H), 5.52 (s, 2H), 5.02 (s, 2H), 3.17-3.19 (m, 2H), 2.99-3.08 (m, 2H), 2.23 (s, 6H) | calc 408.5, found 409.0 [MH]$^+$ | 7 Step 1 |
| 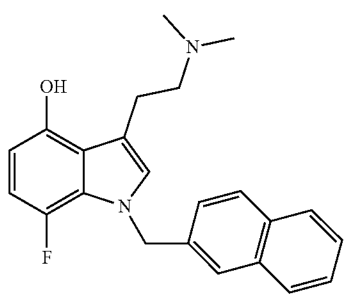 [SMILES: CN(C)CCc1cn(Cc2ccc3ccccc3c2)c2c(F)ccc(O)c12] | 3-(2-(dimethylamino)ethyl)-7-fluoro-1-(naphthalen-2-ylmethyl)-1H-indol-4-ol | 28 | 7-5 | $^1$H NMR (CDCl$_3$) δ (ppm) 7.73-7.81 (m, 3H), 7.56 (s, 1H), 7.43-7.46 (m, 2H), 7.30 (dd, J = 8.3, 1.7 Hz, 1H), 6.74 (s, 1H), 6.72 (dd, J = 12.4, 8.2 Hz, 1H), 6.37 (dd, J = 8.5, 3.6 Hz, 2H), 5.53 (s, 2H), 2.87-2.91 (m, 2H), 2.64-2.67 (m, 2H), 2.36 (s, 6H) | calc 362.2, found 363.1 [MH]$^+$ | 7 |
| 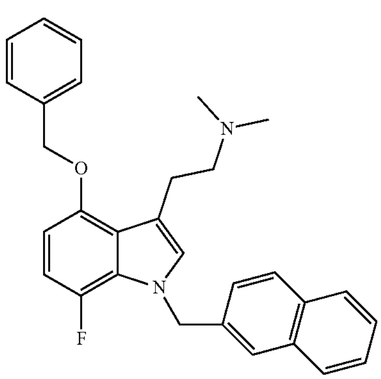 [SMILES: CN(C)CCc1cn(Cc2ccc3ccccc3c2)c2c(F)ccc(OCc3ccccc3)c12] | 2-(4-(benzyloxy)-7-fluoro-1-(naphthalen-2-ylmethyl)-1H-indol-3-yl)-N,N-dimethylethanamine | 29 | 7-6 | $^1$H NMR (CDCl$_3$) (HCl salt) δ (ppm) 12.10 (bs, 1H), 7.62-7.81 (m, 3H), 7.59 (s, 1H), 7.41-7.50 (m, 6H), 7.26-7.29 (m, 1H), 7.00 (s, 1H), 6.77 (dd, J = 12.1, 8.5 Hz, 1H), 6.43 (dd, J = 8.5, 2.7 Hz, 2H), 5.52 (s, 2H), 5.04 (s, 2H), 3.18-3.23 (m, 2H), 2.98-3.12 (m, 2H), 2.23 (s, 6H) | calc 452.2, found 453.1 [MH]$^+$ | 7 Step 1 |

TABLE 7-continued

| Structure | name | Ex. number | ID number | NMR | MS | Procedure of scheme |
|---|---|---|---|---|---|---|
| 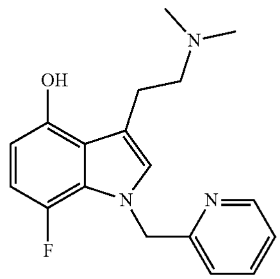 [SMILES: CN(C)CCc1cn(Cc2ccccn2)c2c(F)ccc(O)c12] | 3-(2-(dimethylamino)ethyl)-7-fluoro-1-(pyridin-2-ylmethyl)-1H-indol-4-ol | 30 | 7-7 | ¹H NMR (DMSO-d₆) (HCl salt) δ (ppm) 10.18 (bs, 1H), 9.73 (s, 1H), 8.51 (d, J = 4.9 Hz, 1H), 7.72 (t, J = 7.4 Hz, 1H), 7.27 (t, J = 5.2 Hz, 1H), 7.24 (s, 1H), 6.82 (d, J = 7.7 Hz, 1H), 6.64 (dd, J = 12.6, 8.5 Hz, 1H), 6.28 (dd, J = 8.2, 3.0 Hz, 1H), 5.48 (s, 2H), 3.29-3.36 (m, 2H), 3.16-3.21 (m, 2H), 2.79 (s, 6H) | calc 313.2, found 314.2 [MH]⁺ | 7 |
| 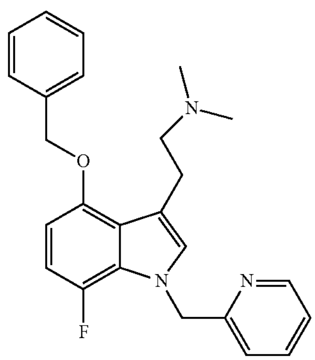 [SMILES: CN(C)CCc1cn(Cc2ccccn2)c2c(F)ccc(OCc3ccccc3)c12] | 2-(4-(benzyloxy)-7-fluoro-1-(pyridin-2-ylmethyl)-1H-indol-3-yl)-N,N-dimethylethanamine | 31 | 7-8 | ¹H NMR (CDCl₃) (HCl salt) δ (ppm) 12.06 (bs, 1H), 8.63 (d, J = 4.4 Hz, 1H), 7.88 (t, J = 8.0 Hz, 1H), 7.41-7.51 (m, 6H), 7.12 (s, 1H), 7.08 (d, J = 7.4 Hz,. 1H), 6.77 (dd, J = 12.1, 8.5 Hz, 1H), 6.46 (dd, J = 8.8, 3.0 Hz, 1H), 5.74 (s, 2H), 5.06 (s, 2H), 3.18-3.24 (m, 2H), 3.06-3.11 (m, 2H), 2.32 (s, 3H), 2.30 (s, 3H) | calc 403.2, found 404.2 [MH]⁺ | 7 Step 1 |
| 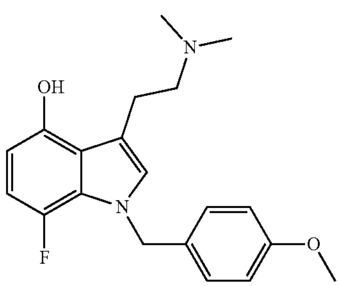 [SMILES: COc1ccc(Cn2cc(CCN(C)C)c3c(O)ccc(F)c32)cc1] | 3-(2-(dimethylamino)ethyl)-7-fluoro-1-(4-methoxybenzyl)-1H-indol-4-ol | 32 | 7-9 | ¹H NMR (DMSO-d₆) (HCl salt) δ (ppm) 10.00 (bs, 1H), 9.69 (bs, 1H), 7.23 (s, 1H), 7.09 (d, J = 8.8 Hz, 2H), 6.86 (d, J = 8.5 Hz, 2H), 6.66 (dd, J = 12.4, 8.3 Hz, 1H), 6.26 (dd, J = 8.5, 3.3 Hz, 1H), 5.29 (s, 2H), 3.69 (s, 3H), 3.27-3.32 (m, 2H), 3.12-3.17 (m, 2H), 2.79 (s, 6H) | calc 342.4, found 343.2 [MH]⁺ | 7 |
| 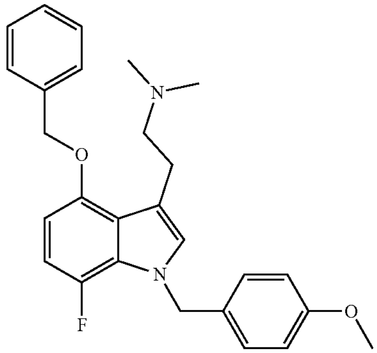 [SMILES: COc1ccc(Cn2cc(CCN(C)C)c3c(OCc4ccccc4)ccc(F)c32)cc1] | 2-(4-(benzyloxy)-7-fluoro-1-(4-methoxybenzyl)-1H-indol-3-yl)-N,N-dimethylethanamine | 33 | 7-10 | ¹H NMR (CDCl₃) (HCl salt) δ (ppm) 12.11 (bs, 1H), 7.38-7.50 (m, 5H), 7.10 (d, J = 8.8 Hz, 2H), 6.90 (s, 1H), 6.82 (d, J = 8.5 Hz, 2H), 6.77 (dd, J = 12.1, 8.5 Hz, 1H), 6.42 (dd, J = 8.3, 2.8 Hz, 1H), 5.29 (s, 2H), 5.03 (s, 2H), 3.77 (s, 3H), 3.15-3.20 (m, 2H), 2.98-3.06 (m, 2H), 2.23 (s, 3H), 2.21 (s, 3H) | calc 433.2, found 433.2 [MH]⁺ | 7 Step 1 |

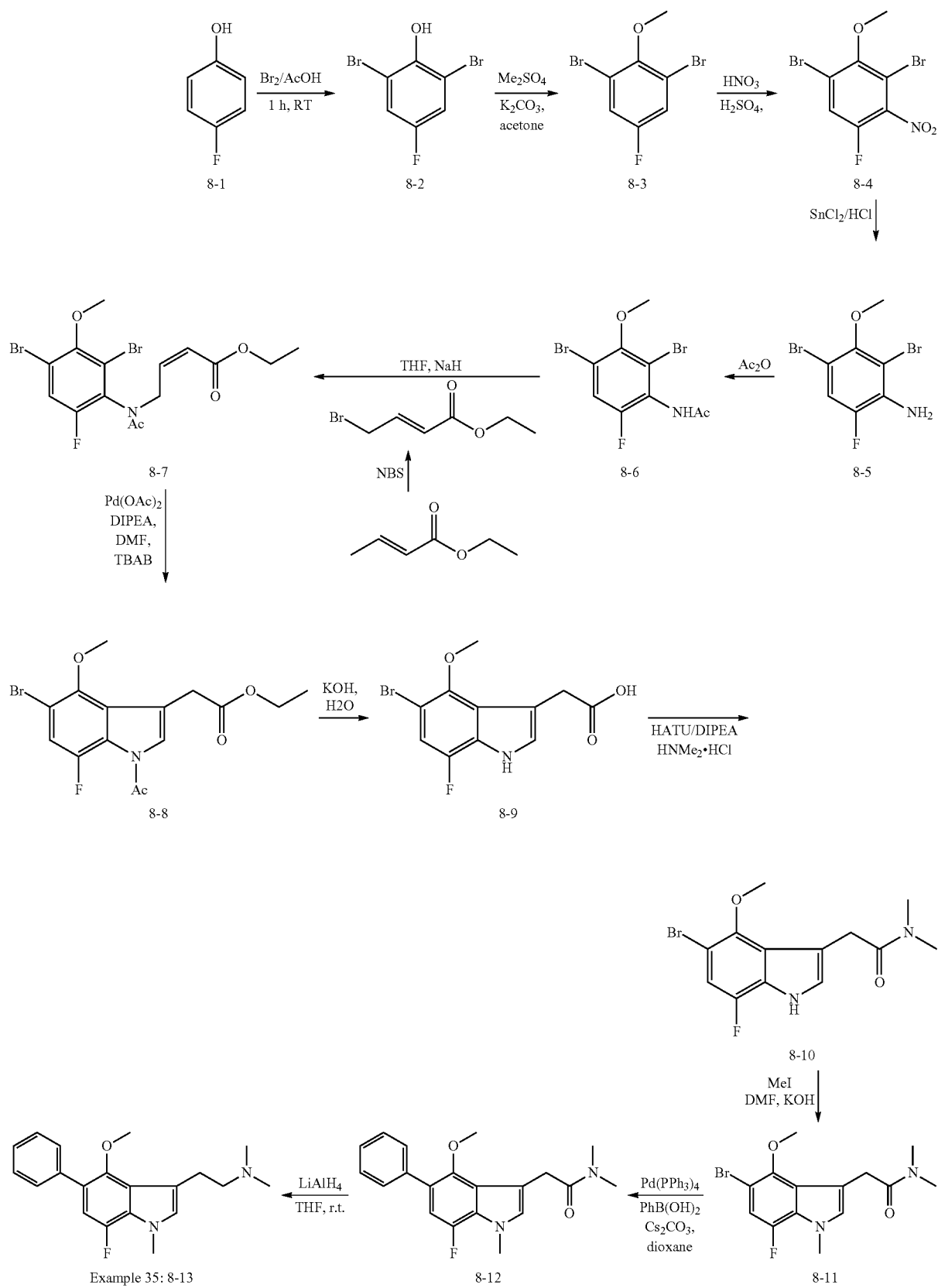
Scheme 8

Example 34

2-(7-fluoro-4-methoxy-1-methyl-5-phenyl-1H-indol-3-yl)-N,N-dimethylethanamine (8-13)

Step 1: 2,6-dibromo-4-fluorophenol (8-2): prepared according to *J. Med. Chem.* 1999, 42, 2007-2020

The solution of 8-1 (112.1 g, 1 mol) in acetic acid (1 L) was added bromine (352 g, 2.2 mol) dropwise over an hour at room temperature. After addition, the mixture was stirred for another 2 h. The reaction mixture was poured onto crushed ice followed by the addition of 500 mL of saturated aqueous $NaHSO_3$. The white precipitate was filtered and dried to afford 8-2 (246.4 g, 91.3%) as a white solid.

Step 2: 1,3-dibromo-5-fluoro-2-methoxybenzene (8-3)

To the mixture of 8-2 (262.6 g, 0.973 mmol) and $K_2CO_3$ (215 g, 1.56 mol) in acetone (1.8 L) was added $Me_2SO_4$ (140.1 g, 1.17 mol) in acetone (300 mL) dropwise via a constant pressure dropping funnel over 20 min. The mixture was stirred for 6 h at room temperature. TLC showed that the reaction was completed. The solid was filtered off and the filtrate was concentrated in vacuo to get 8-3 (273.4 g, 99%) as a white solid which was used for the next step without further purification.

Step 3: 1,3-dibromo-5-fluoro-2-methoxy-4-nitrobenzene (8-4)

The solution of 8-3 (273.4 g, 0.963 mol) dissolved in concentrated $H_2SO_4$ (1.6 L) at 0° C. The mixture of conc.$HNO_3$ (63.2 mL) and conc. $H_2SO_4$ (400 mL) was added dropwise over 1 h. The color of the reaction became orange. TLC monitored the starting material was disappeared. The reaction mixture was poured onto crushed ice and extracted with ethyl acetate (800 mL×3). The combined organic layers were combined and were concentrated in vacuo to 400 mL, which was cooled under ice bath to afforded 8-4 (234.2 g, 73.9%) as a white solid.

Step 4: 2,4-dibromo-6-fluoro-3-methoxyaniline (8-5)

To the solution of 8-4 (234.2 g, 0.784 mol) and concentrated HCl (720 mL) in ethanol (2.2 L) at room temperature, $SnCl_2.H_2O$ (415 g, 2.0 mol) was added by portions. The mixture was stirred for 16 h. TLC showed the reaction was completed. The volatiles were removed in vacuo. The residue was quenched with cooled water (500 mL) and ethyl acetate (1.5 L). The aqueous layer was neutralized with KOH until PH=6~7. The white precipitate was filtered off to get a clear solution, which was extracted with ethyl acetate (600 mL×3). The combined organic layers were washed with brine twice, dried over anhydrous sodium sulfate. After filtration and evaporation, 8-5 (212.7 g, 100%) was obtained as brownish white solid.

Step 5: N-(2,4-dibromo-6-fluoro-3-methoxyphenyl)acetamide (8-6)

Compound 8-5 (212.7 g, 0.711 mol) was added to acetic anhydride (200 mL) in one portion at 20° C. The reaction mixture was stirred for 30 minutes and then was filtered to get 8-6 (192 g, 79.2%) as a white solid.

Step 6: (Z)-ethyl 4-(N-(2,4-dibromo-6-fluoro-3-methoxyphenyl)acetamido)but-2-enoate (8-7)

To the solution of 8-6 (1.3 g, 3.82 mmol) in THF (20 mL) at room temperature was added NaH (100 mg, 4.2 mmol, dispersed in mineral oil, 60%). The mixture was stirred for 30 min until no gas was released. (E)-ethyl 4-brombut-2-enoate (0.88 g, 4.58 mmol) in THF (5 mL) was added. The mixture was stirred overnight at room temperature. TLC showed that the reaction was completed. Water was added to the reaction mixture and extracted with ethyl acetate (50 mL×3). The combined organic layers were combined and were concentrated in vacuo. The residue was purified by flash chromatography (silica gel, elution with ethyl acetate/petroleum=1:8 to 1:2) to afford 8-7 (1.6 g, 92.4%) as yellow oil.

Step 7: ethyl 2-(1-acetyl-5-bromo-7-fluoro-4-methoxy-1H-indol-3-yl)acetate (8-8)

To the solution of 8-7 (20 g, 44.0 mmol) in anhydrous DMF (250 mL) was added $Pd(OAc)_2$ (2.0 g, 8.8 mmol), $Bu_4NBr$ (14.3 g, 44.0 mmol) and DIPEA (14.2 g, 110 mmol) under $N_2$. The mixture was stirred at 80° C. for 3 h. TLC showed that the reaction was completed. The mixture was poured into ice water and extracted with ethyl acetate (150 mL×3). The organic layers were combined and were concentrated in vacuo. The residue was purified by flash chromatography (Silica-gel, petroleum ether/ethyl acetate=10:1) to afford 8-8 (13.0 g, 79%) as a white solid.

Step 8: 2-(5-bromo-7-fluoro-4-methoxy-1H-indol-3-yl)acetic acid (8-9)

To the solution of 8-8 (16.5 g, 44.0 mmol) in water (50 mL) was added 4N KOH (50 mL). The mixture was stirred at room temperature for 1 h. TLC showed that the reaction was completed. The mixture was neutralized with HCl to pH=5. The formed precipitate was collected and washed with water. After drying, 8-7 (11.5 g, 87%) was obtained as a yellowish solid.

Step 9: 2-(5-bromo-7-fluoro-4-methoxy-1H-indol-3-yl)-N,N-dimethylacetamide (8-10)

To the solution of 8-9 (11.5 g, 38.0 mmol) in THF (300 mL) was added HATU (22.0 g, 58.0 mmol) $Me_2NH.HCl$ (3.1 g, 38.0 mmol) at 0° C. After the mixture was stirred for 5 minutes, DIPEA (12.3 g, 95.3 mmol) was added. The mixture was stirred overnight at room temperature. The volatile was removed and the residue was purified by flash chromatography (Silica gel, DCM/MeOH=50:1) to afford 8-10 (9.0 g, 72%) as white solid.

Step 10: 2-(5-bromo-7-fluoro-4-methoxy-1-methyl-1H-indol-3-yl)-N,N-dimethylacetamide (8-11)

To the solution of 8-10 (7.0 g, 21.3 mmol) in anhydrous DMF (20 mL) was added KOH (4.34 g, 78.0 mmol), and MeI (4.55 g, 32.0 mmol) at room temperature. After the mixture was stirred for 1 h, TLC showed that the reaction was completed. The mixture was quenched with water and extracted with ethyl acetate (150 mL×3). The organic layers were combined and concentrated in vacuo. 8-11 (7.2 g, crude) was obtained as yellow oil and used for the next step without further purification.

Step 11: 2-(7-fluoro-4-methoxy-1-methyl-5-phenyl-1H-indol-3-yl)-N,N-dimethylacetamide (8-12)

To the solution of 8-11 (200 mg, 0.58 mmol) in dioxane (10 mL) was added phenylboronic acid (86 mg, 0.70 mmol), Pd(PPh$_3$)$_4$ (68 mg, 0.06 mmol), and Cs$_2$CO$_3$ (760 mg, 2.3 mmol) under nitrogen atmosphere. The reaction mixture was refluxed overnight, poured into water and extracted with ethyl acetate (20 mL×3). The separated organic layer was dried over anhydrous sodium sulfate and concentrated in vacuo. The residue was purified by flash chromatography (elution with petroleum ether:ethyl acetate=1:1) to afford 8-12 (160 mg, 81%) as white solid. LCMS: calc 340.4 and found 341.1 [MH]$^+$.

Step 12: 2-(7-fluoro-4-methoxy-1-methyl-5-phenyl-1H-indol-3-yl)-N,N-dimethylethanamine (8-13)

Following the procedure used to prepare compound 1-7a (step 6 scheme 1), compound 8-12 gave compound 8-13 The compounds in table 8 were made according to processes described in scheme 8.

TABLE 8

| Structure | name | Ex. number | ID number | NMR | MS | Procedure of scheme |
|---|---|---|---|---|---|---|
| 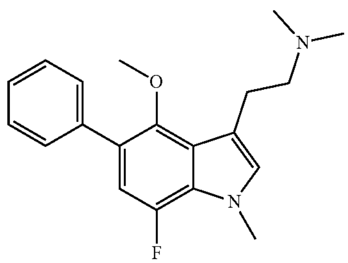 [SMILES: COc1c(-c2ccccc2)cc(F)c2c1c(CCN(C)C)cn2C] | 2-(7-fluoro-4-methoxy-1-methyl-5-phenyl-1H-indol-3-yl)-N,N-dimethylethanamine | 34 | 8-13 | 1H NMR (CDCl3) δ (ppm) 7.52(d, J = 7.2 Hz, 2H), 7.36(t, J = 7.6 Hz, 2H), 7.27(t, J = 7.2 Hz, 1H), 6.89(s, 1H), 6.82(d, J = 8.8 Hz, 1H), 3.87(s, 3H), 3.38(s, 3H), 3.30(s, 4H), 2.79(s, 6H) | calc 326.4, found 327.1 [MH]+ | 8 |
| 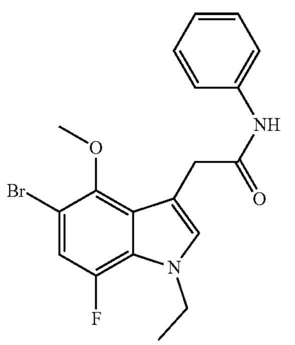 [SMILES: CCn1cc(CC(=O)Nc2ccccc2)c2c(OC)c(Br)cc(F)c21] | 2-(5-bromo-1-ethyl-7-fluoro-4-methoxy-1H-indol-3-yl)-N-phenylacetamide | 35 | 8-14 | 1H NMR (CDCl3) δ (ppm) 8.58(br.s, 1H), 7.45(t, J = 1.2 Hz, 2H), 7.26(t, J = 6.4 Hz, 5H), 7.02-7.08(m, 3H), 4.25(q, J = 7.2 Hz, 2H), 4.02(s, 3H), 3.80(s, 2H), 1.45(t, J = 6.8 Hz, 3H) | calc 406.3, found 407.0 [MH]+ | 8 Step 1-10 |

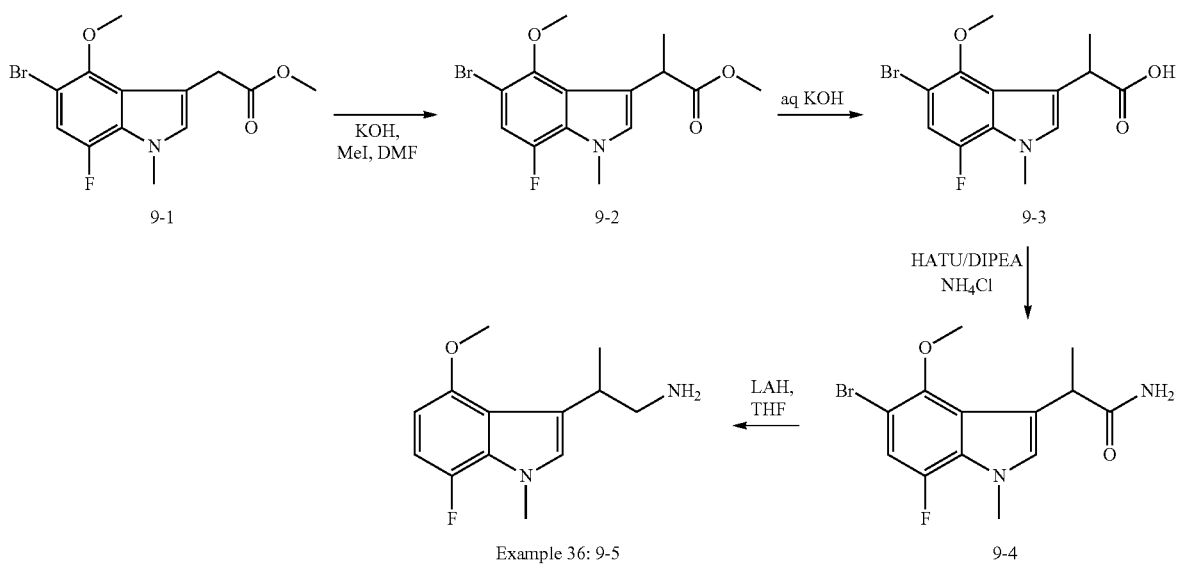

Scheme 9

Example 36: 9-5

Example 36

2-(7-fluoro-4-methoxy-1-methyl-1H-indol-3-yl)propan-1-amine (9-5)

Step 1: methyl 2-(5-bromo-7-fluoro-4-methoxy-1-methyl-1H-indol-3-yl)propanoate (9-2)

To the solution of 9-1 (prepared according to the same procedure of ethyl 2-(5-bromo-7-fluoro-4-methoxy-1H-indol-3-yl)acetate) (2.0 g, 6.3 mmol) in anhydrous DMF (15 mL) was added KOH (1.12 g, 20 mmol), and iodomethane (1.8 g, 12.7 mmol). The mixture was stirred for 1 h at room temperature. After quenching with water, the reaction mixture was extracted with ethyl acetate (150 mL×3). The combined organic layers were dried over anhydrous sodium sulfate. After filtration and concentration, a residue 9-2 (3.0 g, crude) was obtained as yellow oil which was used for the next step without further purification.

Step 2: 2-(5-bromo-7-fluoro-4-methoxy-1-methyl-1H-indol-3-yl)propanoic acid (9-3)

To the solution of 9-2 (0.5 g, 1.5 mmol) in water (10 mL) was added 2N KOH (10 mL). The mixture was stirred at room temperature for 1 h. The mixture was neutralized with HCl to pH:5. The precipitate was filtered and dried. 9-3 (210 mg, crude) was obtained as a yellow solid.

Step 3: 2-(5-bromo-7-fluoro-4-methoxy-1-methyl-1H-indol-3-yl)propanamide (9-4)

To the solution of 9-3 (150 mg, 0.45 mmol), HATU (260 mg, 0.68 mmol) and $NH_4Cl$ (26 mg, 0.49 mmol) in THF (10 mL) was added DIPEA (147 mg, 0.57 mmol) at 0° C. The mixture was stirred overnight at room temperature. The mixture was diluted with ethyl acetate (30 mL) and washed with brine twice. The combined organic layers were dried over anhydrous sodium sulfate. After filtration and concentration, the obtained residue was purified by flash chromatography (Silica gel, DCM:MeOH) to afford 9-4 (90 mg, 84%) as yellow oil.

Step 4: 2-(7-fluoro-4-methoxy-1-methyl-1H-indol-3-yl)propan-1-amine (9-5)

To the solution of 9-4 (154 mg, 0.46 mmol) in anhydrous THF (10 mL) was added $LiAlH_4$ (53 mg, 1.40 mmol). The mixture was heated to reflux for 2 h. $Na_2SO_4.10H_2O$ was added and the solid was filtered off. The filtrate was concentrated in vacuo to get a residue, which was purified by preparative TLC (DCM:MeOH:10:1) to afford compound 9-5 (30 mg, 27% yield) as white solid.

The compound in table 9 was made according to processes described in scheme 9.

TABLE 9

| Structure | name | Ex. number | ID number | NMR | MS | Procedure of scheme |
|---|---|---|---|---|---|---|
| 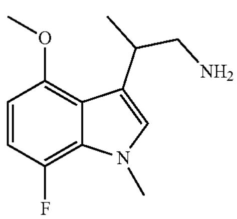 [SMILES: COc1ccc(F)c2c1c(C(C)CN)cn2C] | 2-(7-fluoro-4-methoxy-1-methyl-1H-indol-3-yl)propan-1-amine | 36 | 9-5 | calc 236.3, found 237.1 [MH]+ | 1H NMR (DMSO-d6) δ (ppm) 6.79(s, 1H), 6.73(dd, J1 = 8.8 Hz, J2 = 9.4 Hz, 1H), 6.27(dd, J1 = 2.4 Hz, J2 = 6.5 Hz, 1H), 3.9(d, J = 1.6 Hz, 3H), 3.88(s, 3H), 3.66-3.69(m, 1H), 3.19-3.23(m, 1H), 3.02-3.12(m, 3H), 1.37(d, J = 6.8 Hz, 3H), 1.25(s, 1H). | 9 |

Scheme 11

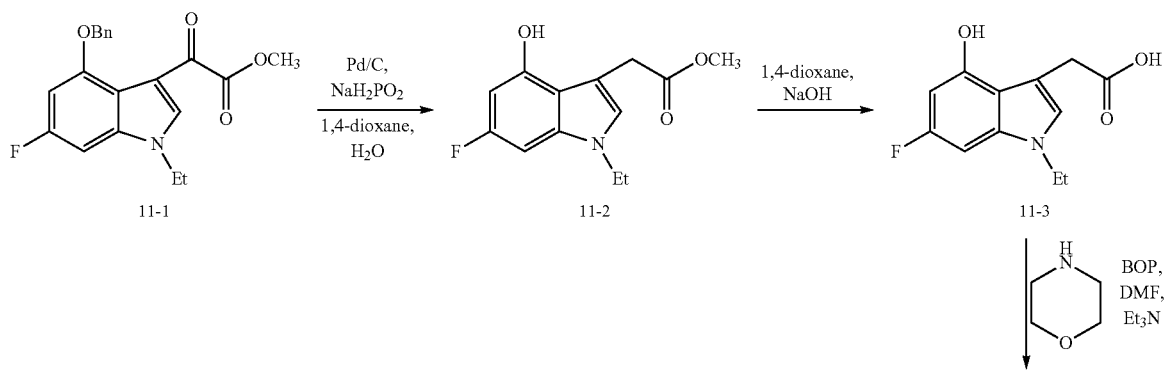

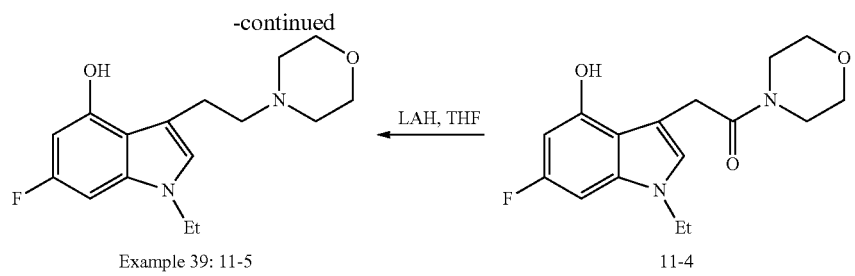

Example 39: 11-5     11-4

Example 39

1-ethyl-6-fluoro-3-(2-morpholinoethyl)-1H-indol-4-ol (11-5)

Step 1: methyl 2-(1-ethyl-6-fluoro-4-hydroxy-1H-indol-3-yl)acetate (11-2)

To a solution of 11-1 (15 g, 42.21 mmol) in dioxane (130 mL) was added Pd/C (10%, 3 g) and $NaH_2PO_2$ (21.5 g, 203 mmol in 21.5 mL of water). The mixture was heated to reflux for 6 days. After cooling, the mixture was filtered through a silica gel pad and washed with methanol (100 mL). The filtrate was concentrated in vacuo to get a residue, which was purified by silica gel chromatography (elution with petroleum:ethyl acetate=2:1) to get 11-2 (5.4 g, 51%) as a white solid. LCMS: calc 251.3 and found 251.9[MH]+.

Step 2: 2-(1-ethyl-6-fluoro-4-hydroxy-1H-indol-3-yl)acetic acid (11-3)

Following the procedure used to prepare compound 8-7 (step 8 scheme 8), NaOH was replaced by KOH, compound 11-2 gave compound 11-3.

Step 3: 2-(1-ethyl-6-fluoro-4-hydroxy-1H-indol-3-yl)-1-morpholinoethanone (11-4)

To a solution of compounds 11-3 (119 mg, 0.5 mmol) in DMF (2 mL) was added morpholine (66 uL, 0.75 mmol), triethylamine (0.24 mL, 1.75 mmol) and BOP (265 mg, 0.6 mmol). The reaction mixture was stirred at room temperature overnight. The solution was diluted with water and extracted with EtOAc. Combined organic layers were washed with 1N HCl, water, brine, dried over $MgSO_4$, filtered and concentrated. The crude material was purified by flash chromatography (silica gel, ethyl acetate:hexanes: 25:75 to 100%) gave pure 11-4 (140 mg, 91%) as a white foam.

Step 4: 1-ethyl-6-fluoro-3-(2-morpholinoethyl)-1H-indol-4-ol (11-5)

Following the procedure used to prepare compound 1-7a (step 6 scheme 1), compound 11-4 gave compound 11-5 (41 mg, 27%) as a white solid.

The compounds in table 11 were made according to processes described in scheme 1 and 11.

TABLE 11

| Structure | name | Ex. number | ID number | NMR | MS | Procedure of scheme |
|---|---|---|---|---|---|---|
| 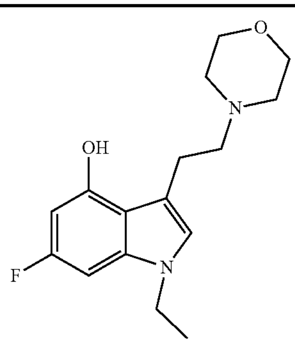 | 1-ethyl-6-fluoro-3-(2-morpholinoethyl)-1H-indol-4-ol | 39 | 11-5 | (300 MHz, DMSO-d6) δ (ppm) (HCl salt) - 10.61 (br. s, 1H), 10.17 (s, 1H), 7.05 (s, 1H), 6.70 (dd, J = 10.2 and 2.1 Hz, 1H), 6.24 (dd, J = 11.4 and 2.1 Hz, 1H), 4.04-3.94 (m, 4H), 3.76 (t, J = 11.7 Hz, 2H), 3.46 (d, J = 12.3 Hz, 2H), 3.33 (br s, 2H), 3.19-3.06 (m, 4H), 1.26 (t, J = 7.2, 3H) | calc 292.4, found 293.0 [MH]+ | 11 |
| 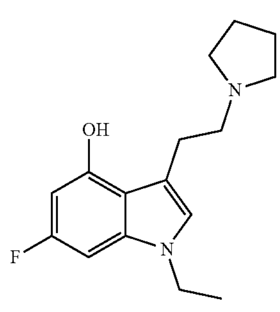 [SMILES: CCn1cc(CCN2CCCC2)c2c(O)cc(F)cc21] | 1-ethyl-6-fluoro-3-(2-(pyrrolidin-1-yl)ethyl)-1H-indol-4-ol | 40 | 11-6 | (300 MHz, DMSO-d6) δ (ppm) (HCl salt) 10.41 (br. s, 1H), 10.20 (s, 1H), 7.06 (s, 1H), 6.70 (dd, J = 10.2 and 2.1 Hz, 1H), 6.25 (dd, J = 11.4 and 2.1 Hz, 1H), 4.01 (q, J = 7.2 Hz, 2H), 3.53 (br. s, 2H), 3.33 (br s, 2H), 3.14-3.00 (m, 4H), 1.98-1.86 (m, 4H), 1.26 (t, J = 7.2 Hz, 3H) | calc 276.4 found 277.1 [MH]+ | 11 |

TABLE 11-continued

| Structure | name | Ex. number | ID number | NMR | MS | Procedure of scheme |
|---|---|---|---|---|---|---|
| 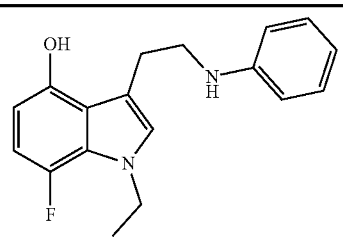 | 1-ethyl-7-fluoro-3-(2-(phenylamino)ethyl)-1H-indol-4-ol | 41 | 11-7 | (300 MHz, DMSO-d6) δ (ppm) 9.52(s, 1H), 7.25-6.63(m, 8H), 6.22(dd, J1 = 2.8 Hz, J2 = 6.2 Hz, 1H), 4.18(q, J = 7.2 Hz, 2H), 3.39(t, 2H, J = 7.2), 3.06(t, 2H, J = 8.0), 1.32(t, 3H, J = 7.2). | calc 298.4, found 299.1 [MH]+ | 11 |
| 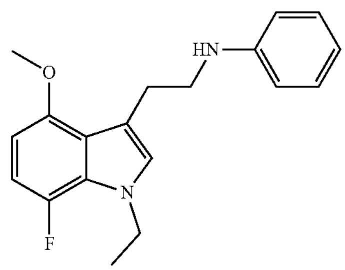 [SMILES: CCn1cc(CCNc2ccccc2)c2c(OC)ccc(F)c21] | N-(2-(1-ethyl-7-fluoro-4-methoxy-1H-indol-3-yl)ethyl)aniline | 42 | 11-8 | (300 MHz, DMSO-d6) δ (ppm) 7.14(s, 1H), 7.07(t, J = 8.0 Hz, 2H), 6.80(dd, J1 = 8.4 Hz, J2 = 9.0 Hz, 1H), 6.61(d, J = 8.0 Hz, 2H), 6.50(t, J = 6.8 Hz, 1H), 6.37(dd, J1 = 2.8 Hz, J2 = 6.3 Hz, 1H), 5.68(t, J = 5.6 Hz, 1H), 4.21(q, J = 6.8 Hz, 2H), 3.86(s, 3H), 3.24(q, J = 6.8 Hz, 2H), 2.99(t, J = 8.0 Hz, 2H), 1.31(t, J = J = 6.8 Hz, 3H) | calc 312.4, found 313.0 [MH]+ | 11 |
| 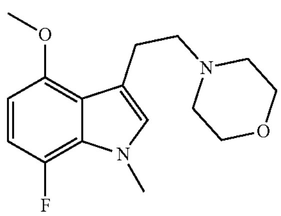 [SMILES: COc1ccc(F)c2c1c(CCN1CCOCC1)cn2C] | 4-(2-(7-fluoro-4-methoxy-1-methyl-1H-indol-3-yl)ethyl)morpholine | 43 | 11-9 | 1H NMR (CDCl3) δ (ppm) 6.71(dd, J1 = 8.4 Hz, J2 = 9.6 Hz, 2H), 6.25(dd, J1 = 2.8 Hz, J2 = 6.3 Hz, 1H), 3.89(d, J = 1.6 Hz, 3H), 3.87(s, 3H), 3.82(s, 4H), 3.08(t, J = 6.8 Hz, 2H), 2.73(s, 3H), 2.64(s, 3H). | calc 292.4, found 293.1 [MH]+ | 11 |
| 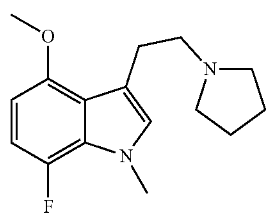 [SMILES: COc1ccc(F)c2c1c(CCN1CCCC1)cn2C] | 7-fluoro-4-methoxy-1-methyl-3-(2-(pyrrolidin-1-yl)ethyl)-1H-indole | 44 | 11-10 | 1H NMR (CDCl3) δ (ppm) 6.80(s, 1H), 6.68(dd, J1 = 8.4 Hz, J2 = 9.1 Hz, 2H), 6.22(dd, J1 = 2.8 Hz, J2 = 6.6 Hz, 1H), 3.83(s, 6H), 3.73-3.80(m, 2H), 3.26-3.37(m, 4H), 2.86-2.87(m, 2H), 1.99-2.18(m, 4H).z | calc 276.4, found 277.1 [MH]+ | 11 |
| 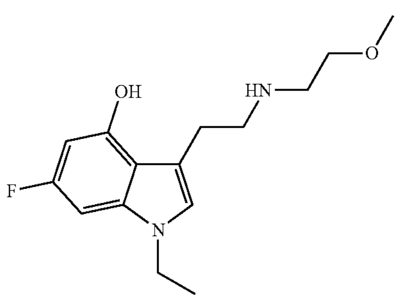 [SMILES: CCn1cc(CCNCCOC)c2c(O)cc(F)cc21] | 1-ethyl-6-fluoro-3-(2-(2-methoxyethylamino)ethyl)-1H-inol-4-ol | 44b | 11-11 | 1H NMR (300 MHz, MeOD) δ (ppm) 6.97 (s, 1H), 6.59 (dd, J = 9.9 and 1.8 Hz, 1H), 6.21 (dd, J = 11.4 and 1.8 Hz, 1H), 4.05 (q, J = 7.2 Hz, 2H), 3.62 (t, J = 4.5 Hz, 2H), 3.40-3.35 (m, 4H), 3.24-3.17 (m, 4H), 1.38 (t, J = 7.2 Hz, 3H) | Calc 280.16, found 281.1 [MH]+ | 11 |
| 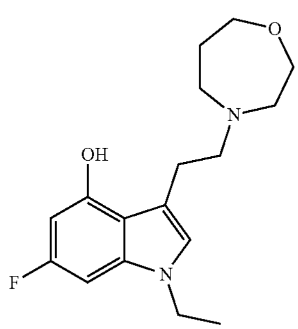 [SMILES: CCn1cc(CCN2CCCOCC2)c2c(O)cc(F)cc21] | 3-(2-(1,4-oxazepan-4-yl)ethyl)-1-ethyl-6-fluoro-1H-indol-4-ol | 44c | 11-12 | 1H NMR (300 MHz, DMSO) δ (ppm) 11.10 (s, 1H), 6.94 (s, 1H), 6.63 (dd, J = 10.2, 2.1 Hz, 1H), 6.13 (dd, J = 11.6, 2.2 Hz, 1H), 3.97 (q, J = 7.1 Hz, 2H), 3.76-3.51 (m, 4H), 2.88-2.80 (m, 4H), 2.76-2.68 (m, 6H), 2.41 (s, 2H), 1.88-1.76 (m, 2H), 1.26 (t, J = 7.2 Hz, 3H). | calc 306.17, found 307.1 [MH]+ | 11 |

TABLE 11-continued

| Structure | name | Ex. number | ID number | NMR | MS | Procedure of scheme |
|---|---|---|---|---|---|---|
| 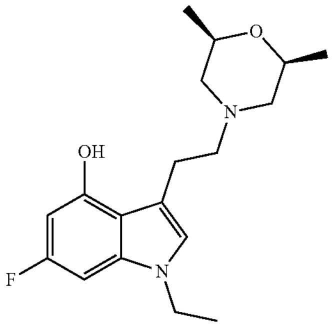 [SMILES: CCn1cc(CCN2C[C@@H](C)O[C@@H](C)C2)c2c(O)cc(F)cc21] | 3-(2-cis-2,6-dimethylmorpholino) ethyl)-1-ethyl-6-fluoro-1H-indol-4-ol | 44e | 11-13 | 1H NMR (300 MHz, DMSO) δ (ppm) 10.69 (s, 1H), 6.94 (s, 1H), 6.64 (dd, J = 10.2, 2.1 Hz, 1H), 6.13 (dd, J = 11.6, 2.1 Hz, 1H), 3.97 (q, J = 7.1 Hz, 2H), 3.84-3.42 (m, 2H), 3.04-2.67 (m, 4H), 1.68 (t, J = 10.8 Hz, 2H), 1.25 (t, J = 7.2 Hz, 3H), 1.04 (d, J = 6.3 Hz, 6H) | calc 320.19, found 321.2 [MH]+ | 11 |
| 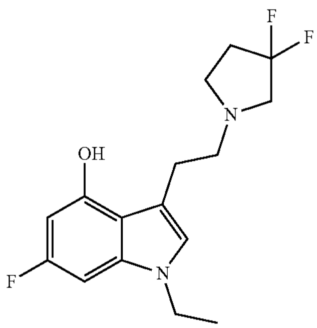 [SMILES: CCn1cc(CCN2CCC(F)(F)C2)c2c(O)cc(F)cc21] | 3-(2-(3,3-difluoropyrrolidin-1-yl)ethyl)-1-ethyl-6-fluoro-1H-indol-4-ol | 44f | 11-14 | 1H NMR (300 MHz, DMSO) δ (ppm) 10.00 (s, 1H), 6.94 (s, 1H), 6.64 (dd, J = 10.3, 2.1 Hz, 1H), 6.15 (dd, J = 11.6, 2.1 Hz, 1H), 3.98 (q, J = 7.2 Hz, 2H), 3.01-2.80 (m, 4H), 2.80-2.52 (m, 4H), 2.33-2.10 (m, 2H), 1.25 (t, J = 7.2 Hz, 3H). | calc 312.14, found 313.1 [MH]+ | 11 |
| 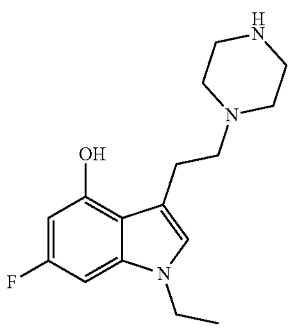 [SMILES: CCn1cc(CCN2CCNCC2)c2c(O)cc(F)cc21] | 1-ethyl-6-fluoro-3-(2-(piperazin-1-yl)ethyl)-1H-indol-4-ol | 44g | 11-15 | 1H NMR (300 MHz, MeOD-d6) δ (ppm) 6.83 (s, 1H), 6.52 (dd, J = 10.0, 2.1 Hz, 1H), 6.15 (dd, J = 11.4, 2.1 Hz, 1H), 4.00 (q, J = 7.2 Hz, 2H), 3.03-2.87 (m, 6H), 2.69 (t, J = 6.7 Hz, 2H), 2.59 (br.s, 4H), 1.35 (t, J = 7.2 Hz, 3H) | calc 291.17, found 292.1 [MH]+ | 11 |

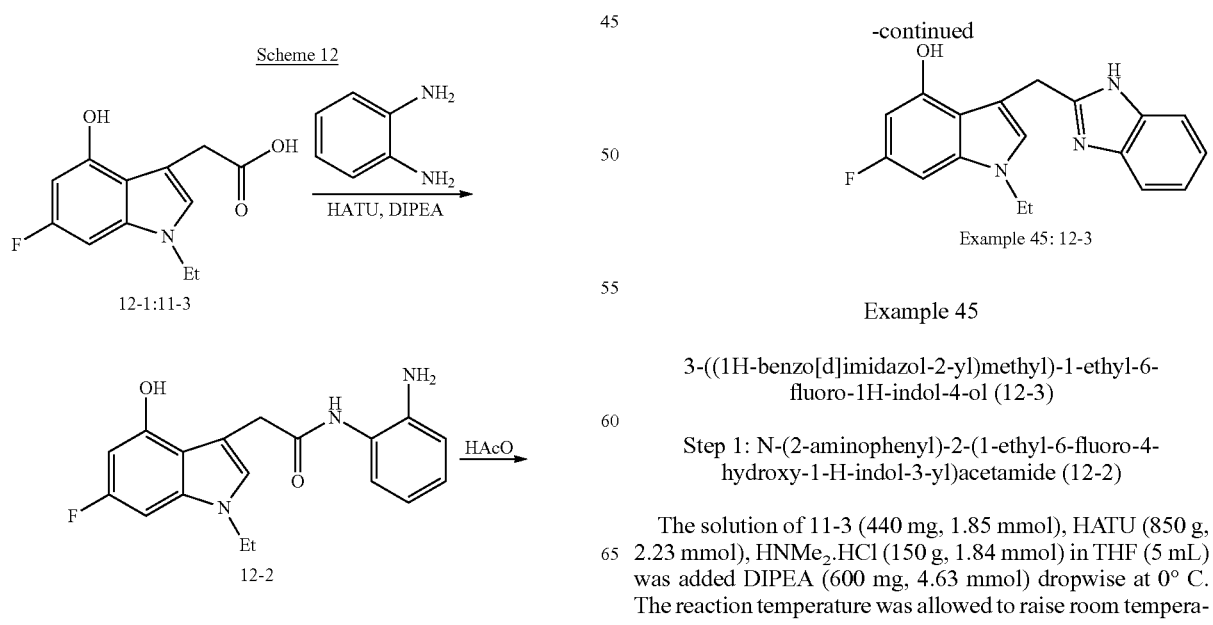

Example 45

3-((1H-benzo[d]imidazol-2-yl)methyl)-1-ethyl-6-fluoro-1H-indol-4-ol (12-3)

Step 1: N-(2-aminophenyl)-2-(1-ethyl-6-fluoro-4-hydroxy-1-H-indol-3-yl)acetamide (12-2)

The solution of 11-3 (440 mg, 1.85 mmol), HATU (850 g, 2.23 mmol), HNMe$_2$.HCl (150 g, 1.84 mmol) in THF (5 mL) was added DIPEA (600 mg, 4.63 mmol) dropwise at 0° C. The reaction temperature was allowed to raise room temperature and stirred overnight. The volatile was removed by evaporation. A white residue was obtained, which was quenched with 100 mL of water and extracted with DCM (50 mL×4). The combined organic layers were dried over anhydrous $Na_2SO_4$. After filtration and concentration, the residue was purified by silica gel chromatography (elution with petroleum:ethyl acetate: 1:1) to get 12-2 (324 mg, 53.5%) as a white solid. LCMS: calc 327.4 and found 328.1 [MH]+.

Step 2: 3-((1H-benzo[d]imidazol-2-yl)methyl)-1-ethyl-6-fluoro-1H-indol-4-ol (12-3)

The solution of 12-2 (0.3 g, 0.92 mmol) in 25 mL of acetic acid was heated to 80° C. for 8 h. The volatile was removed in vacuo and the residue was neutralized with $Na_2CO_3$ solution to pH:7. The mixture was extracted with ethyl acetate (100 mL) and washed with brine. The organic layer was dried over anhydrous $Na_2SO_4$. After filtration and concentration, a residue was obtained, which was purified by preparative TLC to give 12-3 (68 mg, 23.9%)

The compounds in table 12 were made according to processes described in scheme 1 and 12.

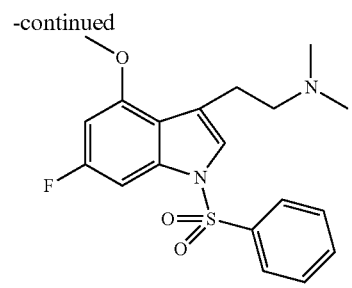

Example 52: 15-2

Example 52

2-(6-fluoro-4-methoxy-1-(phenylsulfonyl)-1H-indol-3-yl)-N,N-dimethylethan amine (15-2)

Step 1: 2-(6-fluoro-4-methoxy-1-(phenylsulfonyl)-1H-indol-3-yl)-N,N-dimethylethan amine (15-2)

To the solution of 15-1 (100 mg, 0.42 mmol) in dry DMF (4 mL) was added NaH (24 mg, 0.6 mmol, dispersed in mineral

TABLE 12

| Structure | name | Ex. number | ID number | NMR | MS | Procedure of scheme |
|---|---|---|---|---|---|---|
| (structure with OH, indole, benzimidazole, F, ethyl) | 3-((1H-benzo[d]imidazol-2-yl)methyl)-1-ethyl-6-fluoro-1H-indol-4-ol | 45 | 12-3 | 1H NMR (CDCl3) δ (ppm) 11.90(br.s, 1H), 7.48(dd, J1 = 3.2 Hz, J2 = 4.0 Hz, 2H), 7.14(dd, J1 = 3.2 Hz, J2 = 4.8 Hz, 2H), 7.06(s, 1H), 6.73(dd, J1 = 2.0 Hz, J2 = 7.8 Hz, 1H), 6.23(dd, J1 = 1.6 Hz, J2 = 9.7 Hz, 1H), 4.33(s, 2H), 4.03(q, J = 7.2 Hz, 2H), 1.26(q, J = 6.8 Hz, 3H) | calc 309.3, found 310.1 [MH]+ | 12 |
| (structure with OH, indole, benzoxazole, F, ethyl) | 3-(benzo[d]oxazol-2-ylmethyl)-1-ethyl-6-fluoro-1H-indol-4-ol | 46 | 12-4 | 1H NMR (CDCl3) δ (ppm) 7.67(dd, J1 = 3.2 Hz, J2 = 4.2 Hz, 1H), 7.50(dd, J1 = 2.4 Hz, J2 = 3.7 Hz, 1H), 7.29-7.33(m, 2H), 6.94(s, 1H), 6.54(40, J1 = 1.8 Hz, J2 = 7.2 Hz, J3 = 7.4 Hz, 2H), 4.42(s, 2H), 3.99(q, J = 7.2 Hz, 2H), 1.40(t, 3H, J = 7.6 Hz) | calc 310.3, found 311.0 [MH]+ | 12 |

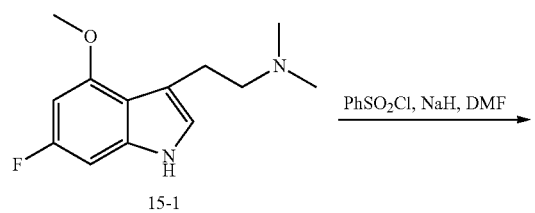

Scheme 15

PhSO₂Cl, NaH, DMF 15-1 oil, 60%) in portions at 0° C. After stirring for 0.5 h, benzenesulfonyl chloride (148 mg, 0.84 mmol) was added dropwise. After stirring for another 2 h, the mixture was quenched with water and extracted with ethyl acetate. The combined organic layers were dried over anhydrous sodium sulfate. After filtration and concentration, a yellow solid was obtained, which was purified by flash chromatography (silica gel, DCM:MeOH 5%) to get 15-2 (30 mg, 19%) as a white solid

TABLE 16

| Structure | name | Ex. number | ID number | NMR | MS | Procedure of scheme |
|---|---|---|---|---|---|---|
| 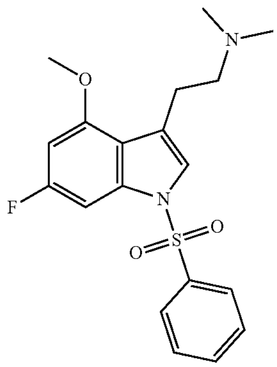 [SMILES: COc1cc(F)cc2c1c(CCN(C)C)cn2S(=O)(=O)c1ccccc1] | 2-(6-fluoro-4-methoxy-1-(phenylsulfonyl)-1H-indol-3-yl)-N,N-dimethylethanamine | 52 | 15-2 | 1H (NMR (CDCl3) δ (ppm): 7.86(d, J = 7.6 Hz, 2H), 7.56(t, J = 7.2 Hz, 1H), 7.46(t, 2H, J = 8 Hz), 7.33(dd, J1 = 2.0 Hz, J2 = 7.5 Hz, 1H), 7.25(s, 1H), 6.43(dd, J1 = 1.6 Hz, L2 = 9.7 Hz, 1H), 3.86(s, 3H), 3.05(t, J = 7.2 Hz, 2H), 2.75(t, J = 8 Hz, 2H), 2.48(s, 6H) | calc 376.5, found 377.1 [MH]+ | 15 |

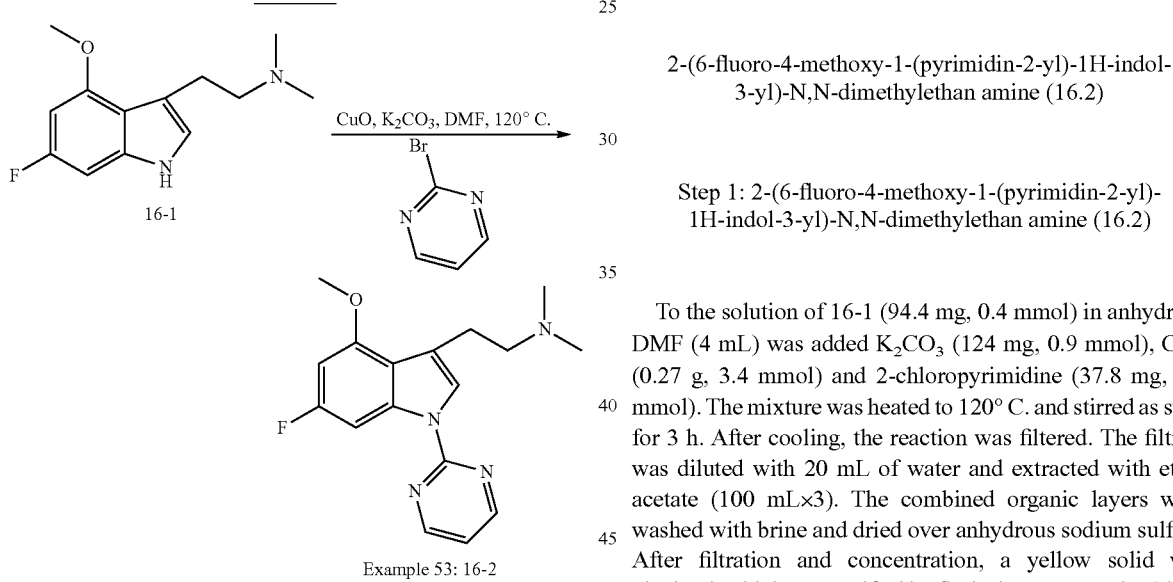

Example 53: 16-2

Example 53

2-(6-fluoro-4-methoxy-1-(pyrimidin-2-yl)-1H-indol-3-yl)-N,N-dimethylethan amine (16.2)

Step 1: 2-(6-fluoro-4-methoxy-1-(pyrimidin-2-yl)-1H-indol-3-yl)-N,N-dimethylethan amine (16.2)

To the solution of 16-1 (94.4 mg, 0.4 mmol) in anhydrous DMF (4 mL) was added K₂CO₃ (124 mg, 0.9 mmol), CuO (0.27 g, 3.4 mmol) and 2-chloropyrimidine (37.8 mg, 0.3 mmol). The mixture was heated to 120° C. and stirred as such for 3 h. After cooling, the reaction was filtered. The filtrate was diluted with 20 mL of water and extracted with ethyl acetate (100 mL×3). The combined organic layers were washed with brine and dried over anhydrous sodium sulfate. After filtration and concentration, a yellow solid was obtained, which was purified by flash chromatography (silica gel, DCM:MeOH 5%) to give 16-2 (22.7 mg, 18.1%)

TABLE 17

| Structure | name | Ex. number | ID number | NMR | MS | Procedure of scheme |
|---|---|---|---|---|---|---|
| 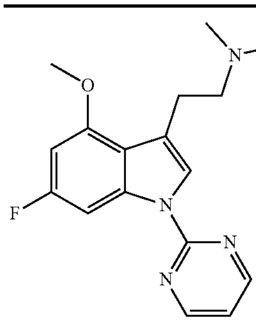 | 2-(6-fluoro-4-methoxy-1-(pyrimidin-2-yl)-1H-indol-3-yl)-N,N-dimethylethanamine | 53 | 16-2 | 1H NMR (CDCl3) δ (ppm) 8.66(d, J = 4.8 Hz, 2H), 8.18(dd, J1 = 1.6 Hz, J2 = 9.3 Hz, 1H), 7.89(s, 1H), 7.02(t, J = 4.8 Hz, 1H), 6.46(dd, J1 = 1.6 Hz, J2 = 9.7 Hz, 1H), 3.91(s, 3H), 3.05(t, J1 = 7.6 Hz, 2H), 2.65(t, J1 = 8.4 Hz, 2H), 2.36(s, 6H). | calc 314.4, found 315.1 [MH]+ | 16 |

Scheme 17

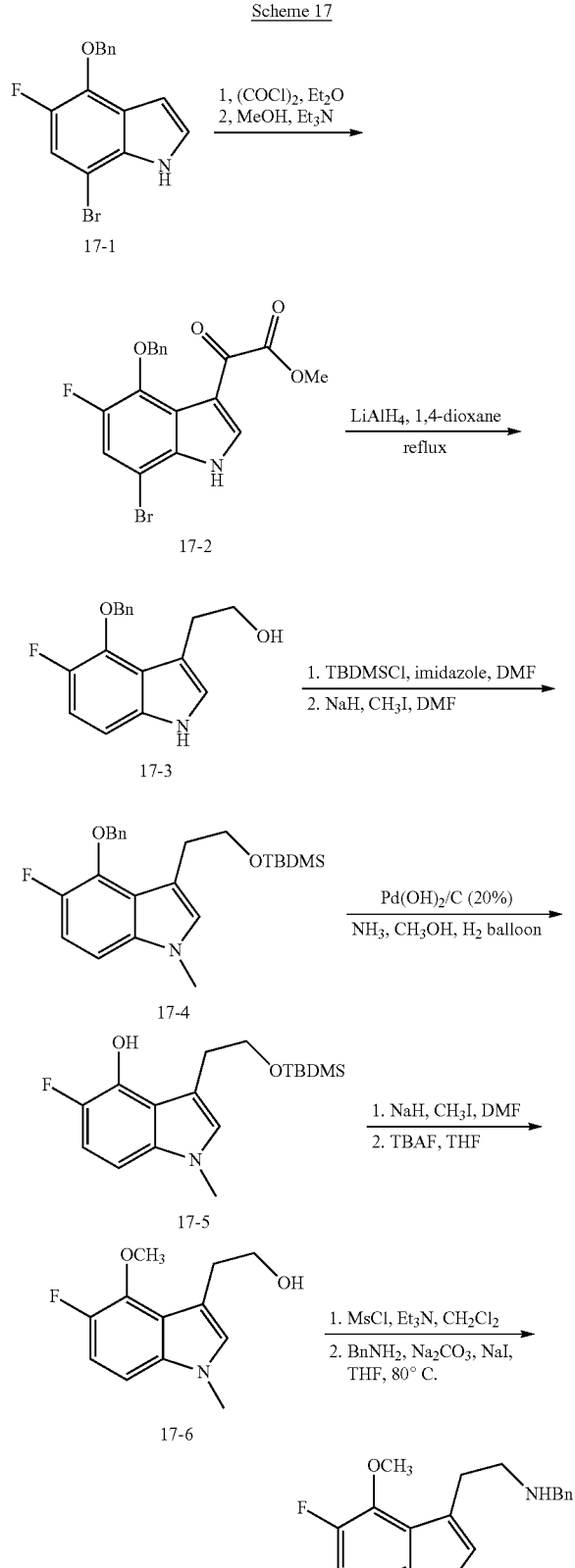

Example 54

N-Benzyl-2-(5-fluoro-4-methoxy-1-methyl-1H-indol-3-yl)ethanamine (17-7)

Step 1: Methyl 2-(4-(benzyloxy)-7-bromo-5-fluoro-1H-indol-3-yl)-2-oxoacetate (17-2)

A solution of oxalyl chloride (0.8 mL, 9.37 mmol) in anhydrous ether (20 mL) was added dropwise over 20 min to a 0° C. solution of 17-1 (2.0 g, 6.247 mmol) (prepared according patent WO2009/103710) in anhydrous ether (20 mL). The reaction mixture was stirred at room temperature overnight, cooled to −20° C., and treated with a mixture of $Et_3N$ in $CH_3OH$. The reaction was diluted with EtOAc, washed with water and brine, and dried over $Na_2SO_4$. After concentration, the resulting residue was recrystallized from EtOAc to afford 17-2 as a white solid in 60% yield (1.5 g). $^1H$ NMR (300 MHz, $CDCl_3$) δ (ppm) 8.90 (br, 1H), 8.23 (d, J=3.3 Hz, 1H), 7.51-7.53 (m, 2H), 7.28-7.35 (m, 4H), 5.18 (s, 2H), 3.80 (s, 3H).

Step 2: 2-(4-(Benzyloxy)-5-fluoro-1H-indol-3-yl)ethanol (17-3)

A solution of 17-2 (1.98 g, 4.874 mmol) in dry 1,4-dioxane (80 mL) was added dropwise to a slurry of $LiAlH_4$ (1.85 g, 48.74 mmol) in dry 1,4-dioxane (40 mL) at reflux. The mixture was held at reflux for 1 h. The mixture was then cooled, quenched with 2 mL $H_2O$, 2 mL NaOH (15%) solution, and 6 mL $H_2O$. After stirring for 20 min, the mixture was filtered and the filtrate was concentrated. The resulting residue was purified by column chromatography on silica gel with hexanes/ethyl acetate (1:0 to 1:1) as eluent to afford 17-3 as a colorless oil in 56% yield (1.0 g). $^1H$ NMR (300 MHz, $CDCl_3$) δ (ppm) 7.97 (br, 1H), 7.47-7.50 (m, 2H), 7.34-7.43 (m, 3H), 6.96-6.98 (m, 3H), 5.27 (d, J=1.1 Hz, 2H), 3.74 (dt, J=6.3, 6.0 Hz, 2H), 2.96 (t, J=6.3 Hz, 2H), 1.47 (t, J=6.3 Hz, 1H). APCI [M+1]: 286.1

Step 3: 4-(Benzyloxy)-3-(2-((tert-butyldimethylsilyl)oxy)ethyl)-5-fluoro-1-methyl-1H-indole (17-4)

To a solution of 17-3 (1.4 g. 4.907 mmol) in DMF (30 mL) were added imidazole (2.67 g, 39.3 mmol) and TBDMSCl (2.96 g, 19.6 mmol) at room temperature. The reaction mixture was stirred overnight. The mixture was concentrated and the residue was diluted with EtOAc, washed with $H_2O$, brine, and dried over anhydrous $Na_2SO_4$. After concentration, the crude product was used in the next step without purification.

To the above crude compound in DMF was added NaH (300 mg) at 0° C. and the reaction mixture was stirred for 15 min. Methyl iodide (0.3 mL) was added, and then the mixture was stirred for 1 h. The mixture was quenched with $H_2O$ and concentrated. The residue was diluted with EtOAc, washed with $H_2O$, brine, dried over anhydrous $Na_2SO_4$. After concentration, the residue was purified by column chromatography on silica gel, eluting with Hexane/EtOAc (10%). A colorless oil 17-4 was obtained in 79% yield (1.6 g). $^1H$ NMR (300 MHz, $CDCl_3$) δ (ppm) 7.48-7.51 (m, 2H), 7.31-7.39 (m, 3H), 6.97 (dd, J=11.8, 8.8 Hz, 1H), 6.87 (dd, J=8.8, 3.6 Hz, 1H), 6.82 (s, 1H), 5.22 (s, 2H), 3.77 (t, J=7.1 Hz, 2H), 3.68 (s, 3H), 3.00 (t, J=6.8 Hz, 2H), 0.84 (s, 9H), 0.01 (s, 6H).

Step 4: 3-(2-((tert-Butyldimethylsilyl)oxy)ethyl)-5-fluoro-1-methyl-1H-indol-4-ol (17-5)

A mixture of 17-4 (454 mg, 1.098 mmol) and Pd(OH)$_2$/C in MeOH (0.5 mL NH$_3$) was hydrogenated at ambient pressure for 30 min at 25° C., then the mixture was filtered through a plug of Celite and washed with EtOAc. The crude product was purified by column chromatography on silica gel eluting with Hexane/EtOAc (20%) to afford a white solid 17-5 in 94% yield (334 mg). $^1$H NMR (300 MHz, CDCl$_3$) δ (ppm) 8.27 (br, 1H), 6.96 (dd, J=10.9, 8.8 Hz, 1H), 6.73 (s, 1H), 6.68 (dd, J=8.8, 3.3 Hz, 1H), 3.90 (t, J=5.2 Hz, 2H), 3.67 (s, 3H), 3.07 (t, J=5.5 Hz, 2H), 0.84 (s, 9H), 0.01 (s, 6H). LRMS: calc 323.2 and found: 324.2 [M+1].

Step 5: 2-(5-Fluoro-4-methoxy-1-methyl-1H-indol-3-yl)ethanol (17-6)

At 0° C., NaH (529 mg, 13.23 mmol) was added to a solution of compound 17-5 (2.14 g, 6.61 mmol) in DMF (30 mL). After 30 min, methyl iodide (0.6 mL, 9.92 mmol) was added, and then the reaction mixture was stirred for 1 h. The mixture was quenched with H$_2$O and concentrated. The residue was diluted with EtOAc, washed with H$_2$O, brine, and dried over anhydrous Na$_2$SO$_4$. After concentration, the crude product was used in the next step without purification.

To the above crude compound in THF (30 mL) was added TBAF (10 mL) and the reaction mixture was stirred for 4 h. The mixture was diluted with EtOAc, washed with H$_2$O, brine, dried over anhydrous Na$_2$SO$_4$. After concentration, the residue was purified by column chromatography on silica gel, eluting with Hexane/EtOAc (10%). A colorless oil 17-6 was obtained in 90% yield (two steps), 1.3 g. $^1$H NMR (300 MHz, CDCl$_3$) δ (ppm) 6.97 (dd, J=11.8, 8.8 Hz, 1H), 6.87 (dd, J=8.8, 3.3 Hz, 1H), 6.86 (s, 1H), 4.04 (d, J=2.2 Hz, 3H), 3.87 (dt, J=6.1, 6.0 Hz, 2H), 3.70 (s, 3H), 3.07 (t, J=6.3 Hz, 2H), 1.81 (t, J=5.6 Hz, 1H).

Step 6: N-Benzyl-2-(5-fluoro-4-methoxy-1-methyl-1H-indol-3-yl)ethanamine (17-7)

MsCl (45 μL, 0.585 mmol) was added dropwise to a solution of compound 17-6 (87 mg, 0.39 mmol) and Et$_3$N (0.2 mL, 1.56 mmol) in 10 mL CH$_2$Cl$_2$ at 0° C. under N$_2$, and then the mixture was stirred at this temperature for 2 h. TLC showed no more starting material left, and the reaction mixture was diluted with CH$_2$Cl$_2$, and washed with brine. After drying the organic layer with Na$_2$SO$_4$, the solvent was removed in vacuo, and the resulting colorless oil used for the next step without purification.

A mixture of the mesylate intermediate, Na$_2$CO$_3$ (413 mg, 3.901 mmol), NaI (10 mg) and BnNH$_2$ (0.4 mL, 3.901 mmol) in 10 mL THF was heated to 80° C. overnight in a pressure bottle. After cooling to room temperature, the reaction mixture was diluted with H$_2$O and extracted with EtOAc (2×75 mL). The combined organic phase was washed with brine and dried over Na$_2$SO$_4$. The residue was purified by column chromatography on silica gel, eluting with CH$_2$Cl$_2$/1% NH$_4$OH to afford 17-7 as colorless oil (80 mg, 66%), which was converted to the hydrochloride salt. $^1$H NMR (DMSO-d$_6$, 300 MHz) δ (ppm) (HCl salt): 9.08 (br, 2H), 7.65 (dd, J=5.0, 1.1 Hz, 1H), 7.32 (m, 1H), 7.18 (s, 1H), 7.08-7.13 (m, 2H), 7.04 (dd, J=11.8, 8.8 Hz, 1H), 4.42 (br, 2H), 3.91 (d, J=2.2 Hz, 3H), 3.70 (s, 3H), 3.1-3.18 (m, 4H). LRMS: calc 318.1 found 319.1[MH]+.

The compounds in Table 18 were made according to processes described in Scheme 17.

TABLE 18

| Structure | name | Ex. number | ID number | NMR | MS | Procedure of scheme |
|---|---|---|---|---|---|---|
| 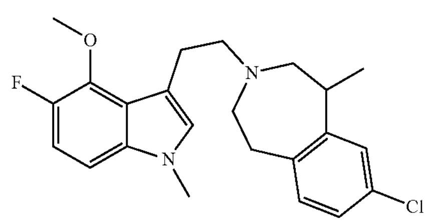 [SMILES: COc1c(F)ccc2c1c(CCN1CCc3ccc(Cl)cc3C(C)C1)cn2C] | 8-chloro-3-(2-(5-fluoro-4-methoxy-1-methyl-1H-indol-3-yl)ethyl)-1-methyl-2,3,4,5-tetrahydro-1H-benzo[d]azepine | 55 | 17-8 | $^1$H NMR (DMSO-d$_6$, 300 MHz) δ (ppm) (HCl salt): 10.64 (br, 1H), 7.30 (s, 1H), 7.31-7.23 (m, 2H), 7.19 (s, 1H), 7.12-7.01 (m, 2H), 3.98 (d, J = 1.9 Hz, 3H), 3.82-3.72 (m, 1H), 3.71 (s, 3H), 3.66-3.58 (m, 1H), 3.56-3.40 (m, 3H), 3.30-3.18 (m, 4H), 3.11-2.96 (m, 2H), 1.42 (d, J = 6.33 Hz, 3H) | Calc 400.2 Found 401.1 (MH)$^+$ | 17 |

TABLE 18-continued

| Structure | name | Ex. number | ID number | NMR | MS | Procedure of scheme |
|---|---|---|---|---|---|---|
| 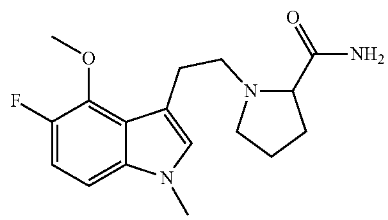 [SMILES: COc1c(F)ccc2c1c(CCN1CCCC1C(N)=O)cn2C] | 1-(2-(5-fluoro-4-methoxy-1-methyl-1H-indol-3-yl)ethyl)pyrrolidine-2-carboxamide | 56 | 17-9 | $^1$H NMR (DMSO-$d_6$, 300 MHz) δ (ppm) (HCl salt): 9.52 (brs, 1H), 8.19 (s, 1H), 7.86 (s, 1H), 7.21 (s, 1H), 7.12-7.00 (m, 2H), 4.13 (m, 1H), 3.98 (d, J = 1.9 Hz, 3H), 3.80-3.71 (m, 1H), 3.70 (s, 3H), 3.50-3.19 (m, 4H), 3.08 (t, J = 8.2 Hz, 2H), 2.11-2.02 (m, 1H), 1.96-1.86 (m, 2H) | Calc 319.2 Found 320.1 (MH)$^+$ | 17 |
| 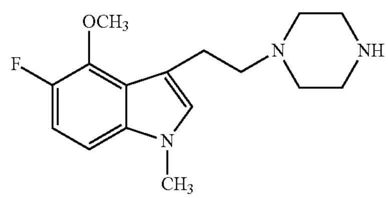 [SMILES: COc1c(F)ccc2c1c(CCN1CCNCC1)cn2C] | 5-fluoro-4-methoxy-1-methyl-3-(2-(piperazin-1-yl)ethyl)-1H-indole | 57 | 17-10 | $^1$H NMR (D$_2$O, 300 MHz) δ (ppm) (HCl salt): 7.12-7.14 (m, 2H), 7.09 (dd, J = 15.7, 8.8 Hz, 1H), 4.01 (d, J = 1.6 Hz, 3H), 3.54 (br, 8H), 3.41-3.46 (m, 2H), 3.21-3.26 (m, 2H) | calc 291.2 found 292.2 [MH]+ | 17 |
| | 2-(2-(5-fluoro-4-methoxy-1-methyl-1H-indol-3-yl)ethyl)-1,2,3,4-tetrahydroisoquinoline | 59 | 17-12 | $^1$H NMR (DMSO-$d_6$, 300 MHz) δ (ppm) (HCl salt): 10.69 (brs, 1H), 7.32-7.24 (m, 5H), 7.15-7.01 (m, 2H), 4.66 (m, 1H), 4.45-4.34 (m, 1H), 3.99 (d, J = 1.9 Hz, 3H), 3.80-3.72 (m, 1H), 3.71 (s, 3H), 3.49-3.20 (m, 6H), 3.09-3.03 (m, 1H) | Calc 338.2 Found 339.1 [MH]$^+$ | 17 |
| 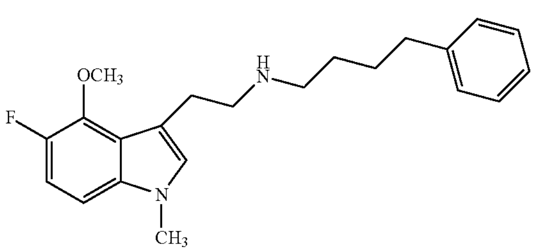 [SMILES: COc1c(F)ccc2c1c(CCNCCCCc1ccccc1)cn2C] | N-(2-(5-fluoro-4-methoxy-1-methyl-1H-indol-3-yl)ethyl)-4-phenylbutan-1-amine | 60 | 17-13 | $^1$H NMR (DMSO-$d_6$, 300 MHz) δ (ppm) (HCl salt): 8.53 (br, 2H), 7.26-7.31 (m, 2H), 7.15-7.22 (m, 4H), 7.11 (dd, J = 8.8, 3.8 Hz, 1H), 7.04 (dd, J = 11.8, 8.8 Hz, 1H), 3.95 (d, J = 1.9 Hz, 3H), 3.69 (s, 3H), 3.07-3.10 (m, 4H), 2.91-2.96 (m, 2H), 2.57-2.60 (m, 2H), 1.60-1.62 (m, 4H) | calc 354.2 found 355.2 [MH]+ | 17 |

TABLE 18-continued

| Structure | name | Ex. number | ID number | NMR | MS | Procedure of scheme |
|---|---|---|---|---|---|---|
| 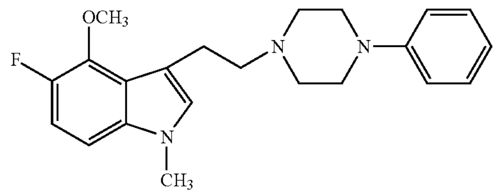 [SMILES: COc1c(F)ccc2c1c(CCN1CCN(c3ccccc3)CC1)cn2C] | 5-fluoro-4-methoxy-1-methyl-3-(2-(4-phenyl-piperazin-1-yl)ethyl)-1H-indole | 61 | 17-14 | $^1$H NMR (DMSO-d$_6$, 300 MHz) δ (ppm) (HCl salt): 10.72 (br, 1H), 7.23-7.30 (m, 3H), 7.00-7.14 (m, 4H), 6.87 (t, J = 7.1 Hz, 1H), 4.01 (d, J = 2.2 Hz, 3H), 3.82-3.86 (m, 2H), 3.71 (s, 3H), 3.65-3.68 (m, 2H), 3.33-3.37 (m, 2H), 3.10-3.26 (m, 6H) | calc 367.2 found 368.1 [MH]+ | 17 |
| 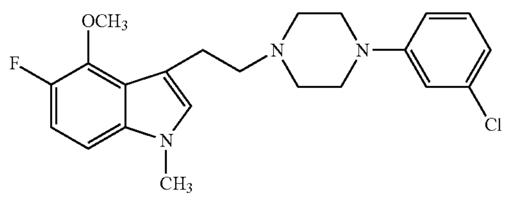 [SMILES: COc1c(F)ccc2c1c(CCN1CCN(c3cccc(Cl)c3)CC1)cn2C] | 3-(2-(4-(3-chlorophenyl)piperazin-1-yl)ethyl)-5-fluoro-4-methoxy-1-methyl-1H-indole | 62 | 17-15 | $^1$H NMR (DMSO-d$_6$, 300 MHz) δ (ppm) (HCl salt): 10.81 (br, 1H), 7.26 (dd, J = 16.2, 8.0 Hz, 1H), 7.22 (s, 1H), 7.04-7.13 (m, 3H), 6.96-7.01 (m, 1H), 6.88 (dd, J = 7.4, 1.6 Hz, 1H), 4.01 (d, J = 2.2 Hz, 3H), 3.90-3.93 (m, 2H), 3.71 (s, 3H), 3.63-3.65 (m, 2H), 3.31-3.36 (m, 2H), 3.16-3.25 (m, 6H) | calc 401.2 found 402.1 [MH]+ | 17 |
| 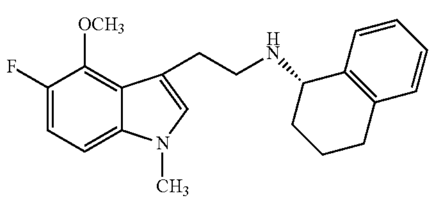 [SMILES: COc1c(F)ccc2c1c(CCN[C@H]1CCCc3ccccc31)cn2C] | (S)-N-(2-(5-fluoro-4-methoxy-1-methyl-1H-indol-3-yl)ethyl)-1,2,3,4-tetrahydro-naphthalen-1-amine | 63 | 17-16 | $^1$H NMR (DMSO-d$_6$, 300MHz) δ (ppm) (HCl salt): 9.14 (br, 2H), 7.60 (d, J = 7.1 Hz, 1H), 7.19-7.33 (m, 4H), 7.10 (dd, J = 8.8, 3.6 Hz, 1H), 7.03 (dd, J = 11.8, 8.8 Hz, 1H), 4.52 (m, 1H), 3.92 (d, J = 1.9 Hz, 3H), 3.70 (s, 3H), 3.18 (m, 4H), 2.70-2.88 (m, 2H), 1.74-2.15 (m, 4H) | calc 352.2 found 353.2 [MH]+ | 17 |
| 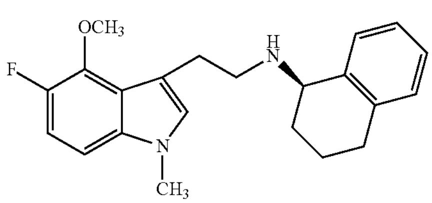 [SMILES: COc1c(F)ccc2c1c(CCN[C@@H]1CCCc3ccccc31)cn2C] | (R)-N-(2-(5-fluoro-4-methoxy-1-methyl-1H-indol-3-yl)ethyl)-1,2,3,4-tetrahydro-naphthalen-1-amine | 64 | 17-17 | $^1$H NMR (DMSO-d$_6$, 300 MHz) ppm (HCl salt): 9.19 (br, 2H), 7.61 (d, J = 7.1 Hz, 1H), 7.19-7.33 (m, 4H), 7.10 (dd, J = 8.8, 3.8 Hz, 1H), 7.03 (dd, J = 11.8, 8.8 Hz, 1H), 4.52 (m, 1H), 3.92 (d, J = 2.2 Hz, 3H), 3.70 (s, 3H), 3.12-3.21 (m, 4H), 2.74-2.84 (m, 2H), 1.74-2.16 (m, 4H) | calc 352.2 found 353.2 [MH]+ | 17 |

TABLE 18-continued

| Structure | name | Ex. number | ID number | NMR | MS | Procedure of scheme |
|---|---|---|---|---|---|---|
| 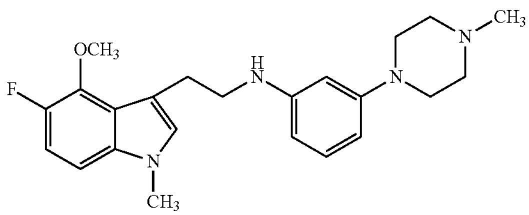 [SMILES: COc1c(F)ccc2c1c(CCNc1cccc(N3CCN(C)CC3)c1)cn2C] | N-(2-(5-fluoro-4-methoxy-1-methyl-1H-indol-3-yl)ethyl)-3-(4-methyl-piperazin-1-yl)aniline | 65 | 17-18 | $^1$H NMR (D$_2$O, 300 MHz) δ (ppm) (HCl salt): 7.25-7.30 (m, 1H), 7.01-7.04 (m, 2H), 6.95 (s, 1H), 6.87 (d, J = 8.2 Hz, 1H), 6.78 (d, J = 8.0 Hz, 3H), 6.59 (m, 1H), 3.82 (d, J = 1.1 Hz, 3H), 3.72 (t, J = 6.8 Hz, 2H), 3.59 (s, 3H), 3.53-3.57 (m, 4H), 3.10-3.17 (m, 4H), 2.90-2.96 (m, 2H), 2.90 (s, 3H) | calc 396.2 found 397.2 [MH]+ | 17 |
| 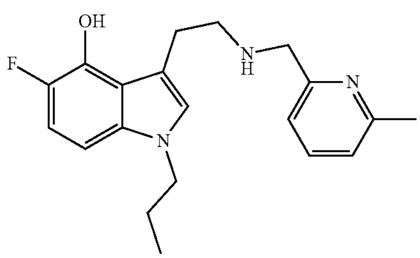 [SMILES: CCCn1cc(CCNCc2cccc(C)n2)c2c(O)c(F)ccc21] | 5-fluoro-3-(2-(((6-methyl-pyridin-2-yl)methyl)amino)ethyl)-1-propyl-1H-indol-4-ol | 65a | 17-19 | $^1$H NMR (D$_2$O, 300 MHz) δ (ppm) (HCl salt): 8.01 (t, J = 7.9 Hz, 1H), 7.50 (d, J = 7.9 Hz, 1H), 7.47 (d, J = 7.7 Hz, 1H), 7.12 (s, 1H), 7.0 (dd, J = 10.9, 8.8 Hz, 1H), 6.9 (dd, J = 9.1, 3.9 Hz, 1H), 4.42 (s, 2H), 3.99 (t, J = 6.9 Hz, 2H), 3.50 (t, J = 6.6 Hz, 2H), 3.16 (t, J = 6.3 Hz, 2H), 2.50 (s, 3H), 1.73 (m, 2H), 0.77 (t, J = 7.4 Hz, 3H) | calc 341.2 found 342.2 [MH]+ | 17 From 17-4 steps 5-2, 6, 4 |
| 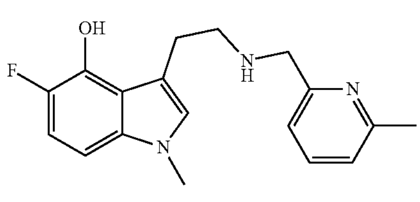 [SMILES: Cc1cccc(CNCCc2cn(C)c3ccc(F)c(O)c23)n1] | 5-fluoro-1-methyl-3-(2-(((6-methyl-pyridin-2-yl)methyl)amino)ethyl)-1H-indol-4-ol | 65b | 17-20 | $^1$H NMR (D$_2$O, 300 MHz) δ (ppm) (HCl salt): 8.02 (t, J = 7.9 Hz, 1H), 7.52 (d, J = 7.9 Hz, 1H), 7.47 (d, J = 7.7 Hz, 1H), 7.03 (s, 1H), 7.0 (dd, J = 10.9, 9.1 Hz, 1H), 6.84 (dd, J = 8.8, 3.3 Hz, 1H), 4.42 (s, 2H), 3.64 (s, 3H), 3.51 (t, J = 6.3 Hz, 2H), 3.15 (t, J = 6.3 Hz, 2H), 2.51 (s, 3H) | calc 313.2 found 314.2 [MH]+ | 17 From 17-4 steps 5-2, 6, 4 |

Scheme 18:

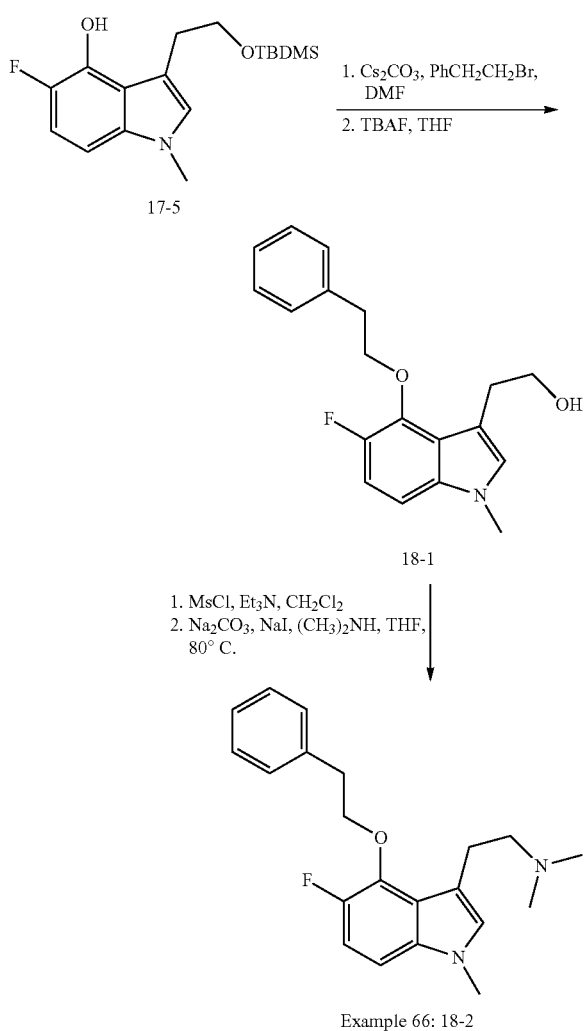

Example 66

2-(5-fluoro-1-methyl-4-phenethoxy-1H-indol-3-yl)-N,N-dimethylethanamine (18-2)

Step 1: 2-(5-fluoro-1-methyl-4-phenethoxy-1H-indol-3-yl)ethanol (18-1)

To a solution of compound 17-5 (150 mg, 0.464 mmol) in DMF (10 mL) was added $Cs_2CO_3$ (181.5 mg, 0.557 mmol) and 2-bromoethylbenzene (70 uL, 0.511 mmol). Then the reaction mixture was stirred at room temperature overnight. The mixture was quenched with $H_2O$ and concentrated. The residue was diluted with EtOAc, washed with $H_2O$, brine, and dried over anhydrous $Na_2SO_4$. After concentration, the crude product was used in the next step without purification.

To the above crude compound in THF (10 mL) was added TBAF (3.0 mL) and the reaction mixture was stirred for 4 h. The mixture was diluted with EtOAc, washed with $H_2O$, brine, and dried over anhydrous $Na_2SO_4$. After concentration, the residue was purified by column chromatography, eluting with Hexane/EtOAc (30%) to afford 18-1 as a colorless oil (78 mg, 54% yield). $^1$H NMR ($CDCl_3$, 300 MHz) δ (ppm): 7.29-7.32 (m, 5H), 6.96 (dd, J=12.1, 9.1 Hz, 1H), 6.85 (dd, J=8.8, 3.6 Hz, 1H), 6.81 (s, 1H), 4.46 (dt, J=6.9, 1.4 Hz, 2H), 3.68 (dt, J=6.3, 6.1 Hz, 2H), 3.67 (s, 3H), 3.15 (t, J=7.1 Hz, 2H), 2.82 (t, J=6.3 Hz, 2H), 1.54 (t, J=6.3 Hz, 1H).

Step 2: 2-(5-fluoro-1-methyl-4-phenethoxy-1H-indol-3-yl)-N,N-dimethylethanamine (18-2)

Following the procedure (step 6, scheme 17) used to prepare compound 17-7, compound 18-1 gave compound 18-2 in 72% yield as a colorless oil, which was converted to the hydrochloride salt. $^1$H NMR (DMSO-$d_6$, 300 MHz) δ (ppm) (HCl salt): 9.92 (br, 1H), 7.23-7.32 (m, 5H), 7.21 (s, 1H), 7.10 (dd, J=9.1, 4.1 Hz, 1H), 7.04 (dd, J=12.1, 8.8 Hz, 1H), 4.40 (td, J=7.4, 1.6 Hz, 2H), 3.70 (s, 3H), 3.16-3.21 (m, 2H), 3.11 (t, J=7.1 Hz, 2H), 3.00-3.06 (m, 2H), 2.73 (s, 6H). LRMS: calc 340.2 found 341.2 [MH]+.

The compounds in Table 19 were made according to processes described in Scheme 18.

TABLE 19

| Structure | name | Ex. number | ID number | NMR | MS | Procedure of scheme |
|---|---|---|---|---|---|---|
| (4-chlorobenzyl structure) | 2-(4-((4-chlorobenzyl)oxy)-5-fluoro-1-propyl-1H-indol-3-yl)ethanamine | 66b | 18-3 | $^1$H NMR (DMSO-d6, 300 MHz) δ (ppm) (HCl salt): 7.73 (br, 3H), 7.51 (d, J = 8.2 Hz, 2H), 7.46 (d, J = 8.8 Hz, 2H), 7.22 (s, 1H), 7.18 (dd, J = 9.1, 3.6 Hz, 1H), 7.03 (dd, J = 12.1, 8.8 Hz, 1H), 5.19 (s, 2H), 4.03 (t, J = 6.9 Hz, 2H), 3.01 (br, 4H), 1.72 (m, 2H), 0.83 (t, J = 7.1 Hz, 3H) | calc 360.1 found 361.1 [MH]$^+$ | 18 Step 1 from N1Pr of 17-5 Step 1 and 3 |

Scheme 19:

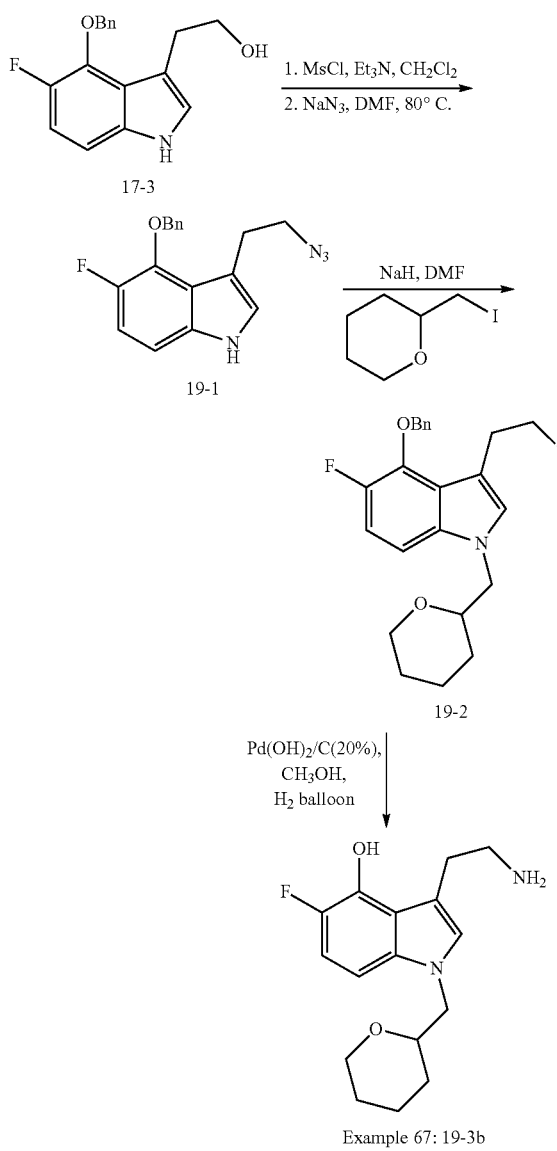

Example 67: 19-3b

Example 67

3-(2-Aminoethyl)-5-fluoro-1-((tetrahydro-2H-pyran-2-yl)methyl)-1H-indol-4-ol (19-3b)

Step 1: 3-(2-Azidoethyl)-4-(benzyloxy)-5-fluoro-1H-indole (19-1)

Following the procedure (step 6, scheme 17) used to prepare compound mesylate intermediate; compound 17-3 gave the mesylte analog used for the next step without purification.

A mixture of the mesylate intermediate, NaN$_3$ (131 mg, 2.018 mmol) in 10 mL DMF was heated at 80° C. overnight. After cooling to room temperature, the reaction mixture was diluted with H$_2$O and extracted with EtOAc (2×75 mL). The combined organic phase was washed by brine and dried over Na$_2$SO$_4$. The crude was purified by flash column chromatography, eluting with Hexane/EtOAc (10%) to give the product 19-1 in 80% yield as a colorless oil. $^1$H NMR (CDCl$_3$, 300 MHz) ┃ ppm: 7.94 (br, 1H), 7.45-7.47 (m, 2H), 7.34-7.41 (m, 3H), 6.95-6.99 (m, 3H), 5.27 (d, J=1.1 Hz, 2H), 3.42 (t, J=7.1 Hz, 2H), 2.98 (t, J=6.9 Hz, 2H).

Step 2: 3-(2-Azidoethyl)-4-(benzyloxy)-5-fluoro-1-((tetrahydro-2H-pyran-2-yl)methyl)-1H-indole (19-2)

Following the procedure (step 5, scheme 17, TBAF deprotection step unnecessary) used to prepare compound 17-6, compound 19-1 gave compound 19-2 in 82% yield as a colorless oil. $^1$H NMR (CDCl$_3$, 300 MHz) δ (ppm): 7.25-7.47 (m, 5H), 6.91-6.97 (m, 3H), 3.91-4.04 (m, 3H), 3.58 (m, 1H), 3.36-3.43 (m, 3H), 2.97 (t, J=6.9 Hz, 2H), 1.23-1.48 (m, 6H).

Step 3: 3-(2-Aminoethyl)-5-fluoro-1-((tetrahydro-2H-pyran-2-yl)methyl)-1H-indol-4-ol (19-3)

Following the procedure (step 4, scheme 17) used to prepare compound 17-5, compound 19-2 was used as starting material, using Pd(OH)$_2$/C (20%) as source of Pd to afford 19-3 (45% yield) as a white solid. The compound was then converted to the hydrochloride salt. $^1$H NMR (D$_2$O, 300 MHz) δ (ppm) (HCl salt): 7.06 (s, 1H), 7.03 (dd, J=11.2, 9.1 Hz, 1H), 6.89 (dd, J=9.1, 3.6 Hz, 1H), 4.10 (dd, J=15.1, 4.1 Hz, 1H), 4.04 (dd, J=15.1, 7.7 Hz, 1H), 3.75-3.84 (m, 2H), 3.27-3.36 (m, 3H), 3.12-3.17 (m, 2H), 1.63-1.79 (m, 2H), 1.40-1.50 (m, 3H), 1.20-1.28 (m, 1H). LRMS: calc 292.2 found 293.1 [MH]$^+$.

The compounds in Table 20 were made according to processes described in Scheme 19.

TABLE 20

| Structure | name | Ex. number | ID number | NMR | MS | Procedure of scheme |
|---|---|---|---|---|---|---|
| 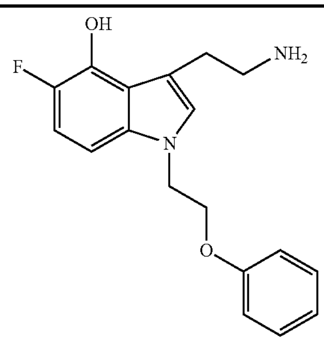 | 3-(2-aminoethyl)-5-fluoro-1-(2-phenoxyethyl)-1H-indol-4-ol | 68a | 19-4 | $^1$H NMR (DMSO-d$_6$, 300 MHz) δ (ppm) (HCl salt): 9.63 (br, 1H), 7.88 (br, 2H), 7.25 (dd, J = 8.5, 7.7 Hz, 2H), 7.18 (s, 1H), 6.86-7.00 (m, 5H), 4.43 (t, J = 5.2 Hz, 2H), 4.23 (t, J = 5.0 Hz, 2H), 3.07 (br, 4H) | calc 314.1 found 315.1 [MH]+ | 19 |

TABLE 20-continued

| Structure | name | Ex. number | ID number | NMR | MS | Procedure of scheme |
|---|---|---|---|---|---|---|
| (structure with 5-fluoro-4-hydroxyindole, 3-(2-aminoethyl), N-substituted with (2,3-dihydrobenzo[b][1,4]dioxin-2-yl)methyl) | 3-(2-aminoethyl)-1-((2,3-dihydrobenzo[b][1,4]dioxin-2-yl)methyl)-5-fluoro-1H-indol-4-ol | 68b | 19-5 | $^1$H NMR (D$_2$O, 300 MHz) δ (ppm) (HCl salt): 7.03 (s, 1H), 6.97 (dd, J = 11.3, 9.1 Hz, 1H), 6.83-6.87 (m, 3H), 6.72-6.78 (m, 2H), 4.55 (m, 1H), 4.30 (d, J = 5.8 Hz, 2H), 4.22 (dd, J = 11.8, 2.5 Hz, 1H), 3.97 (dd, J = 11.8, 5.0 Hz, 1H), 3.25 (t, J = 7.4 Hz, 2H), 3.11 (t, J = 6.6 Hz, 2H) | calc 342.1 found 343.1 [MH]+ | 19 |
| (structure with N,N-diethylacetamide group on N1) | (2-(3-(2-aminoethyl)-5-fluoro-4-hydroxy-1H-indol-1-yl)-N,N-diethylacetamide | 68c | 19-6 | 1H NMR (DMSO-d6, 300 MHz) δ (ppm) (HCl salt): 8.03 (brs, 3H), 7.04 (s, 1H), 6.95 (dd, J = 11.2 Hz, 8.79 Hz, 1H), 6.68 (dd, J = 8.79 Hz, 3.5 Hz, 1H), 4.97 (s, 2H), 3.44-3.35 (m, 2H), 3.31-3.22 (m, 2H), 3.07 (s, 4H), 1.18 (t, J = 7.0 Hz, 3H), 1.03 (t, J = 7.0 Hz, 3H) | calc 307.2 found 308.2 [MH]+ | 19 |
| (structure with acetamide group on N1) | 2-(3-(2-aminoethyl)-5-fluoro-4-hydroxy-1H-indol-1-yl)acetamide | 68d | 19-7 | 1H NMR (DMSO-d6, 300 MHz) δ (ppm) (HCl salt): 9.67 (s, 1H), 7.84 (brs, 3H), 7.34 (s, 1H), 7.26 (s, 1H), 7.06 (s, 1H), 6.99 (dd, J = 11.5 Hz, 8.79 Hz, 1H), 6.73 (dd, J = 8.79 Hz, 3.5 Hz, 1H), 4.65 (s, 2H), 3.16-3.02 (m, 4H). | Calc 251.1 Found 252.1 (MH)+ | 19 |

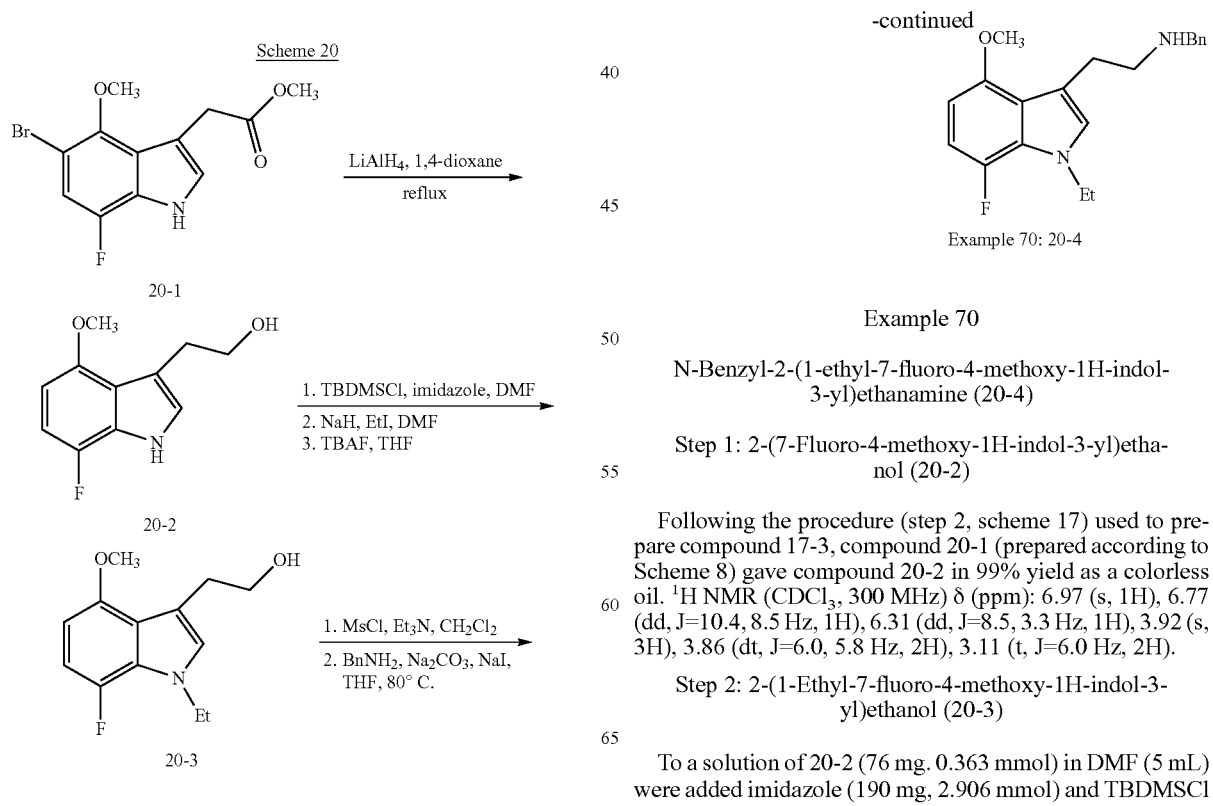

Example 70

N-Benzyl-2-(1-ethyl-7-fluoro-4-methoxy-1H-indol-3-yl)ethanamine (20-4)

Step 1: 2-(7-Fluoro-4-methoxy-1H-indol-3-yl)ethanol (20-2)

Following the procedure (step 2, scheme 17) used to prepare compound 17-3, compound 20-1 (prepared according to Scheme 8) gave compound 20-2 in 99% yield as a colorless oil. $^1$H NMR (CDCl$_3$, 300 MHz) δ (ppm): 6.97 (s, 1H), 6.77 (dd, J=10.4, 8.5 Hz, 1H), 6.31 (dd, J=8.5, 3.3 Hz, 1H), 3.92 (s, 3H), 3.86 (dt, J=6.0, 5.8 Hz, 2H), 3.11 (t, J=6.0 Hz, 2H).

Step 2: 2-(1-Ethyl-7-fluoro-4-methoxy-1H-indol-3-yl)ethanol (20-3)

To a solution of 20-2 (76 mg, 0.363 mmol) in DMF (5 mL) were added imidazole (190 mg, 2.906 mmol) and TBDMSCl (220 mg, 1.453 mmol) at room temperature. The reaction mixture was stirred overnight. The mixture was concentrated and the residue was diluted with EtOAc, washed with H$_2$O, brine, and dried over anhydrous Na$_2$SO$_4$. After concentration, the crude product was used in the next step without purification.

To the above crude compound in DMF (10 mL) was added NaH (31 mg, 0.774 mmol) at 0° C. and the reaction mixture was stirred for 15 min. Ethyl iodide (46 μL, 0.581 mmol) was added, and then the mixture was stirred for 1 h. The mixture was quenched with H$_2$O and concentrated. The residue was diluted with EtOAc, washed with H$_2$O, brine, dried over anhydrous Na$_2$SO$_4$. After concentration, the crude compound was dissolved in THF (5 mL) and TBAF (2 mL) was added at room temperature. The reaction mixture was stirred for 2 h, and then the mixture was diluted with EtOAc, washed with H$_2$O, brine, dried over anhydrous Na$_2$SO$_4$. After concentration, the residue was purified by column chromatography, eluting with hexane/EtOAc (50%). A colorless oil 20-3 was obtained in 77% yield, 66 mg. $^1$H NMR (CDCl$_3$, 300 MHz) δ (ppm): 6.80 (s, 1H), 6.73 (dd, J=12.4, 8.5 Hz, 1H), 6.27 (dd, J=8.5, 3.0 Hz, 1H), 4.24 (q, J=7.1 Hz, 2H), 3.82-3.87 (m, 5H), 3.08 (t, J=6.1 Hz, 2H), 1.84 (t, J=5.8 Hz, 1H), 1.41 (t, J=7.1 Hz, 3H).

Step 3: N-Benzyl-2-(1-ethyl-7-fluoro-4-methoxy-1H-indol-3-yl)ethanamine (20-4)

Following the procedure (step 6, scheme 17) used to prepare compound 17-7, compound 20-3 was used as starting material, giving compound 20-4 in 68% yield as a white solid, which was converted to the hydrochloride salt. $^1$H NMR (DMSO-d$_6$, 300 MHz) δ (ppm) (HCl salt): 9.25 (br, 2H), 7.54-7.57 (m, 2H), 7.42-7.44 (m, 3H), 7.16 (s, 1H), 6.82 (dd, J=12.4, 8.5 Hz, 1H), 6.35 (dd, J=8.5, 2.7 Hz, 1H), 4.21 (q, J=7.1 Hz, 2H), 4.17 (s, 2H), 3.75 (s, 3H), 3.12 (br, 4H), 1.32 (t, J=7.1 Hz, 3H). LRMS: calc 326.2 found 327.2 [MH]$^+$.

The compounds in Table 21 were made according to processes described in Scheme 20.

TABLE 21

| Structure | name | Ex. number | ID number | NMR | MS | Procedure of scheme |
|---|---|---|---|---|---|---|
| 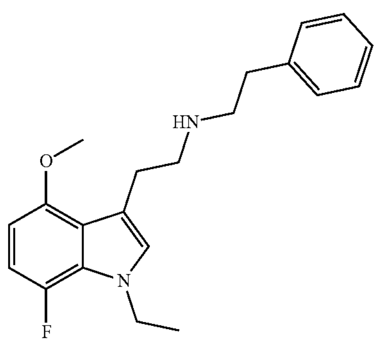 [SMILES: CCn1cc(CCNCCc2ccccc2)c2c(OC)ccc(F)c21] | 2-(1-ethyl-7-fluoro-4-methoxy-1H-indol-3-yl)-N-phenethylanamine | 72 | 20-7 | $^1$H NMR (DMSO-d$_6$, 300 MHz) δ (ppm) (HCl salt): 8.91 (br, 2H), 7.25-7.37 (m, 5H), 7.17 (s, 1H), 6.83 (dd, J = 12.6, 8.5 Hz, 1H), 6.39 (dd, J = 8.5, 2.5 Hz, 1H), 4.22 (q, J = 7.1 Hz, 2H), 3.84 (s, 3H), 3.10-3.19 (m, 6H), 2.93-2.99 (m, 2H), 1.33 (t, J = 7.1 Hz, 3H) | calc 340.2 found 341.2 [MH]+ | 20 |
| 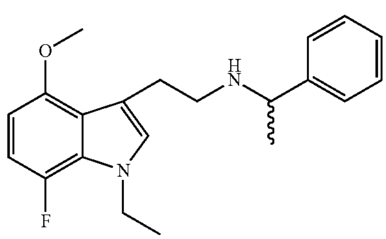 [SMILES: CCn1cc(CCNC(C)c2ccccc2)c2c(OC)ccc(F)c21] | 2-(1-ethyl-7-fluoro-4-methoxy-1H-indol-3-yl)-N-(1-phenylethyl)ethanamine | 73 | 20-8 | $^1$H NMR (DMSO-d$_6$, 300 MHz) δ (ppm) (HCl salt): 9.43 (br, 2H), 9.07 (br, 1H), 7.52-7.54 (m, 2H), 7.39-7.46 (m, 3H), 7.12 (s, 1H), 6.79 (dd, J = 12.6, 8.3 Hz, 1H), 6.30 (dd, J = 8.8, 3.0 Hz, 1H), 4.38 (br, 1H), 4.18 (q, J = 7.4 Hz, 2H), 3.66 (s, 3H), 2.82-3.05 (m, 4H), 1.58 (d, J = 6.3 Hz, 3H), 1.29 (t, J = 7.1 Hz, 3H) | calc 340.2 found 341.2 [MH]+ | 20 |
| 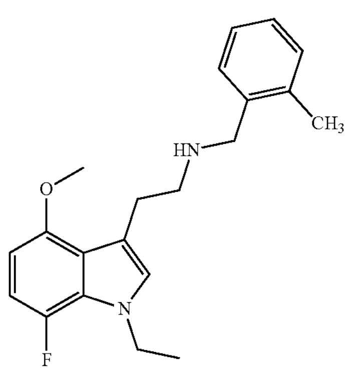 [SMILES: CCn1cc(CCNCc2ccccc2C)c2c(OC)ccc(F)c21] | 2-(1-ethyl-7-fluoro-4-methoxy-1H-indol-3-yl)-N-(2-methylbenzyl)ethanamine | 74 | 20-9 | $^1$H NMR (DMSO-d$_6$, 300 MHz) δ (ppm) (HCl salt): 8.97 (br, 2H), 7.46-7.48 (m, 1H), 7.26-7.31 (m, 3H), 7.18 (s, 1H), 6.83 (dd, J = 12.4, 8.3 Hz, 1H), 6.37 (dd, J = 8.8, 3.0 Hz, 1H), 4.21 (q, J = 6.9 Hz, 2H), 4.17 (s, 2H), 3.79 (s, 3H), 3.11-3.20 (m, 4H), 2.37 (s, 3H), 1.32 (t, J = 7.1 Hz, 3H) | calc 340.2 found 341.2 [MH]+ | 20 |

TABLE 21-continued

| Structure | name | Ex. number | ID number | NMR | MS | Procedure of scheme |
|---|---|---|---|---|---|---|
| 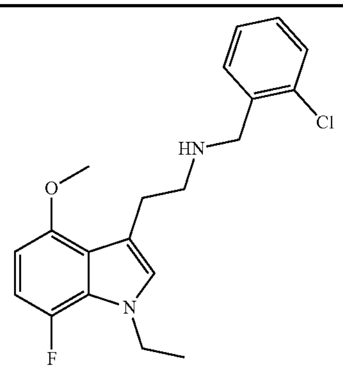 | N-(2-chlorobenzyl)-2-(1-ethyl-7-fluoro-4-methoxy-1H-indol-3-yl)ethanamine | 75 | 20-10 | ¹H NMR (DMSO-d₆, 300 MHz) δ (ppm) (HCl salt): 9.19 (br, 2H), 7.69-7.72 (m, 1H), 7.55-7.58 (m, 1H), 7.44-7.47 (m, 2H), 7.18 (s, 1H), 6.82 (dd, J = 12.6, 8.5 Hz, 1H), 6.37 (dd, J = 8.8, 3.0 Hz, 1H), 4.30 (s, 2H), 4.21 (q, J = 7.1 Hz, 2H), 3.78 (s, 3H), 3.11-3.19 (m, 4H), 1.32 (t, J = 6.9 Hz, 3H). | calc 360.1 found 361.1 [MH]+ | 20 |

Scheme 22

Example 77

2-(7-Fluoro-4-methoxy-1-methyl-5-phenyl-1H-indol-3-yl)-N-methylethanamine (22-5)

Step 1: Methyl 2-(7-fluoro-4-methoxy-5-phenyl-1H-indol-3-yl)acetate (22-2)

Following the procedure for preparing the compound 6-6 in (Step 5, Scheme 6), using 22-1 (prepared according to Scheme 8 but RCOOMe in place of RCOOEt), phenylboronic acid, sodium carbonate and [1,1'-bis(diphenylphosphino)ferrocene]dichloropalladium(II) in a microwave reactor (150° C., 30 min) to give 22-2 as a white solid (93%). ¹H NMR (CDCl₃) δ (ppm) 8.24 (bs, 1H), 7.58-7.62 (m, 2H), 7.38-7.44 (m, 2H), 7.30-7.35 (m, 1H), 7.15 (d, J=2.2 Hz, 1H), 6.89 (d, J=11.3 Hz, 1H), 3.96 (s, 2H), 3.73 (s, 3H), 3.37 (s, 3H).

Step 2: 2-(7-Fluoro-4-methoxy-5-phenyl-1H-indol-3-yl)ethanol (22-3)

Following the procedure (step 2, scheme 17) used to prepare compound 17-3, compound 22-2 gave compound 22-3 in 69% yield as a white solid. ¹H NMR (CDCl₃) δ ppm: 8.21 (bs, 1H), 7.58-7.62 (m, 2H), 7.39-7.45 (m, 2H), 7.30-7.35 (m, 1H), 7.08 (d, J=2.5 Hz, 1H), 6.91 (d, J=11.3 Hz, 1H), 3.95 (q, J=6.0 Hz, 2H), 3.45 (s, 3H), 3.13 (t, J=6.0 Hz, 2H), 2.14 (t, J=5.5 Hz, 1H).

Step 3: 2-(7-Fluoro-4-methoxy-1-methyl-5-phenyl-1H-indol-3-yl)ethanol (22-4)

Following the procedure (step 2, scheme 20) used to prepare compound 20-3, compound 22-3 gave compound 22-4 in 90% yield as a colorless oil. ¹H NMR (CDCl₃) δ ppm: 7.58-7.62 (m, 2H), 7.39-7.45 (m, 2H), 7.30-7.35 (m, 1H), 6.88 (s, 1H), 6.83 (d, J=1.9 Hz, 1H), 3.94 (d, J=1.9 Hz, 3H), 3.87-3.92 (m, 2H), 3.43 (s, 3H), 3.08 (t, J=6.1 Hz, 2H), 2.15 (t, J=5.5 Hz, 1H).

Step 4: 2-(7-fluoro-4-methoxy-1-methyl-5-phenyl-1H-indol-3-yl)-N-methylethanamine (22-5)

Following the procedure (step 6, scheme 17) used to prepare compound 17-7, compound 22-4 was used as starting material, giving compound 22-5 in 47% yield as a colorless oil, which was converted to the hydrochloride salt. $^1$H NMR (DMSO-d$_6$, 300 MHz) δ (ppm) (HCl salt): 8.63 (br, 2H), 7.57-7.60 (m, 2H), 7.45 (t, J=7.4 Hz, 2H), 7.30-7.36 (m, 1H), 7.23 (s, 1H), 6.93 (d, J=12.9 Hz, 1H), 3.90 (d, J=1.9 Hz, 3H), 3.36 (s, 3H), 3.16-3.21 (m, 2H), 3.06-3.11 (m, 2H), 2.59 (s, 3H). LRMS: calc 312.2 found 313.1 [MH]$^+$.

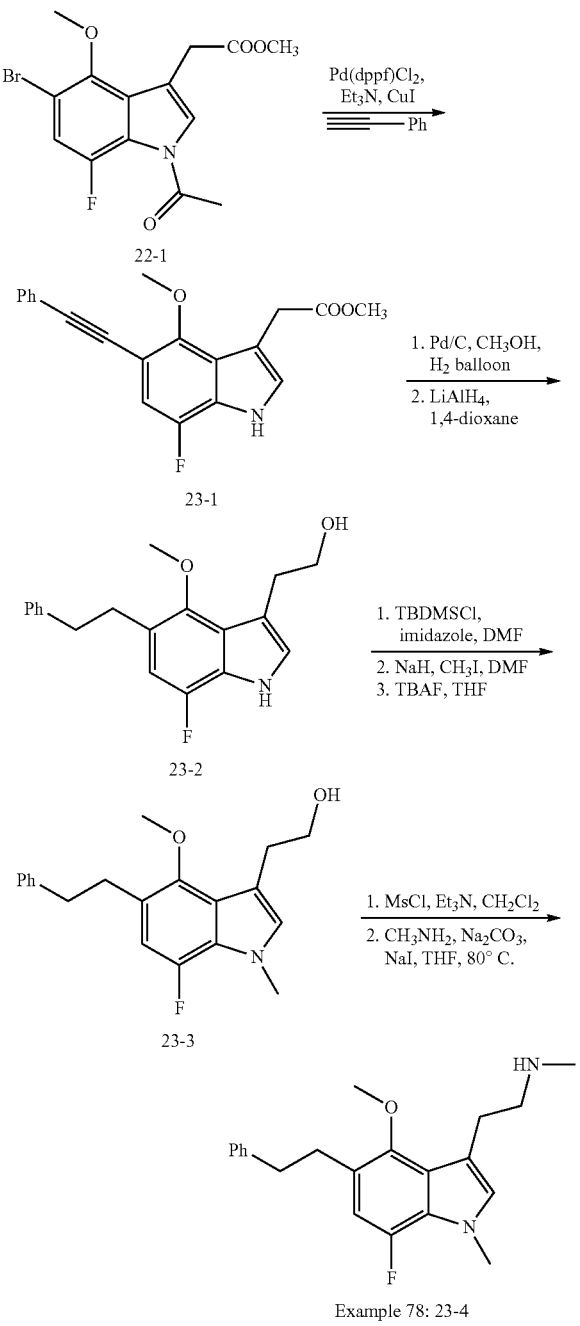

Scheme 23

Example 78: 23-4

Example 78

2-(7-Fluoro-4-methoxy-1-methyl-5-phenethyl-1H-indol-3-yl)-N-methylethanamine (23-4)

Step 1: Methyl 2-(7-fluoro-4-methoxy-5-(phenylethynyl)-1H-indol-3-yl)acetate (23-1)

A mixture of 22-1 (358 mg, 1.0 mmol), phenylacetylene (0.55 mL, 5.0 mmol), Pd(dppf)Cl$_2$·CH$_2$Cl$_2$ (163 mg, 0.2 mmol), CuI (38 mg, 0.2 mmol) in 10 mL Et$_3$N was heated at 110° C. overnight under nitrogen. The reaction mixture was concentrated to dryness and purified by flash column chromatography, eluting with hexanes/EtOAc to afford 23-1 as a brown oil (530 mg).

Step 2: 2-(7-Fluoro-4-methoxy-5-phenethyl-1H-indol-3-yl)ethanol (23-2)

A mixture of compound 23-1 (530 mg) and Pd/C (5%, 300 mg) in 100 mL of MeOH/EtOAc (1:1) was stirred at room temperature overnight. The mixture was filtered through Celite and concentrated to obtain a brown oil (460 mg), which was used in the next step without purification.

To a solution of the intermediate (460 mg) in 20 mL dioxane, LiAlH$_4$ (380 mg, 10 mmol) was added and the resulting mixture was heated to reflux for 2 h. After cooled to 0° C., the mixture was quenched by water, 15% NaOH and water, then filtered and dried over Na$_2$SO$_4$. After the concentration, the black oil was purified by flash column chromatography eluting with hexanes/EtOAc to afford 23-2 as a brown oil (246 mg, 79%). $^1$H NMR (CDCl$_3$) δ ppm: 8.15 (bs, 1H), 7.18-7.32 (m, 5H), 7.03 (d, J=2.2 Hz, 1H), 6.75 (d, J=11.3 Hz, 1H), 3.87-3.94 (m, 2H), 3.78 (s, 3H), 2.89-3.04 (m, 4H), 2.12 (t, J=5.8 Hz, 1H).

Step 3: 2-(7-Fluoro-4-methoxy-1-methyl-5-phenethyl-1H-indol-3-yl)ethanol (23-3)

Following the procedure (step 2, scheme 20) used to prepare compound 20-3, compound 23-2 gave compound 23-3 in 69% yield as a colorless oil. $^1$H NMR (CDCl$_3$, 300 MHz) δ ppm: 7.22-7.29 (m, 5H), 6.79 (s, 1H), 6.70 (d, J=12.9 Hz, 1H), 3.90 (d, J=1.92 Hz, 3H), 3.84-3.89 (m, 2H), 3.74 (s, 3H), 3.05 (d, J=6.0 Hz, 2H), 2.9-2.96 (m, 4H), 2.11 (t, J=5.8 Hz, 1H).

Step 4: 2-(7-Fluoro-4-methoxy-1-methyl-5-phenethyl-1H-indol-3-yl)-N-methylethanamine (23-4)

Following the procedure (step 6, scheme 17) used to prepare compound 17-7, compound 23-3 was used as starting material, giving compound 23-4 in 62% yield as a colorless oil, which was converted to the hydrochloride salt. $^1$H NMR (DMSO-d$_6$, 300 MHz) δ (ppm) (HCl salt): 8.62 (br, 2H), 7.18-7.31 (m, 5H), 7.15 (s, 1H), 6.87 (d, J=13.4 Hz, 1H), 3.85 (d, J=1.7 Hz, 3H), 3.69 (s, 3H), 3.05-3.13 (m, 4H), 2.88 (br, 4H), 2.57 (s, 3H). LRMS: calc 340.2 found 341.1[MH]$^+$.

The compounds in Table 24 was made according to processes described in Scheme 23.

TABLE 24

| Structure | name | Ex. number | ID number | NMR | MS | Procedure of scheme |
|---|---|---|---|---|---|---|
| 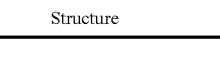 | 2-(5-(2-cyclohexylethyl)-7-fluoro-4-methoxy-1-methyl-1H-indol-3-yl)-N-methylethanamine | 79 | 23-5 | $^1$H NMR (DMSO-d$_6$, 300 MHz) δ (ppm) (HCl salt): 8.66 (br, 2H), 7.14 (s, 1H), 6.75 (d, J = 13.5 Hz, 1H), 3.85 (d, J = 1.6 Hz, 3H), 3.72 (s, 3H), 3.05-3.16 (m, 4H), 2.58-2.63 (m, 2H), 2.57 (s, 3H), 1.64-1.78 (m, 5H), 1.41-1.48 (m, 2H), 1.14-1.25 (m, 4H), 0.89-0.97 (m, 2H) | calc 346.2 found 347.2 [MH]+ | 23 |

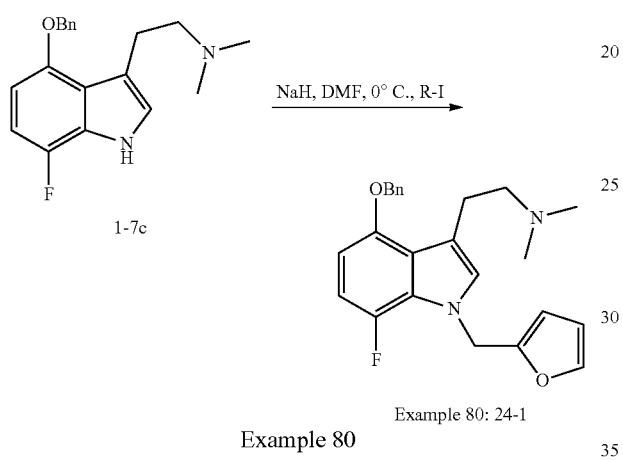

Example 80

2-(4-(benzyloxy)-7-fluoro-1-(furan-2-ylmethyl)-1H-indol-3-yl)-N,N-dimethylethanamine (24-1)

Step 1: 2-(4-(benzyloxy)-7-fluoro-1-(furan-2-ylmethyl)-1H-indol-3-yl)-N,N-dimethylethanamine (24-1)

Following the procedure (step 5-1, scheme 17) used to prepare compound 17-6, the compound 1-7c, gave compound 24-1 in 40% yield as a colorless oil, which was converted to the hydrochloride salt. $^1$H NMR (CDCl$_3$, 300 MHz) δ (ppm) (HCl salt): 12.09 (br, 2H), 7.34-7.49 (m, 6H), 6.94 (s, 1H), 6.88 (dd, J=12.1, 8.3 Hz, 1H), 6.43 (dd, J=8.8, 3.0 Hz, 1H), 6.29-6.30 (m, 2H), 5.33 (s, 2H), 5.02 (s, 2H), 3.15-3.20 (m, 2H), 3.00-3.04 (m, 2H), 2.23 (s, 3H), 2.22 (s, 3H). LRMS: calc 392.2 found 393.2 [MH]+.

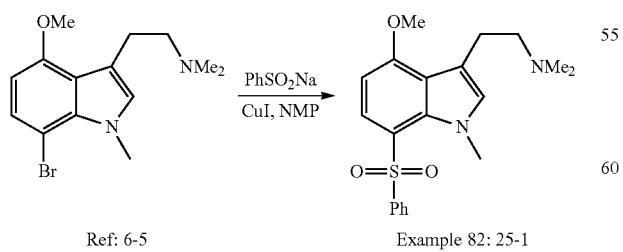

Example 82

2-(4-Methoxy-1-methyl-7-(phenylsulfonyl)-1H-indol-3-yl)-N,N-dimethylethanamine hydrochloride (25-1)

Step 1: 2-(4-Methoxy-1-methyl-7-(phenylsulfonyl)-1H-indol-3-yl)-N,N-dimethylethanamine hydrochloride (25-1)

A mixture of compound 6-5 (100 mg, 0.32 mmol), sodium benzenesulfinate (264 mg, 1.6 mmol), CuI (306 mg, 1.6 mmol) in 10 mL NMP was heated at 150° C. for 3 h under argon. After cooling to room temperature, the reaction mixture was diluted with MeOH and filtered. The filtrate was concentrated and purified by flash column chromatography, eluting with CH₂Cl²/MeOH/NH₄OH to give the product as a brown oil (35 mg), which was converted to the HCl salt to afford 25-1 as a yellow solid (32 mg), mp 200-203° C. ¹H NMR (CDCl₃, 300 MHz) δ (ppm) 7.92 (d, J=8.5 Hz, 1H), 7.77-7.82 (m, 2H), 7.47-7.61 (m, 3H), 6.83 (s, 1H), 6.59 (d, J=8.5 Hz, 1H), 4.06 (s, 3H), 3.77 (s, 3H), 3.42 (bs, 2H), 3.26 (bs, 2H), 2.84 (bs, 6H). LRMS: Calc 372.2. found 373.2 [MH]⁺.

Example 83

(E)-Methyl 3-(3-(2-(dimethylamino)ethyl)-4-methoxy-1-methyl-1H-indol-7-yl)acrylate hydrochloride (25-2)

Step 1: (E)-Methyl 3-(3-(2-(dimethylamino)ethyl)-4-methoxy-1-methyl-1H-indol-7-yl)acrylate hydrochloride (25-2)

In a seal tube, a mixture of 6-5 (311 mg, 1.0 mmol), methyl acrylate (0.90 mL, 10 mmol), Pd₂(dba)₃ (46 mg, 0.05 mmol), P(t-Bu)₃ (50 µL, 0.2 mmol) and Cs₂CO₃ (652 mg, 2.0 mmol) in 15 mL dioxane was heated at 100° C. overnight. Since MS showed incomplete reaction, methyl acrylate (0.90 mL), Pd₂ (dba)₃ (125 mg), PᵗBu₃ (2.0 mL) was added and the mixture was heated for another 6 h. After cooling to room temperature, the reaction mixture was filtered, and the filtrate was concentrated. The brown oil was purified by flash column chromatography, eluting with CH₂Cl₂/NH₄OH (1%) to afford 25-2 as yellow solid (303 mg, 87%). The final product showed 10% cis isomer by ¹H NMR and 34% cis isomer by HPLC. ¹H NMR (CDCl₃, 300 MHz) δ (ppm) 8.47 (d, J=15.4 Hz, 1H), 7.35 (d, J=8.2 Hz, 1H), 6.68 (s, 1H), 6.48 (d, J=8.2 Hz, 1H), 6.27 (d, J=15.4 Hz, 1H), 3.95 (s, 3H), 3.92 (s, 3H), 3.80 (s, 3H), 2.97-3.03 (m, 2H), 2.53-2.59 (m, 2H), 2.32 (s, 6H). LRMS: Calc 316.2. found 317.2 [MH]⁺.

Example 84

3-(3-(2-(Dimethylamino)ethyl)-4-methoxy-1-methyl-1H-indol-7-yl)propan-1-ol hydrochloride (25-4)

Step 1: Methyl 3-(3-(2-(dimethylamino)ethyl)-4-methoxy-1-methyl-1H-indol-7-yl)propanoate (25-3)

A mixture of 25-2 (78.6 mg, 0.25 mmol) and Pd/C (5%, 50 mg) in MeOH was purged with nitrogen and hydrogen, and then the reaction was stirred at room temperature. After 6 h, the reaction mixture was filtered and concentrated to give the compound 25-3 as a pale yellow semi-solid (67 mg), which was used for the next step without purification. ¹H NMR (CDCl, 300 MHz) δ (ppm) 6.82 (d, J=8.0 Hz, 1H), 6.64 (s, 1H), 6.37 (d, J=8.0 Hz, 1H), 3.93 (s, 3H), 3.87 (s, 3H), 3.28-3.34 (m, 2H), 2.99-3.05 (m, 2H), 2.57-2.69 (m, 4H), 2.35 (s, 6H).

Step 2: 3-(3-(2-(Dimethylamino)ethyl)-4-methoxy-1-methyl-1H-indol-7-yl)propan-1-ol hydrochloride (25-4)

To a suspension of 25-3 in 10 mL THF, a solution of LiAlH₄ (1.0 M in THF, 1.1 mL) was added and the mixture was stirred at room temperature for 5 h. The reaction was quenched by water and extracted by EtOAc (2×50 mL), and the combined organic phase was washed by brine and dried over Na₂SO₄. After concentration, the brown oil was purified by flash column chromatography, eluting with CH₂Cl₂/5% NH₄OH/2% MeOH to afford 25-4 as a colorless oil (44 mg), and then it was converted to the HCl salt to give the product as a white solid, mp 182-185° C. ¹H NMR (DMSO-d₆ 300 MHz) δ (ppm): 9.84 (bs, 1H), 6.98 (s, 1H), 6.78 (d, J=8.0 Hz, 1H), 6.42 (d, J=8.0 Hz, 1H), 4.54 (t, J=5.0 Hz, 1H), 3.92 (s, 3H), 3.84 (s, 3H), 3.47 (q, J=6.0 Hz, 2H), 3.17-3.25 (m, 2H), 3.06-3.14 (m, 2H), 2.96 (t, J=9.0 Hz, 2H), 1.66-1.74 (m, 2H). LRMS: Calc 290.2. found 291.2 [MH]⁺.

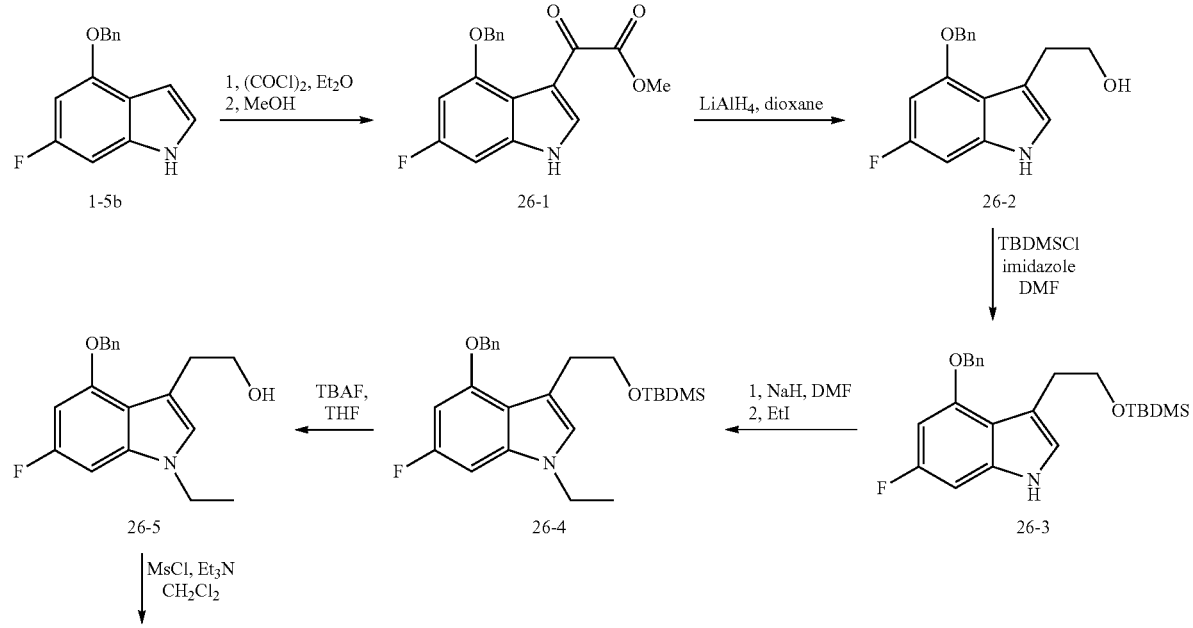

Scheme 26

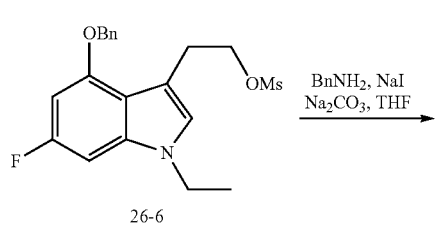 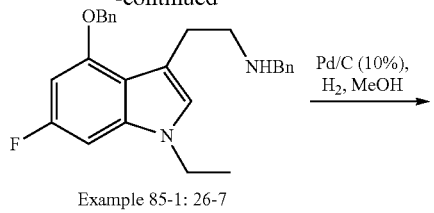

Example 85-1

N-Benzyl-2-(4-(benzyloxy)-1-ethyl-6-fluoro-1H-indol-3-yl)ethanamine (26-7)

Step 1: Methyl 2-(4-(benzyloxy)-6-fluoro-1H-indol-3-yl)-2-oxoacetate (26-1)

To a solution of compound 1-5b (559 mg, 2.32 mmol) in 70 mL ether, oxalyl chloride was added slowly at 0° C. After 10 min, the reaction mixture was warmed to room temperature and stirred for 6 h. After the mixture was cooled to 0° C., $Et_3N$ (3.0 mL) and MeOH (3.0 mL) were introduced and the resulting mixture was stirred overnight. The reaction mixture was diluted with water and extracted with EtOAc 2×100 mL, the combined organic phase was washed by brine and dried over $Na_2SO_4$. After concentration, the crude product 26-1 was obtained as a brown oil (897 mg), which was used in the next step without purification. $^1$H NMR ($CDCl_3$, 300 MHz) δ (ppm): 9.09 (bs, 1H), 8.00 (d, J=3.0 Hz, 1H), 7.50 (d, J=7.1 Hz, 2H), 7.28-7.41 (m, 3H), 6.72 (dd, J=1.9, 8.3 Hz, 1H), 6.51 (dd, J=1.9, 11.7 Hz, 1H), 5.20 (s, 2H), 3.67 (s, 3H).

Step 2: 2-(4-(Benzyloxy)-6-fluoro-1H-indol-3-yl)ethanol (26-2)

A crude of 26-1 (2.32 mmol) and $LiAlH_4$ (1.32 g, 34.8 mmol) in 100 mL dioxane was heated at reflux for 2 h. The reaction mixture was cooled to 0° C. and quenched by water, 15% NaOH and then water. The resulting suspension was stirred for 30 min, and then filtered. After dried over $Na_2SO_4$, the organic phase was concentrated to give a brown oil, which was purified by flash column chromatography, eluting with hexanes/EtOAc (8:1 to 1:1) to afford 26-2 as a white solid (259 mg, 39%). $^1$H NMR ($CDCl_3$) δ (ppm): 7.98 (bs, 1H), 7.35-7.48 (m, 5H), 6.91 (d, J=2.5 Hz, 1H), 6.68 (dd, J1=1.9 Hz, J2=9.2 Hz, 1H), 6.39 (dd, J1=1.9 Hz, J2=11.5 Hz, 1H), 5.14 (s, 2H), 6.81 (q, J=6.3 Hz, 2H), 3.07 (t, J=6.3 Hz, 2H), 1.47 (t, J=6.0 Hz, 1H).

Step 3, 4 and 5: 2-(4-(Benzyloxy)-1-ethyl-6-fluoro-1H-indol-3-yl)ethanol (26-5)

To a solution of 26-2 (259 mg, 0.91 mmol) and imidazole (494 mg, 7.26 mmol) in 25 mL DMF, TBDMSCl (547 mg, 3.63 mmol) was added and the reaction mixture was stirred at room temperature overnight. The reaction mixture was partitioned with EtOAc and brine, and the combined organic phase was washed by brine and dried over $Na_2SO_4$. After concentration, the product 26-3 was obtained as brown oil, which was used for the next step without purification.

The crude 26-3 was dissolved in 50 mL DMF and the mixture was cooled to 0° C. NaH (730 mg, 18.2 mmol) was added at once and stirred at this temperature for 20 min. Then MeI (1.46 mL, 18.2 mmol) was added and stirred for 2 h. The reaction mixture was quenched by water, and extracted with EtOAc 2×150 mL. The combined organic phase was washed by brine and dried over $Na_2SO_4$. After concentration, the product 26-4 was obtained as brown liquid, and it was used in the next step without purification.

To a solution of the crude 26-4 in 15 mL THF, TBAF solution (1.0 M in THF, 5.5 mL) was introduced via syringe and the mixture was stirred for 2 h. After diluted with EtOAc, the mixture was washed with water, brine, and dried over $Na_2SO_4$, then concentrated in vacuo to give a brown oil, which was purified by flash column chromatography, eluting with hexanes/EtOAc (8:1 to 1:1) to afford the product 26-5 as a pale yellow oil (259 mg, 91%). $^1$H NMR ($CDCl_3$) δ (ppm): 7.34-7.48 (m, 5H), 6.82 (s, 1H), 6.62 (dd, J=2.2, 9.6 Hz, 1H), 6.37 (dd, J=1.9, 11.5 Hz, 1H), 5.14 (s, 2H), 4.01 (q, J=7.4 Hz, 2H), 3.79 (q, J=6.3 Hz, 2H), 3.05 (t, J=6.3 Hz, 2H), 1.48 (t, J=6.0 Hz, 1H), 1.41 (t, J=7.4 Hz, 3H).

Step 6 and 7: N-Benzyl-2-(4-(benzyloxy)-1-ethyl-6-fluoro-1H-indol-3-yl)ethanamine (26-7)

To a solution of 26-5 (60 mg, 0.19 mmol) and $Et_3N$ (0.16 mL, 1.15 mmol) in 12 mL $CH_2Cl_2$, MsCl (23 µL, 0.29 mmol) was added dropwise and the reaction mixture was stirred for 2 h. The reaction mixture was diluted with $CH_2Cl_2$ and washed with brine. The organic phase was dried over $Na_2SO_4$ and concentrated to get 26-6 as a colorless oil.

Crude 26-6 was dissolved in 5 mL THF and transferred to a sealed tube. $BnNH_2$ solution (2.1 mL, 19 mmol), NaI (10 mg), $Na_2CO_3$ (201 mg, 1.9 mmol) were added. The tube was sealed and heated at 80° C. overnight. After cooling to room temperature, the reaction mixture was partitioned with EtOAc and water, and the organic phase was washed with brine and dried over $Na_2SO_4$. After concentration, the brown oil was purified by flash column chromatography, eluting with $CH_2Cl_2$/MeOH/$NH_4OH$ to afford 26-7 as a yellow oil which was converted into the HCl salt to give a yellow solid, mp 167-171° C. $^1$H NMR (DMSO-$d_6$, 300 MHz) δ (ppm): 9.04 (bs, 1H), 7.30-7.51 (m, 10H), 7.12 (s, 1H), 6.93 (dd, J=1.9, 9.9 Hz, 1H), 6.53 (dd, J=1.9, 12.0 Hz, 1H), 5.21 (s, 2H), 4.04 (q, J=7.4 Hz, 2H), 5.95-4.00 (m, 2H), 3.14 (bs, 4H), 1.29 (t, J=7.4 Hz, 3H). LRMS: Calc 402.2. found 403.2 $[MH]^+$.

Example 85-2

3-(2-(benzylamino)ethyl)-1-ethyl-6-fluoro-1H-indol-4-ol (26-8)

Step 7: 3-(2-(benzylamino)ethyl)-1-ethyl-6-fluoro-1H-indol-4-ol (26-8)

Following the procedure (step 2-1, scheme 23) used to prepare compound 23-2, compound 26-7 gave compound 26-8 in 37% yield (67.5 mg) as off-white solid. $^1$H NMR (300 MHz, MeOD-d6) δ (ppm): 7.41 (d, J=20.1 Hz, 5H), 6.96 (s, 1H), 6.59 (dd, J=9.9, 2.1 Hz, 1H), 6.19 (dd, J=11.2, 2.0 Hz, 1H), 4.20 (s, 2H), 4.05 (q, J=7.3 Hz, 2H), 3.37 (dd, J=13.4, 6.1 Hz, 2H), 3.26-3.16 (m, 2H), 1.37 (t, J=7.2 Hz, 3H). LRMS: calc 312.16. found 313.1 $[MH]+$.

The compound in Table 27 was made according to processes described in Scheme 26.

TABLE 27

| Structure | name | Ex. number | ID number | NMR | MS | Procedure of scheme |
|---|---|---|---|---|---|---|
| 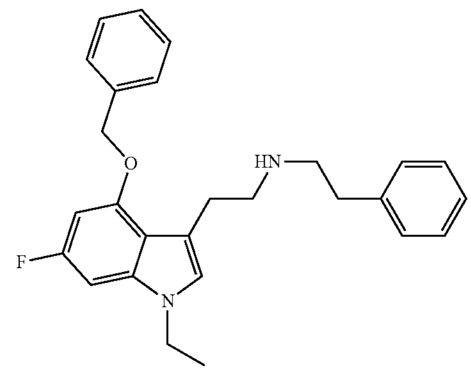 [SMILES: CCn1cc(CCNCCc2ccccc2)c2c(OCc3ccccc3)cc(F)cc21] | 2-(4-(benzyl-oxy)-1-ethyl-6-fluoro-1H-indol-3-yl)-N-phenethyl-ethanamine | 85-3 | 26-9 | $^1$H NMR δ (ppm): (300 MHz, MeOD-d6) δ (ppm): 7.52-7.43 (m, 2H), 7.41-7.28 (m, 3H), 7.22-7.11 (m, 3H), 7.08-7.00 (m, 2H), 6.73 (s, 1H), 6.67 (dd, J = 9.8, 2.0 Hz, 1H), 6.41 (dd, J = 11.8, 1.9 Hz, 1H), 5.12 (s, 2H), 3.99 (q, J = 7.2 Hz, 2H), 2.93 (t, J = 6.9 Hz, 2H), 2.80 (t, J = 6.7 Hz, 2H), 2.67 (dt, J = 5.3, 4.3 Hz, 4H), 1.31 (t, J = 7.2 Hz, 3H) | calc 416.23, found 417.3 [MH]+ | 26 Step 1-6 |
| 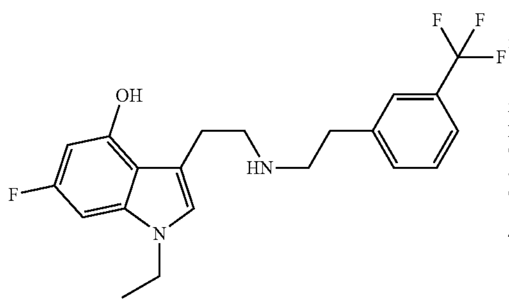 [SMILES: CCn1cc(CCNCCc2cccc(C(F)(F)F)c2)c2c(O)cc(F)cc21] | 1-ethyl-6-fluoro-3-(2-(3-(trifluoro-methyl)phen-ethyl-amino)ethyl)-1H-indol-4-ol | 85-4 | 26-10 | $^1$H NMR (300 MHz, MeOD-d6) δ (ppm): 7.56-7.28 (m, 4H), 6.77 (s, 1H), 6.49 (dd, J = 10.0, 2.1 Hz, 1H), 6.15 (dd, J = 11.6, 2.1 Hz, 1H), 6.15 (dd, J = 11.6, 2.1Hz, 1H), 3.98 (q, J = 7.2 Hz, 2H), 2.97 (dt, J = 9.7, 4.8 Hz, 4H), 2.86 (s, 4H), 1.32 (t, J = 7.2 Hz, 3H) | calc 394.17, found 395.1 [MH]+ | 26 |
| 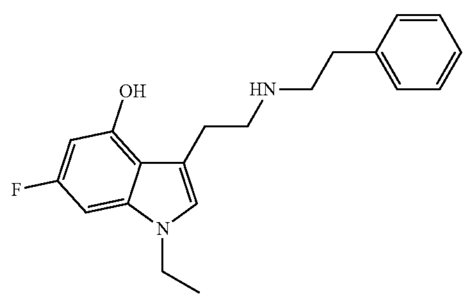 [SMILES: CCn1cc(CCNCCc2ccccc2)c2c(O)cc(F)cc21] | 1-ethyl-6-fluoro-3-(2-(phenyl-ethylamino)ethyl)-1H-indol-4-ol | 85-5 | 26-1 | $^1$H NMR (300 MHz, MeOD-d6) δ (ppm): 7.15 (40, J = 19.7, 10.9, 4.9 Hz, 5H), 6.74 (s, 1H), 6.48 (dd, J = 10.0, 2.1 Hz, 1H), 6.14 (dd, J = 11.6, 2.1 Hz, 1H), 3.97 (dt, J = 9.3, 4.6 Hz, 4H), 2.82 (td, J = 11.5, 6.9 Hz, 4H), 1.32 (t, J = 7.2 Hz, 3H) | calc 326.18, found 327.2 [MH]+ | 26 |

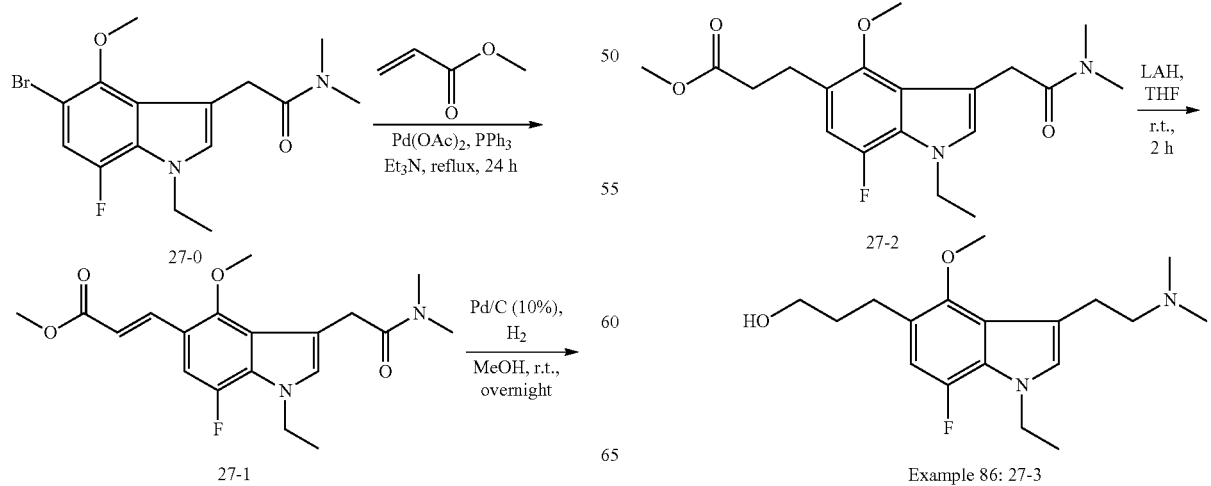

Scheme 27

Example 86

Synthesis of 3-(3-(2-(dimethylamino)ethyl)-7-fluoro-4-methoxy-1-ethyl-1H-indol-5-yl)propan-1-ol (27-3)

Step 1: (E)-methyl3-(7-fluoro-4-methoxy-1-ethyl-3-(2-(methylamino)-2-oxoethyl)-1H-indol-5-yl)acrylate (27-1)

To a solution of 27-0 (7.5 g, 21.0 mmol) (prepared as 8-11 scheme 8) in anhydrous Et$_3$N (20 mL) was added Pd(OAc)$_2$ (471 mg, 2.1 mmol), PPh$_3$ (1100 mg, 4.2 mmol) and methyl acrylate (2.7 g, 31.3 mmol). The mixture was refluxed for 24 h. After cooled to room temperature, the mixture was filtered, and the residue was evaporated to obtain 27-1 (7.5 g, 20.7 mmol) as red oil, which was used in the next step without further purification. LRMS: calc 362.1 and found 363.1 [MH]$^+$.

Step 2: methyl 3-(3-(2-(dimethylamino)-2-oxoethyl)-7-fluoro-4-methoxy-1-ethyl-1H-indol-5-yl)propanoate (27-2)

To a solution of 27-1 (200 mg, 0.57 mmol) in 20 mL of MeOH was added 0.1 g of Pd/C (10%). The mixture was stirred over night under H$_2$ atmosphere at room temperature. The mixture was filtered and the filtrate was to afford 27-2 (150 mg, 0.42 mmol, 74%) as a white solid. LRMS: calc 364.1 and found: 365.1 [MH]$^+$.

Step 3: 3-(3-(2-(dimethylamino)ethyl)-7-fluoro-4-methoxy-1-ethyl-1H-indol-5-yl)propan-1-ol (27-3)

To a solution of 27-2 (150 mg, 0.42 mmol) in anhydrous THF (20 mL) was added LiAlH$_4$ (78 mg, 2.05 mmol) and the mixture was stirred at room temperature for two hours. Na$_2$SO$_4$.10H$_2$O was added, the solid was filtered off and washed with ethylacetate (20 mL). The filtrate was concentrated in under vacuum. The resulting residue was purified by column chromatographyon (DCM:MeOH=50:1) to afford compound 27-3 (30 mg, 23%) as a white solid. $^1$H-NMR (400 MHz, MeOD-d6): δ (ppm) 7.02 (s, 1H), 6.65 (d, J=13.2 Hz, 1H), 4.16 (q, J=6.8 Hz, 2H), 3.72 (s, 3H), 3.51 (t, J=6.6 Hz, 2H), 3.22-3.17 (m, 2H), 3.10-3.03 (m, 2H), 2.74 (s, 6H), 2.72-2.64 (m, 2H), 1.79-1.72 (m, 2H), 1.30 (t, J=7.2 Hz, 3H). LRMS: calc 322.4 and found: 323.0 [MH]$^+$.

Scheme 28

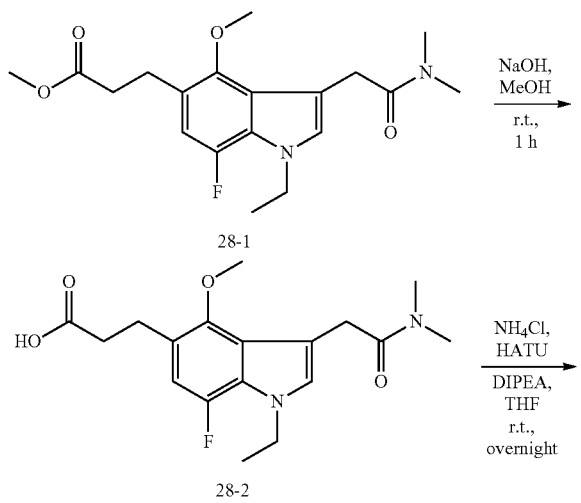

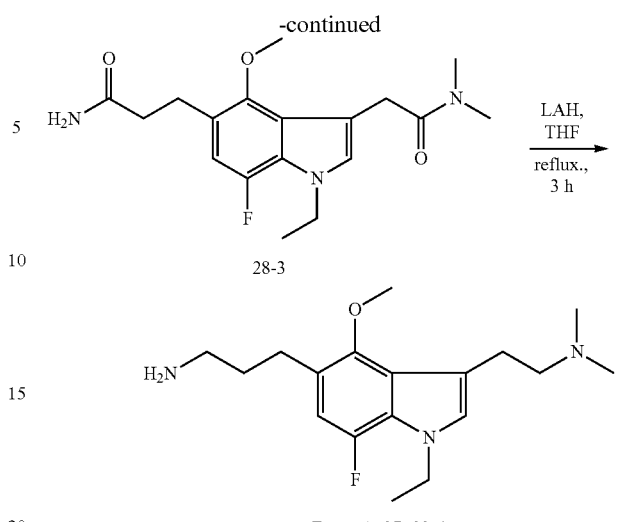

Example 87: 28-4

Example 87

3-(3-(2-(dimethylamino)ethyl)-1-ethyl-7-fluoro-4-methoxy-1H-indol-5-yl)propan-1-amine (28-4)

Step 1: 3-(3-(2-(dimethylamino)-2-oxoethyl)-1-ethyl-7-fluoro-4-methoxy-1H-indol-5-yl) propanoic acid (28-2)

To a solution of 28-1 (200 mg, 0.55 mmol) (prepared using similar synthetic scheme as 27-2) in MeOH (4 mL) was added 2N NaOH (4 mL), and then the mixture was stirred at room temperature for one hour. The reaction mixture was neutralized with 1N HCl to pH=7, then extracted with ethyl acetate (3×100 mL). The organic layer was concentrated under vacuum to afford 28-2 (180 mg, 94%) as a yellow solid. LRMS: calc 350.2 and found: 351.1 [MH]$^+$.

Step 2: 3-(3-(2-(dimethylamino)-2-oxoethyl)-1-ethyl-7-fluoro-4-methoxy-1H-indol-5-yl)propanamide (28-3)

A mixture of 28-2 (180 mg, 0.51 mmol), HATU (388 mg, 1.02 mmol), DIPEA (220 mg, 1.7 mmol) and ammonium chloride (73 mg, 1.36 mmol) in THF (10 mL) was stirred at room temperature overnight. Water (10 mL) was added, and the reaction mixture was extracted with ethyl acetate (3×20 mL). The combined organic phase was dried over MgSO$_4$, filtered and evaporated to give crude product, which was purified by preparative TLC (petroleum ether/ethyl acetate=1:1) to afford 28-3 (150 mg, 84%) as a yellow solid. LRMS: calc 349.2 and found: 350.0 [M+1].

Step 3: 3-(3-(2-(dimethylamino)ethyl)-1-ethyl-7-fluoro-4-methoxy-1H-indol-5-yl)propan-1-amine (28-4)

To a solution of 28-3 (100 mg, 0.28 mmol) in THF (10 mL) was added lithium aluminum hydride (44 mg, 1.15 mmol) in portions. The mixture was stirred at room temperature overnight. NaSO$_4$.10H$_2$O was added, then the mixture was filtered and the filtrate was evaporated. The crude product was purified by preparative HPLC (acid conditions) to afford 28-4 (10 mg, 11%) as a yellow solid. $^1$H-NMR (400 MHz, CDCl$_3$):

δ (ppm) 6.83 (s, 1H), 6.66 (d, J=6.6 Hz, 1H), 4.21 (q, J=7.2 Hz, 2H), 3.80 (s, 3H), 3.04 (t, J=7.2 Hz, 2H), 2.77-2.69 (m, 6H), 2.62-2.60 (br.s, 2H), 2.40 (s, 6H), 1.85-1.78 (m, 2H), 1.42 (t, J=6.8 Hz, 3H). LRMS: calc 321.4 and found: 322.0 [M+1].

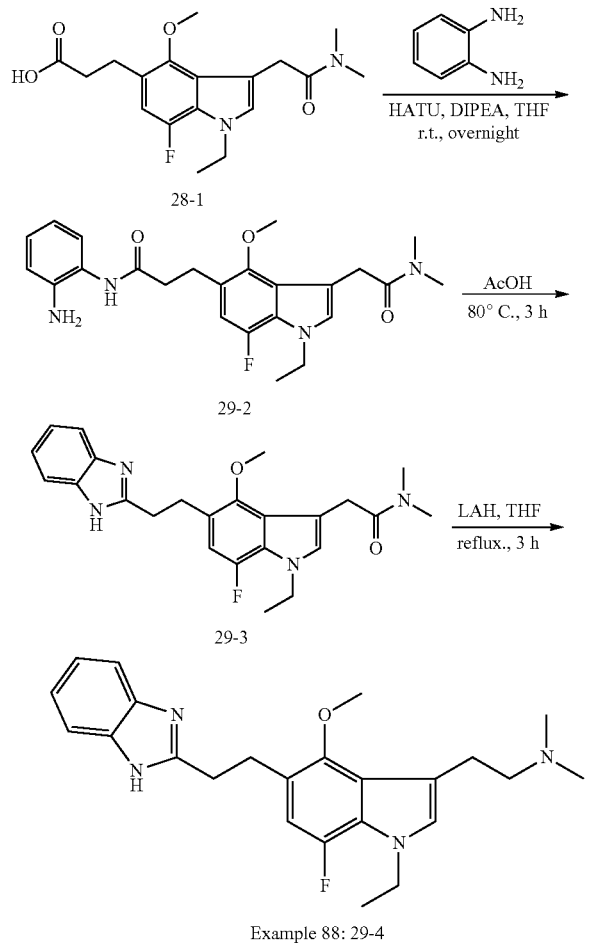

Example 88: 29-4

Example 88

2-(5-(2-(1H-benzo[d]imidazol-2-yl)ethyl)-1-ethyl-7-fluoro-4-methoxy-1H-indol-3-yl)-N,N-dimethylethanamine (29-4)

Step 1: N-(2-aminophenyl)-3-(3-(2-(dimethylamino)-2-oxoethyl)-1-ethyl-7-fluoro-4-methoxy-1H-indol-5-yl)propanamide (29-2)

A mixture of 28-1 (300 mg, 0.86 mmol), HATU (490 mg, 1.29 mmol), DIPEA (278 mg, 2.15 mmol) and benzene-1,2-diamine (140 mg, 1.29 mmol) in THF (10 mL) was stirred at room temperature overnight. Water (10 mL) was added, and the reaction mixture was extracted with ethyl acetate (3×20 mL). The combined organic phase was dried over MgSO₄, filtered and evaporated to give crude product, which was purified by preparative TLC (petroleum ether/ethyl acetate=1:1) to afford 29-2 (250 mg, 66%) as a light yellow solid. LRMS: calc 440.2 and found: 441.2 [M+1].

Step 2: 2-(5-(2-(1H-benzo[d]imidazol-2-yl)ethyl)-1-ethyl-7-fluoro-4-methoxy-1H-indol-3-yl)-N,N-dimethylacetamide (29-3)

A solution of 29-2 (230 mg, 0.52 mmol) in acetic acid (10 mL) was heated to 80° C. for 3 h. After cooled to room temperature, water (10 mL) and sat. aqueous NaHCO₃ (30 mL) were added. The mixture was extracted with ethyl acetate (3×20 mL). The combined organic layer was dried with MgSO₄, filtered and evaporated to afford 29-3 (150 mg, 68%) as yellow oil. LRMS: calc 422.5 and found: 423.2 [M+1].

Step 3: 2-(5-(2-(1H-benzo[d]imidazol-2-yl)ethyl)-1-ethyl-7-fluoro-4-methoxy-1H-indol-3-yl)-N,N-dimethylethanamine (29-4)

To a solution of 29-3 (100 mg, 0.24 mmol) in THF (10 mL) was added lithium aluminum hydride (19 mg, 0.48 mmol). The mixture was stirred at room temperature overnight. Na₂SO₄.10H₂O was added and the reaction mixture was filtered and the filtrate was evaporated to give the crude product which was purified by preparative HPLC (basic condition, water/CH₃CN, 43-53% CH₃CN in 7.5 min, RT=7.3 min) to afford 29-4 (22 mg, 23%) as a yellow solid. ¹H-NMR (400 MHz, CDCl₃): δ (ppm) 7.52-7.50 (br.s, 2H), 7.20-7.16 (m, 2H), 6.76 (s, 1H), 6.66 (d, J=12.8 Hz, 1H), 3.96 (q, J=7.2 Hz, 2H), 3.81 (s, 3H), 3.14 (t, J=7.2 Hz, 2H), 3.06-2.98 (m, 4H), 2.69 (t, J=7.6 Hz, 2H), 2.38 (s, 6H) 1.30 (t, J=7.2 Hz, 3H). LRMS: calc 408.5 and found: 409.2 [M+1].

Scheme 30

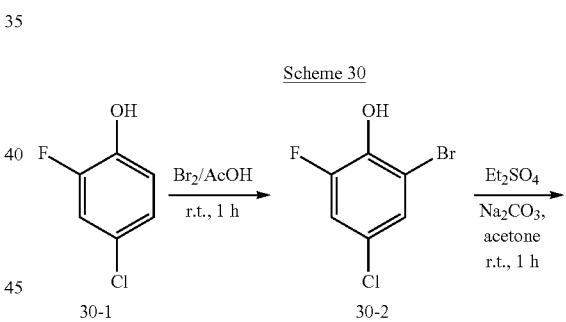

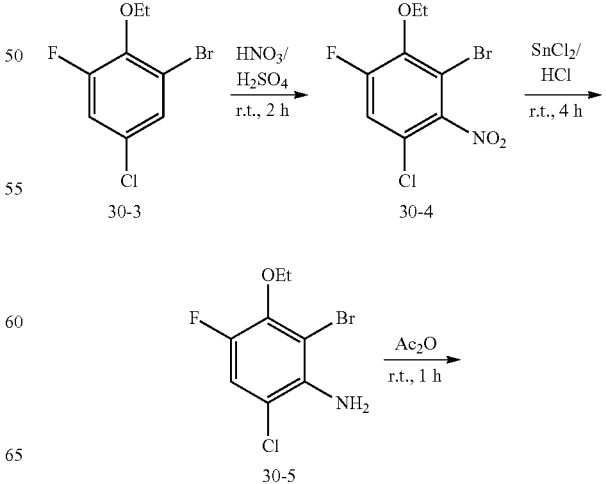

-continued

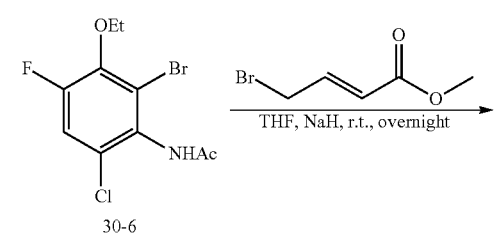
30-6

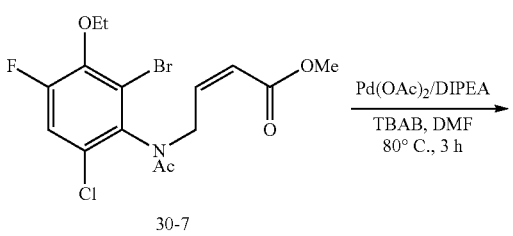
30-7

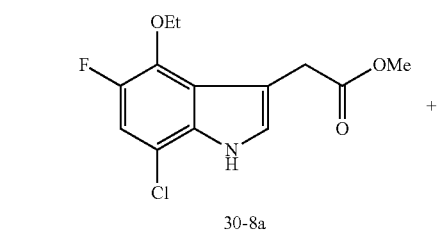
30-8a
+

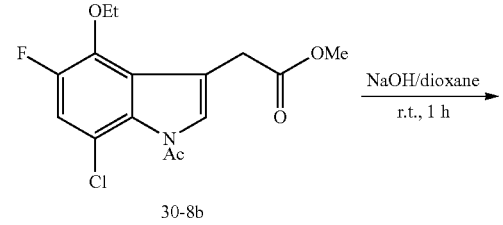
30-8b

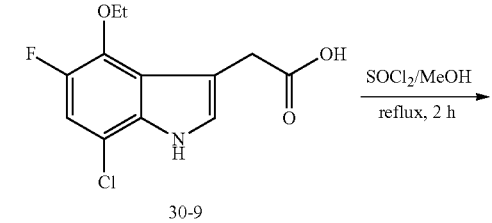
30-9

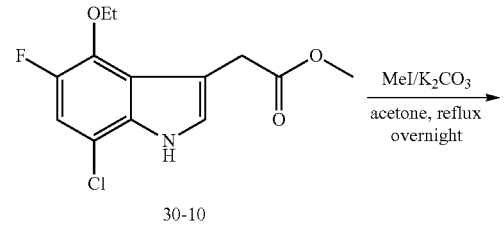
30-10

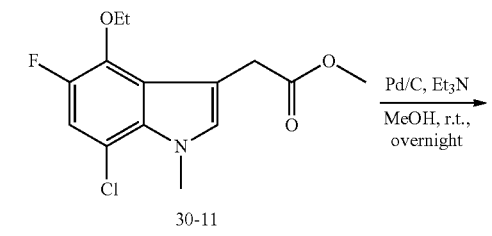
30-11

-continued

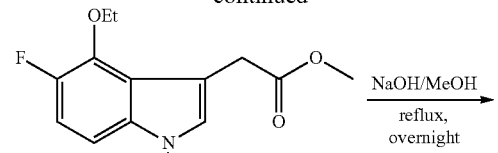
30-12

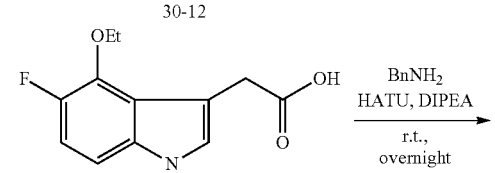
30-13

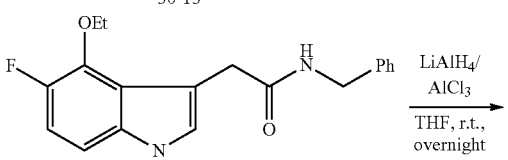
30-14

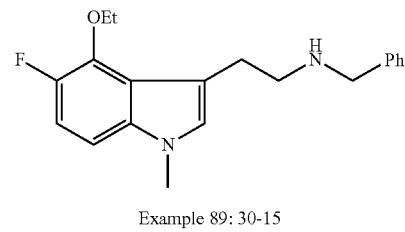
Example 89: 30-15

Example 89

N-benzyl-2-(4-ethoxy-5-fluoro-1-methyl-1H-indol-3-yl)ethanamine (30-15)

Step 1: 2-bromo-4-chloro-6-fluorophenol (30-2)

To a solution of 30-1 (29.31 g, 200 mmol) in acetic anhydride (200 mL) was added bromine (32 g, 200 mmol) dropwise. After the addition, the mixture was stirred at room temperature overnight and then was poured into ice water. 100 mL of saturated aqueous $NaHSO_3$ aqueous was added. The precipitate was filtered and dried over $Na_2SO_4$ to afford 30-2 (48.1 g) as a white solid. LRMS: calc 223.9 and found: 224.9 [M+1].

Step 2: 1-bromo-5-chloro-2-ethoxy-3-fluorobenzene (30-3)

To a mixture of 30-2 (48.1 g, 214 mmol) and $Na_2CO_3$ (34 g, 321 mmol) in acetone (300 mL) was added a solution of $Et_2SO_4$ (39.6 g, 257 mmol) in acetone (100 mL) dropwise over 20 minutes and then the mixture was stirred at room temperature for one hour. The solid was filtered off and the filtrate was concentrated under vacuum to afford 30-3 (48.6 g, 90%) as a white solid. LRMS: calc 251.9 and found: 252.9 [M+1].

Step 3: 3-bromo-1-chloro-4-ethoxy-5-fluoro-2-nitrobenzene (30-4)

To a solution of 30-3 (48.6 g, 192 mmol) in concentrated $H_2SO_4$ (240 mL) stirred at room temperature was added $HNO_3$ (19 mL) dropwise. The mixture was allowed to stir at room temperature for two hours. The reaction mixture was then poured into ice water and extracted with ethyl acetate (3×800 mL). The organic layer was combined and concentrated under vacuum to get a crude product which was purified on silica gel column chromatography eluting with petroleum ether/ethyl acetate (10:1 to 1:1) to afford 30-4 (22.9 g, 40%) as a yellow solid. LRMS: calc 296.9 and found: 297.9 [M+1].

Step 4: 2-bromo-6-chloro-3-ethoxy-4-fluorobenzenamine (30-5)

To a solution of 30-4 (22.9 g, 77 mmol) in ethanol (100 mL) at room temperature was added concentrated HCl (74 mL) and $SnCl_2$ (44 g, 231 mmol). The mixture was allowed to stir at room temperature for 4 hours. The reaction mixture was poured into water and extracted with ethyl acetate (3×150 mL), the organic layer was combined and was concentrated under vacuum to get a crude product which was purified on silica gel column chromatography eluting with petroleum ether/ethyl acetate (5:1 to 1:1) to afford 30-5 (16 g, 78%) as a white solid. LRMS: calc 266.9 and found: 267.9 [M+1].

Step 5: N-(2-bromo-6-chloro-3-ethoxy-4-fluorophenyl)acetamide (30-6)

A solution of 30-5 (16 g, 59.7 mmol) in acetic anhydride (50 mL) was stirred at room temperature for one hour. The precipitate was filtered and washed with ether to afford 30-6 (14 g, 76%) as a white solid. LRMS: calc 308.9 and found: 309.9 [M+1].

Step 6: (Z)-methyl 4-(N-(2-bromo-6-chloro-3-ethoxy-4-fluorophenyl)acetamido) but-2-enoate (30-7)

To a solution of 30-6 (12.42 g, 40 mmol) in THF (100 mL) was added NaH (1.92 g, 80 mmol) in portions, the mixture was stirred at room temperature for 30 min before (E)-methyl 4-bromobut-2-enoate (8.6 g, 48 mmol) was added. The mixture was stirred overnight. Water (150 mL) was added to the reaction mixture and extracted with ethyl acetate (3×200 mL). The combined organic layers were concentrated under vacuum to obtain a yellow residue, which was purified on silica gel column chromatography eluting with petroleum ether/ethyl acetate (5:1 to 1:1) to afford 30-7 (11.8 g, 72%) as a white solid. LRMS: calc 407.0 and found: 408.0 [M+1].

Step 7: methyl 2-(7-chloro-4-ethoxy-5-fluoro-1H-indol-3-yl)acetate (30-8a) and methyl 2-(1-acetyl-7-chloro-4-ethoxy-5-fluoro-1H-indol-3-yl)acetate (30-8b)

To a solution of 30-7 (11.8 g, 28.9 mmol) in anhydrous DMF (250 mL) was added Pd(OAc)$_2$ (0.64 g, 2.87 mmol), Bu$_4$NBr (18.36 g, 57.4 mmol) and DIPEA (5.8 g, 57.4 mmol) under $N_2$. The mixture was stirred at 80° C. for three hours before it was cooled to room temperature. Then the reaction mixture was poured into ice water and extracted with ethyl acetate (3×150 mL). The combined organic layer was concentrated to get a crude product which was purified on silica gel column chromatography eluting with petroleum ether/ethyl acetate (10:1 to 51:1) to afford a mixture 30-8a and 30-8b (6 g) as light yellow oil. LRMS (8-30-8a): calc 285.0 and found: 286.0 [M+1]. LRMS (30-8b): calc 327.07 and found: 328.0 [M+1].

Step 8: 2-(7-chloro-4-ethoxy-5-fluoro-1H-indol-3-yl) acetic acid (30-9)

To a solution of mixture 30-8a and 30-8b (500 mg, 1.53 mmol) in water (50 mL) was added 2N NaOH (8 mL), then the mixture was stirred at room temperature for one hour. The mixture was neutralized with HCl to pH=7, then extracted with ethyl acetate (3×100 mL). The combined organic layer was concentrated under vacuum to afford 30-9 (582 mg) as a yellow solid. LRMS: calc 271.0 and found: 272.1 [M+1].

Step 9: methyl 2-(7-chloro-4-ethoxy-5-fluoro-1H-indol-3-yl)acetate (30-10)

To a solution of 30-9 (582 mg, 6.4 mmol) in CH$_3$OH (20 mL) was added SOCl$_2$ (1 mL). The mixture was refluxed for 2 h before it was cooled to room temperature, the solvent was removed under reduce pressure. The resulting residue was partitioned between water (30 mL) and ethyl acetate (30 mL). The organic layer was separated and the aqueous layer was extracted with ethyl acetate (3×20 mL). The combined organic layers were combined, washed with brine (3×20 mL), dried over Na$_2$SO$_4$, filtered and concentrated to afford 30-10 (500 mg, 82%) as a light yellow solid. LRMS: calc 285.0 and found: 286.1 [M+1].

Step 10: methyl 2-(7-chloro-4-ethoxy-5-fluoro-1-methyl-1H-indol-3-yl)acetate (30-11)

To a solution of 30-10 (2 g, 7 mmol) in acetone (40 mL) was added K$_2$CO$_3$ (3 g, 21 mmol) and MeI (1.2 g, 8.4 mmol). The reaction mixture was refluxed overnight before it was cooled to room temperature. The solid was filtered off and the filtrate was evaporated to give the crude product, which was purified on silica gel column chromatography eluting with hexane/ethyl acetate (1:5) to afford 30-11 (1.4 g, 67%) as a yellow solid. LRMS: calc 299.1 and found: 300.1 [M+1].

Step 11: methyl 2-(4-ethoxy-5-fluoro-1-methyl-1H-indol-3-yl)acetate (30-12)

A mixture of 30-11 (1.4 g, 4.7 mmol), Pd/C (280 mg, 20%) and Et$_3$N (1.42 g, 14.1 mmol) in MeOH (20 mL) was stirred under hydrogen atmosphere at room temperature overnight. The mixture was filtered and the filtrate was concentrated to afford 30-12 (1 g, 92%) as a yellow solid. LRMS: calc 265.1 and found: 266.1 [M+1].

Step 12: 2-(4-ethoxy-5-fluoro-1-methyl-1H-indol-3-yl)acetic acid (30-13)

To a solution of 30-12 (45 mg, 0.17 mmol) in MeOH (10 mL) was added 2N NaOH (8 mL). The mixture was refluxed for one hour. After cooled to room temperature, the mixture was neutralized with hydrochloric acid to pH=7, extracted with ethyl acetate (3×100 mL). The combined organic layer was washed with brine (30 mL), dried over MgSO$_4$ and concentrated to afford 30-13 (40 mg, 94%) as a yellow solid. LRMS: calc 251.1 and found: 252.0 [M+1].

Step 13: N-benzyl-2-(4-ethoxy-5-fluoro-1-methyl-1H-indol-3-yl)acetamide (30-14)

A solution of 30-13 (30 mg, 0.12 mmol), HATU (76 mg, 0.2 mmol), DIPEA (39 mg, 0.3 mmol) and phenylmethanamine (17 mg, 0.16 mmol) in THF (5 mL) was stirred at room temperature overnight. Water (5 mL) and ethyl acetate (10 mL) were added to the mixture. The organic layer was separated, washed with brine (3×20 mL), dried over MgSO4, filtered and evaporated to give a crude product, which was purified by preparative TLC (petroleum ether/ethyl acetate=1:1) to afford 30-14 (28 mg, 69%) as a light yellow solid. LRMS: calc 340.2 and found: 341.1 [M+1].

Step 14: N-benzyl-2-(4-ethoxy-5-fluoro-1-methyl-1H-indol-3-yl)ethanamine (30-15)

To a solution of LiAlH$_4$ (5 mg, 0.12 mmol) and AlCl$_3$ (16 mg, 0.12 mmol) in THF (5 mL) was added a solution of 30-14 (14 mg, 0.04 mmol) in THF (5 mL) dropwise, the mixture was stirred at room temperature overnight before Na$_2$SO$_4$.10H$_2$O was added. The mixture was filtered and the filtrate was evaporated to give a crude product which was purified by preparative HPLC (acid condition, water/CH$_3$CN, 25-30% CH$_3$CN in 7.5 min, RT=6.5 min) to afford 30-15 (8 mg, 61%) as a yellow solid. $^1$H-NMR (400 MHz, CDCl$_3$): δ (ppm) 7.30-7.28 (m, 5H), 7.00-6.95 (m, 1H), 6.87-6.84 (m, 2H), 4.24 (q, J=7.2 Hz, 2H), 4.01-3.98 (br.s, 2H), 3.67 (s, 3H), 3.27-3.22 (br.s, 2H), 3.15-3.11 (br.s, 2H), 1.34 (t, J=6.8 Hz, 3H). LRMS: calc 326.2 and found: 327.0 [M+1].

The compounds in Table 28 were made according to processes described in Scheme 30.

TABLE 28

| Structure | name | Ex. number | ID number | NMR | MS | Procedure of scheme |
|---|---|---|---|---|---|---|
| 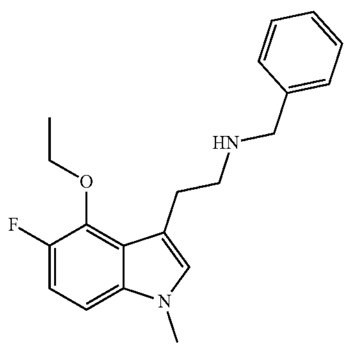 [SMILES: CCOc1c(F)ccc2c1c(CCNCc1ccccc1)cn2C] | N-benzyl-2-(4-ethoxy-5-fluoro-1-methyl-1H-indol-3-yl)ethanamine | 89 | 30-15 | $^1$H-NMR (400 MHz, CDCl$_3$): δ (ppm) 7.30-7.28 (m, 5H), 7.00-6.95 (m, 1H), 6.87-6.84 (m, 2H), 4.24 (q, 2H), 4.01-3.98 (br.s, 2H), 3.67 (s, 3H), 3.27-3.22 (br.s, 2H), 3.15-3.11 (br.s, 2H), 1.34 (t, J = 6.8 Hz, 3H). | calc 326.2, found 327.0 [MH]+ | 30 |
| 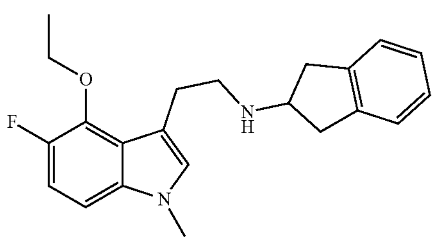 [SMILES: CCOc1c(F)ccc2c1c(CCNC1Cc3ccccc3C1)cn2C] | N-(2-(4-ethoxy-5-fluoro-1-methyl-1H-indol-3-yl)ethyl)-2,3-dihydro-1H-inden-2-amine | 90 | 30-16 | $^1$H-NMR (400 MHz, CDCl$_3$): δ (ppm) 7.16-7.11 (m, 4H), 6.99-6.94 (m, 1H), 6.86 (d, J = 3.2 Hz, 1H), 6.84 (s, 1H), 4.29 (q, 2H), 3.72-3.68 (m, 1H), 3.67 (s, 3H), 3.21-3.15 (m, 2H), 3.07 (s, 3H), 3.09-3.06 (m, 1H), 2.85-2.79 (m, 2H), 1.43 (t, J = 6.8 Hz, 3H). | calc 352.2, found 353.2 [MH]+ | 30 |
| 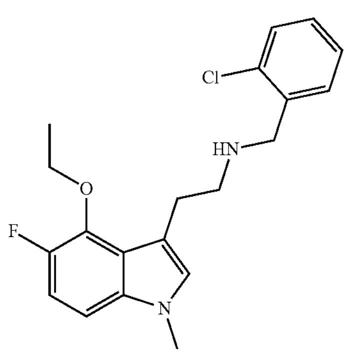 [SMILES: CCOc1c(F)ccc2c1c(CCNCc1ccccc1Cl)cn2C] | N-(2-chlorobenzyl)-2-(4-ethoxy-5-fluoro-1-methyl-1H-indol-3-yl)ethanamine | 91 | 30-17 | $^1$H-NMR (400 MHz, CDCl$_3$): δ (ppm) 7.39-7.37 (m, 1H), 7.34-7.32 (m, 1H), 7.22-7.19 (m, 2H), 6.97-6.94 (m, 1H), 6.87-6.83 (m, 2H), 4.26 (q, 2H), 3.94 (s, 2H), 3.69 (s, 3H), 3.09 (t, J = 6.4 Hz, 2H), 3.01 (t, J = 6.4 Hz, 2H), 1.43 (d, J = 7.2 Hz, 3H). | calc 360.8, found 361.0, 362.9 [MH]+ | 30 |

TABLE 28-continued

| Structure | name | Ex. number | ID number | NMR | MS | Procedure of scheme |
|---|---|---|---|---|---|---|
| 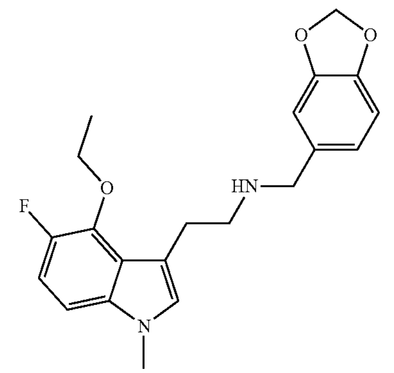 [SMILES: CCOc1c(F)ccc2c1c(CCNCc1ccc3c(c1)OCO3)cn2C] | N-(benzo[d][1,3] dioxol-5-ylmethyl)-2-(4-ethoxy-5-fluoro-1-methyl-1H-indol-3-yl)ethanamine | 92 | 30-18 | $^1$H-NMR (400 MHz, CDCl$_3$): δ (ppm) 7.00-6.95 (m, 1H), 6.88-6.85 (m, 3H), 6.77-6.72 (m, 2H), 5.93 (s, 2H), 4.28 (q, 2H), 3.79 (s, 2H), 3.70 (s, 3H), 3.12 (t, J = 6.0 Hz, 2H), 3.06(t, J = 6.0 Hz, 2H), 1.43 (t, J = 7.0 Hz, 3H). | calc 370.4, found 370.9 [MH]+ | 30 |
| 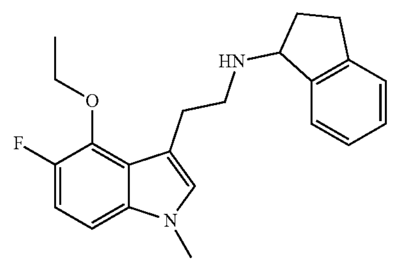 [SMILES: CCOc1c(F)ccc2c1c(CCNC1CCc3ccccc31)cn2C] | N-(2-(4-ethoxy-5-fluoro-1-methyl-1H-indol-3-yl)ethyl)-2,3-dihydro-1H-inden-1-amine | 93 | 30-19 | $^1$H-NMR (400 MHz, MeOD-d6): δ (ppm) 7.50 (d, J = 7.6 Hz, 1H), 7.42-7.38 (m, 2H), 7.32-7.28 (m, 1H), 7.08 (s, 1H), 7.05-6.97 (m, 2H), 4.98-4.84 (m, 1H), 4.25 (q, 2H), 3.75 (s, 3H), 3.50-3.37 (m, 2H), 3.28-3.16 (m, 3H), 3.05-2.97 (m, 1H), 2.64-2.55 (m, 1H), 2.27-2.21 (m, 1H), 1.37 (t, J = 7.0 Hz, 3H). | calc 352.4, found 353.0 [MH]+ | 30 |
| 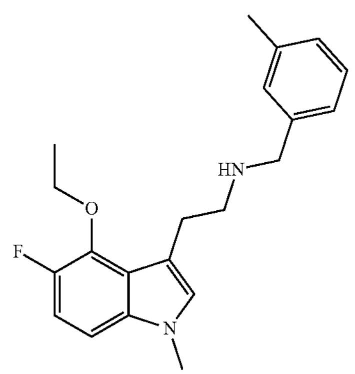 [SMILES: CCOc1c(F)ccc2c1c(CCNCc1cccc(C)c1)cn2C] | 2-(4-ethoxy-5-fluoro-1-methyl-1H-indol-3-yl)-N-(3-methylbenzyl)ethanamine | 94 | 30-20 | $^1$H-NMR (400 MHz, CDCl$_3$): δ (ppm) 7.19 (t, J = 7.2 Hz, 1H), 7.11-7.04 (m, 3H), 6.98-6.93 (m, 1H), 6.85 (dd, J = 8.8, 3.2 Hz, 1H), 6.81 (s, 1H), 4.25 (q, 2H), 3.80 (s, 2H), 3.68 (s, 3H), 3.08 (t, J = 7.2 Hz, 2H), 2.99 (t, J = 6.8 Hz, 2H), 2.32 (s, 3H), 1.41 (t, J = 7.2 Hz, 3H). | calc 340.4, found 341.0 [MH]+ | 30 |
| 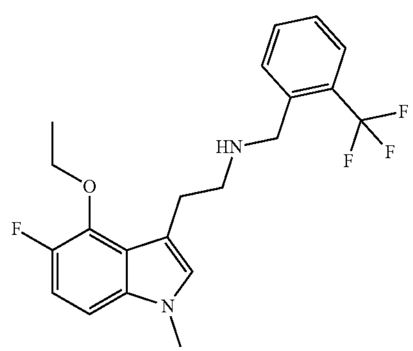 [SMILES: CCOc1c(F)ccc2c1c(CCNCc1ccccc1C(F)(F)F)cn2C] | 2-(4-ethoxy-5-fluoro-1-methyl-1H-indol-3-yl)-N-(2-(trifluoromethyl)benzyl)ethanamine | 95 | 30-21 | $^1$H-NMR (400 MHz, CDCl$_3$): δ (ppm) 7.63-7.59 (m, 2H), 7.52-7.41 (m, 2H), 6.99-6.84 (m, 3H), 4.27 (s, 2H), 4.21 (q, 2H), 3.66 (s, 3H), 3.41 (t, J = 6.0 Hz, 2H), 3.18 (t, J = 6.4 Hz, 2H), 1.32 (t, J = 7.2 Hz, 3H). | calc 394.2, found 394.9 [MH]+ | 30 |

TABLE 28-continued

| Structure | name | Ex. number | ID number | NMR | MS | Procedure of scheme |
|---|---|---|---|---|---|---|
| | 2-(4-ethoxy-5-fluoro-1-methyl-1H-indol-3-yl)-N-(3-(trifluoromethyl)benzyl)ethanamine | 96 | 30-22 | $^1$H-NMR (400 MHz, CDCl$_3$): δ (ppm) 7.59 (s, 1H), 7.51 (t, J = 6.8 Hz, 2H), 7.41 (t, J = 7.6 Hz, 1H), 6.99-6.94 (m, 1H), 6.87-6.83 (m, 2H), 4.26 (q, 2H), 3.89 (s, 2H), 3.68 (s, 3H), 3.09 (t, J = 6.8 Hz, 2H), 3.01 (t, J = 6.4 Hz, 2H), 1.41 (t, J = 7.2 Hz, 3H). | calc 394.4, found 395.1 [MH]+ | 30 |
| 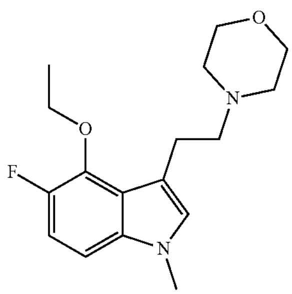 [SMILES: CCOc1c(F)ccc2c1c(CCN1CCOCC1)cn2C] | 4-(2-(4-ethoxy-5-fluoro-1-methyl-1H-indol-3-yl)ethyl)morpholine | 97 | 30-23 | $^1$H-NMR (400 MHz, CDCl$_3$): δ (ppm) 7.06-6.96 (m, 1H), 6.92 (s, 1H), 6.88 (dd, J = 9.2, 3.6 Hz, 1H), 4.33 (q, 2H), 4.05-3.98 (m, 4H), 3.69 (s, 3H), 3.58 (d, J = 11.6 Hz, 2H), 3.33-3.30 (m, 4H), 2.88 (t, J = 9.2 Hz, 2H), 1.41 (t, J = 7.0 Hz, 3H). | calc 306.4, found 307.0 [MH]+ | 30 |
| 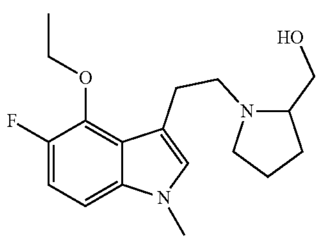 [SMILES: CCOc1c(F)ccc2c1c(CCN1CCCC1CO)cn2C] | (1-(2-(4-ethoxy-5-fluoro-1-methyl-1H-indol-3-yl)ethyl)pyrrolidin-2-yl)methanol | 98 | 30-24 | $^1$H-NMR (400 MHz, CDCl$_3$): δ (ppm) 7.00-6.86 (m, 3H), 4.31 (q, 2H), 3.99-3.97 (br.s, 2H), 3.78 (d, J = 4.0 Hz, 1H), 3.68-3.66 (m, 4H), 3.58-3.56 (br.s, 1H), 3.36-3.26 (m, 3H), 2.97 (d, J = 6.4 Hz, 1H), 2.15-2.02 (m, 3H), 1.98 (d, J = 5.6 hz, 1H), 1.40 (d, J = 7.0 Hz, 3H). | calc 320.2, found 321.0 [MH]+ | 30 |
| 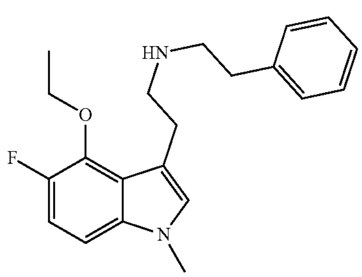 [SMILES: CCOc1c(F)ccc2c1c(CCNCCc1ccccc1)cn2C] | 2-(4-ethoxy-5-fluoro-1-methyl-1H-indol-3-yl)-N-phenethyl-ethanamine | 99 | 30-25 | $^1$H-NMR (400 MHz, CDCl$_3$): δ (ppm) 7.19-7.02 (br.s, 5H), 6.99-6.96 (m, 2H), 6.87-6.85 (m, 1H), 4.33 (q, 2H), 3.59 (s, 3H), 3.45-3.17 (m, 8H), 1.42-1.40 (br.s, 3H). | calc 340.2, found 341.0 [MH]+ | 30 |
| 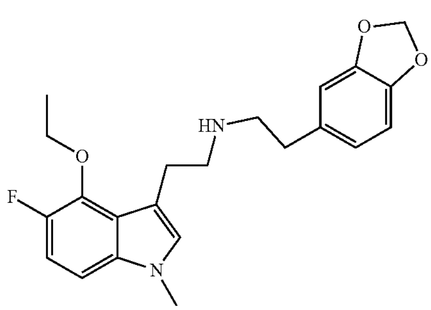 [SMILES: CCOc1c(F)ccc2c1c(CCNCCc1ccc3c(c1)OCO3)cn2C] | 2-(benzo[d][1,3]dioxol-5-yl)-N-(2-(4-ethoxy-5-fluoro-1-methyl-1H-indol-3-yl)ethyl)ethanamine | 100 | 30-26 | $^1$H-NMR (400 MHz, CDCl$_3$): δ (ppm) 6.99-6.94 (m, 1H), 6.87-6.84 (m, 2H), 6.58 (d, J = 7.6 Hz, 1H), 6.53 (s, 1H), 6.47 (d, J = 8.0 Hz, 1H), 5.88 (s, 2H), 4.29 (q, 2H), 3.63 (s, 3H), 3.36-3.34 (br.s, 2H), 3.21-3.13 (m, 4H), 2.88 (t, J = 7.2 Hz, 2H), 1.38 (t, J = 7.2 Hz, 3H). | calc 384.2, found 385.0 [MH]+ | 30 |

TABLE 28-continued

| Structure | name | Ex. number | ID number | NMR | MS | Procedure of scheme |
|---|---|---|---|---|---|---|
| 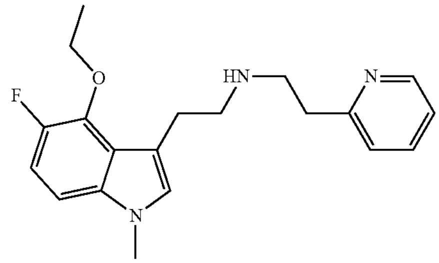 [SMILES: CCOc1c(F)ccc2c1c(CCNCCc1ccccn1)cn2C] | 2-(4-ethoxy-5-fluoro-1-methyl-1H-indol-3-yl)-N-(2-(pyridin-2-yl)ethyl)ethanamine | 101 | 30-27 | $^{1}$H-NMR (400 MHz, CDCl$_3$): δ (ppm) 7.89 (t, J = 7.6 Hz, 1H), 7.80 (d, J = 4.4 Hz, 1H), 7.42 (d, J = 7.6 Hz, 1H), 7.32 (t, J = 6.0 Hz, 1H), 7.01-6.96 (m, 2H), 6.90 (dd, J = 8.8, 3.2 Hz, 1H), 4.27 (q, 2H), 3.69 (s, 3H), 3.44 (d, J = 5.6 Hz, 4H), 3.33-3.30 (m, 2H), 3.21 (t, J = 6.0 Hz, 2H), 1.38 (t, J = 6.8 Hz, 3H). | calc 341.2, found 342.1 [MH]+ | 30 |
| 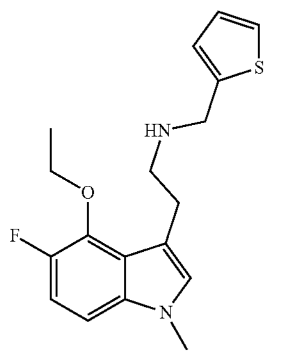 [SMILES: CCOc1c(F)ccc2c1c(CCNCc1cccs1)cn2C] | 2-(4-ethoxy-5-fluoro-1-methyl-1H-indol-3-yl)-N-(thiophen-2-ylmethyl)ethanamine | 102 | 30-28 | $^{1}$H-NMR (400 MHz, CDCl$_3$): δ (ppm) 7.19-7.18 (m, 1H), 6.95-6.80 (m, 5H), 4.25 (q, 2H), 4.01 (s, 2H), 3.67 (s, 3H), 3.05-2.99 (m, 4H), 1.41 (t, J = 7.0 Hz, 3H). | calc 332.1, found 333.1 [MH]+ | 30 |
| 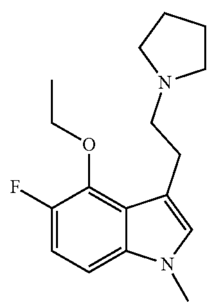 [SMILES: CCOc1c(F)ccc2c1c(CCN1CCCC1)cn2C] | 4-ethoxy-5-fluoro-1-methyl-3-(2-(pyrrolidin-1-yl)ethyl)-1H-indole | 103 | 30-29 | $^{1}$H-NMR (400 MHz, CDCl$_3$): δ (ppm) 7.01-6.87 (m, 3H), 4.32 (q, 2H), 3.83-3.81 (m, 2H), 3.69 (s, 3H), 3.40-3.25 (m, 4H), 2.83-2.79 (m, 2H), 2.12-2.03 (m, 4H), 1.41 (t, J = 7.0 Hz, 3H). | calc 290.1, found 291.0 [MH]+ | 30 |

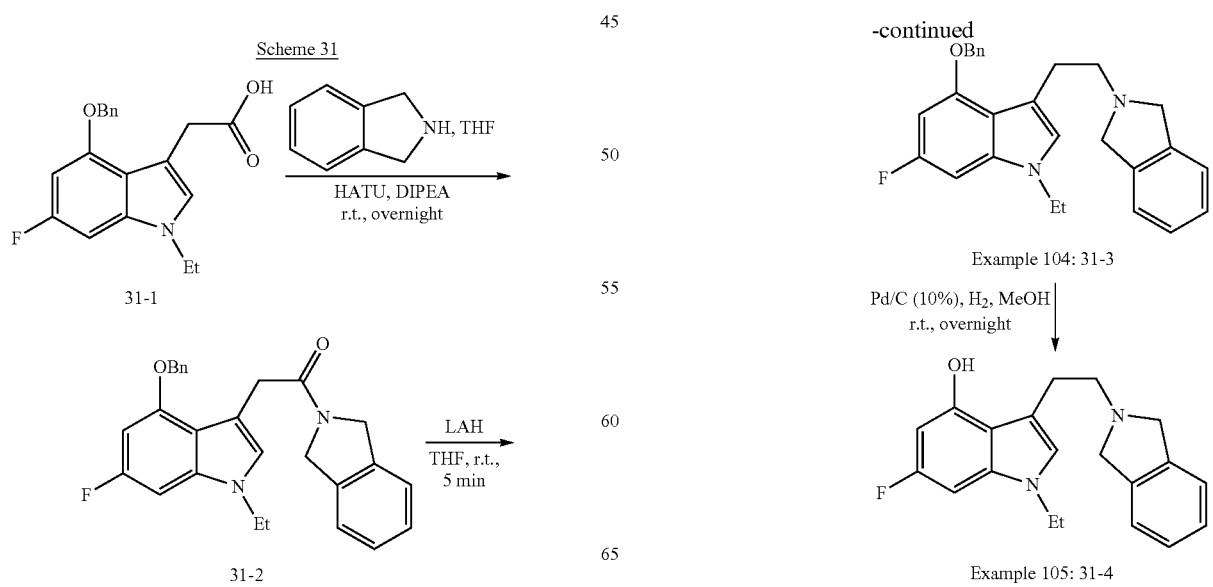

Example 105

1-ethyl-6-fluoro-3-(2-(isoindolin-2-yl)ethyl)-1H-indol-4-ol (31-4)

Step 1: 2-(4-(benzyloxy)-1-ethyl-6-fluoro-1H-indol-3-yl)-1-(isoindolin-2-yl)ethanone (31-2)

A mixture of 31-1 (100 mg, 0.306 mmol), isoindoline (47 mg, 0.398 mmol) and HATU (232 mg, 0.611 mmol) in THF (10 mL) was stirred for 10 min at room temperature. DIPEA (99 mg, 0.764 mmol) was added and the reaction mixture was stirred overnight. The volatiles were evaporated and the resulting residue was partitioned between ethyl acetate (10 mL) and water (10 mL). The organic layer was separated and washed with brine (3×10 mL), dried over $Na_2SO_4$ and concentrated under vacuum. The resulting residue was purified on silica gel column chromatography eluting with dichloromethane/methanol (100:1) to afford 31-2 (180 mg, 70%) as a white solid. LRMS: calc 428.2 and found: 429.1 [M+1].

General conditions for step 1: amine, BOP, TEA in DMF.

Example 104

Step 2: 4-(benzyloxy)-1-ethyl-6-fluoro-3-(2-(isoindolin-2-yl)ethyl)-1H-indole (31-3)

To a solution of $LiAlH_4$ (100 mg, 2.6 mmol) in THF (30 mL) was added aluminum trichloride (463 mg, 3.51 mmol) at 0° C. After stirring for 10 min, a solution of 31-2 (180 mg, 0.42 mmol) in THF (5 mL) was added dropwise. The reaction mixture was stirred for 5 min before $Na_2SO_4.10H_2O$ was added to quench the reaction. The solid was filtered off and the filtrate was evaporated. The resulting residue was purified on silica gel column chromatography eluting with dichloromethane/methanol (10:1) to get 31-3 (100 mg, 57%) as a yellow solid. $^1$H-NMR (400 MHz, $CDCl_3$): δ (ppm) 7.46 (d, J=7.2 Hz, 2H), 7.31-7.26 (m, 4H), 7.27 (t, J=3.6 Hz, 1H), 7.09-7.06 (m, 2H), 6.93 (s, 1H), 6.65 (d, J=7.2 Hz, 1H), 6.42 (d, J=7.2 Hz, 1H), 5.06 (s, 2H), 4.02-4.00 (m, 6H), 3.27 (s, 4H), 1.41 (t, J=7.4 Hz, 3H). LRMS: calc 414.2 and found: 414.9 [M+1].

Example 105

Step 3: 1-ethyl-6-fluoro-3-(2-(isoindolin-2-yl)ethyl)-1H-indol-4-ol (31-4)

To a solution of 31-3 (30 mg, 0.072 mmol) in methanol (10 mL) was added 10% Pd/C (20 mg) under hydrogen atmosphere. The reaction mixture was stirred at room temperature overnight and then filtered through a pad of celite. The filtrate was concentrated to give a pale yellow residue, which was purified on silica gel column chromatography eluting with dichloromethane/methanol (9:1) to give 31-4 (25 mg, 70%) as a white solid. $^1$H-NMR (400 MHz, $CDCl_3$): δ (ppm) 7.29 (d, J=2.4 Hz, 2H), 7.17 (d, J=3.2 Hz, 2H), 6.76 (s, 1H), 6.50 (d, J=8.8 Hz, 1H), 6.30 (d, J=10.8 Hz, 1H), 5.00-4.96 (br.s, 2H), 4.34-4.32 (br.s, 2H), 3.96 (q, 2H), 3.59-3.57 (br.s, 2H), 3.32-3.30 (br.s, 2H), 1.37 (t, J=7.6 Hz, 3H). LRMS: calc 324.2 and found: 325.1 [M+1].

The compounds in Table 29 were made according to processes described in Scheme 31.

TABLE 29

| Structure | name | Ex. number | ID number | NMR | MS | Procedure of scheme |
|---|---|---|---|---|---|---|
| 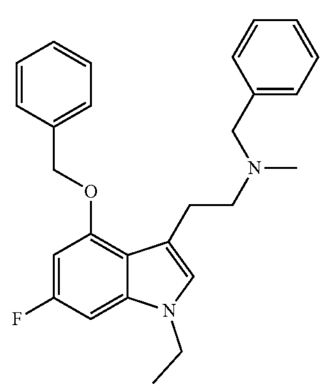 [SMILES: CCn1cc(CCN(C)Cc2ccccc2)c2c(OCc3ccccc3)cc(F)cc21] | N-benzyl-2-(4-(benzyloxy)-1-ethyl-6-fluoro-1H-indol-3-yl)-N-methyl-ethanamine | 107 | 31-6 | $^1$H-NMR (400 MHz, $CDCl_3$): δ (ppm) 7.47 (d, J = 7.2 Hz, 2H), 7.36 (t, J = 7.2 Hz, 2H), 7.31-7.26 (m, 3H), 7.25-7.22 (m, 3H), 6.76 (s, 1H), 6.60 (dd, J = 9.6, 1.2 Hz, 1H), 6.34 (dd, J = 11.6, 1.6 Hz, 1H), 5.11 (s, 2H), 4.00 (q, 2H), 3.42 (s, 2H), 3.08 (t, J = 7.6 Hz, 2H), 2.71 (t, J = 8.4 Hz, 2H), 2.10 (s, 3H), 1.41 (t, J = 7.2 Hz, 3H). | calc 416.5, found 417.0 [MH]+ | 31 Step 1-2 |

TABLE 29-continued

| Structure | name | Ex. number | ID number | NMR | MS | Procedure of scheme |
|---|---|---|---|---|---|---|
| 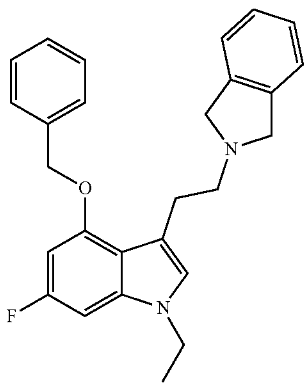 [SMILES: CCn1cc(CCN2Cc3ccccc3C2)c2c(OCc3ccccc3)cc(F)cc21] | 4-(benzyloxy)-1-ethyl-6-fluoro-3-(2-(isoindolin-2-yl)ethyl)-1H-indole | 104 | 31-3 | ¹H-NMR (400 MHz, CDCl₃): δ (ppm) 7.46 (d, J = 7.2 Hz, 2H), 7.31-7.26 (m, 4H), 7.27 (t, J = 3.6 Hz, 1H), 7.09-7.06 (m, 2H), 6.93 (s, 1H), 6.65 (d, J = 7.2 Hz, 1H), 6.42 (d, J = 7.2 Hz, 1H), 5.06 (s, 2H), 4.02-4.00 (m, 6H), 3.27 (s, 4H), 1.41 (t, J = 7.4 Hz, 3H). | calc 414.2, found 414.9 [MH]+ | 31 Step 1-2 |
| 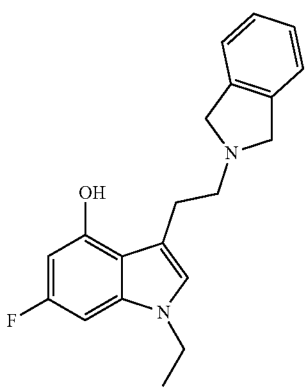 [SMILES: CCn1cc(CCN2Cc3ccccc3C2)c2c(O)cc(F)cc21] | 1-ethyl-6-fluoro-3-(2-(isoindolin-2-yl)ethyl)-1H-indol-4-ol | 105 | 31-4 | ¹H-NMR (400 MHz, CDCl₃): δ (ppm) 7.29 (d, J = 2.4 Hz, 2H), 7.17 (d, J = 3.2 Hz, 2H), 6.76 (s, 1H), 6.50 (d, J = 8.8 Hz, 1H), 6.30 (d, J = 10.8 Hz, 1H), 5.00-4.96 (br.s, 2H), 4.34-4.32 (br.s, 2H), 3.96 (q, 2H), 3.59-3.57 (br.s, 2H), 3.32-3.30 (br.s, 2H), 1.37 (t, J = 7.6 Hz, 3H). | calc 324.2, found 325.1 [MH]+ | 31 |
| 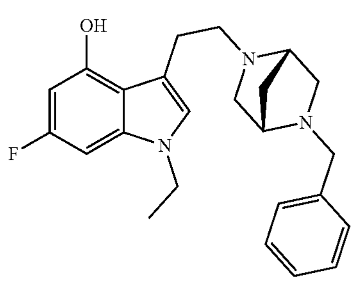 [SMILES: CCn1cc(CCN2C[C@@H]3C[C@H]2CN3Cc2ccccc2)c2c(O)cc(F)cc21] | 3-(2-((1S,4S)-5-benzyl-2,5-diazabicyclo[2.2.1]heptan-2-yl)ethyl)-1-ethyl-6-fluoro-1H-indol-4-ol | 108 | 31-7 | ¹H-NMR (400 MHz, MeOD-d6): δ (ppm) 7.29-7.21 (m, 4H), 7.16 (t, J = 7.2 Hz, 1H), 6.75 (s, 1H), 6.43 (d, J = 10.0 Hz, 1H), 6.10 (dd, J = 11.6, 1.6 Hz, 1H), 3.91 (q, 2H), 3.70 (d, J = 13.2 Hz, 1H), 3.60 (d, J = 12.8 Hz, 1H), 3.43 (s, 1H), 3.28 (s, 1H), 3.03-2.97 (m, 2H), 2.90-2.79 (m, 4H), 2.72 (dd, J = 10.8, 2.4 Hz, 1H), 2.58 (dd, J = 10.4, 2.4 Hz, 1H), 1.78 (t, J = 13.2 Hz, 2H), 1.26 (t, J = 7.2 Hz, 3H). | calc 393.4, found 394.0 [MH]+ | 31 Starting from 11-3 step 1-2 |

TABLE 29-continued

| Structure | name | Ex. number | ID number | NMR | MS | Procedure of scheme |
|---|---|---|---|---|---|---|
| | (2-(4-(benzyloxy)-1-ethyl-6-fluoro-1H-indol-3-yl)-N-(3-(trifluoromethyl)benzyl)ethanamine | 109 | 31-8 | $^1$H-NMR (400 MHz, CDCl$_3$): δ (ppm) 7.45 (d, J = 7.6 Hz, 1H), 7.41-7.28 (m, 8H), 6.77 (s, 1H), 6.62 (dd, J = 9.6, 1.6 Hz, 1H), 6.36 (dd, J = 11.6, 1.6 Hz, 1H), 5.05 (s, 2H), 3.99-3.94 (m, 2H), 3.56 (s, 2H), 3.02 (s, 4H), 1.37 (t, J = 7.2 Hz, 3H). | calc 470.1, found 471.0 [MH]+ | 31 Step 1-2 |
| | 2-(4-(benzyloxy)-1-ethyl-6-fluoro-1H-indol-3-yl)-N-(3-chlorobenzyl)ethanamine | 110 | 31-9 | $^1$H-NMR (400 MHz, CDCl$_3$): δ (ppm) 7.39-7.36 (m, 4H), 7.33-7.27 (m, 1H), 7.16 (d, J = 8.0 Hz, 1H), 7.10 (t, J = 7.6 Hz, 2H), 7.03 (d, J = 7.2 Hz, 1H), 6.78 (s, 1H), 6.61 (dd, J = 9.6, 2.0 Hz, 1H), 6.34 (dd, J = 11.2, 1.6 Hz, 1H), 5.05 (s, 2H), 3.99-3.94 (m, 2H), 3.53 (s, 2H), 3.03 (s, 4H), 1.37 (t, J = 7.2 Hz, 3H). | calc 436.1, found 437.0 [MH]+ | 31 Step 1-2 |
| | 3-(2-(benzhydrylamino)ethyl)-1-ethyl-6-fluoro-1H-indol-4-ol | 111 | 31-10 | $^1$H-NMR (400 MHz, MeOD-d6): δ (ppm) 7.48-7.40 (m, 10H), 6.94 (s, 1H), 6.61 (dd, J = 10.0, 2.4 Hz, 1H), 6.19 (dd, J = 11.2, 1.6 Hz, 1H), 5.50 (s, 1H), 4.05 (q, 2H), 3.32 (t, J = 6.8 Hz, 2H), 3.25 (t, J = 7.4 Hz, 2H), 1.37 (t, J = 7.2 Hz, 3H). | calc 388.1, found 389.0 [MH]+ | 31 Starting from 11-3 step 1-2 |
| | 3-(2-(3-chlorobenzylamino)ethyl)-1-ethyl-6-fluoro-1H-indol-4-ol | 112 | 31-11 | $^1$H-NMR (400 MHz, MeOD-d6): δ (ppm) 7.52 (s, 1H), 7.47-7.39 (m, 2H), 7.40-7.37 (m, 1H), 6.98 (s, 1H), 6.61 (dd, J = 9.6, 1.6 Hz, 1H), 6.22 (dd, J = 11.2, 2.0 Hz, 1H), 4.22 (s, 2H), 4.07 (q, 2H), 3.42 (t, J = 7.4 Hz, 2H), 3.24 (t, J = 7.4 Hz, 2H), 1.40 (t, J = 7.2 Hz, 3H). | calc 346.1, found 346.9 [MH]+ | 31 Starting from 11-3 step 1-2 |

TABLE 29-continued

| Structure | name | Ex. number | ID number | NMR | MS | Procedure of scheme |
|---|---|---|---|---|---|---|
| (structure: 1-ethyl-6-fluoro-4-hydroxyindole with 3-(trifluoromethyl)benzylaminoethyl side chain) | 1-ethyl-6-fluoro-3-(2-(3-(trifluoromethyl)benzylamino)ethyl)-1H-indol-4-ol | 113 | 31-12 | $^1$H-NMR (400 MHz, MeOD-d6): δ (ppm) 7.51 (s, 1H), 7.45-7.42 (m, 2H), 7.37 (d, J = 7.6 Hz, 1H), 6.72 (s, 1H), 6.42 (dd, J = 10.0, 2.0 Hz, 1H), 6.04 (dd, J = 11.2, 1.6 Hz, 1H), 3.90 (q, 2H), 3.73 (s, 2H), 2.92 (t, J = 6.4 Hz, 2H), 2.83 (t, J = 6.2 Hz, 2H), 1.24 (t, J = 7.2 Hz, 3H). | calc 380.4, found 381.0 [MH]+ | 31 |
| (structure: 4-benzyloxy-1-ethyl-6-fluoroindole with N-(3-(trifluoromethyl)phenethyl)ethanamine side chain) | 2-(4-(benzyloxy)-1-ethyl-6-fluoro-1H-indol-3-yl)-N-(3-(trifluoromethyl)phenethyl)ethanamine | 114 | 31-13 | $^1$H-NMR (300 MHz, MeOD-d6): δ (ppm) 7.62-7.08 (m, 9H), 6.79 (s, 1H), 6.68 (dd, J = 9.8, 2.0 Hz, 1H), 6.42 (dd, J = 11.8, 2.0 Hz, 1H), 5.12 (s, 2H), 4.00 (q, J = 7.2 Hz, 2H), 2.98-2.90 (m, 2H), 2.85-2.78 (m, 2H), 2.74-2.64 (dd, J = 9.5, 5.0 Hz, 4H), 1.32 (t, J = 8.5 Hz, 3H) | calc 484.21, found 485.3 [MH]+ | 31 |

Scheme 32

1-9b → (PhBr/CuI/pyridine, K$_2$CO$_3$/dioxane, reflux, overnight) → Example 115: 32-2

Example 115

2-(1-ethyl-6-fluoro-4-phenoxy-1H-indol-3-yl)-N,N-dimethylethanamine (32-2)

Step 1: 2-(1-ethyl-6-fluoro-4-phenoxy-1H-indol-3-yl)-N,N-dimethylethanamine (32-2)

A mixture of 1-9b (80 mg, 0.32 mmol), bromobenzene (100 mg, 0.64 mmol), K$_2$CO$_3$ (110 mg, 0.8 mmol) and CuI (152 mg, 0.8 mmol) in 10 mL of dioxane was stirred at reflux overnight. After cooled to room temperature, the volatiles were evaporated under vacuum and the resulting residue was partitioned between water (10 mL) and ethyl acetate (10 mL). The organic layer was separated and the aqueous layer was extracted with ethyl acetate (3×15 mL). The organic layers were combined, washed with brine (2×30 mL), dried over MgSO$_4$ and evaporated. The resulting brown residue was purified by preparative HPLC (acid condition, water/CH$_3$CN, 25-30% CH$_3$CN in 7.5 min, RT=6.5 min) to give 32-2 (3 mg, 3%) as a white solid. $^1$H-NMR (400 MHz, MeOD-d6): δ (ppm) 7.34 (t, J=8.0 Hz, 2H), 7.13-7.09 (m, 2H), 7.02 (d, J=8.0 Hz, 2H), 6.85 (d, J=11.2 Hz, 1H), 6.10 (d, J=11.2 Hz, 1H), 4.05 (q, 2H), 3.33-3.28 (m, 2H), 3.11-3.07 (m, 2H), 2.74 (s, 6H), 1.33 (t, J=7.2 Hz, 3H). LRMS: calc 326.2 and found: 327.1 [M+1].

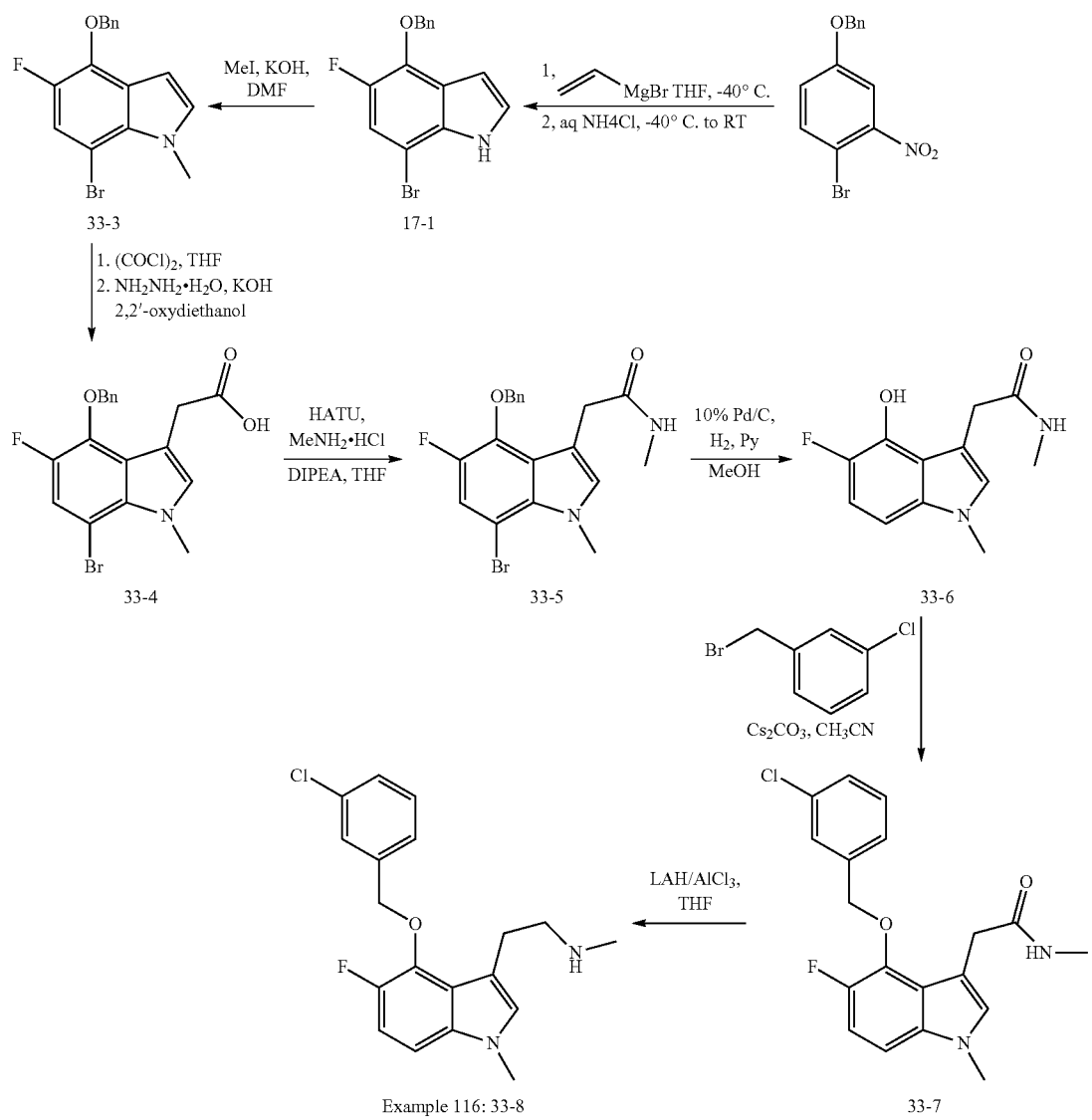

Scheme 33

Example 116

2-(4-(3-chlorobenzyloxy)-5-fluoro-1-methyl-1H-indol-3-yl)-N-methylethanamine (33-12a)

Step 1: 4-(benzyloxy)-7-bromo-5-fluoro-1H-indole (17-1)

To a solution of 4-(benzyloxy)-1-bromo-2-nitrobenzene (2 g, 6.13 mmol) (prepared according patent WO2009/103710) in THF (20 mL) at −40° C. was added vinylmagnesium bromide (19 mL, 18.4 mmol) dropwise. The temperature was kept constant at 40° C. during the addition. The mixture was stirred at this temperature for 2 h. and then saturated aqueous NH$_4$Cl was added to quench the reaction. The mixture was extracted with ethyl acetate (3×40 mL). The combined organic layers were washed with water (2×50 mL), dried over MgSO$_4$, filtered, and evaporated to afford a brown solid which was purified on silica gel column chromatography eluting with petroleum ether/ethylacetate (5:1) to afford 17-1 (650 mg, 33%) as a yellow solid. LRMS: calc 319.0 and found: 320.1 [M+1].

Step 2: 4-(benzyloxy)-7-bromo-5-fluoro-1-methyl-1H-indole (33-3)

A solution of 17-1 (9 g, 28 mmol), potassium hydroxide (2.36 g, 42 mmol) and methyl iodide (6 g, 42 mmol) in DMF (30 mL) was stirred at room temperature for 2 h. The mixture was poured into water (50 mL), extracted with ethyl acetate (3×50 mL). The extracts were washed with water (3×50 mL) and brine (2×50 mL), dried over MgSO4, filtered, and evaporated to afford 33-3 (8 g, 90%) which was used directly in next step. LRMS: calc 333.0 and found: 334.0 [M+1].

Step 3: 2-(4-(benzyloxy)-7-bromo-5-fluoro-1-methyl-1H-indol-3-yl)acetic acid (33-4)

To the solution of 33-3 (8 g, 24 mmol) in THF (30 mL) was added oxalyl chloride (15.4 g, 120 mmol) dropwised at 0° C.

The mixture was stirred at room temperature overnight. The volatiles were evaporated to get a yellow residue, which was dissolved in 2,2'-oxydiethanol (50 mL). To the resulting solution were added hydrazine hydrate (6 mL) and potassium hydroxide (6.72 g, 120 mmol). The mixture was heated at 190° C. for 2 h before it was cooled to room temperature. Water (100 mL) was added to the mixture and neutralized with hydrochloric acid to pH=5, then extracted with ethyl acetate (2×50 mL). The organic layers were combined, washed with brine (4×50 mL), dried over MgSO$_4$, filtered, and concentrated under vacuum. The resulting residue was purified on silica gel column chromatography eluting with dichloromethane/methanol (10:1) to afford 33-4 (5 g, 58%) as a yellow solid. LRMS: calc 391.0 and found: 392.1 [M+1].

Step 4: 2-(4-(benzyloxy)-7-bromo-5-fluoro-1-methyl-1H-indol-3-yl)-N-methyl acetamide (33-5)

Following the procedure (step 1, scheme 31) used to prepare compound 31-2, compound 33-4 gave compound 33-5 in 96% yield as a yellow solid. LRMS: calc 404.0 and found: 405.0 [M+1].

Step 5: 2-(5-fluoro-4-hydroxy-1-methyl-1H-indol-3-yl)-N-methylacetamide (33-6)

A mixture of 33-5 (1.4 g, 4.5 mmol), pyridine (2 mL) and Pd/C (140 mg, 10%) in methanol (20 mL) was stirred at room temperature overnight under hydrogen atmosphere. The mixture was adjusted with hydrochloric acid to pH=5-6. The solid was filtered off and the filtrate was concentrated. The resulting residue was partitioned between water (20 mL) and ethylacetate (20 mL). The organic layer was separated, washed with brine (3×30 mL), dried over MgSO4, filtered and evaporated to obtain 33-6 (700 mg, 85%) as a brown solid. LRMS: calc 236.1 and found: 237.1 [M+1].

Step 6: 2-(4-(3-chlorobenzyloxy)-5-fluoro-1-methyl-1H-indol-3-yl)-N-methyl acetamide (33-7)

A mixture of 33-6 (40 mg, 0.17 mmol), 1-(bromomethyl)-3-chlorobenzene (35 mg, 0.17 mmol) and Cesium carbonate (166 mg, 0.51 mmol) in acetonitrile (20 mL) was refluxed for 2 h. After cooled to room temperature, the mixture was filtered and the filtrate was evaporated under vacuum. The resulting residue was purified by Preparative TLC (petroleum ether/ethyl acetate=1:3) to give 33-7 (50 mg, 82%) as a white solid. LRMS: calc 360.1 and found: 361.1 [M+1].

Step 7: 2-(4-(3-chlorobenzyloxy)-5-fluoro-1-methyl-1H-indol-3-yl)-N-methyl ethanamine (33-8)

A solution of 33-7 (50 mg, 0.139 mmol) in THF (10 mL) was added dropwise into the solution of lithium aluminum hydride (19 mg, 0.417 mmol) and AlCl$_3$ (41 mg, 0.381 mmol) in THF (10 mL). The mixture was stirred at room temperature for 1 h. Na$_2$SO$_4$.10 H$_2$O was added to quench the reaction. The solid was filtered off and washed with ethyl acetate (20 mL). The organic solvent was washed with brine (3×30 mL), dried over MgSO$_4$, filtered and evaporated. The resulting residue was purified by preparative HPLC (acid condition, water/CH$_3$CN, 30-35% CH$_3$CN in 7.5 min, RT=6.5 min) to give 33-8 (11 mg, 23%) as a yellow solid. $^1$H-NMR (400 MHz, CDCl$_3$): δ (ppm) 8.80-8.60 (brs, 1H), 7.47 (s, 1H), 7.34 (s, 2H), 7.28 (s, 1H), 7.02-6.99 (m, 1H), 6.92-6.89 (m, 2H), 5.25 (s, 2H), 3.66 (s, 3H), 3.13-3.05 (m, 4H), 2.45 (s, 3H). LRMS: calc and found: 347.1 [M+1].

The compounds in Table 30 were made according to processes described in Scheme 33.

TABLE 30

| Structure | name | Ex. number | ID number | NMR | MS | Procedure of scheme |
|---|---|---|---|---|---|---|
| 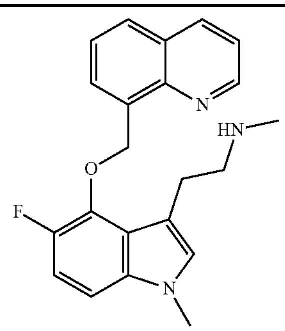 | 2-(5-fluoro-1-methyl-4-(quinolin-8-ylmethoxy)-1H-indol-3-yl)-N-methylethanamine | 117 | 33-13 | 1H-NMR (400 MHz, MeOD-d6): δ (ppm) 8.87-8.85 (m, 1H), 8.40-8.38 (m, 1H), 7.91-7.84 (m, 2H), 7.56-7.52 (m, 2H), 6.97-6.90 (m, 3H), 5.85 (s, 2H), 3.62 (s, 3H), 2.99 (t, J = 6.8 Hz, 2H), 2.82 (t, J = 7.2 Hz, 2H), 2.35 (s, 3H). | calc 363.4, found 364.0 [MH]+ | 33 |
|  | 2-(5-fluoro-1-methyl-4-(2-phenoxyethoxy)-1H-indol-3-yl)-N-methylethanamine | 118 | 33-14 | 1H-NMR (400 MHz, MeOD-d6): δ (ppm) 7.27 (t, J = 8.0 Hz, 2H), 7.05-6.99 (m, 3H), 6.96-6.93 (m, 3H), 4.60-4.58 (m, 2H), 4.32-4.30 (m, 2H), 3.72 (s, 3H), 3.30-3.28 (m, 2H), 3.23 (t, J = 5.6 Hz, 2H), 2.56 (s, 3H). | calc 342.4, found 343.0 [MH]+ | 33 |

TABLE 30-continued

| Structure | name | Ex. number | ID number | NMR | MS | Procedure of scheme |
|---|---|---|---|---|---|---|
| 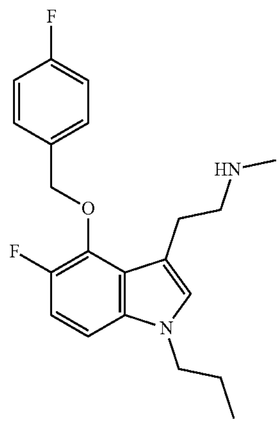 [SMILES: CCCn1cc(CCNC)c2c(OCc3ccc(F)cc3)c(F)ccc21] | 2-(5-fluoro-4-(4-fluorobenzyl-oxy)-1-propyl-1H-indol-3-yl)-N-methylethan-amine | 119 | 33-15 | 1H-NMR (400 MHz, MeOD-d6): δ (ppm) 7.51-7.48 (m, 2H), 7.13-6.98 (m, 5H), 5.25 (s, 2H), 4.05 (t, J = 6.8 Hz, 2H), 3.20 (t, J = 7.6, Hz, 2H), 3.08 (t, J = 6.4 Hz, 2H), 2.55 (s, 3H), 1.85-1.80 (m, 2H), 0.91 (t, J = 7.2 Hz, 3H). | calc 358.4, found 359.0 [MH]+ | 33 |
| 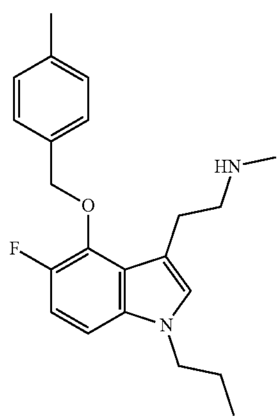 [SMILES: CCCn1cc(CCNC)c2c(OCc3ccc(C)cc3)c(F)ccc21] | 2-(5-fluoro-4-(4-methylbenzyl-oxy)-1-propyl-1H-indol-3-yl)-N-methylethan-amine | 120 | 33-16 | 1H-NMR (400 MHz, MeOD-d6): δ (ppm) 7.35 (d, J = 7.6 Hz, 2H), 7.21 (d, J = 6.8 Hz, 2H), 7.10-7.00 (m, 3H), 5.22 (d, J = 3.6 Hz, 2H), 4.05 (t, J = 6.8 Hz, 2H), 3.15 (d, J = 5.6 Hz, 2H), 3.04 (t, J = 6.4 Hz, 2H), 2.47 (d, J = 4.4 Hz, 3H), 2.35 (d, J = 4.4 Hz, 3H), 1.84-1.81 (m, 2H), 0.92 (t, J = 7.2 Hz, 3H). | calc 354.5, found 355.0 [MH]+ | 33 |
| 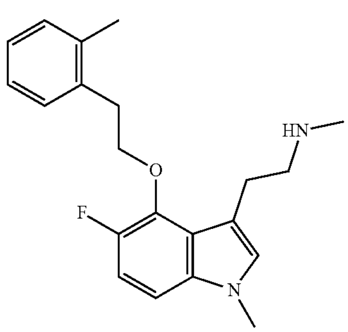 [SMILES: CNCCc1cn(C)c2ccc(F)c(OCCc3ccccc3C)c12] | 2-(5-fluoro-1-methyl-4-(2-methylphen-ethoxy)-1H-indol-3-yl)-N-methylethan-amine | 121 | 33-17 | 1H-NMR (400 MHz, MeOD-d6): δ (ppm) 7.27-7.23 (m, 1H), 7.20-7.14 (m, 3H), 7.07-6.99 (m, 3H), 4.47-4.43 (m, 2H), 3.73 (s, 3H), 3.17 (t, J = 7.2 Hz, 2H), 3.05 (t, J = 6.4 Hz, 2H), 2.94 (t, J = 6.4 Hz, 2H), 2.57 (s, 3H), 2.35 (s, 3H). | calc 340.4, found 341.1 [MH]+ | 33 |

TABLE 30-continued

| Structure | name | Ex. number | ID number | NMR | MS | Procedure of scheme |
|---|---|---|---|---|---|---|
| 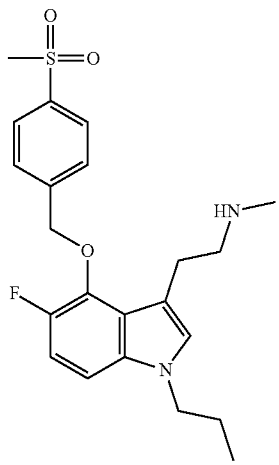 | 2-(5-fluoro-4-(4-(methylsulfonyl)benzyloxy)-1-propyl-1H-indol-3-yl)-N-methylethanamine | 122 | 33-18 | 1H-NMR (400 MHz, MeOD-d6): δ (ppm) 7.89 (d, J = 8.0 Hz, 2H), 7.66 (d, J = 8.4 Hz, 2H), 7.04-6.99 (m, 1H), 5.30 (s, 2H), 3.97 (t, J = 6.8 Hz, 2H), 3.13 (t, J = 7.2 Hz, 2H), 3.05 (t, J = 2.0 Hz, 3H), 3.02 (t, J = 7.6 Hz, 2H), 2.47 (s, 3H), 1.75-1.70 (m, 2H), 0.81 (t, J = 7.2 Hz, 3H). | calc 418.5, found 419.1 [MH]+ | 33 |
| 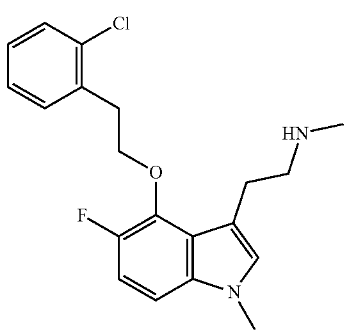 [SMILES: CNCCc1cn(C)c2ccc(F)c(OCCc3ccccc3Cl)c12] | 2-(4-(2-chlorophenethoxy)-5-fluoro-1-methyl-1H-indol-3-yl)-N-methylethanamine | 123 | 33-19 | 1H-NMR (400 MHz, MeOD-d6): δ (ppm) 7.45-7.40 (m, 2H), 7.29-7.27 (m, 2H), 7.06-7.01 (m, 3H), 4.49 (t, J = 6.8 Hz, 2H), 3.75 (s, 3H), 3.33-3.30 (m, 2H), 3.15 (t, J = 6.4 Hz, 2H), 3.01 (t, J = 6.4 Hz, 2H), 2.62 (s, 3H). | calc 360.8, found 361.1 [MH]+ | 33 |
| 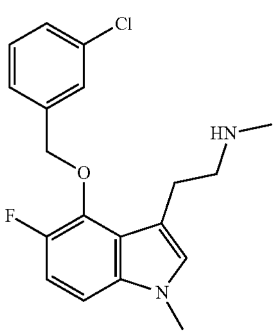 [SMILES: CNCCc1cn(C)c2ccc(F)c(OCc3cccc(Cl)c3)c12] | 2-(4-(3-chlorobenzyloxy)-5-fluoro-1-methyl-1H-indol-3-yl)-N-methylethanamine | 116 | 33-8 | $^1$H-NMR (400 MHz, CDCl3): δ 8.80-8.60 (brs, 1H), 7.47 (s, 1H), 7.34 (s, 2H), 7.28 (s, 1H), 7.02-6.99 (m, 1H), 6.92-6.89 (m, 2H), 5.25 (s, 2H), 3.66 (s, 3H), 3.13-3.05 (m, 4H), 2.45 (s, 3H). | calc 346.8, found 347.1, 349.1 [MH]+ | 33 |
| 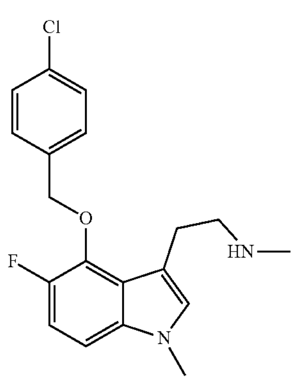 [SMILES: CNCCc1cn(C)c2ccc(F)c(OCc3ccc(Cl)cc3)c12] | 2-(4-(4-chlorobenzyloxy)-5-fluoro-1-methyl-1H-indol-3-yl)-N-methylethanamine | 124 | 33-20 | $^1$H-NMR (400 MHz, CDCl$_3$): δ (ppm) 8.78-8.90 (brs, 2H), 7.35 (q, 4H), 6.98 (dd, J = 9.2, 1.2 Hz, 1H), 6.87 (dd, J = 8.8, 3.2 Hz, 1H), 6.84 (s, 1H), 5.23 (s, 2H), 3.63 (s, 3H), 3.09-3.03 (m, 4H), 2.41 (s, 3H). | calc 346.8, found 347.1, 349.1 [MH]+ | 33 |

TABLE 30-continued

| Structure | name | Ex. number | ID number | NMR | MS | Procedure of scheme |
|---|---|---|---|---|---|---|
| | 2-(5-fluoro-1-methyl-4-(3-(trifluoromethyl)benzyloxy)-1H-indol-3-yl)-N-methylethanamine | 125 | 33-21 | $^1$H-NMR (400 MHz, CDCl$_3$): δ (ppm) 9.10-8.90 (brs, 1H), 7.71 (s, 1H), 7.65-7.47 (m, 3H), 7.01-6.96 (m, 1H), 6.90-6.86 (m, 2H), 5.31 (s, 2H), 3.63 (s, 3H), 3.10-3.04 (m, 4H), 2.39 (s, 3H). | calc 380.4, found 381.1 [MH]+ | 33 |
| | 2-(5-fluoro-1-methyl-4-(2-methylbenzyloxy)-1H-indol-3-yl)-N-methylethanamine | 126 | 33-22 | $^1$H-NMR (400 MHz, CDCl$_3$): δ (ppm) 8.60-8.40 (brs, 1H), 7.37 (d, J = 7.2 Hz, 1H), 7.26-7.20 (m, 3H), 7.03-6.98 (m, 1H), 6.87 (dd, J = 6.0, 3.2 Hz, 1H), 6.81 (s, 1H), 5.29 (s, 2H), 3.62 (s, 3H), 2.98-2.94 (m, 4H), 2.71 (s, 3H), 2.42 (s, 3H). | calc 326.4, found 327.0 [MH]+ | 33 |
| | 2-(4-(2-chlorobenzyloxy)-5-fluoro-1-methyl-1H-indol-3-yl)-N-methylethanamine | 127 | 33-23 | $^1$H-NMR (400 MHz, CDCl$_3$): δ (ppm) 8.64-8.43 (brs, 1H), 7.57 (d, J = 3.2 Hz, 1H), 7.45 (t, J = 4.0 Hz, 1H), m 7.30 (t, J = 4.0 Hz, 2H), 7.07-7.01 (m, 1H), 6.92 (dd, J = 6.0, 2.8 Hz, 2H), 5.41 (s, 2H), 3.67 (s, 3H), 3.14-3.03 (m, 4H), 2.41 (s, 3H). | calc 346.8, found 347.1, 349.1 [MH]+ | 33 |
| | 2-(5-fluoro-4-(2-fluorobenzyloxy)-1-methyl-1H-indol-3-yl)-N-methylethanamine | 128 | 33-24 | $^1$H-NMR (400 MHz, MeOD-d6): δ (ppm) 7.54-7.50 (m, 1H), 7.42-7.40 (m, 1H), 7.22-7.19 (m, 2H), 7.05-7.02 (m, 3H), 5.36 (s, 2H), 3.73 (s, 3H), 3.21-3.19 (m, 2H), 3.07-3.04 (m, 2H), 2.55 (s, 3H). | calc 330.4, found 331.1 [MH]+ | 33 |

TABLE 30-continued

| Structure | name | Ex. number | ID number | NMR | MS | Procedure of scheme |
|---|---|---|---|---|---|---|
| | 2-(5-fluoro-4-(4-methoxyphen-ethoxy)-1-methyl-1H-indol-3-yl)-N-methylethan-amine | 129 | 33-25 | ¹H-NMR (400 MHz, MeOD-d6): δ (ppm) 7.22 (d, J = 8.4 Hz, 2H), 7.03-7.00 (m, 3H), 6.49 (d, J = 8.4 Hz, 2H), 4.47 (t, J = 6.6 Hz, 2H), 3.79 (s, 3H), 3.74 (s, 3H), 3.08 (t, J = 6.4 Hz, 4H), 2.93 (t, J = 6.6 Hz, 2H), 2.58 (s, 3H). | calc 356.4, found 357.1 [MH]+ | 33 |
| | 2-(5-fluoro-1-methyl-4-phenethoxy-1H-indol-3-yl)-N-methylethan-amine | 130 | 33-26 | ¹H-NMR (400 MHz, MeOD-d6): δ (ppm) 7.34-7.32 (m, 4H), 7.28-7.24 (m, 1H), 7.05-6.99 (m, 3H), 4.52 (t, J = 6.8 Hz, 2H), 3.74 (s, 3H), 3.15 (t, J = 6.8 Hz, 2H), 3.04 (t, J = 6.4 Hz, 2H), 2.89 (t, J = 6.4 Hz, 2H), 2.56 (s, 3H). | calc 326.4, found 327.1 [MH]+ | 33 |
| | 2-(5-fluoro-1-methyl-4-(4-methylbenzyl-oxy)-1H-indol-3-yl)-N-methylethan-amine | 131 | 33-27 | ¹H-NMR (400 MHz, MeOD-d6): δ (ppm) 7.34 (d, J = 8.0 Hz, 2H), 7.20 (d, J = 8.0 Hz, 2H), 7.03 (t, J = 4.6 Hz, 3H), 5.23 (s, 2H), 3.73 (s, 3H), 3.15 (t, J = 6.8 Hz, 2H), 3.02 (t, J = 6.6 Hz, 2H), 2.49 (s, 3H), 2.35 (s, 3H). | calc 326.4, found 327.1 [MH]+ | 33 |
| | 2-(5-fluoro-4-(4-fluorophen-ethoxy)-1-methyl-1H-indol-3-yl)-N-methylethan-amine | 132 | 33-28 | ¹H-NMR (400 MHz, MeOD-d6): δ (ppm) 7.32-7.38 (m, 2H), 7.06-6.98 (m, 5H), 4.46 (t, J = 6.6 Hz, 2H), 3.72 (s, 3H), 3.14-3.09 (m, 4H), 2.97 (t, J = 6.6 Hz, 2H), 2.61 (s, 3H). | calc 344.4, found 345.0 [MH]+ | 33 |

TABLE 30-continued

| Structure | name | Ex. number | ID number | NMR | MS | Procedure of scheme |
|---|---|---|---|---|---|---|
| 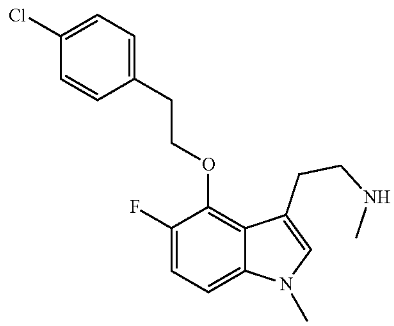 [SMILES: CNCCc1cn(C)c2ccc(F)c(OCCc3ccc(Cl)cc3)c12] | 2-(4-(4-chlorophen-ethoxy)-5-fluoro-1-methyl-1H-indol-3-yl)-N-methylethan-amine | 133 | 33-29 | ¹H-NMR (400 MHz, MeOD-d6): δ (ppm) 7.32-7.26 (m, 4H), 7.03-6.98 (m, 3H), 4.46 (t, J = 6.2 Hz, 2H), 3.71 (s, 3H), 3.12-3.08 (m, 4H), 2.95 (t, J = 6.6 Hz, 2H), 2.60 (s, 3H). | calc 360.8, found 361.1, 363.1 [MH]+ | 33 |
| 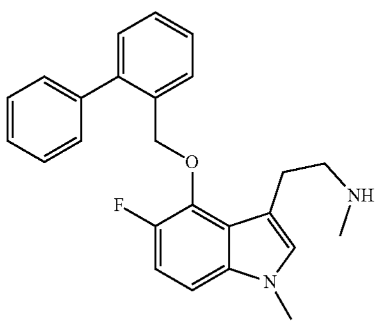 [SMILES: CNCCc1cn(C)c2ccc(F)c(OCc3ccccc3-c3ccccc3)c12] | 2-(4-(biphenyl-2-ylmethoxy)-5-fluoro-1-methyl-1H-indol-3-yl)-N-methylethan-amine | 134 | 33-30 | ¹H-NMR (400 MHz, MeOD-d6): δ (ppm) 7.68-7.66 (m, 1H), 7.47-7.42 (m, 2H), 7.39-7.35 (m, 6H), 7.03-6.93 (m, 3H), 5.24 (s, 2H), 3.73 (s, 3H), 3.10 (t, J = 6.8 Hz, 2H), 2.91 (t, J = 6.8 Hz, 2H), 2.45 (s, 3H). | calc 388.4, found 389.0 [MH]+ | 33 |
| 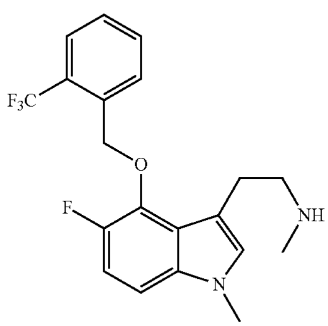 [SMILES: CNCCc1cn(C)c2ccc(F)c(OCc3ccccc3C(F)(F)F)c12] | 2-(5-fluoro-1-methyl-4-(2-(trifluoro-methyl)benzyloxy)-1H-indol-3-yl)-N-methylethan-amine | 135 | 33-31 | ¹H-NMR (400 MHz, MeOD-d6): δ (ppm) 7.83 (dd, J = 10.8, 8.0 Hz, 2H), 7.70 (t, J = 7.6 Hz, 1H), 7.57 (t, J = 7.6 Hz, 1H), 7.12-7.03 (m, 3H), 5.48 (s, 2H), 3.76 (s, 3H), 3.16 (t, J = 6.8 Hz, 2H), 3.01 (t, J = 6.8 Hz, 2H), 2.50 (s, 3H). | calc 380.4, found 381.0 [MH]+ | 33 |
| 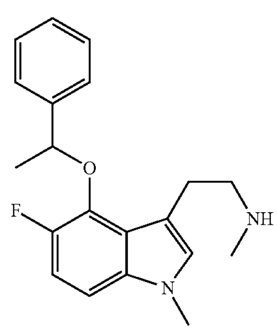 [SMILES: CNCCc1cn(C)c2ccc(F)c(OC(C)c3ccccc3)c12] | 2-(5-fluoro-1-methyl-4-(1-phenylethoxy)-1H-indol-3-yl)-N-methylethan-amine | 136 | 33-32 | ¹H-NMR (400 MHz, MeOD-d6): δ (ppm) 7.42 (d, J = 6.8 Hz, 2H), 7.34-7.27 (m, 2H), 7.03 (s, 1H), 6.99-6.95 (m, 2H), 5.63 (q, 1H), 3.71 (s, 3H), 3.29-3.24 (m, 2H), 3.08 (t, J = 6.8 Hz, 2H), 2.60 (s, 3H), 1.70 (d, J = 6.4 Hz, 3H). | calc 326.4, found 327.1 [MH]+ | 33 |

TABLE 30-continued

| Structure | name | Ex. number | ID number | NMR | MS | Procedure of scheme |
|---|---|---|---|---|---|---|
| | 2-(5-fluoro-4-(5-fluoro-2-methylbenzyloxy)-1-methyl-1H-indol-3-yl)-N-methylethanamine | 137 | 33-33 | ¹H-NMR (400 MHz, MeOD-d6): δ (ppm) 7.26-7.19 (m, 2H), 7.08-7.00 (m, 4H), 5.25 (s, 2H), 3.74 (s, 3H), 3.17 (t, J = 6.8 Hz, 2H), 3.06 (t, J = 6.8 Hz, 2H), 2.51 (s, 3H), 2.36 (s, 3H). | calc 344.4, found 345.1 [MH]+ | 33 |
| | 2-(5-fluoro-1-methyl-4-(2-(trifluoromethoxy)benzyloxy)-1H-indol-3-yl)-N-methylethanamine | 138 | 33-34 | ¹H-NMR (400 MHz, MeOD-d6): δ (ppm) 7.68 (d, J = 7.2 Hz, 1H), 7.50-7.48 (m, 1H), 7.43-7.37 (m, 2H), 7.07-7.03 (m, 3H), 5.37 (s, 2H), 3.75 (s, 3H), 3.19 (t, J = 6.8 Hz, 2H), 3.05 (t, J = 6.8 Hz, 2H), 2.54 (s, 3H). | calc 396.4, found 397.1 [MH]+ | 33 |
| | 2-(5-fluoro-4-(4-fluorobenzyloxy)-1-methyl-1H-indol-3-yl)-N-methylethanamine | 139 | 33-35 | ¹H-NMR (400 MHz, MeOD-d6): δ (ppm) 7.48-7.44 (m, 2H), 7.11-6.99 (m, 5H), 5.22 (s, 2H), 3.70 (s, 3H), 3.20-3.16 (t, J = 6.8 Hz, 2H), 3.07-3.03 (t, J = 7.0 Hz, 2H), 2.54 (s, 3H). | calc 330.4, found 331.1 [MH]+ | 33 |
| | 2-(5-fluoro-1-methyl-4-(naphthalen-1-ylmethoxy)-1H-indol-3-yl)-N-methylethanamine | 140 | 33-36 | ¹H-NMR (400 MHz, MeOD-d6): δ (ppm) 8.28 (dd, J = 7.2, 2.0 Hz, 1H), 7.94 (t, J = 8.4 Hz, 2H), 7.60-7.53 (m, 3H), 7.48 (t, J = 7.6 Hz, 1H), 7.13-7.05 (m, 2H), 6.99 (s, 1H), 5.72 (s, 2H), 3.71 (s, 3H), 2.86 (t, J = 6.8 Hz, 2H), 2.77 (t, J = 6.8 Hz, 2H), 2.16 (s, 3H). | calc 362.4, found 363.1 [MH]+ | 33 |

TABLE 30-continued

| Structure | name | Ex. number | ID number | NMR | MS | Procedure of scheme |
|---|---|---|---|---|---|---|
| 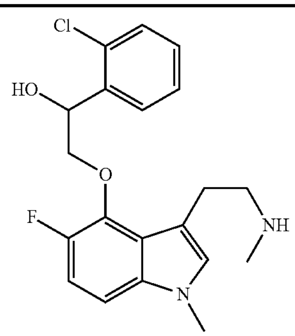 | 1-(2-chlorophenyl)-2-(5-fluoro-1-methyl-3-(2-(methylamino)ethyl)-1H-indol-4-yloxy)ethanol | 141 | 33-37 | ¹H-NMR (400 MHz, MeOD-d6): δ (ppm) 7.61 (dd, J = 6.0, 1.4 Hz, 1H), 7.31-7.21 (m, 3H), 6.98 (s, 1H), 6.96-6.86 (m, 2H), 5.44 (dd, J = 5.2, 2.8 Hz, 1H), 4.36-4.33 (m, 1H), 4.14-4.09 (m, 1H), 3.64 (s, 3H), 3.43 (t, J = 6.0 Hz, 2H), 3.18 (t, J = 6.0 Hz, 2H), 2.60 (s, 3H). | calc 376.8, found 377.1, 379.1 [MH]+ | 33 |
| 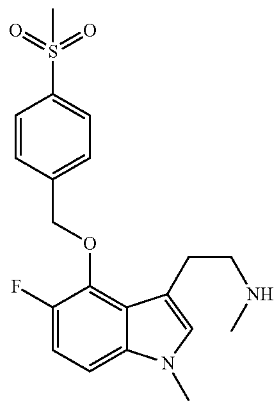 [SMILES: CNCCc1cn(C)c2ccc(F)c(OCc3ccc(S(C)(=O)=O)cc3)c12] | 2-(5-fluoro-1-methyl-4-(4-(mehtylsulfonyl)benzyloxy)-1H-indol-3-yl)-N-methylethanamine | 142 | 33-38 | ¹H-NMR (400 MHz, MeOD-d6): δ (ppm) 7.99 (d, J = 8.0 Hz, 2H), 7.76 (d, J = 8.0 Hz, 2H), 7.11-7.01 (m, 3H), 5.41 (s, 2H), 3.76 (s, 3H), 3.24 (t, J = 6.8 Hz, 2H), 3.15 (s, 3H), 3.11 (t, J = 6.8 Hz, 2H), 2.59 (s, 3H). | calc 390.4, found 391.1 [MH]+ | 33 |
| 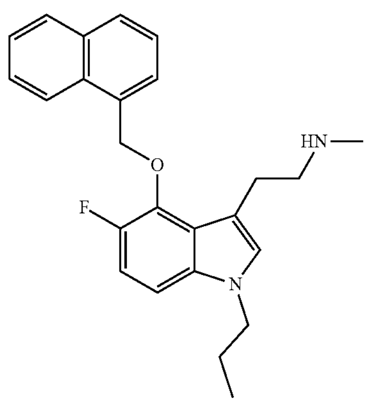 [SMILES: CCCn1cc(CCNC)c2c(OCc3cccc4ccccc34)c(F)ccc21] | 2-(5-fluoro-4-(naphthalen-1-ylmethoxy)-1-propyl-1H-indol-3-yl)-N-methylethanamine | 143 | 33-39 | ¹H-NMR (400 MHz, CDCl₃): δ (ppm) 8.33 (dd, J = 7.2, 2.0 Hz, 1H), 7.99-7.95 (m, 2H), 7.66-7.50 (m, 4H), 7.15-7.07 (m, 3H), 5.78 (d, J = 1.2 Hz, 2H), 4.08 (t, J = 7.2 Hz, 2H), 2.89 (t, J = 6.8 Hz, 2H), 2.79 (t, J = 6.8 Hz, 2H), 2.16 (s, 3H), 1.84 (q, 2H), 0.93 (t, J = 7.2 Hz, 3H). | calc 390.4, found 391.0 [MH]+ | 33 |
| 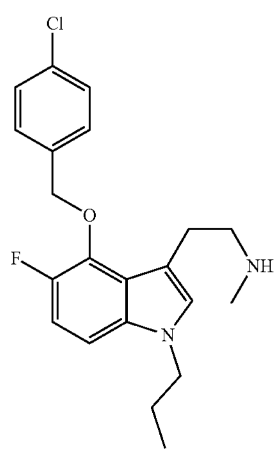 [SMILES: CCCn1cc(CCNC)c2c(OCc3ccc(Cl)cc3)c(F)ccc21] | 2-(4-(4-chlorobenzyloxy)-5-fluoro-1-propyl-1H-indol-3-yl)-N-methylethanamine | 144 | 33-40 | ¹H-NMR (400 MHz, MeOD-d6): δ (ppm) 7.47 (d, J = 8.0 Hz, 2H), 7.38 (d, J = 8.4 Hz, 2H), 7.12-7.07 (m, 2H), 7.03-6.98 (m, 1H), 5.26 (s, 2H), 4.06 (t, J = 7.0 Hz, 2H), 3.20 (t, J = 7.0 Hz, 2H), 3.07 (t, J = 6.8 Hz, 2H), 3.08 (t, J = 6.8 Hz, 2H), 2.56 (s, 3H), 1.86-1.80 (m, 2H), 0.92 (t, J = 7.4 Hz, 3H). | calc 374.8, found 375.1, 377.1 [MH]+ | 33 |

TABLE 30-continued

| Structure | name | Ex. number | ID number | NMR | MS | Procedure of scheme |
|---|---|---|---|---|---|---|
| 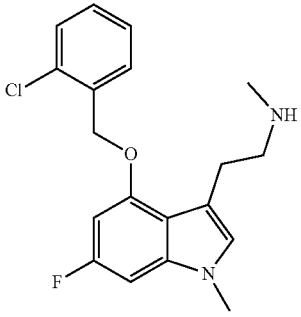 [SMILES: CNCCc1cn(C)c2cc(F)cc(OCc3ccccc3Cl)c12] | 2-(4-(2-chlorobenzyl-oxy)-6-fluoro-1-methyl-1H-indol-3-yl)-N-methylethan-amine | 148 | 33-44 | ¹H-NMR (400 MHz, MeOD-d6): δ (ppm) 7.63-7.60 (m, 1H), 7.54-7.52 (m, 1H), 7.44-7.40 (m, 2H), 6.96 (s, 1H), 6.77 (dd, J = 9.6, 2.0 Hz, 1H), 6.54 (dd, J = 9.6, 2.0 Hz, 1H), 5.31 (s, 2H), 3.71 (d, J = 2.0 Hz, 3H), 3.21 (t, J = 7.2 Hz, 2H), 3.11 (t, J = 6.4 Hz, 2H), 2.50 (s, 3H). | calc 346.8, found 347.1, 349.1 [MH]+ | 33 step 4-6-7 from SM 11-3 |
| 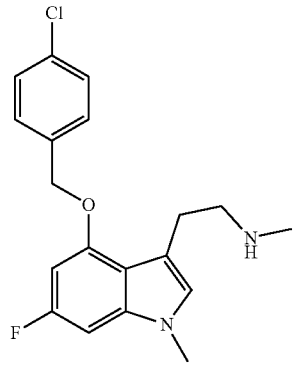 [SMILES: CNCCc1cn(C)c2cc(F)cc(OCc3ccc(Cl)cc3)c12] | 2-(4-(4-chlorobenzyl-oxy)-6-fluoro-1-methyl-1H-indol-3-yl)-N-methylethan-amine | 149 | 33-45 | ¹H-NMR (400 MHz, MeOD-d6): δ (ppm) 7.51 (d, J = 8.4 Hz, 2H), 7.46-7.44 (m, 2H), 6.97 (s, 1H), 6.77 (dd, J = 9.6, 2.0 Hz, 1H), 6.53 (dd, J = 9.6, 2.0 Hz, 1H), 5.20 (s, 2H), 3.70 (s, 3H), 3.22-3.20 (m, 2H), 3.16-3.12 (m, 2H), 2.53 (s, 3H). | calc 346.8, found 347.1, 349.1 [MH]+ | 33 step 4-6-7 from SM 11-3 |
| 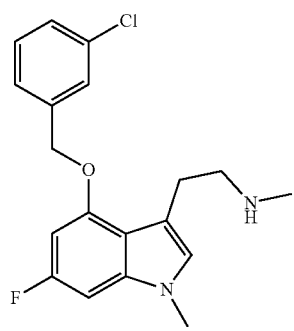 [SMILES: CNCCc1cn(C)c2cc(F)cc(OCc3cccc(Cl)c3)c12] | 2-(4-(3-chlorobenzyl-oxy)-6-fluoro-1-methyl-1H-indol-3-yl)-N-methylethan-amine | 150 | 33-46 | ¹H-NMR (400 MHz, MeOD-d6): δ (ppm) 7.56 (s, 1H), 7.48-7.39 (m, 3H), 6.98 (s, 1H), 6.76 (dd, J = 9.6, 2.0 Hz, 1H), 6.51 (dd, J = 11.6, 1.2 Hz, 1H), 5.23 (s, 2H), 3.71 (s, 3H), 3.24 (t, J = 6.4 Hz, 2H), 3.18-3.15 (m. 2H), 2.56 (s, 3H). | calc 346.8, found 347.1, 349.1 [MH]+ | 33 step 4-6-7 from SM 11-3 |
| 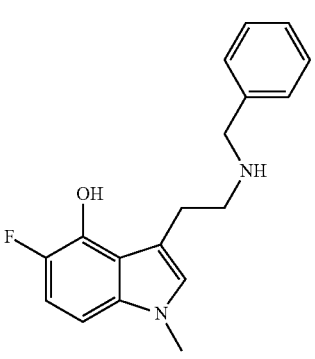 [SMILES: Cn1cc(CCNCc2ccccc2)c2c(O)c(F)ccc21] | 3-(2-(benzylamino)ethyl)-5-fluoro-1-methyl-1H-indol-4-ol | 151 | 33-47 | ¹H-NMR (400 MHz, MeOD-d6): δ (ppm) 7.46 (s, 5H), 6.99-6.93 (m, 2H), 6.78 (dd, J = 8.8, 3.2 Hz, 1H), 4.23 (s, 2H), 3.72 (s, 3H), 3.43 (t, J = 7.4 Hz, 2H), 3.27 (t, J = 7.4 Hz, 2H). | calc 298.1, found 299.0 [MH]+ | 33 step 4-5-7 |

TABLE 30-continued

| Structure | name | Ex. number | ID number | NMR | MS | Procedure of scheme |
|---|---|---|---|---|---|---|
| 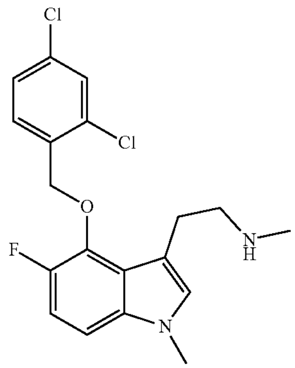 [SMILES: CNCCc1cn(C)c2ccc(F)c(OCc3ccc(Cl)cc3Cl)c12] | 2-(4-(2,4-dichlorobenzyl-oxy)-5-fluoro-1-methyl-1H-indol-3-yl)-N-methylethan-amine | 152 | 33-48 | $^1$H-NMR (400 MHz, MeOD-d6): δ (ppm) 7.60 (d, J = 8.0 Hz, 1H), 7.56 (s, 1H), 7.39 (dd, J = 8.0 Hz, 1.6 Hz, 1H), 7.10-7.01 (m, 3H), 5.37 (s, 2H), 3.75 (s, 3H), 3.23 (t, J = 6.8 Hz, 2H), 3.07 (t, J = 6.4 Hz, 2H), 2.58 (s, 3H). | calc 380.0, found 381.0 [MH]+ | 33 |
| 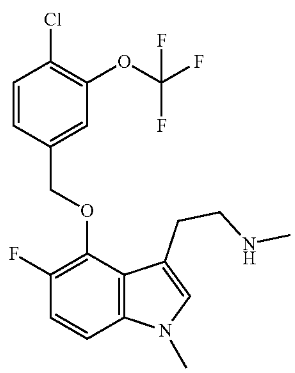 [SMILES: CNCCc1cn(C)c2ccc(F)c(OCc3ccc(Cl)c(OC(F)(F)F)c3)c12] | 2-(4-(4-chloro-3-(trifluoro-methoxy)benzyloxy)-5-fluoro-1-methyl-1H-indol-3-yl)-N-methylethan-amine | 153 | 33-49 | $^1$H-NMR (400 MHz, MeOD-d6): δ (ppm) 7.60 (d, J = 8.0 Hz, 1H), 7.55 (s, 1H), 7.48 (dd, J = 8.0 Hz, 1.6 Hz, 1H), 7.11-7.01 (m, 3H), 5.32 (s, 2H), 3.76 (s, 3H), 3.24 (t, J = 6.8 Hz, 2H), 3.10 (t, J = 6.8 Hz, 2H), 2.01 (s, 3H). | calc 430.1, found 431.0 [MH]+ | 33 |

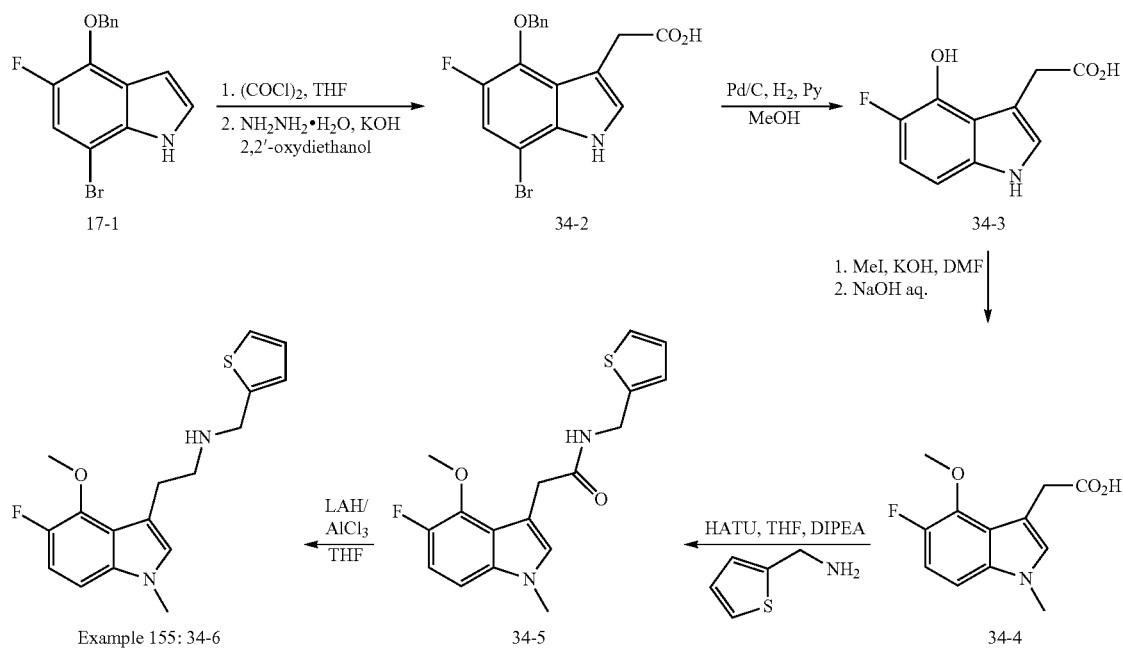

Scheme 34

Example 155

2-(5-fluoro-4-methoxy-1-methyl-1H-indol-3-yl)-N-(thiophen-2-ylmethyl)ethanamine (34-6)

Step 1: 2-(4-(benzyloxy)-7-bromo-5-fluoro-1H-indol-3-yl)acetic acid (34-2)

Following the procedure (step 3, scheme 33) used to prepare compound 33-4, compound 17-1 gave compound 34-2 in 58% yield as a yellow solid after column chromatography on silica gel eluting with dichloromethane/methanol (5:1). LRMS: calc 377.0 and found: 378.0 [M+1].

Step 2: 2-(5-fluoro-4-hydroxy-1H-indol-3-yl)acetic acid (34-3)

Following the procedure (step 9, scheme 13) used to prepare compound 33-10, compound 34-2 gave compound 34-3 in 90% yield as a yellow solid. The crude product was used in the next step without purification. LRMS: calc 209.2 and found: 210.1 [M+1].

Step 3: 2-(5-fluoro-4-methoxy-1-methyl-1H-indol-3-yl)acetic acid (34-4)

A mixture of compound 34-3 (1 g, 4.78 mmol), KOH (1 g, 19.14 mmol), MeI (2.7 g, 19.14 mmol) in DMF (20 mL) was stirred at room temperature for 2 h. Water (50 mL) and ethyl acetate (50 mL) were added to the mixture. The organic layer was separated and the aqueous layer was extracted with ethyl acetate (3×30 mL). The organic layers were combined, dried over MgSO$_4$, filtered, and evaporated to afford crude product (600 mg). To this crude product was added methanol (10 mL) and NaOH aq. (2 N, 8 mL) and then the reaction mixture was stirred and refluxed for 1 h. The mixture was allowed to cool to room temperature and neutralized with hydrochloric acid to pH=7 before it was extracted with ethyl acetate (2×30 mL). The organic layers were combined, dried over MgSO$_4$, filtered, and concentrated under reduce pressure to afford 34-4 (250 mg, 85%) as yellow oil. LRMS: calc 237.2 and found: 238.1 [M+1].

Step 4: N2-(5-fluoro-4-methoxy-1-methyl-1H-indol-3-yl)-N-(thiophen-2-ylmethyl)acetamide (34-5)

Following the procedure (step 4, scheme 33) used to prepare compound 33-5, compound 34-4 gave compound 34-5 in 82% yield as yellow solid. LRMS: calc 332.1 and found: 333.0 [M+1].

Step 5: 2-(5-fluoro-4-methoxy-1-methyl-1H-indol-3-yl)-N-(thiophen-2-ylmethyl)ethanamine (34-6)

Following the procedure (step 7, scheme 33) used to prepare compound 33-8, compound 34-5 gave compound 34-6. $^1$H-NMR (400 MHz, MeOD-d6): δ (ppm) 7.57 (d, J=4.8 Hz, 1H), 7.30 (d, J=3.6 Hz, 1H), 7.13-7.09 (m, 2H), 7.05-6.97 (m, 2H), 4.48 (s, 2H), 4.01 (d, J=2.4 Hz, 3H), 3.75 (s, 3H), 3.38-3.33 (m, 2H), 3.21 (t, J=7.4 Hz, 2H). LCMS calc 318.1. found 319.0 [MH]+.

The compounds in Table 31 were made according to processes described in Scheme 34.

TABLE 31

| Structure | name | Ex. number | ID number | NMR | MS | Procedure of scheme |
|---|---|---|---|---|---|---|
| 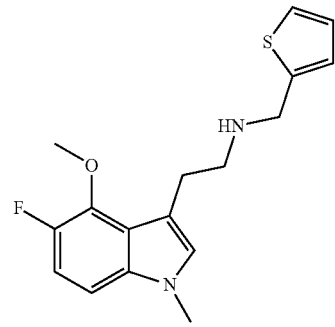 [SMILES: COc1c(F)ccc2c1c(CCNCc1cccs1)cn2C] | 2-(5-fluoro-4-methoxy-1-methyl-1H-indol-3-yl)-N-(thiophen-2-ylmethyl)ethanamine | 154 | 34-6 | $^1$H-NMR (400 MHz, MeOD-d6): δ (ppm) 7.57 (d, J = 4.8 Hz, 1H), 7.30 (d, J = 3.6 Hz, 1H), 7.13-7.09 (m, 2H), 7.05-6.97 (m, 2H), 4.48 (s, 2H), 4.01 (d, J = 2.4 Hz, 3H), 3.75 (s, 3H), 3.38-3.33 (m, 2H), 3.21 (t, J = 7.4 Hz, 2H). | calc 318.1, found 319.0 [MH]+ | 34 |
| 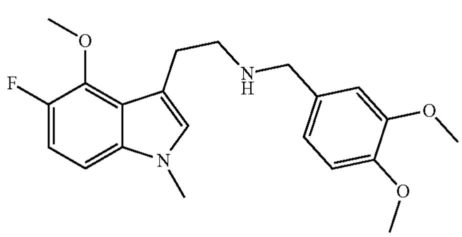 [SMILES: COc1ccc(CNCCc2cn(C)c3ccc(F)c(OC)c23)cc1OC] | N-(3,4-dimethoxybenzyl)-2-(5-fluoro-4-methoxy-1-methyl-1H-indol-3-yl)ethanamine | 156 | 34-8 | $^1$H-NMR (400 MHz, MeOD-d6): δ (ppm) 7.07-7.00 (m, 6H), 4.17 (s, 2H), 4.00 (d, J = 2.0 Hz, 3H), 3.86 (d, J = 5.2 Hz, 6H), 3.75 (s, 3H), 3.34-3.32 (m, 2H), 3.20 (t, J = 7.6 Hz, 2H). | calc 372.1, found 373.0 [MH]+ | 34 |

TABLE 31-continued

| Structure | name | Ex. number | ID number | NMR | MS | Procedure of scheme |
|---|---|---|---|---|---|---|
| 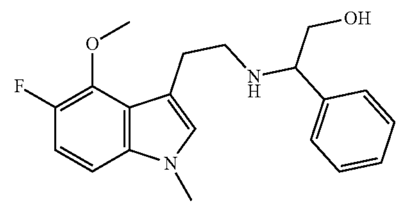 [SMILES: COc1c(F)ccc2c1c(CCNC(CO)c1ccccc1)cn2C] | 2-(2-(5-fluoro-4-methoxy-1-methyl-1H-indol-3-yl)ethylamino)-2-phenylethanol | 157 | 34-9 | $^1$H-NMR (400 MHz, MeOD-d6): δ (ppm) 7.40-7.30 (m, 5H), 6.99-6.94 (m, 1H), 6.88-6.84 (m, 2H), 5.38-5.30 (br.s, 1H), 5.33-5.30 (m, 1H), 4.16-4.08 (m, 2H), 3.91 (d, J = 2.8 Hz, 4H), 3.68 (s, 3H), 3.16 (s, 4H). | calc 342.1, found 343.0 [MH]+ | 34 |
| 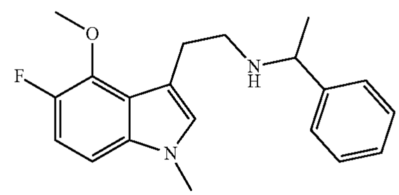 [SMILES: COc1c(F)ccc2c1c(CCNC(C)c1ccccc1)cn2C] | 2-(5-fluoro-4-methoxy-1-methyl-1H-indol-3-yl)-N-(1-phenylethyl)ethanamine | 158 | 34-10 | $^1$H-NMR (400 MHz, MeOD-d6): δ (ppm) 7.50-7.44 (m, 5H), 7.02-6.94 (m, 3H), 4.42 (q, 1H), 3.89 (d, J = 2.8 Hz, 3H), 3.72 (s, 3H), 3.24-3.10 (m, 4H), 1.70 (d, J = 6.4 Hz, 3H). | calc 326.1, found 327.0 [MH]+ | 34 |

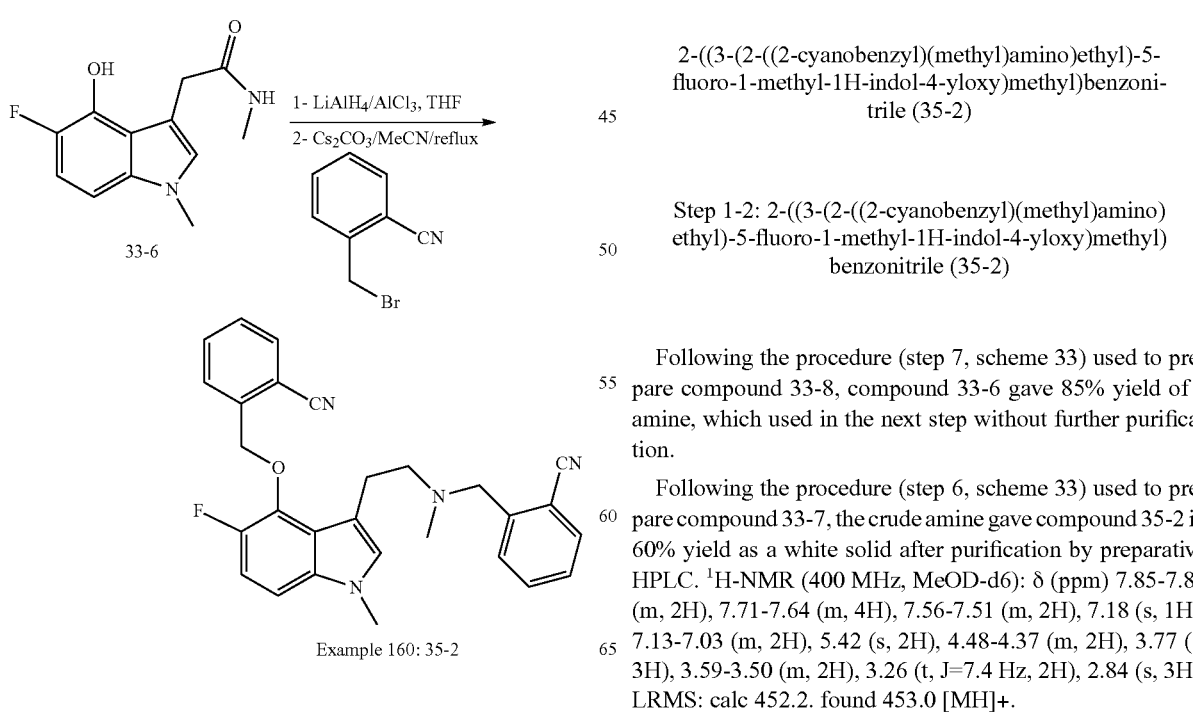

Example 160

2-((3-(2-((2-cyanobenzyl)(methyl)amino)ethyl)-5-fluoro-1-methyl-1H-indol-4-yloxy)methyl)benzonitrile (35-2)

Step 1-2: 2-((3-(2-((2-cyanobenzyl)(methyl)amino)ethyl)-5-fluoro-1-methyl-1H-indol-4-yloxy)methyl)benzonitrile (35-2)

Following the procedure (step 7, scheme 33) used to prepare compound 33-8, compound 33-6 gave 85% yield of a amine, which used in the next step without further purification.

Following the procedure (step 6, scheme 33) used to prepare compound 33-7, the crude amine gave compound 35-2 in 60% yield as a white solid after purification by preparative HPLC. $^1$H-NMR (400 MHz, MeOD-d6): δ (ppm) 7.85-7.82 (m, 2H), 7.71-7.64 (m, 4H), 7.56-7.51 (m, 2H), 7.18 (s, 1H), 7.13-7.03 (m, 2H), 5.42 (s, 2H), 4.48-4.37 (m, 2H), 3.77 (s, 3H), 3.59-3.50 (m, 2H), 3.26 (t, J=7.4 Hz, 2H), 2.84 (s, 3H). LRMS: calc 452.2. found 453.0 [MH]+.

Scheme 36

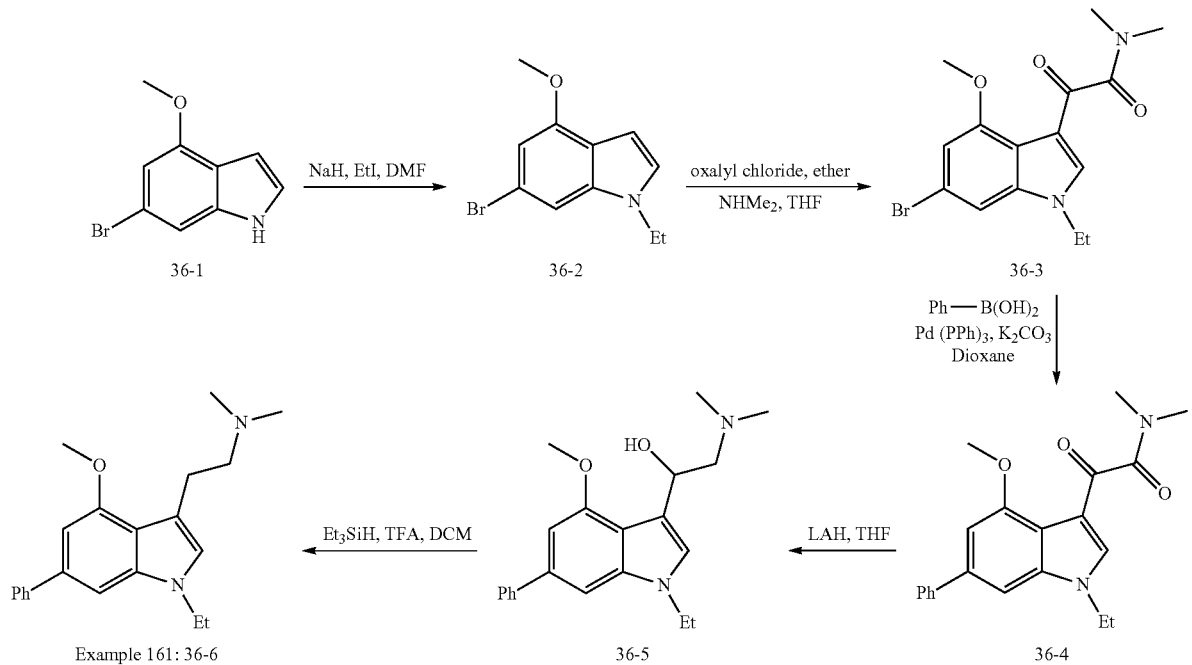

Example 161

2-(1-ethyl-4-methoxy-6-phenyl-1H-indol-3-yl)-N,N-dimethylethanamine (36-6)

Step 1: 6-bromo-1-ethyl-4-methoxy-1H-indole (36-2)

NaH (96 mg, 4 mmol) was suspended in 7 mL DMF in a round bottom flask and cooled to 0° C. 6-bromo-4-methoxy-1H-indole (0.75 g, 3.3 mmol) was added dropwise as a solution in DMF (1 mL). Ethyl iodide (0.28 mL, 3.5 mmol) was added dropwise and the reaction mixture was stirred for 10 min. Volatiles were removed under reduced pressure and the residue partitioned between DCM and water. The aqueous layer was extracted with DCM and the combined organics layers were dried over MgSO$_4$, filtered, and evaporated to give a red oil. The resulting residue was purified on silica gel column chromatography eluting with hexanes/ethyl acetate (0-10%) to afford pure 36-2 (584 mg, 70%) as a white solid.

Step 2: 2-(6-bromo-1-ethyl-4-methoxy-1H-indol-3-yl)-N,N-dimethyl-2-oxo acetamide (36-3)

Following the procedure (step 5, scheme 1) used to prepare compound 1-6a, compound 36-2 gave compound 36-3 (669 mg, 88%) as a pale pink solid. LCMS: calc 352.0 and found: 353.0 [MH]$^+$.

Step 3: 2-(1-ethyl-4-methoxy-6-phenyl-1H-indol-3-yl)-N,N-dimethyl-2-oxoacetamide (36-4)

To a sealable vessel was added 36-3 (100 mg, 0.28 mmol), phenylboronic acid (1042 mg, 0.86 mmol), Pd(PPh$_3$)$_4$ (66 mg, 10 mol %), and potassium carbonate (117 mg, 0.85 mmol). Dioxane (1.5 mL) was added and the reaction heated at 100° C. two days. The reaction mixture was diluted with ethyl acetate, filtered through celite and concentrated. The resulting residue was purified on silica gel column chromatography eluting with hexanes/ethylacetate (50-100%) to afford 79 mg of 36-4. LCMS: calc 350.2 and found: 351.1 [MH]$^+$.

Step 4: 2-(dimethylamino)-1-(1-ethyl-4-methoxy-6-phenyl-1H-indol-3-yl)ethanol (36-5)

Following the procedure (step 6, scheme 1) used to prepare compound 1-7a, compound 36-4 gave compound 36-5 (68%), which was taken on to the final step without further purification. LCMS: calc 338.2 and found: 313.1 [MH−water]$^+$.

Step 5: 2-(1-ethyl-4-methoxy-6-phenyl-1H-indol-3-yl)-N,N-dimethylethanamine (36-6)

36-5 (68 mg, 0.2 mmol) was dissolved in DCM (2 mL) and triethylsilane (0.32 mL, 2.0 mmol) was added at 0° C. Trifluoroacetic acid (126 uL, 1.6 mmol) was added dropwise. After 20 minutes, the reaction mixture was quenched with saturated aqueous sodium bicarbonate and then diluted with DCM. The organic layer was dried over MgSO$_4$, filtered, and evaporated. The resulting residue was purified on silica gel column chromatography eluting with DCM/methanol (0-10%) containing 0.1% NH$_4$OH to give the desired product. The product was acidified with HCl to afford 36-6 (19.6 mg, 27%) as an off-white solid. $^1$H NMR (300 MHz, D$_2$O): δ (ppm) 7.62 (m, 2H), 7.42-7.24 (m, 4H), 7.06 (s, 1H), 6.78 (s, 1H), 4.04 (q, J=7.5 Hz, 2H), 3.88 (s, 3H), 3.31 (t, J=8.4 Hz, 2H), 3.12 (t, J=7.5 Hz, 2H), 2.76 (s, 6H), 1.24 (s, 7.5 Hz, 3H). LCMS: calc 322.4 and found: 323.1 [MH]$^+$.

Scheme 37

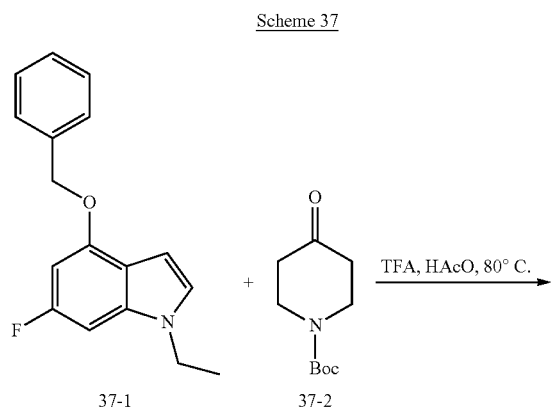

37-1 + 37-2 →(TFA, HAcO, 80° C.)

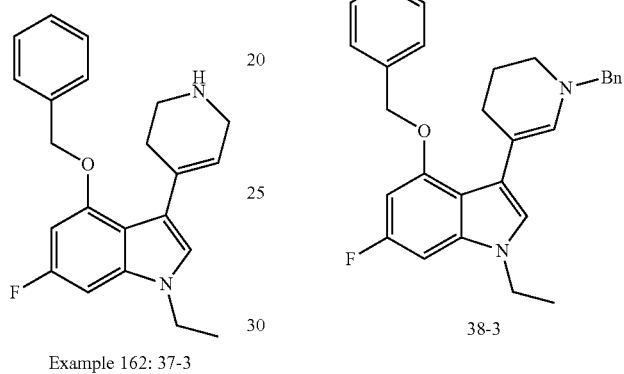

Example 162: 37-3

Example 162

4-(benzyloxy)-1-ethyl-6-fluoro-3-(1,2,3,6-tetrahydropyridin-4-yl)-1H-indole (37-3)

Step 1: 4-(benzyloxy)-1-ethyl-6-fluoro-3-(1,2,3,6-tetrahydropyridin-4-yl)-1H-indole (37-3)

In pressure vessel, tert-butyl 4-oxopiperidine-1-carboxylate (370 mg, 1.86 mmol) was dissolved in acetic acid (3 mL) and then 4-(benzyloxy)-1-ethyl-6-fluoro-1H-indole (200 mg, 0.74 mmol) was added, followed by trifluoroacetic acid (1 mL). The reaction mixture was heated to 80° C. for 1 hour. Volatiles were evaporated and then water was added. The pH was adjusted to ~12 with 15% aqueous NaOH and partitioned between EtOAc-water. The organic layer was washed with brine, dried over MgSO$_4$, filtered and concentrated to give a crude product. The resulting residue was purified on alumina column chromatography eluting with DCM/methanol (0-6%) to afford 37-3 (84 mg, 32%). 1H NMR (300 MHz, DMSO-d6) δ (ppm) 8.78 (br. s, 2H), 7.51-7.41 (m, 5H), 7.27 (s, 1H), 6.99 (dd, J=9.9 Hz and 2.1 Hz, 1H), 6.63 (dd, J=11.8 Hz and 2.1 Hz, 1H), 5.84, (br. s, 1H), 5.16 (s, 2H), 4.11 (q, J=7.2 Hz, 2H), 3.46 (br. s, 2H), 2.93 (br.s, 2H), 2.61 (br. s, 2H), 1.31 (t, J=7.2 Hz, 3H). LCMS: calc 350.4 and found: 351.1 [MH]$^+$.

Scheme 38

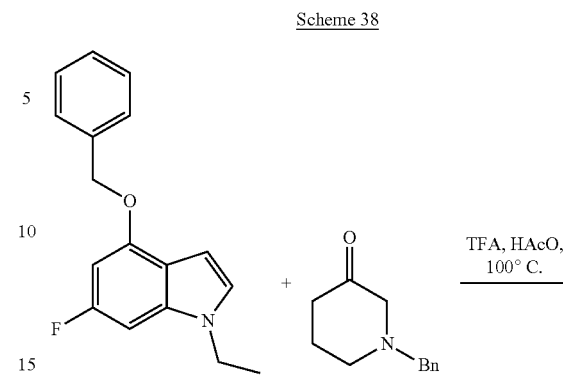

37-1 + 38-2 →(TFA, HAcO, 100° C.)

38-3 →(Pd/C (10%), H$_2$ / MeOH, HAcO)

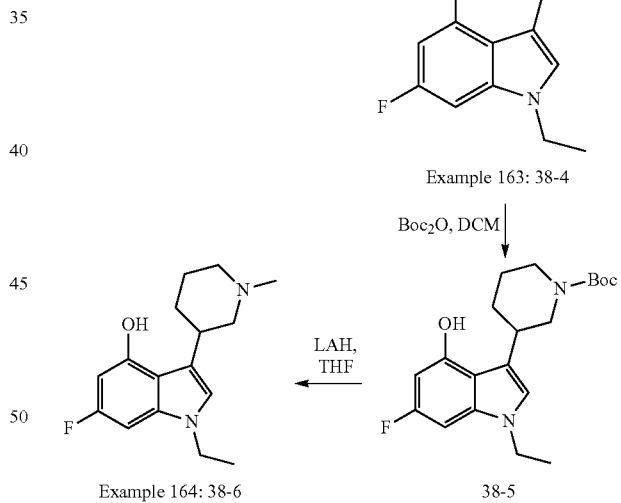

Example 163: 38-4

Boc$_2$O, DCM ↓

38-5 →(LAH, THF)→ Example 164: 38-6

Example 163

1-ethyl-6-fluoro-3-(piperidin-3-yl)-1H-indol-4-ol (38-4)

Step 1: 3-(1-benzyl-1,4,5,6-tetrahydropyridin-3-yl)-4-(benzyloxy)-1-ethyl-6-fluoro-1H-indole (38-3)

Following the procedure (step 1, scheme 37) used to prepare compound 37-3, compound 37-1 gave compound 38-3

(98%) as a brown oil that was taken on to the next step without purification. LCMS: calc 440.2 and found: 439.3 [MH]⁻.

Example 163

Step 2: 1-ethyl-6-fluoro-3-(piperidin-3-yl)-1H-indol-4-ol (38-4)

Following the procedure (step 3 scheme 31 used to prepare compound 31-4 compound 38-3 gave compound 38-4 (113 mg, 59%) as a light tan-colored solid. $^1$H NMR (300 MHz, MeOD-d6): δ (ppm) 6.80 (s, 1H), 6.49 (dd, J=10.0, 2.1 Hz, 1H), 6.13 (dd, J=11.4, 2.1 Hz, 1H), 4.01 (q, J=7.2 Hz, 2H), 3.53-3.40 (m, 2H), 3.05 (d, J=11.4 Hz, 1H), 2.55 (dt, J=23.0, 11.7 Hz, 2H), 2.14 (dd, J=8.8, 6.1 Hz, 1H), 1.85-1.56 (m, 3H), 1.34 (t, J=7.2 Hz, 3H). LCMS: calc 262.1 and found: 263.1 [MH]⁺.

Example 164

1-ethyl-6-fluoro-3-(1-methylpiperidin-3-yl)-1H-indol-4-ol (38-6)

Step 3: tert-butyl 3-(1-ethyl-6-fluoro-4-hydroxy-1H-indol-3-yl)piperidine-1-carboxylate (38-5)

38-4 (350 mg, 1.1 mmol) was dissolved in DCM (6 mL) and di-tert-butyl-dicarbonate (284 mg, 1.3 mmol) was added. The reaction mixture was stirred at room temperature for 30 minutes and then diluted with DCM, washed with aqueous sodium bicarbonate, dried over MgSO₄, filtered and concentrated to give the crude product. The resulting residue was purified on silica gel column chromatography eluting with hexanes/ethylacetate (5-30%) to afford 224 mg (57%) of 38-5 as a white crystalline solid. LCMS: calc 362.2 and found: 363.2 [MH]⁺.

Step 3: 1-ethyl-6-fluoro-3-(1-methylpiperidin-3-yl)-1H-indol-4-ol (38-6)

Following the procedure (step 6, scheme 1) used to prepare compound 1-7a, compound 38-5 gave compound 38-6 (20 mg, 22%) as a white solid. $^1$H NMR (300 MHz, DMSO-d6) δ (ppm) 9.91 (s, 1H), 6.92 (s, 1H), 6.63 (dd, J=10.2, 2.1 Hz, 1H), 6.14 (dd, J=11.5, 2.1 Hz, 1H), 3.98 (q, J=7.1 Hz, 2H), 3.31 (m, 1H), 3.02 (d, J=10.1 Hz, 1H), 2.71 (s, 1H), 2.14 (s, 3H), 2.01-1.42 (m, 5H), 1.25 (m, J=7.2 Hz, 4H). LCMS: calc 276.2 and found: 277.1 [MH]⁺.

Scheme 39:

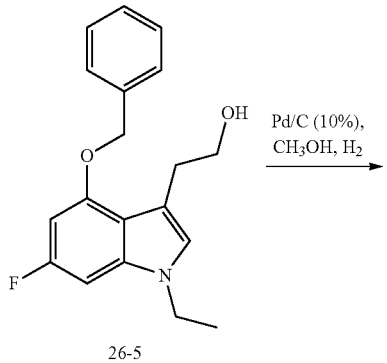

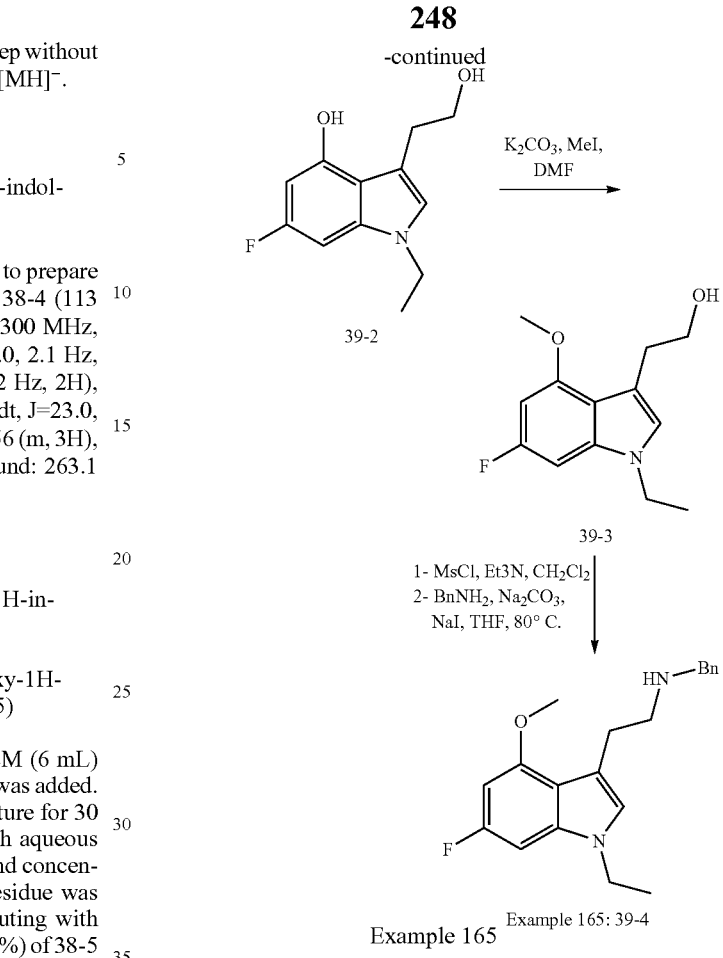

Example 165

N-benzyl-2-(1-ethyl-6-fluoro-4-methoxy-1H-indol-3-yl)ethanamine (39-4)

Step 1: 1-ethyl-6-fluoro-3-(2-hydroxyethyl)-1H-indol-4-ol (39-2)

Following the procedure (step 3 scheme 31 used to prepare compound 31-4 compound 26-5 gave compound 39-2 (318 mg, 99%) as a light purple solid.

Step 2: 2-(1-ethyl-6-fluoro-4-methoxy-1H-indol-3-yl)ethanol (39-3)

39-2 (318 mg, 1.43 mmol) was dissolved in DMF (5 mL) and then potassium carbonate (236 mg, 1.71 mmol) and methyl iodide (98 uL, 1.56 mmol) were added. The reaction mixture was stirred at room temperature overnight, concentrated under vacuum and then water added. A solid was filtered to afford 39-3 (313 mg, 90%) as a light purple solid. LCMS: calc 326.2. found 327.1 [MH]⁺.

Step 3-4: N-benzyl-2-(1-ethyl-6-fluoro-4-methoxy-1H-indol-3-yl)ethanamine (39-4)

Following the procedure used to prepare compound 23-4a (scheme 23, step 3-4), compound 39-4 was prepared from 39-3. Compound 39-4 was obtained as yellow oil (26 mg, 40%). $^1$H NMR (300 MHz, DMSO-d6) δ (ppm) 7.31-7.15 (m, 5H), 6.95 (s, 1H), 6.82 (dd, J=10.1, 2.0 Hz, 1H), 6.34 (dd, J=12.1, 2.0 Hz, 1H), 4.01 (t, J=7.2 Hz, 2H), 3.77 (s, 3H), 3.70 (s, 2H), 2.86 (t, J=6.6 Hz, 2H), 2.71 (t, J=7.4 Hz, 2H), 1.24 (t, J=7.2 Hz, 3H). LCMS: calc calc 326.18. found 327.1 [MH]+.

The compounds in Table 33 were made according to processes described in Scheme 39.

TABLE 33

| Structure | name | Ex. number | ID number | NMR | MS | Procedure of scheme |
|---|---|---|---|---|---|---|
| 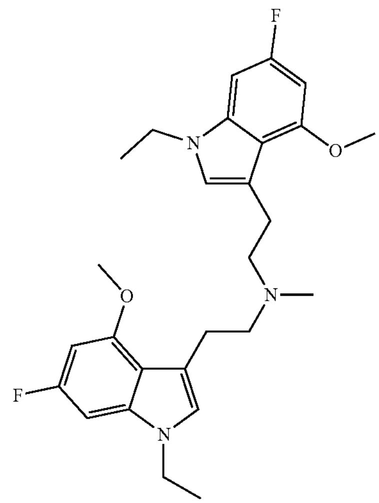 [SMILES: CCn1cc(CCN(C)CCc2cn(CC)c3cc(F)cc(OC)c23)c2c(OC)cc(F)cc21] | 2-(1-ethyl-6-fluoro-4-methoxy-1H-indol-3-yl)-N-(2-(1-ethyl-6-fluoro-4-methoxy-1H-indol-3-yl)ethyl)-N-methylethanamine | 166 | 39-5 | $^1$H NMR (300 MHz, MeOD-d6): δ (ppm) 6.86 (s, 2H), 6.66 (dd, J = 9.8, 2.0 Hz, 2H), 6.31 (dd, J = 11.9, 2.0 Hz, 2H), 4.10-3.97 (m, 4H), 3.81 (s, 6H), 3.03 (dd, J = 10.2, 6.1 Hz, 4H), 2.79 (dd, J = 10.2, 5.9 Hz, 4H), 2.48 (s, 3H), 1.35 (s, 6H) | calc 469.25, found 470.2 [MH]+ | 29 Starting material 0.5 eq MeNH2 |
| | 1-ethyl-6-fluoro-3-(2-(2-phenylpropylamino)ethyl)-1H-indol-4-ol | 166b | 39-6 | $^1$H NMR (300 MHz, MeOD-d6): δ (ppm) 7.24-7.01 (m, 5H), 6.64 (s, 1H), 6.48 (dd, J = 10.0, 2.1 Hz, 1H), 6.14 (dd, J = 11.5, 2.1 Hz, 1H), 3.94 (q, J = 7.2 Hz, 2H), 3.05-2.68 (m, 7H), 1.29 (t, J = 7.2 Hz, 3H), 1.20 (d, J = 6.9 Hz, 3H). | calc 340.2, found 341.2 [MH]+ | |

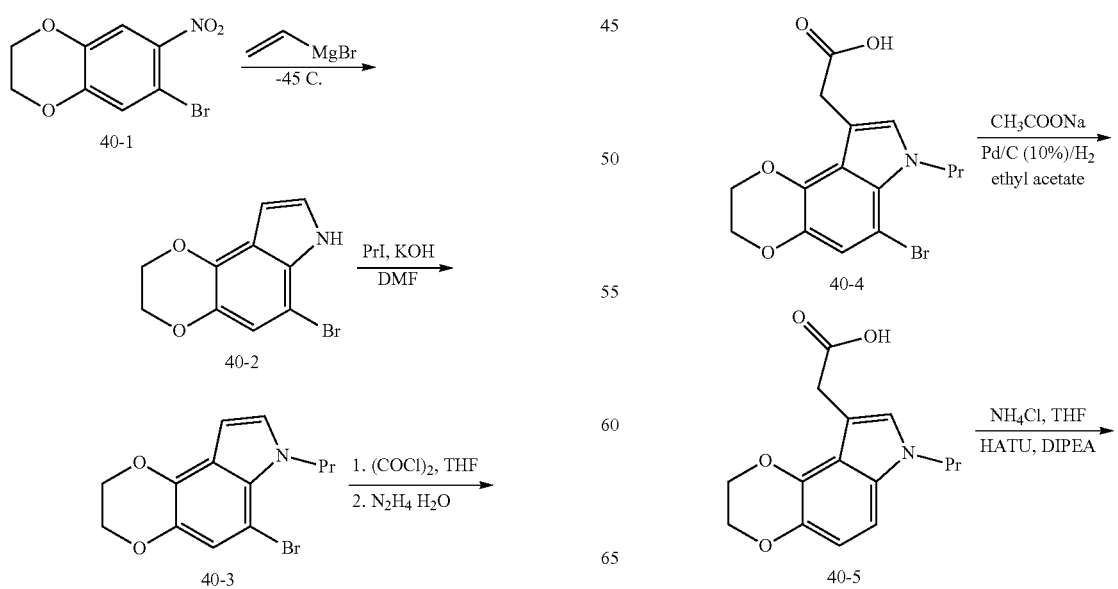

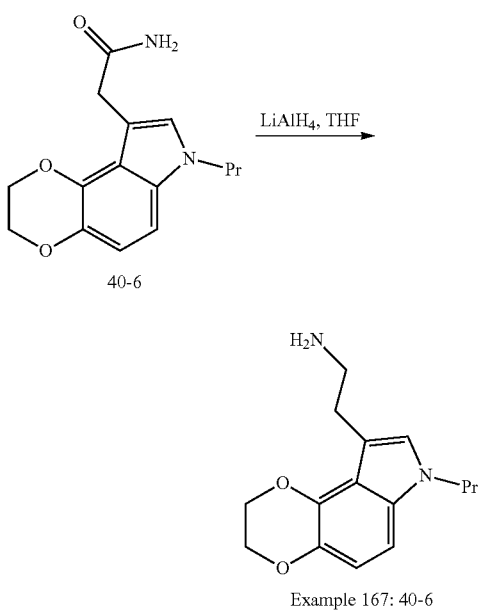

Example 167

2-(7-propyl-3,7-dihydro-2H-[1,4]dioxino[2,3-e]indol-9-yl)ethanamine (40-7)

Step 1: 6-bromo-3,7-dihydro-2H-[1,4]dioxino[2,3-e]indole (40-2)

Following the procedure (step 1, scheme 33) used to prepare compound 17-1, compound 40-1 gave compound 40-2 in 35% yield as a yellow solid. LCMS: calc 253.0. found 254.8 [MH]$^+$.

Step 2: 6-bromo-7-propyl-3,7-dihydro-2H-[1,4]dioxino[2,3-e]indole (40-3)

Following the procedure (step 2, scheme 33) used to prepare compound 33-3, compound 40-2 gave compound 40-3 in 90% yield as a yellow solid. LCMS: calc 295.0 found 296.0 [MH]$^+$.

Step 3: 2-(6-bromo-7-propyl-3,7-dihydro-2H-[1,4]dioxino[2,3-e]indol-9-yl)acetic acid (40-4)

Following the procedure (step 3, scheme 333) used to prepare compound 33-4, compound 40-3 gave compound 40-4 in 74% yield as a yellow solid. LCMS: calc 353.0 found 353.9 [MH]$^+$.

Step 4: 2-(7-propyl-3,7-dihydro-2H-[1,4]dioxino[2,3-e]indol-9-yl)acetic acid (40-5)

A mixture of 40-4 (0.16 g, 0.45 mmol), NaOAc (0.9 g, 0.74 mmol) and 10% Pd/C (0.2 g) in ethyl acetate (20 mL) was stirred under H$_2$ at room temperature for 12 h. The solid was filtered off and the filtrate was concentrated to obtain the desired product 40-5 (0.12 g, 97%) as a yellow solid, which was used in the next step without further purification. LCMS: calc 275.0 found 276.0 [MH]$^+$.

Step 5: 2-(7-propyl-3,7-dihydro-2H-[1,4]dioxino[2,3-e]indol-9-yl)acetamide (40-6)

Following the procedure (step 1, scheme 31) used to prepare compound 31-2, compound 40-5 gave compound 40-6 in 100% yield as yellow oil. LCMS: calc 274.1 found 275.0 [MH]$^+$.

Step 6: 2-(7-propyl-3,7-dihydro-2H-[1,4]dioxino[2,3-e]indol-9-yl)ethanamine (40-7)

Following the procedure (step 6, scheme 1) used to prepare compound 1-7a, compound 40-6 gave compound 40-7 (5 mg, 9%) as yellow oil. $^1$H NMR (300 MHz, MeOD-d6): δ (ppm) 6.87 (s, 1H), 6.73 (d, J=8.8 Hz, 1H), 6.61 (d, J=8.8 Hz, 1H), 4.26-4.24 (m, 2H), 4.16-1.15 (m, 2H), 3.91 (t, J=7.2 Hz, 2H), 3.13 (t, J=7.2 Hz, 2H), 3.02 (t, J=7.2 Hz, 2H), 1.71 (q, J=7.2 Hz, 2H), 0.80 (t, J=7.2 Hz, 3H). LCMS: calc 260.2 found 261.1 [MH]$^+$.

Example 41

LCMS Methods

Standard conditions for Analytical LCMS conditions are as follows:
Standard Conditions Column type: Waters Symmetry C18 100×4.6 mm IC, 3.5 μm
Run time: 10.00 minute run
QC Conditions Column type: Waters symmetry C18 50×4.6 mm ID, 3.5 μm
Run time: 5.00 minute run
NH$_4$OAc (AA) Standard Conditions:
Solvent A:
10 mM NH$_4$OAc
98% water
2% Isopropyl alcohol
Solvent B:
10 mM NH$_4$OAc
25% Methanol
75% MeCN
NH$_4$OAc (AA) OC conditions:
Solvent A:
10 mM NH$_4$OAc
99% water
1% MeCN
Solvent B:
10 mM NH$_4$OAc
5% water
95% MeCN
HCOOH (FA) Standard and OC Conditions:
Solvent C:
0.1% HCOOH
99% water
1% MeCN
Solvent D:
0.1% HCOOH
5% water
95% MeCN
Standard Gradient (Ammonium Acetate and Formic Acid Conditions):

| Time [min] | Solvent A % | Solvent B % | Flow rate [ml/min] |
|---|---|---|---|
| 0.00 | 95.0 | 5.0 | 1.0 |
| 7.50 | 0.0 | 100.0 | 1.0 |
| 8.00 | 0.0 | 100.0 | 1.0 |
| 9.75 | 0.0 | 100.0 | 1.0 |
| 9.80 | 95.0 | 5.0 | 1.0 |
| 10.00 | 95.0 | 5.0 | 1.0 |

QC Gradient (Ammonium Acetate and Formic Acid Conditions):

| Time [min] | Solvent A % | Solvent B % | Flow rate [ml/min] |
|---|---|---|---|
| 0.00 | 95.0 | 5.0 | 1.0 |
| 3.50 | 0.0 | 100.0 | 1.0 |
| 4.90 | 0.0 | 100.0 | 1.0 |
| 5.0 | 95.0 | 5.0 | 1.0 |

System: Agilent 1200 HPLC/MSD, DAD Wavelength Range (nm) detector; A 6110 Quadrupole MS, electrospray ion source (ESI).

1. QA Project LCMS/HPLC Base Methods

| | |
|---|---|
| Column | XBridge C18 4.6 × 150 mm, 3.5 μm |
| Solvent A | Water (10 mM NH₄HCO3) |
| Solvent B | MeCN |
| Col Temp | 40 degrees centigrade |
| Split ratio ELSD:MS | 10:1 |
| DAD Wavelength Range (nm) | 210 to 350 |
| Mass range | 100 to 1000 |

Gradient

| Time (min) | Solvent A % | Solvent B % | Flow rate (mL/min) |
|---|---|---|---|
| 0.0 | 80.0 | 20.0 | 1.2 |
| 1.5 | 80.0 | 20.0 | 1.2 |
| 8.0 | 20.0 | 80.0 | 1.2 |
| 8.1 | 5.0 | 95.0 | 1.2 |
| 16.0 | 5.0 | 95.0 | 1.2 |

2 QA Project LCMS/HPLC Acid Method

| | |
|---|---|
| Column | Agilent Eclipse XDB-C18 (4.6 × 150 mm, 5 μm) |
| Solvent A | Water (0.01% TFA) |
| Solvent B | MeCN (0.01% TFA) |
| Col Temp | 35 degrees centigrade |
| Split ratio ELSD:MS | 10:1 |
| DAD Wavelength Range (nm) | 210 to 350 |
| mass range | 100 to 1000 amu |

Gradient

| Time (min) | Solvent A % | Solvent B % | Flow rate (mL/min) |
|---|---|---|---|
| 0.0 | 80.0 | 20.0 | 1.2 |
| 1.5 | 80.0 | 20.0 | 1.2 |
| 8.0 | 20.0 | 80.0 | 1.2 |
| 8.1 | 5.0 | 95.0 | 1.2 |
| 16.0 | 5.0 | 95.0 | 1.2 |

Example 42

Preparative HPLC Methods

| | | |
|---|---|---|
| Instrument | Glison 281(PHG005) | |
| Column | Waters Sunfire Prep C18 OBD, 30 * 100 mm, 5 um | |
| Wavalength (nm) | 214/254 | |
| Flow Rate (ml/min) | 30.00 | |
| Method | Acid condition | Basic condition |
| Mobile Phase | A: Water (0.05% TFA), B: ACN | : Water (0.1% NH3H2O); B: ACN (0.1% NH3H2O) |
| Gradient | % B in 7.5 min, stop at 12 min | % B in 7.5 min, stop at 12 min |

Example 43

Aequorin Assays Dose Response

Testing Protocol:

For Aequorin technology Aequorin human serotonin 5-HT2A, 5-HT2C(e) and 5-HT2C(ne) cells grown 18 hours prior to the test in media without antibiotics are detached by gentle flushing with PBS-EDTA (5 mM EDTA), recovered by centrifugation and resuspended in "assay buffer" (DMEM/HAM's F12 with HEPES+0.1% BSA protease free). Cells are incubated at room temperature for at least 4 h with Coelenterazine h (Molecular Probes). Dose response curves with the reference compounds are performed before testing the compounds. 5-HT2A reference agonist and antagonist are -methyl-5-HT and ketanserin, respectively. 5-HT2C(e) and 5-HT2C(ne) reference agonists are -methyl-5-HT and 5-HT, respectively. 5-HT2C(e) and 5-HT2C(ne) reference antagonist is RS102221. For agonist testing, 50 μl of cell suspension will be injected on 50 μl of test compound or reference agonist plated in a 96-well plate. The resulting emission of light will be recorded using the Hamamatsu Functional Drug Screening System 6000 (FDSS 6000). Following an incubation of 15 mM after the first injection, 100 μl of the reference agonist at a concentration corresponding to its EC80 will be injected on the 100 μl of the mixture of cell suspension and test compound, for antagonist testing. The resulting emission of light will be recorded using FDSS6000. To standardize the emission of recorded light (determination of the "100% signal") across plates and across different experiments, some of the wells will contain 100 μM digitonin or a saturating concentration of ATP (20 μM). Plates will also contain the reference agonist at a concentration equivalent to the EC80 obtained during the test validation. Agonist activity of test compound will be expressed as a percentage of the activity of the reference agonist at its EC100 concentration. Antagonist activity of test compound will be expressed as a percentage of the inhibition of reference agonist activity at its EC80 concentration.

Example 44 cAMP Assays Dose Response

Testing Protocol:

Recombinant 5-HT6 cells grown to mid-log phase in culture media without antibiotics are detached with PBS-EDTA, centrifuged and resuspended in assay buffer (KRH, 1 mM IBMX) at a concentration of 2.1×105 cells/ml. The test is performed in 96 well plates. For agonist testing, 12 μl of cells (2,500 cells/well) are mixed with 12 μl of test compound at increasing concentrations. For antagonist testing, 12 μl of cells (2,500 cells/well) are mixed with 6 μl of the test compound at increasing concentrations. After incubation for 10 mM at room temperature, 6 μl of the reference agonist are added at a final agonist concentration corresponding to the historical EC80. The plates are then incubated for 30 min at room temperature. After addition of the lysis buffer, cAMP concentrations are estimated, according to the manufacturer specification, with the HTRF kit from Cis-Bio International (cat no 62AM2PEB). 5-HT6 reference agonist and antagonist are 5-HT and mianserin, respectively.

Quality Control for Compound Testing:

On each day of experimentation and prior to the testing of compounds, reference compounds were tested at several concentrations in duplicate (n=2) to obtain a dose-response curve and an estimated EC50 and/or IC50 values. Reference values thus obtained for the test will be compared to historical values obtained from the same receptor and used to validate the experimental session. A session was considered as valid only if the reference value was found to be within a 0.5 logs interval from the historical value. For replicate determinations, the maximum variability tolerated in the test will be of +/−20% around the average of the replicates.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

Example 45 cAMP Agonist and Antagonist Mode at 5-HT6

For assessment of 5-HT6 activity, 1321N1 cells stably expressing human 5-HT6 were grown to ~90% confluence in a humidified atmosphere at 37° C. with 5% $CO_2$ in F12 nutrient mixture (Ham) containing 10% dialyzed FBS, 400 □g/ml G418, 100 U/ml penicillin, and 100 □g/ml streptomycin. Medium was removed by aspiration, cells were washed 1× with PBS, and dissociated using PBS-EDTA for 5 mM at room temperature. Cells were then diluted with PBS and pelleted by centrifugation for 5 mM at 1000 rpm. Cells were suspended in assay buffer containing 3000 □M Ro-20-1724 (Sigma, St. Louis, Mo.), a phosphodiesterase inhibitor. Cells were seeded using a microplate dispenser at a density of 3,750 cells/well in a volume of 5 □l onto 384 well white wall/opaque bottom, small volume plates (Greiner Bio One, Monroe, N.C.).

Compound plates for cAMP assays were prepared at 8 mM in 100% DMSO and diluted in assay buffer to the appropriate test concentrations. The final in-well concentration of DMSO was 0.5%. Compounds were tested in duplicate wells using a range of twelve concentrations.

Test compounds were transferred to assay plates using an automated liquid handling workstation (Janus; PerkinElmer, Waltham, Mass.). After the addition of test compounds, plates were incubated for 15 mM in a humidified atmosphere at 37° C. with 5% $CO_2$. After that, either assay buffer (for agonist mode) or the $EC_{80}$ (15 nM in assay buffer) of 5-HT (for antagonist mode) was added, and the plates incubated for an additional 30 min in a humidified atmosphere at 37° C. with 5% $CO_2$.

Homogeneous time-resolved fluorescence (HTRF) (cAMP dynamic 2 kit; Cisbio, Bedford, Mass.) was used to measure the formation of 3',5'-cyclic adenosine monophosphate (cAMP) per the manufacturer's instructions. HTRF signal was measured at 620 and 665 nm using an EnVision Multilabel Plate Reader (PerkinElmer). Compounds were first tested in agonist mode, with $E_{max}$ defined as percent activation relative to the $EC_{100}$ (10 □M) of 5-HT. Only compounds lacking significant (i.e. <25%) activity in agonist mode were tested in antagonist mode. Maximum inhibition ($I_{max}$) in antagonist mode was defined as percent inhibition relative to 10 □M of a 5-HT6 antagonist reference compound (SB 258585; Tocris, Ellisville, Mo.). Minimum inhibition in antagonist mode was defined by the $EC_{80}$ (15 nM) of 5-HT.

Example 46

Binding Assay 5-HT2A, 5-HT2B, 5-HT2C(VSV) and 5-HT6 (Agonist and Antagonist Ligand)

All radioligand binding assays were performed at Euroscreen SA (Gosselies, Belgium). Membrane extracts were prepared at Euroscreen from Chinese Hamster Ovary (CHOK1) cells stably expressing human 5-HT2A, 5-HT2B, 5-HT2C(VSV), or 5-HT6 using standard methods. Compounds were solubilized in 100% DMSO at a concentration of 10 mM (master solution). Serial dilutions were made from master solutions in 100% DMSO to obtain intermediate concentrations 200-fold higher than the final concentrations to be tested. Each sample was then diluted 100-fold in the appropriate assay buffer (see below) and dispensed onto the test plate. Compounds were tested in duplicate wells in 8 point dose-response curves at the following concentrations: 0.00001, 0.0001, 0.001, 0.01, 0.1, 1, 10, and 100 μM. The competitive displacement of radioligand was used to measure the $IC_{50}$ of test compound. $IC_{50}$s were converted to absolute inhibition constants (Kis) using the Cheng-Prusoff equation.

Human 5-HT2A radioligand binding assays were performed by the successive addition of 1) 50 μl of either test compound or reference ligand (5-HT) at increasing concentrations, 2) 25 μl of either diluted agonist ([$^{125}$I]DOI; Perkin Elmer ET62690) or antagonist ([3H]ketanserin; Perkin Elmer NET-791) radioligand, and 3) 25 μl membrane extracts (5 μg/well) into the wells of a 96 well plate (Master Block; Greiner Bio One). All necessary dilutions were made in assay buffer (50 mM Tris, 5 mM CaCl2, 0.1% ascorbic acid, pH 7.4). The final concentrations of [$^{125}$I]DOI and [3H]ketanserin were 0.4 and 1 nM, respectively. Plates were incubated for 60 mM at 25° C. in a water bath, and then filtered over GF/B filters (Perkin Elmer) presoaked for 2 hr at room temperature in 0.5% polyethyleneimine (PEI) with a Filtermate Harvester (PerkinElmer). Filters were washed 3× with 0.5 ml of ice-cold wash buffer (50 mM Tris). 50 μA of Microscint 20 (Packard Instrument, Meriden, Conn.) was then added, the plates were incubated for 15 min at room temperature on an orbital shaker, and counted using either a TopCount™ or MicroBeta™ (PerkinElmer) for 1 min/well.

Human 5-HT2B radioligand binding assays were performed by the successive addition of 1) 50 μA of either test compound or reference ligand (5-HT and methysergide) at increasing concentrations, 2) 25 μA of either diluted agonist ([$^{125}$I]DOI) or antagonist ([$^3$H]mesulergine; Amersham TRK845) radioligand, and 3) 25 μA membrane extracts (7 μg/well) into the wells of a 96 well plate. All necessary dilutions were made in assay buffer (50 mM Tris, 4 mM CaCl2, 0.1% ascorbic acid, pH 7.4). The final concentrations of [$^{125}$I]DOI and [3H]mesulergine were 0.2 and 1 nM, respectively. Plates were incubated for 30 mM at 37° C. (for agonist) and 60 mM at 25° C. (for antagonist) in a water bath, and then filtered over either GF/C filters presoaked in 0.5% PEI for 2 hr at room temperature (for agonist) or GF/B filters presoaked in 0.5% BSA for 2 hr at room temperature (for antagonist) with a Filtermate Harvester. Filters were washed 3× with 0.5 ml of ice-cold wash buffer (50 mM Tris). 50 µA of Microscint 20 was then added, the plates were incubated for 15 mM at room temperature on an orbital shaker, and counted using either a TopCount™ or MicroBeta™ for 1 min/well.

Human 5-HT2C(VSV) radioligand binding assays were performed by the successive addition of 1) 50 µA of either test compound or reference ligand (5-HT) at increasing concentrations, 2) 25 µA of either diluted agonist ([$^{125}$I]DOI) or antagonist ([$^3$H]mesulergine) radioligand, and 3) 25 µA membrane extracts (8 or 1 µg/well for agonist and antagonist radioligands, respectively) into the wells of a 96 well plate. All necessary dilutions were made in assay buffer (50 mM Tris, 0.1% ascorbic acid, pH 7.4). The final concentrations of [$^{125}$I]DOI and [3H]mesulergine were 0.35 and 1.5 nM, respectively. Plates were incubated for 60 mM at either 25° C. (for agonist) or 37° C. (for antagonist) in a water bath, and then filtered over GF/B filters presoaked in 0.5% PEI for 2 hr at room temperature with a Filtermate Harvester. Filters were washed 3× with 0.5 ml of ice-cold wash buffer (50 mM Tris). 50 µl of Microscint 20 was then added, the plates were incubated for 15 mM at room temperature an orbital shaker, and counted using either a TopCount™ or MicroBeta™ for 1 min/well.

Human 5-HT6 radioligand binding assays were performed by the successive addition of 1) 50 µA of either test compound or reference ligand (5-HT) at increasing concentrations, 2) 25 µl of diluted radioligand ([$^3$H]LSD; PerkinElmer NET638), and 3) 25 µA membrane extracts (2.5 µg/well) into the wells of a 96 well plate. All necessary dilutions were made in assay buffer (50 mM Tris, 4 mM CaCl2, 0.1% ascorbic acid, 10 □g/ml saponin, pH 7.4). The final concentration of [$^3$H] LSD was 1 nM. Plates were incubated for 60 min at 25° C. in a water bath, and then filtered over GF/B filters presoaked in 0.5% PEI for 2 hr at room temperature with a Filtermate Harvester. Filters were washed 6× with 0.5 ml of ice-cold wash buffer (50 mM Tris). 50 µA of Microscint 20 was then added, the plates were incubated for 15 mM at room temperature an orbital shaker, and counted using either a TopCount™ or MicroBeta™ for 1 min/well.

Example 47

Flipr Assays

Agonist Mode at Human 5-HT2A, 5-HT2B and 5-HT2C(VSV)

For assessment of 5-HT2 agonism, Chinese Hamster Ovary (CHOK1) cells stably expressing human 5-HT2A, 5-HT2B, 5-HT2C(VSV), or 5-HT2C(INI) were grown to ~80-90% confluence in a humidified atmosphere at 37° C. with 5% $CO_2$ in UltraCHO Medium (Lonza, Walkersville, Md.) containing 1% dialyzed fetal bovine serum (FBS), 400 □g/ml G418 (Geneticin; Invitrogen, Carlsbad, Calif.), 100 U/ml penicillin, and 100 □g/ml streptomycin. Medium was removed by aspiration, cells were washed 1× with PBS, and trypsinized for 5 mM at room temperature. After trypsinization, cells were diluted with UltraCHO Medium containing 1% dialyzed FBS (with no G418 or antibiotics) and seeded using a microplate dispenser (Matrix WellMate; Thermo Fisher Scientific, Hudson, N.H.) at a density of 22,500 cells/well in a volume of 30 □l/well onto 384 well black wall/clear bottom, poly-d-lysine coated plates (BD Biocoat; BD Biosciences, San Jose, Calif.). Plates were then incubated overnight in a humidified atmosphere at 37° C. with 5% $CO_2$.

On the day of the experiment, cells were loaded with a membrane-permeable, calcium-sensitive dye (FLIPR Calcium 4 Assay Kit; Molecular Devices, Sunnyvale, Calif.) (prepared according to the manufacturer's instructions) containing 2.5 mM probenecid and incubated for 1 hr at 37° C. Plates were removed from the incubator and allowed to cool to room temperature prior to assay (~15 mM). Response to test compound was measured using a fluorometric imaging plate reader (FLIPR384, Molecular Devices).

Compound plates for FLIPR assays were prepared at either 2 mM (for 5-HT2A and 5-HT2C) or 8 mM (for 5-HT2B) in 100% dimethyl sulphoxide (DMSO) and diluted in assay buffer (1×HBSS/20 mM HEPES, pH 7.4) to the appropriate test concentrations. The final in-well concentration of DMSO in all assays was 0.5%. Compounds were tested in duplicate wells using a range of twelve concentrations.

The statistical parameter exported from each well was the maximum peak height of the response to test compound. The minimum peak height was then subtracted from this value, and expressed as a percentage of the mean maximal response to 10 □M 5-HT. Dose-response curves were generated (GraphPad Prism 4; La Jolla, Calif.) and both potency ($EC_{50}$) and efficacy ($E_{max}$) were determined for each test compound.

Example 48

Compound Testing Aequorin Assay

Compounds were tested in duplicate at 10 µM concentration, for agonist activity and 5 µM concentration for antagonist activity at human serotonin 5-HT2A, 5-HT2C (edited (e)) and 5-HT2C (non-edited (ne)) receptors with Aequorin Assay and at human 5-HT6 with cAMP assay. DOI was tested in parallel on 5-HT2A, 5-HT2C(e) and 5-HT2C(ne) receptors with Aequorin Assay.

All the compounds exemplified in the examples modulated (i.e. activated or inhibited) at least one of 5HT2C, 5HT6, and/or 5HT2A more than or equal to 50% at 10 uM concentration.

Compound Testing Flipr assay: Compounds were tested in duplicate, for agonist activity at human serotonin 5-HT2A, 5-HT2B, and 5-HT2C(VSV) Representative examples of the present invention are found to have low nM potency for 5-HT2C receptor and are relatively selective for 5-HT2C receptor in comparison to other 5-HT receptor subtype and specifically 5-HT2A and 5-HT2B. Selectivity is demonstrated in agonist activity assay and receptor binding assays.

Compound Testing binding assay: Compounds were tested in duplicate, in human serotonin 5-HT2A, 5-HT2B, 5-HT2C (VSV) and 5-HT6. Representative examples of the present invention are found to have low nM affinity for 5-HT2C and/or 5-HT6 receptor with Ki's less or equal to 200 nM. More preferred are those with Ki's less or equal to 60 nM.

Compound Testing cAMP assay: Compounds were tested in duplicate, for agonist and antagonist activity at human serotonin 5-HT6. Representative examples of the present invention are found to have nM EC50 or IC50 for 5-HT6.

Representative examples of the present invention are found to have antagonist activity at 5-HT2A and/or 5-HT2B.

Biological Data

5-HT2C EC$_{50}$ values of representatives compounds described in the examples are compiled in table 34. The values have been obtained as described above. A<10 uM, B: 1–<500 nM and C: 500 nM-10 uM. 5-HT6 IC$_{50}$ and/or 5-HT6 EC$_{50}$ values of representatives compounds in the examples have values of <5 uM.

TABLE 34

| | Ex | Cpd ID | 5-HT2C EC50 |
|---|---|---|---|
| 2-(1-ethyl-6-fluoro-4-(4-fluorobenzyloxy)-1H-indol-3-yl)-N,N-dimethylethanamine | 5 | 1-14b | B |
| 2-(1-ethyl-6-fluoro-4-(4-methoxybenzyloxy)-1H-indol-3-yl)-N,N-dimethylethanamine | 6 | 1-15b | B |
| 2-(4-(4-chlorobenzyloxy)-1-ethyl-6-fluoro-1H-indol-3-yl)-N,N-dimethylethanamine | 1 | 1-10b | C |
| 2-(1-ethyl-6-fluoro-4-(4-(trifluoromethoxy)benzyloxy)-1H-indol-3-yl)-N,N-dimethylethanamine | 2 | 1-11b | C |
| 2-(1-ethyl-6-fluoro-4-(4-(trifluoromethyl)benzyloxy)-1H-indol-3-yl)-N,N-dimethylethanamine | 3 | 1-12b | C |
| 2-(1-ethyl-6-fluoro-4-(2-(trifluoromethyl)benzyloxy)-1H-indol-3-yl)-N,N-dimethylethanamine | 4 | 1-13b | C |
| 2-(1-ethyl-6-fluoro-4-(3-(trifluoromethyl)benzyloxy)-1H-indol-3-yl)-N,N-dimethylethanamine | 7 | 1-16b | C |
| 2-(3-(2-(dimethylamino)ethyl)-1-ethyl-7-fluoro-1H-indol-4-yloxy)aniline | 12 | 2-3 | B |
| 2-(1-ethyl-7-fluoro-4-(2-nitrophenoxy)-1H-indol-3-yl)-N,N-dimethylethanamine | 11 | 2-2 | C |
| 2-(1-ethyl-6-fluoro-4-(5-fluoro-2-methylbenzyloxy)-1H-indol-3-yl)-N,N-dimethylethanamine | 8 | 1-17b | B |
| 2-(4-methoxy-1-methyl-7-(pyridin-3-yl)-1H-indol-3-yl)-N,N-dimethylethanamine | 24 | 6-14 | B |
| 2-(4-methoxy-1-methyl-7-phenyl-1H-indol-3-yl)-N,N-dimethylethanamine | 16 | 6-6 | B |
| 1-ethyl-7-fluoro-3-(2-(phenylamino)ethyl)-1H-indol-4-ol | 41 | 11-7 | C |
| 2-(1-benzyl-4-(benzyloxy)-7-fluoro-1H-indol-3-yl)-N,N-dimethylethanamine | 25 | 7-2 | C |
| 1-benzyl-3-(2-(dimethylamino)ethyl)-7-fluoro-1H-indol-4-ol | 26 | 7-3 | C |
| 2-(7-fluoro-4-methoxy-1-methyl-1H-indol-3-yl)propan-1-amine | 36 | 9-5 | B |
| 4-(2-(7-fluoro-4-methoxy-1-methyl-1H-indol-3-yl)ethyl)morpholine | 43 | 11-9 | B |
| 2-(6-fluoro-4-methoxy-1-(pyrimidin-2-yl)-1H-indol-3-yl)-N,N-dimethylethanamine | 52 | 15-2 | C |
| 1-ethyl-6-fluoro-3-(2-morpholinoethyl)-1H-indol-4-ol | 39 | 11-5 | B |
| 1-ethyl-6-fluoro-3-(2-(2-methoxyethylamino)ethyl)-1H-indol-4-ol | 44b | 11-11 | B |
| 1-ethyl-6-fluoro-3-(2-(pyrrolidin-1-yl)ethyl)-1H-indol-4-ol | 40 | 11-6 | B |
| 7-fluoro-4-methoxy-1-methyl-3-(2-(pyrrolidin-1-yl)ethyl)-1H-indole | 44 | 11-10 | B |
| 2-(4-methoxy-1-methyl-7-(thiophen-3-yl)-1H-indol-3-yl)-N,N-dimethylethanamine | 23 | 6-13 | C |
| 2-(4-methoxy-1-methyl-7-(thiophen-2-yl)-1H-indol-3-yl)-N,N-dimethylethanamine | 17 | 6-7 | C |
| 2-(7-(furan-2-yl)-4-methoxy-1-methyl-1H-indol-3-yl)-N,N-dimethylethanamine | 18 | 6-8 | C |
| 2-(7-(furan-3-yl)-4-methoxy-1-methyl-1H-indol-3-yl)-N,N-dimethylethanamine | 19 | 6-9 | C |
| 2-(4-methoxy-1-methyl-7-(1H-pyrrol-2-yl)-1H-indol-3-yl)-N,N-dimethylethanamine | 20 | 6-10 | C |
| 3-(3-(2-(dimethylamino)ethyl)-4-methoxy-1-methyl-1H-indol-7-yl)prop-2-yn-1-ol | 21 | 6-11 | B |
| 3-(2-(dimethylamino)ethyl)-4-methoxy-1-methyl-N-phenyl-1H-indol-7-amine | 22 | 6-12 | B |
| 2-(4-(benzyloxy)-7-fluoro-1-(naphthalen-2-ylmethyl)-1H-indol-3-yl)-N,N-dimethylethanamine | 29 | 7-6 | B |
| 2-(4-(benzyloxy)-7-fluoro-1-(thiophen-2-ylmethyl)-1H-indol-3-yl)-N,N-dimethylethanamine | 27 | 7-4 | B |
| (E)-methyl 3-(3-(2-(dimethylamino)ethyl)-4-methoxy-1-methyl-1H-indol-7-yl)acrylate | 83 | 25-2 | B |
| 3-(3-(2-(dimethylamino)ethyl)-1-ethyl-7-fluoro-4-methoxy-1H-indol-5-yl)propan-1-ol | 86 | 27-3 | B |
| 2-(4-(benzyloxy)-7-fluoro-1-(furan-2-ylmethyl)-1H-indol-3-yl)-N,N-dimethylethanamine | 80 | 24-1 | B |
| 2-(1-ethyl-4-methoxy-6-phenyl-1H-indol-3-yl)-N,N-dimethylethanamine | 161 | 36-6 | C |
| 4-(benzyloxy)-1-ethyl-6-fluoro-3-(1,2,3,6-tetrahydropyridin-4-yl)-1H-indole | 162 | 37-2 | C |
| 3-(2-(1,4-oxazepan-4-yl)ethyl)-1-ethyl-6-fluoro-1H-indol-4-ol | 44c | 11-12 | C |
| 3-(2-((2S,6R)-2,6-dimethylmorpholino)ethyl)-1-ethyl-6-fluoro-1H-indol-4-ol | 44e | 11-13 | C |
| 3-(2-(3,3-difluoropyrrolidin-1-yl)ethyl)-1-ethyl-6-fluoro-1H-indol-4-ol | 44f | 11-14 | C |
| 2-(1-ethyl-6-fluoro-4-(pyridin-4-ylmethoxy)-1H-indol-3-yl)-N,N-dimethylethanamine | 9 | 1-18b | C |
| N-benzyl-2-(1-ethyl-7-fluoro-4-methoxy-1H-indol-3-yl)ethanamine | 70 | 20-4 | B |
| 1-ethyl-6-fluoro-3-(piperidin-3-yl)-1H-indol-4-ol | 163 | 38-4 | B |

TABLE 34-continued

| | Ex | Cpd ID | 5-HT2C EC50 |
|---|---|---|---|
| 2-(1-ethyl-6-fluoro-4-(thiophen-3-ylmethoxy)-1H-indol-3-yl)-N,N-dimethylethanamine | 10 | 1-19b | B |
| 3-(3-(2-(dimethylamino)ethyl)-1-ethyl-7-fluoro-4-methoxy-1H-indol-5-yl)propan-1-amine | 87 | 28-4 | B |
| 2-(5-(2-(1H-benzo[d]imidazol-2-yl)ethyl)-1-ethyl-7-fluoro-4-methoxy-1H-indol-3-yl)-N,N-dimethylethanamine | 88 | 29-4 | B |
| 1-ethyl-6-fluoro-3-(1-methylpiperidin-3-yl)-1H-indol-4-ol | 164 | 38-6 | C |
| 3-(2-(benzylamino)ethyl)-1-ethyl-6-fluoro-1H-indol-4-ol | 85-2 | 26-8 | B |
| 2-(4-methoxy-1-methyl-7-(phenylsulfonyl)-1H-indol-3-yl)-N,N-dimethylethanamine | 82 | 25-1 | B |
| 2-(4-(benzyloxy)-1-ethyl-6-fluoro-1H-indol-3-yl)-N-(3-(trifluoromethyl)phenethyl)ethanamine | 114 | 31-13 | B |
| 1-ethyl-6-fluoro-3-(2-(piperazin-1-yl)ethyl)-1H-indol-4-ol | 44g | 11-15 | C |
| 1-ethyl-6-fluoro-3-(2-(3-(trifluoromethyl)phenethylamino)ethyl)-1H-indol-4-ol | 85-4 | 26-10 | B |
| 1-ethyl-6-fluoro-3-(2-(2-phenylpropylamino)ethyl)-1H-indol-4-ol | 166b | 39-6 | B |
| N-benzyl-2-(4-(benzyloxy)-1-ethyl-6-fluoro-1H-indol-3-yl)ethanamine | 85-1 | 26-7 | C |
| N-benzyl-2-(4-ethoxy-5-fluoro-1-methyl-1H-indol-3-yl)ethanamine | 89 | 30-15 | B |
| N-(2-(4-ethoxy-5-fluoro-1-methyl-1H-indol-3-yl)ethyl)-2,3-dihydro-1H-inden-2-amine | 90 | 30-16 | B |
| 3-(3-(2-(dimethylamino)ethyl)-4-methoxy-1-methyl-1H-indol-7-yl)propan-1-ol | 84 | 25-4 | C |
| 2-(4-(benzyloxy)-1-ethyl-6-fluoro-1H-indol-3-yl)-N-phenethylethanamine | 85-3 | 26-9 | C |
| N-(2-chlorobenzyl)-2-(4-ethoxy-5-fluoro-1-methyl-1H-indol-3-yl)ethanamine | 91 | 30-17 | B |
| N-(benzo[d][1,3]dioxol-5-ylmethyl)-2-(4-ethoxy-5-fluoro-1-methyl-1H-indol-3-yl)ethanamine | 92 | 30-18 | B |
| N-(2-(4-ethoxy-5-fluoro-1-methyl-1H-indol-3-yl)ethyl)-2,3-dihydro-1H-inden-1-amine | 93 | 30-19 | B |
| 1-ethyl-6-fluoro-3-(2-(phenethylamino)ethyl)-1H-indol-4-ol | 85-5 | 26-11 | B |
| 2-(4-ethoxy-5-fluoro-1-methyl-1H-indol-3-yl)-N-(3-methylbenzyl)ethanamine | 94 | 30-20 | B |
| N-benzyl-2-(4-(benzyloxy)-1-ethyl-6-fluoro-1H-indol-3-yl)-N-methylethanamine | 107 | 31-6 | B |
| 4-(benzyloxy)-1-ethyl-6-fluoro-3-(2-(isoindolin-2-yl)ethyl)-1H-indole | 104 | 31-3 | C |
| 1-ethyl-6-fluoro-3-(2-(isoindolin-2-yl)ethyl)-1H-indol-4-ol | 105 | 31-4 | C |
| 2-(4-ethoxy-5-fluoro-1-methyl-1H-indol-3-yl)-N-(2-(trifluoromethyl)benzyl)ethanamine | 95 | 30-21 | B |
| 2-(4-ethoxy-5-fluoro-1-methyl-1H-indol-3-yl)-N-(3-(trifluoromethyl)benzyl)ethanamine | 96 | 30-22 | B |
| 4-(2-(4-ethoxy-5-fluoro-1-methyl-1H-indol-3-yl)ethyl)morpholine | 97 | 30-23 | C |
| (1-(2-(4-ethoxy-5-fluoro-1-methyl-1H-indol-3-yl)ethyl)pyrrolidin-2-yl)methanol | 98 | 30-24 | C |
| 2-(4-ethoxy-5-fluoro-1-methyl-1H-indol-3-yl)-N-phenethylethanamine | 99 | 30-25 | B |
| 2-(1-ethyl-7-fluoro-4-methoxy-1H-indol-3-yl)-N-phenethylethanamine | 72 | 20-7 | B |
| 2-(5-fluoro-1-methyl-4-(thiophen-2-ylmethoxy)-1H-indol-3-yl)-N,N-dimethylethanamine | 11 | 1-20a | B |
| 2-(benzo[d][1,3]dioxol-5-yl)-N-(2-(4-ethoxy-5-fluoro-1-methyl-1H-indol-3-yl)ethyl)ethanamine | 100 | 30-26 | B |
| N-benzyl-2-(1-ethyl-6-fluoro-4-methoxy-1H-indol-3-yl)ethanamine | 165 | 39-4 | B |
| 2-(4-ethoxy-5-fluoro-1-methyl-1H-indol-3-yl)-N-(2-(pyridin-2-yl)ethyl)ethanamine | 101 | 30-27 | B |
| 2-(4-ethoxy-5-fluoro-1-methyl-1H-indol-3-yl)-N-(thiophen-2-ylmethyl)ethanamine | 102 | 30-28 | B |
| 4-ethoxy-5-fluoro-1-methyl-3-(2-(pyrrolidin-1-yl)ethyl)-1H-indole | 103 | 30-29 | B |
| 5-fluoro-4-methoxy-1-methyl-3-(2-(piperazin-1-yl)ethyl)-1H-indole | 57 | 17-10 | C |
| 2-(5-fluoro-4-methoxy-1-methyl-1H-indol-3-yl)-N-(thiophen-2-ylmethyl)ethanamine | 154 | 34-6 | B |
| N-benzyl-2-(5-fluoro-4-methoxy-1-methyl-1H-indol-3-yl)ethanamine | 155 | 34-6 | B |
| 2-(5-fluoro-1-methyl-4-phenethoxy-1H-indol-3-yl)-N,N-dimethylethanamine | 66 | 18-2 | B |
| 2-(1-ethyl-6-fluoro-4-phenoxy-1H-indol-3-yl)-N,N-dimethylethanamine | 115 | 32-2 | C |
| 3-((1S,4S)-5-benzyl-2,5-diazabicyclo[2.2.1]heptan-2-yl)ethyl)-1-ethyl-6-fluoro-1H-indol-4-ol | 108 | 31-7 | C |
| 2-(1-ethyl-6-fluoro-4-methoxy-1H-indol-3-yl)-N-(2-(1-ethyl-6-fluoro-4-methoxy-1H-indol-3-yl)ethyl)-N-methylethanamine | 166 | 39-5 | B |
| 2-(4-(2-chlorobenzyloxy)-6-fluoro-1-methyl-1H-indol-3-yl)-N-methylethanamine | 148 | 33-44 | B |
| 2-(4-(benzyloxy)-1-ethyl-6-fluoro-1H-indol-3-yl)-N-(3-(trifluoromethyl)benzyl)ethanamine | 109 | 31-8 | C |
| 2-(4-(benzyloxy)-1-ethyl-6-fluoro-1H-indol-3-yl)-N-(3-chlorobenzyl)ethanamine | 110 | 31-9 | C |
| 2-(1-ethyl-7-fluoro-4-methoxy-1H-indol-3-yl)-N-(1-phenylethyl)ethanamine | 73 | 20-8 | B |
| 2-(7-fluoro-4-methoxy-1-methyl-5-phenyl-1H-indol-3-yl)-N-methylethanamine | 77 | 22-5 | B |

TABLE 34-continued

| | Ex | Cpd ID | 5-HT2C EC50 |
|---|---|---|---|
| 2-(1-ethyl-7-fluoro-4-methoxy-1H-indol-3-yl)-N-(2-methylbenzyl)ethanamine | 74 | 20-9 | B |
| N-(2-chlorobenzyl)-2-(1-ethyl-7-fluoro-4-methoxy-1H-indol-3-yl)ethanamine | 75 | 20-10 | B |
| N-(3,4-dimethoxybenzyl)-2-(5-fluoro-4-methoxy-1-methyl-1H-indol-3-yl)ethanamine | 156 | 34-8 | B |
| 2-(4-(4-chlorobenzyloxy)-6-fluoro-1-methyl-1H-indol-3-yl)-N-methylethanamine | 149 | 33-45 | B |
| 2-(4-(3-chlorobenzyloxy)-6-fluoro-1-methyl-1H-indol-3-yl)-N-methylethanamine | 150 | 33-46 | B |
| 3-(2-(benzhydrylamino)ethyl)-1-ethyl-6-fluoro-1H-indol-4-ol | 111 | 31-10 | B |
| 2-(2-(5-fluoro-4-methoxy-1-methyl-1H-indol-3-yl)ethylamino)-2-phenylethanol | 157 | 34-9 | B |
| 2-(5-fluoro-4-methoxy-1-methyl-1H-indol-3-yl)-N-(1-phenylethyl)ethanamine | 158 | 34-10 | B |
| 2-(4-(3-chlorobenzyloxy)-5-fluoro-1-methyl-1H-indol-3-yl)-N-methylethanamine | 116 | 33-8 | B |
| 3-(2-(3-chlorobenzylamino)ethyl)-1-ethyl-6-fluoro-1H-indol-4-ol | 112 | 31-11 | B |
| 1-ethyl-6-fluoro-3-(2-(3-(trifluoromethyl)benzylamino)ethyl)-1H-indol-4-ol | 113 | 31-12 | B |
| 2-(4-(4-chlorobenzyloxy)-5-fluoro-1-methyl-1H-indol-3-yl)-N-methylethanamine | 124 | 33-20 | B |
| 2-(5-fluoro-1-methyl-4-(3-(trifluoromethyl)benzyloxy)-1H-indol-3-yl)-N-methylethanamine | 125 | 33-21 | B |
| 2-(5-fluoro-1-methyl-4-(2-methylbenzyloxy)-1H-indol-3-yl)-N-methylethanamine | 126 | 33-22 | B |
| 2-(4-(2-chlorobenzyloxy)-5-fluoro-1-methyl-1H-indol-3-yl)-N-methylethanamine | 127 | 33-23 | B |
| 2-(7-fluoro-4-methoxy-1-methyl-5-phenethyl-1H-indol-3-yl)-N-methylethanamine | 78 | 23-4 | C |
| N-(2-(5-fluoro-4-methoxy-1-methyl-1H-indol-3-yl)ethyl)-4-phenylbutan-1-amine | 60 | 17-13 | B |
| 2-(5-fluoro-4-(2-fluorobenzyloxy)-1-methyl-1H-indol-3-yl)-N-methylethanamine | 128 | 33-24 | B |
| 2-(5-fluoro-4-(4-methoxyphenethoxy)-1-methyl-1H-indol-3-yl)-N-methylethanamine | 129 | 33-25 | B |
| 2-(5-fluoro-1-methyl-4-phenethoxy-1H-indol-3-yl)-N-methylethanamine | 130 | 33-26 | B |
| 3-(2-(benzylamino)ethyl)-5-fluoro-1-methyl-1H-indol-4-ol | 151 | 33-47 | B |
| 2-(5-fluoro-1-methyl-4-(4-methylbenzyloxy)-1H-indol-3-yl)-N-methylethanamine | 131 | 33-27 | B |
| 2-(5-fluoro-4-(4-fluorophenethoxy)-1-methyl-1H-indol-3-yl)-N-methylethanamine | 152 | 33-28 | B |
| 2-(4-(4-chlorophenethoxy)-5-fluoro-1-methyl-1H-indol-3-yl)-N-methylethanamine | 133 | 33-29 | B |
| 2-(5-(2-cyclohexylethyl)-7-fluoro-4-methoxy-1-methyl-1H-indol-3-yl)-N-methylethanamine | 79 | 23-5 | B |
| 2-(4-(biphenyl-2-ylmethoxy)-5-fluoro-1-methyl-1H-indol-3-yl)-N-methylethanamine | 134 | 33-30 | B |
| 2-(5-fluoro-1-methyl-4-(2-(trifluoromethyl)benzyloxy)-1H-indol-3-yl)-N-methylethanamine | 135 | 33-31 | B |
| 2-(5-fluoro-1-methyl-4-(1-phenylethoxy)-1H-indol-3-yl)-N-methylethanamine | 136 | 33-32 | B |
| 2-((3-(2-((2-cyanobenzyl)(methyl)amino)ethyl)-5-fluoro-1-methyl-1H-indol-4-yloxy)methyl)benzonitrile | 160 | 35-2 | C |
| 2-(5-fluoro-4-(5-fluoro-2-methylbenzyloxy)-1-methyl-1H-indol-3-yl)-N-methylethanamine | 137 | 33-33 | B |
| 5-fluoro-4-methoxy-1-methyl-3-(2-(4-phenylpiperazin-1-yl)ethyl)-1H-indole | 61 | 17-14 | C |
| 3-(2-(4-(3-chlorophenyl)piperazin-1-yl)ethyl)-5-fluoro-4-methoxy-1-methyl-1H-indole | 62 | 17-15 | B |
| 2-(5-fluoro-1-methyl-4-(2-(trifluoromethoxy)benzyloxy)-1H-indol-3-yl)-N-methylethanamine | 138 | 33-34 | B |
| 2-(5-fluoro-4-(4-fluorobenzyloxy)-1-methyl-1H-indol-3-yl)-N-methylethanamine | 139 | 33-35 | B |
| 2-(5-fluoro-1-methyl-4-(naphthalen-1-ylmethoxy)-1H-indol-3-yl)-N-methylethanamine | 140 | 33-36 | B |
| 1-(2-chlorophenyl)-2-(5-fluoro-1-methyl-3-(2-(methylamino)ethyl)-1H-indol-4-yloxy)ethanol | 141 | 33-37 | B |
| 2-(5-fluoro-1-methyl-4-(4-(methylsulfonyl)benzyloxy)-1H-indol-3-yl)-N-methylethanamine | 142 | 33-38 | B |
| (S)-N-(2-(5-fluoro-4-methoxy-1-methyl-1H-indol-3-yl)ethyl)-1,2,3,4-tetrahydronaphthalen-1-amine | 63 | 17-16 | B |
| (S)-N-(2-(5-fluoro-4-methoxy-1-methyl-1H-indol-3-yl)ethyl)-1,2,3,4-tetrahydronaphthalen-1-amine | 64 | 17-17 | B |
| 2-(5-fluoro-4-(naphthalen-1-ylmethoxy)-1-propyl-1H-indol-3-yl)-N-methylethanamine | 143 | 33-39 | B |
| 3-(2-aminoethyl)-5-fluoro-1-((tetrahydro-2H-pyran-2-yl)methyl)-1H-indol-4-ol | 67 | 19-3 | B |

TABLE 34-continued

| | Ex | Cpd ID | 5-HT2C EC50 |
|---|---|---|---|
| 3-(2-aminoethyl)-5-fluoro-1-(2-phenoxyethyl)-1H-indol-4-ol | 68a | 19-4 | B |
| N-(2-(5-fluoro-4-methoxy-1-methyl-1H-indol-3-yl)ethyl)-3-(4-methylpiperazin-1-yl)aniline | 65 | 17-18 | B |
| 2-(5-fluoro-1-methyl-4-(quinolin-8-ylmethoxy)-1H-indol-3-yl)-N-methylethanamine | 117 | 33-13 | B |
| 2-(5-fluoro-1-methyl-4-(2-phenoxyethoxy)-1H-indol-3-yl)-N-methylethanamine | 118 | 33-14 | B |
| 8-chloro-3-(2-(5-fluoro-4-methoxy-1-methyl-1H-indol-3-yl)ethyl)-1-methyl-2,3,4,5-tetrahydro-1H-benzo[d]azepine | 55 | 17-8 | B |
| 2-(5-fluoro-4-(4-fluorobenzyloxy)-1-propyl-1H-indol-3-yl)-N-methylethanamine | 119 | 33-15 | B |
| 2-(5-fluoro-4-(4-methylbenzyloxy)-1-propyl-1H-indol-3-yl)-N-methylethanamine | 120 | 33-16 | B |
| 2-(5-fluoro-1-methyl-4-(2-methylphenethoxy)-1H-indol-3-yl)-N-methylethanamine | 121 | 33-17 | B |
| 3-(2-aminoethyl)-1-((2,3-dihydrobenzo[b][1,4]dioxin-2-yl)methyl)-5-fluoro-1H-indol-4-ol | 68b | 19-5 | B |
| 1-(2-(5-fluoro-4-methoxy-1-methyl-1H-indol-3-yl)ethyl)pyrrolidine-2-carboxamide | 56 | 17-9 | C |
| 2-(4-(2-chlorophenethoxy)-5-fluoro-1-methyl-1H-indol-3-yl)-N-methylethanamine | 123 | 33-19 | C |
| 2-(4-(2,4-dichlorobenzyloxy)-5-fluoro-1-methyl-1H-indol-3-yl)-N-methylethanamine | 152 | 33-48 | A |
| 2-(3-(2-aminoethyl)-5-fluoro-4-hydroxy-1H-indol-1-yl)-N,N-diethylacetamide | 68c | 19-6 | A |
| 2-(3-(2-aminoethyl)-5-fluoro-4-hydroxy-1H-indol-1-yl)acetamide | 68d | 19-7 | A |
| 5-fluoro-3-(2-((6-methylpyridin-2-yl)methylamino)ethyl)-1-propyl-1H-indol-4-ol | 65a | 17-19 | A |
| 5-fluoro-1-methyl-3-(2-((6-methylpyridin-2-yl)methylamino)ethyl)-1H-indol-4-ol | 65b | 17-20 | A |
| 2-(4-(4-chlorobenzyloxy)-5-fluoro-1-propyl-1H-indol-3-yl)ethanamine | 66b | 18-3 | A |
| 2-(7-propyl-3,7-dihydro-2H-[1,4]dioxino[2,3-e]indol-9-yl)ethanamine | 167 | 40-6 | A |
| 2-(4-(4-chloro-3-(trifluoromethoxy)benzyloxy)-5-fluoro-1-methyl-1H-indol-3-yl)-N-methylethanamine | 153 | 33-49 | A |

Example 47

Acute Food Intake Assay

Male, Sprague Dawley rats, weighing between 280 and 320 g serve as subjects in this experiment. All rats are allowed to acclimate to the vivarium for at least 1 week prior to study start. Rats are housed singularly in home cages with a layer of absorbent paper covering the floor. The cage does not contain any form of bedding. Water is available at all times by water bottle and food is returned to each animal in the form of pelleted chow. The container along with the food contents is weighed prior to adding it to the cage and is then reweighed at 1, 2, 6 and 24 hours later. Any spilled food is collected and returned to the feeding container prior to weighing. All animals are fasted for 16 hours overnight prior to a single oral gavage dosing (vehicle, plus one to three dose groups). Body weight is measured prior to dosing. Food is returned to all animals ad libitum 2 hours after dosing. Total amount of food consumed is measured for each animal at t=1, 2, 6 and 24 hours after return of food. Body weight is measured again at 24 hours. All animals are clinically observed throughout the study for unusual behavior, mortality or morbidity. The amount of food consumed at each time point and body weight are used as dependent measures in the study.

Conditioned Avoidance Response

Conditioned Avoidance Response (CAR) training is conducted in Coulbourn two way shuttle chambers. Male, Wistar rats, weighing between 250 and 300 g serve as subjects in the experiments. Rats are habituated to the testing room for 60 minutes prior to behavioral testing. Training consists of a 5 minute habituation period, where the animals are allowed to freely explore both left and right hand chambers. The habituation period is followed by repeated pairings of a CS (light and 80 dB tone) followed 10 seconds later by a 0.8 mA footshock which is terminated upon the animal's escape to the adjacent chamber, or after 10 seconds. If the rat moves to the safe, adjacent chamber within 10 seconds, before the termination of the CS, the shock is avoided and the trial is recorded as an avoidance. If the rat moves to the safe compartment within the first 10 seconds of the shock, the trial is recorded as an escape. If the rat fails to move to the safe compartment during the entire 10 seconds of the shock, the trial is recorded as a failure. Thirty trials are given in each daily training session, and rats are trained until they have reached a criterion of 80% correct avoidance responses on three consecutive days. A test session in which rats are tested on CAR in the presence of compound is conducted after criterion is achieved. On the test day, rats are habituated to the room, then weighed and gavaged with compound (vehicle, plus three dose groups) 30 to 60 minutes before training. Training is conducted as described above. The number of crossings made between chambers during the habituation period, as well as the number of avoidances, escapes and failures is recorded for each rat across training days and on the test day. Percent avoidance, failure and escape are calculated and means and SEM's generated. Data are analyzed using one-way ANOVA and SNK post-hoc analysis as appropriate.

Prepulse Inhibition

Male, Wistar rats, weighing between 250 and 300 g serve as subjects in the experiments. Rats are habituated to the testing room for 60-120 minutes prior to behavioral testing. Rats are randomized to treatment groups based on a pre-determined startle response, weighed, gavaged with compound (vehicle, plus three dose groups) and then placed in prepulse inhibition chambers. Kinder Scientific chambers are used for the experiment. Kinder software controls the delivery of all stimuli to the animals and records the response. Training consists of a 5 minute habituation period during which a 65 dB background noise is continuously present. This background noise remains present throughout the entire testing session. After the habituation period, the rats receive a series of five, 40-ms, 120 dB bursts of white noise to partially habituate the animals to the startle-eliciting stimulus. After these stimuli are presented, the training session proper begins. For the training session, a 10-ms prepulse at 68, 71 or 80 dB, followed 100-ms later by a 120 dB, 40-ms startle stimulus is presented. Startle stimulus and no-stimulus trials are also included in the testing session. The stimuli are presented in random order with interstimulus intervals averaging 15 seconds. Levels of prepulse inhibition are determined by the formula (100−((prepulse pulse/alone×100)) and are expressed as percent inhibition.

Spontaneous Locomotion

Male, Wistar rats, weighing between 250 and 300 g serve as subjects in the experiments. Rats are habituated to the testing room for 60-120 minutes prior to behavioral testing. Rats are weighed and gavaged with compound (vehicle, plus three dose groups) and are then placed in automated activity monitoring chambers (Kinder Scientific). The activity levels of the rat, including horizontal movements, total distance moved, total rest time, fine movements and rears are recorded for two consecutive hours. The rats are then removed from the apparatus and returned to their home cages.

Drug-Induced Hyperlocomotion

Male, Wistar rats, weighing between 250 and 300 g serve as subjects in the experiments. Rats are habituated to the testing room for 60-120 minutes prior to behavioral testing. Fifteen to thirty minutes prior to testing, rats are weighed and gavaged with compound (vehicle, plus three dose groups) and are placed in automated activity monitoring chambers (Kinder Scientific) for a 30 minute baseline period. At the end of the baseline period, the animals are removed from the chamber and injected with a psychotomimetic (eg, PCP or d-amphetamine). The rats are then returned to the chambers where their activity levels are monitored for two consecutive hours.

Novel Object Recognition

Male, Wistar rats, weighing between 250 and 300 g serve as subjects for the experiments. Rats are habituated to the testing room for 60-120 minutes prior to behavioral testing. Testing is conducted in large, circular arenas (80 cm in diameter). Training consists of three sessions: habituation, sample and test. For habituation, the rats are placed into an empty test chamber and allowed to explore for a 10 minute period. The sample trial, in which two large, identical objects are placed inside the arena, takes place 24 hours after habituation. The animal is placed inside the arena with the two identical objects and allowed to explore for 5 minutes. The number of approaches and the time spent sniffing each of the objects is recorded by automated software (CleverSys, Inc). Twenty-four hours after the sample phase, the rat is returned to the arena for the test trial. For the test trial, two objects, one familiar object that the animal saw in the sample phase, and one novel object that the animal has not seen before, are placed inside the arena. The animal is placed into the arena with the objects and allowed to explore for a 5 minute period. The number of approaches and time spent sniffing each of the objects is recorded. Compound (vehicle plus three dose groups, via oral gavage) may be administered either before or after the sample trial, or before the test trial. The time the rat spends sniffing each object is used to calculate a discrimination index ((time exploring novel−time exploring familiar)/total exploration time) that is used to determine preference for the familiar versus the novel objects.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A compound of formula (I):

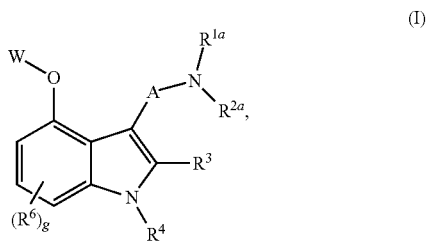

wherein

R$^{1a}$ and R$^{2a}$ are each independently selected from H and optionally substituted C$_{1-8}$ alkyl;

R$^3$ is selected from H and optionally substituted C$_{1-8}$ alkyl;

W is optionally substituted arylC$_2$-C$_6$alkyl, optionally substituted with —OR$^d$, —NR$^d$R$^{d'}$, or —C(O)NR$^d$R$^{d'}$, optionally substituted arylheteroalkyl, optionally substituted heteroarylheteroalkyl, -alkyl-O—O$_{0-2}$alkyl-aryl, -alkyl-O—C$_{0-2}$alkyl-heteroaryl, —(CH$_2$)$_2$—O-phenyl, or is selected from the group:

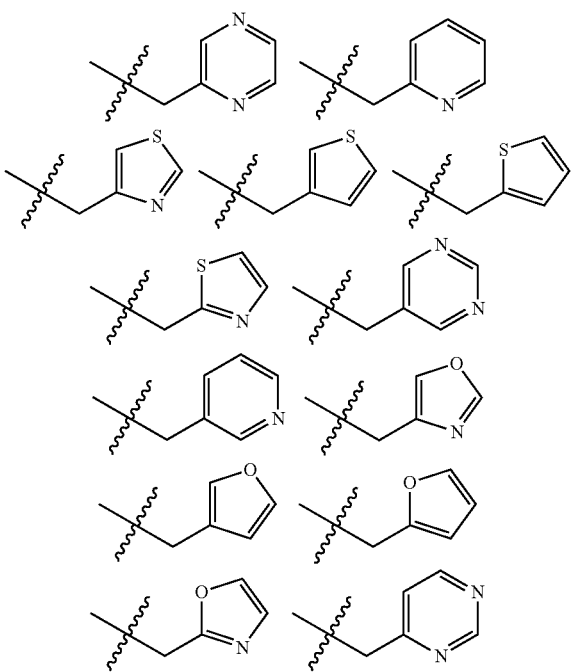

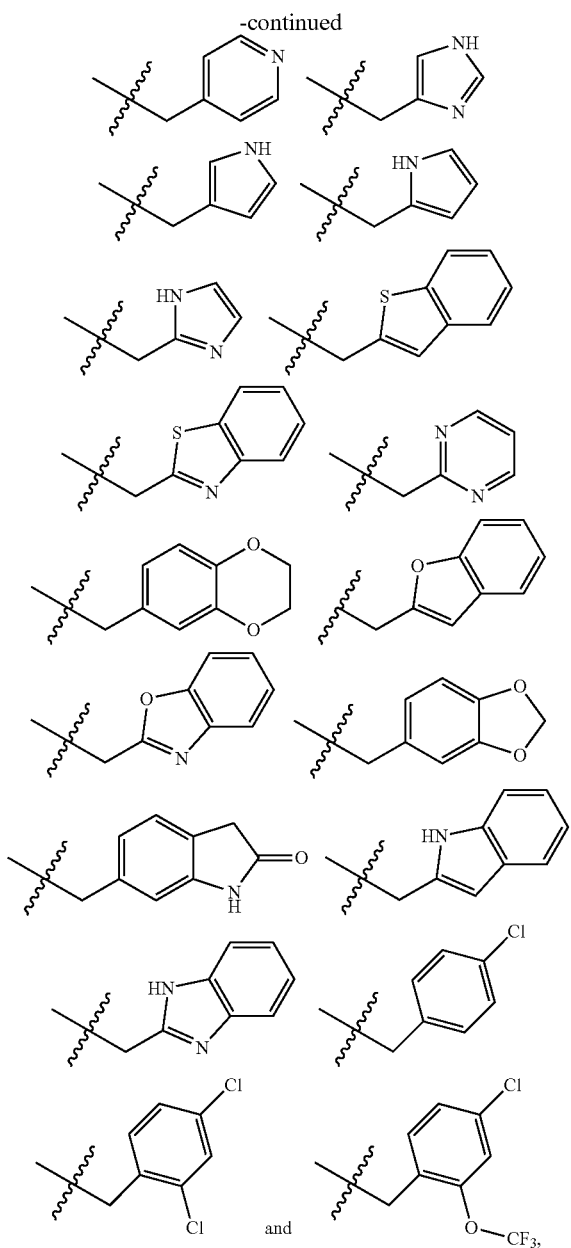

A is optionally substituted C_{1-4} alkylene, wherein alkylene is optionally substituted with 1-3 substituents, each of which is independently selected from the group consisting of halogen, oxo, optionally substituted C_{1-6} alkyl, —S(O)_{0-2}alkyl, —OR$^d$—NR$^d$R$^{d'}$, aryl, heteroaryl, C_3-C_8 cycloalkyl and 4-8 membered heterocycle;

R$^4$ is selected from optionally substituted C_{1-8} alkyl, optionally substituted C_{1-8} heteroalkyl, C_{3-8} cycloalkyl, and cycloalkylalkyl, wherein the alkyl and cycloalkyl are optionally substituted with 1-3 substituents, halo, alkyl, haloalkyl, heteroalkyl, —OR$^d$, —NR$^d$R$^{d'}$;

each R$^6$ is independently selected from halo, C_{1-8} alkyl, aryl, heteroaryl, heteroalkyl, C_{3-8} cycloalkyl, heterocyclyl, arylalkyl, heteroarylalkyl, cycloalkylalkyl, heterocycloalkyl, —SH, —OR$^d$, C_{1-8} haloalkoxy, C_{1-8} haloalkyl, —S(O)_{0-2} C_{1-8} alkyl, —S(O)_{0-2} aryl, —S(O)_{0-2} heteroaryl, —S(O)_{0-2} arylalkyl, —S(O)_{0-2} heteroarylalkyl, —S(O)_{0-2} cycloalkyl, —S(O)_{0-2} hetero-cycloalkyl, —S(O)_{0-2} heterocycloalkylalkyl, —S(O)_{0-2} cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)_2alkyl, —NR$^d$S(O)_2aryl, —NR$^d$S(O)_2heteroaryl, —NR$^d$S(O)_2cycloalkyl, —NR$^d$S(O)_2heterocycloalkyl, —NR$^d$S(O)_2—C_{1-4}alkyl-aryl, —NR$^d$S(O)_2-heteroarylalkyl, —NR$^d$S(O)_2-cycloalkylalkyl, —NR$^a$S(O)_2-heterocycloalkyl, —SO_2NR$^d$R$^{d'}$, cyano, nitro, C_{1-6} haloalkyl, C_{1-6} haloalkoxy, —NR$^d$R$^{d'}$, —C_{1-4}alkyl-NR$^d$R$^{d'}$, optionally substituted C_{1-6} alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

each R$^a$ is independently selected from optionally substituted C_{1-8} alkyl, optionally substituted aryl, optionally substituted heteroaryl, optionally substituted C_{3-8} cycloalkyl, optionally substituted arylalkyl, optionally substituted heteroarylalkyl, optionally substituted cycloalkylalkyl and optionally substituted heterocycloalkyl;

R$^d$, R$^{d'}$, and R$^{d''}$ are each independently selected from H and R$^a$, or when taken together with the atom to which they are attached, two of R$^d$, R$^{d'}$ and R$^{d''}$ form a 4-8 membered heterocyclic moiety; and g is 1, 2 or 3.

2. The compound of claim 1, wherein A is optionally substituted with 1-3 substituents, each of which is independently selected from the group consisting of halogen, hydroxyl, optionally substituted C_{1-6} alkyl, C_{1-8} alkoxy, —SO_2 alkyl, and —NR$^d$R$^{d''}$.

3. The compound of claim 1, wherein each R$^6$ is selected from halogen, C_{1-8} alkyl, hydroxyl, —C_{1-8} fluoroalkyl, C_{1-8} haloalkoxy, and —NR$^d$R$^{d'}$.

4. The compound of claim 1, wherein each R$^6$ is halogen.

5. A compound selected from the group consisting of:
2-(1-ethyl-6-fluoro-4-(4-fluorobenzyloxy)-1H-indol-3-yl)-N,N-dimethylethanamine,
2-(1-ethyl-6-fluoro-4-(4-methoxybenzyloxy)-1H-indol-3-yl)-N,N-dimethylethanamine,
2-(4-(4-chlorobenzyloxy)-1-ethyl-6-fluoro-1H-indol-3-yl)-N,N-dimethylethanamine,
2-(1-ethyl-6-fluoro-4-(4-(trifluoromethoxy)benzyloxy)-1H-indol-3-yl)-N,N-dimethylethanamine,
2-(1-ethyl-6-fluoro-4-(4-(trifluoromethyl)benzyloxy)-1H-indol-3-yl)-N,N-dimethylethanamine,
2-(1-ethyl-6-fluoro-4-(2-(trifluoromethyl)benzyloxy)-1H-indol-3-yl)-N,N-dimethylethanamine,
2-(1-ethyl-6-fluoro-4-(3-(trifluoromethyl)benzyloxy)-1H-indol-3-yl)-N,N-dimethylethanamine,
2-(3-(2-(dimethylamino)ethyl)-1-ethyl-7-fluoro-1H-indol-4-yloxy)aniline,
2-(1-ethyl-7-fluoro-4-(2-nitrophenoxy)-1H-indol-3-yl)-N,N-dimethylethanamine,
2-(1-ethyl-6-fluoro-4-(5-fluoro-2-methylbenzyloxy)-1H-indol-3-yl)-N,N-dimethylethanamine,
2-(1-ethyl-6-fluoro-4-(pyridin-4-ylmethoxy)-1H-indol-3-yl)-N,N-dimethylethanamine,
2-(1-ethyl-6-fluoro-4-(thiophen-3-ylmethoxy)-1H-indol-3-yl)-N,N-dimethylethanamine,
2-(5-fluoro-1-methyl-4-phenethoxy-1H-indol-3-yl)-N,N-dimethylethanamine,
2-(1-ethyl-6-fluoro-4-phenoxy-1H-indol-3-yl)-N,N-dimethylethanamine,
2-(4-(2-chlorobenzyloxy)-6-fluoro-1-methyl-1H-indol-3-yl)-N-methylethanamine,
2-(4-(4-chlorobenzyloxy)-6-fluoro-1-methyl-1H-indol-3-yl)-N-methylethanamine, 2-(4-(3-chlorobenzyloxy)-6-fluoro-1-methyl-1H-indol-3-yl)-N-methylethanamine,
2-(4-(3-chlorobenzyloxy)-5-fluoro-1-methyl-1H-indol-3-yl)-N-methylethanamine,
2-(4-(4-chlorobenzyloxy)-5-fluoro-1-methyl-1H-indol-3-yl)-N-methylethanamine,
2-(5-fluoro-1-methyl-4-(3-(trifluoromethyl)benzyloxy)-1H-indol-3-yl)-Nmethylethanamine,
2-(5-fluoro-1-methyl-4-(2-methylbenzyloxy)-1H-indol-3-yl)-N-methylethanamine,
2-(4-(2-chlorobenzyloxy)-5-fluoro-1-methyl-1H-indol-3-yl)-N-methylethanamine,
2-(5-fluoro-4-(2-fluorobenzyloxy)-1-methyl-1H-indol-3-yl)-N-methylethanamine,
2-(5-fluoro-4-(4-methoxyphenethoxy)-1-methyl-1H-indol-3-yl)-N-methylethanamine,
2-(5-fluoro-1-methyl-4-phenethoxy-1H-indol-3-yl)-N-methylethanamine,
2-(5-fluoro-1-methyl-4-(4-methylbenzyloxy)-1H-indol-3-yl)-N-methylethanamine,
2-(5-fluoro-4-(4-fluorophenethoxy)-1-methyl-1H-indol-3-yl)-N-methylethanamine,
2-(4-(4-chlorophenethoxy)-5-fluoro-1-methyl-1H-indol-3-yl)-N-methylethanamine,
2-(4-(biphenyl-2-ylmethoxy)-5-fluoro-1-methyl-1H-indol-3-yl)-N-methylethanamine,
2-(5-fluoro-1-methyl-4-(2-(trifluoromethyl)benzyloxy)-1H-indol-3-yl)-N-methylethanamine,
2-(5-fluoro-1-methyl-4-(1-phenylethoxy)-1H-indol-3-yl)-N-methylethanamine,
2-((3-(2-((2-cyanobenzyl)(methyl)amino)ethyl)-5-fluoro-1-methyl-1H-indol-4-yloxy)methyl)benzonitrile,
2-(5-fluoro-4-(5-fluoro-2-methylbenzyloxy)-1-methyl-1H-indol-3-yl)-N-methylethanamine,
2-(5-fluoro-1-methyl-4-(2-(trifluoromethoxy)benzyloxy)-1H-indol-3-yl)-N-methylethanamine,
2-(5-fluoro-4-(4-fluorobenzyloxy)-1-methyl-1H-indol-3-yl)-N-methylethanamine,
2-(5-fluoro-1-methyl-4-(naphthalen-1-ylmethoxy)-1H-indol-3-yl)-N-methylethanamine,
1-(2-chlorophenyl)-2-(5-fluoro-1-methyl-3-(2-(methylamino)ethyl)-1H-indol-4-yloxy)ethanol,
2-(5-fluoro-1-methyl-4-(4-(methylsulfonyl)benzyloxy)-1H-indol-3-yl)-N-methylethanamine,
2-(5-fluoro-4-(naphthalen-1-ylmethoxy)-1-propyl-1H-indol-3-yl)-N-methylethanamine,
2-(4-(4-chlorobenzyloxy)-5-fluoro-1-propyl-1H-indol-3-yl)-N-methylethanamine,
2-(5-fluoro-1-methyl-4-(quinolin-8-ylmethoxy)-1H-indol-3-yl)-N-methylethanamine,
2-(5-fluoro-1-methyl-4-(2-phenoxyethoxy)-1H-indol-3-yl)-N-methylethanamine,
2-(5-fluoro-4-(4-fluorobenzyloxy)-1-propyl-1H-indol-3-yl)-N-methylethanamine,
2-(5-fluoro-4-(4-methylbenzyloxy)-1-propyl-1H-indol-3-yl)-N-methylethanamine,
2-(5-fluoro-1-methyl-4-(2-methylphenethoxy)-1H-indol-3-yl)-N-methylethanamine,
2-(5-fluoro-4-(4-(methylsulfonyl)benzyloxy)-1-propyl-1H-indol-3-yl)-N-methylethanamine,
2-(4-(2-chlorophenethoxy)-5-fluoro-1-methyl-1H-indol-3-yl)-N-methylethanamine,
2-(4-(2,4-dichlorobenzyloxy)-5-fluoro-1-methyl-1H-indol-3-yl)-N-methylethanamine,
2-(4-(4-chlorobenzyloxy)-5-fluoro-1-propyl-1H-indol-3-yl)ethanamine 2-(4-(4-chloro-3-(trifluoromethoxy)benzyloxy)-5-fluoro-1-methyl-1H-indol-3-yl)-N-methylethanamine, and
2-(5-fluoro-1-methyl-4-(thiophen-2-ylmethoxy)-1H-indol-3-yl)-N,N-dimethylethanamine.

6. A compound of formula (VIII):

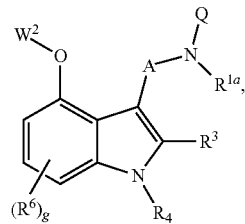

wherein
g is 1, 2 or 3;
$R^{1a}$ is selected from H, optionally substituted $C_{1-8}$ alkyl, and optionally substituted aryl;
Q is selected from aryl, heteroaryl, arylalkyl, heterocycloalkyl, and heteroarylalkyl, wherein Q is optionally substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl, —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^dR^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$SO_2NR^dR^{d'}$, cyano, nitro, $C_{1-6}$ haloalkyl, —$NR^dR^{d'}$, optionally substituted —$C_{1-6}$ alkyl, —$NR^dC(O)R^a$, —$C(O)NR^dR^{d'}$, and —$C(O)$, wherein $R^e$ and $R^f$ are each independently selected from H, $C_{1-8}$ alkyl, optionally substituted aryl, optionally substituted heteroaryl, optionally substituted arylalkyl, optionally substituted heteroarylalkyl, optionally substituted cycloalkyl, optionally substituted heterocyclyl, optionally substituted cycloalkylalkyl, optionally substituted heterocycloalkyl or when taken together with the nitrogen atom to which they are attached, $R^1$ and $R^2$ form a 3-8 membered heterocyclic moiety or when taken together with the nitrogen atom to which they are attached $R^1$ or $R^2$ and A form an optionally substituted 4-8 membered heterocyclyl or heteroaryl moiety;
$R^3$ is selected from H, optionally substituted $C_{1-8}$ alkyl, optionally substituted $C_{3-8}$ cycloalkyl, optionally substituted aryl, optionally substituted heteroaryl, optionally substituted heterocyclyl, halogen, and $C(O)NR^dR^{d'}$;
$W^2$ is hydrogen, optionally substituted $C_{1-8}$ alkyl, optionally substituted aryl, optionally substituted arylalkyl, optionally substituted heteroaryl, optionally substituted heterocyclyl, optionally substituted heteroarylalkyl, optionally substituted cycloalkyl, optionally substituted cycloalkylalkyl, optionally substituted heterocycloalkyl, or —$C(O)NR^dR^{d'}$;
A is optionally substituted $C_{1-4}$ alkylene, wherein the $C_{1-4}$ alkylene is optionally substituted with 1-3 substituents, each of which is independently selected from the group consisting of halogen, hydroxyl, optionally substituted $C_{1-6}$ alkyl, $C_{1-8}$ alkoxy, —$SO_2$ alkyl, and —$NR^dR^{d'}$;

R⁴ is selected from optionally substituted $C_{1-8}$ alkyl, optionally substituted $C_{1-8}$ heteroalkyl, $C_{2-8}$ alkenyl, $C_{2-8}$ alkynyl, —S(O)₂ alkyl, —S(O)₂ heteroalkyl, —S(O)₂ heteroaryl, —S(O)₂ cycloalkyl, —S(O)₂ heterocyclyl, —S(O)₂ heterocycloalkyl, —S(O)₂ arylalkyl, —S(O)₂ heteroarylalkyl, —S(O)₂ cycloalkyalkyl, formyl, —OR$^d$, —NR$^d$R$^{d'}$, —C(O)OR$^a$, —C(O)NR$^d$R$^{d'}$, —S(O)₂NR$^d$R$^{d'}$, $C_{3-8}$ cycloalkyl, heterocyclyl, cycloalkylalkyl, heteocyclylalkyl, aryl, heteroaryl, arylalkyl, and heteroarylalkyl, wherein the alkyl, cycloalkyl and heterocyclyl are optionally substituted with 1-3 substituents, halo, alkyl, haloalkyl, heteroalkyl, —OR$^d$, —NR$^d$R$^{d'}$, and wherein aryl and herteroaryl are optionally substituted with 1-3 substituents, each of which is independently selected from the group consisting of halogen, alkyl, heteroalkyl, cycloalkyl, heterocyclyl, —OR$^d$, —SH, $C_{1-8}$ haloalkoxy, —S(O)$_{0-2}$ $C_{1-8}$ alkyl, —S(O)$_{0-2}$ aryl, —S(O)$_{0-2}$ heteroaryl, —S(O)$_{0-2}$-arylalkyl, —S(O)$_{0-2}$-heteroarylalkyl, —OC(O)NR$^d$R$^{d'}$, —NR$^d$C(O)NR$^{d'}$R$^{d''}$, —NR$^d$C(O)OR$^b$, —OR$^d$, —NR$^d$S(O)₂alkyl, —NR$^d$S(O)₂aryl, —NR$^d$S(O)₂heteroaryl, —NR$^d$S(O)₂cycloalkyl, —NR$^d$S(O)₂heterocycloalkyl, —NR$^d$S(O)₂-arylalkyl, —NR$^d$S(O)₂-heteroarylalkyl, —NR$^d$S(O)₂-cycloalkylalkyl, —NR$^d$S(O)₂-heterocycloalkyl, —SO₂NR$^d$R$^{d'}$, optionally substituted —C₁alkyl-C(O)NR$^e$R$^f$, —C₁alkyl-O-aryl, —C₁alkyl-O-heteroaryl, —C₁alkyl-heterocyclyl, —C₁alkyl-cycloalkyl, cyano, nitro, $C_{1-6}$ haloalkyl, $C_{1-6}$ haloalkoxy, —NR$^d$R$^{d'}$, optionally substituted $C_{1-6}$ alkyl, —NR$^d$C(O)R$^a$, —C(O)NR$^d$R$^{d'}$, and —C(O)OR$^d$;

each R⁶ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —OR$^d$, $C_{1-8}$ haloalkoxy, $C_{1-8}$ haloalkyl, —S(O)$_{0-2}$ $C_{1-8}$ alkyl, —S(O)$_{0-2}$ aryl, —S(O)$_{0-2}$ heteroaryl, —S(O)$_{0-2}$ arylalkyl, —S(O)$_{0-2}$ heteroarylalkyl, —S(O)$_{0-2}$ cycloalkyl, —S(O)$_{0-2}$ heterocycloalkyl, —S(O)$_{0-2}$ heterocycloalkylalkyl, —S(O)$_{0-2}$ cycloalkylalkyl, —OC(O)NR$^d$R$^{d'}$, —NR$^d$C(O)NR$^{d'}$R$^{d''}$, —NR$^d$C(O)OR$^a$, —NR$^d$S(O)₂alkyl, —NR$^d$S(O)₂aryl, —NR$^d$S(O)₂heteroaryl, —NR$^d$S(O)₂cycloalkyl, —NR$^d$S(O)₂heterocycloalkyl, —NR$^d$S(O)₂-arylalkyl, —NR$^d$S(O)₂-heteroarylalkyl, —NR$^d$S(O)₂-cycloalkylalkyl, —NR$^d$S(O)₂-heterocycloalkyl, —SO₂NR$^d$R$^{d'}$, cyano, nitro, $C_{1-6}$ haloalkyl, $C_{1-6}$ haloalkoxy, —NR$^d$R$^{d'}$, —C$_{1-4}$alkyl-NR$^d$R$^{d'}$, optionally substituted $C_{1-6}$ alkyl, —NR$^d$C(O)R$^a$, —C(O)NR$^d$R$^{d'}$, and —C(O)OR$^d$; wherein alkyl, aryl, heteroaryl, cycloalkyl and heterocyclyl are optionally substituted;

R$^a$ and R$^b$ are each independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocycloalkyl; and R$^d$, R$^{d'}$, and R$^{d''}$ are each independently selected from H and R$^a$, or when taken together with the atom to which they are attached, two of R$^d$, R$^{d'}$ and R$^{d''}$ form a 4-8 membered heterocyclic moiety.

7. The compound of claim 6, wherein the compound is N-(2-(1-ethyl-7-fluoro-4-methoxy-1H-indol-3-yl)ethyl)aniline or 1-ethyl-7-fluoro-3-(2-(phenylamino)ethyl)-1H-indol-4-ol.

8. The compound of claim 6, wherein R³ is selected from hydrogen, halogen, and optionally substituted $C_{1-8}$ alkyl.

9. The compound of claim 6, wherein R⁴ is selected from optionally substituted $C_{1-8}$ alkyl, aryl, heteroaryl, arylalkyl, heteroarylalkyl, —S(O)₂ alkyl, —S(O)₂ arylalkyl, —S(O)₂ heteroarylalkyl, —S(O)₂ cycloalkyl, —S(O)₂ heterocycloalkyl, —S(O)₂ heterocycloalkylalkyl, —S(O)₂ cycloalkylalkyl and —S(O)₂ heteroaryl.

10. The compound of claim 6, wherein W² is H or $C_{1-8}$ alkyl optionally substituted with —OR$^d$, —NR$^d$R$^{d'}$, —C(O)NR$^d$R$^{d'}$.

11. The compound of claim 6, wherein Q is optionally substituted aryl, optionally substituted heteroarylalkyl, or optionally substituted arylalkyl.

12. The compound of claim 6, wherein Q is optionally substituted arylalkyl or optionally substituted six-membered heteroarylalkyl wherein the substitution is at the ortho or para position.

13. The compound of claim 6, wherein R⁶ is selected from halogen, $C_{1-8}$ alkyl, hydroxyl, —$C_{1-8}$ fluoroalkyl, amino, and —NR$^d$R$^{d'}$.

14. The compound of claim 6, wherein the compound is selected from

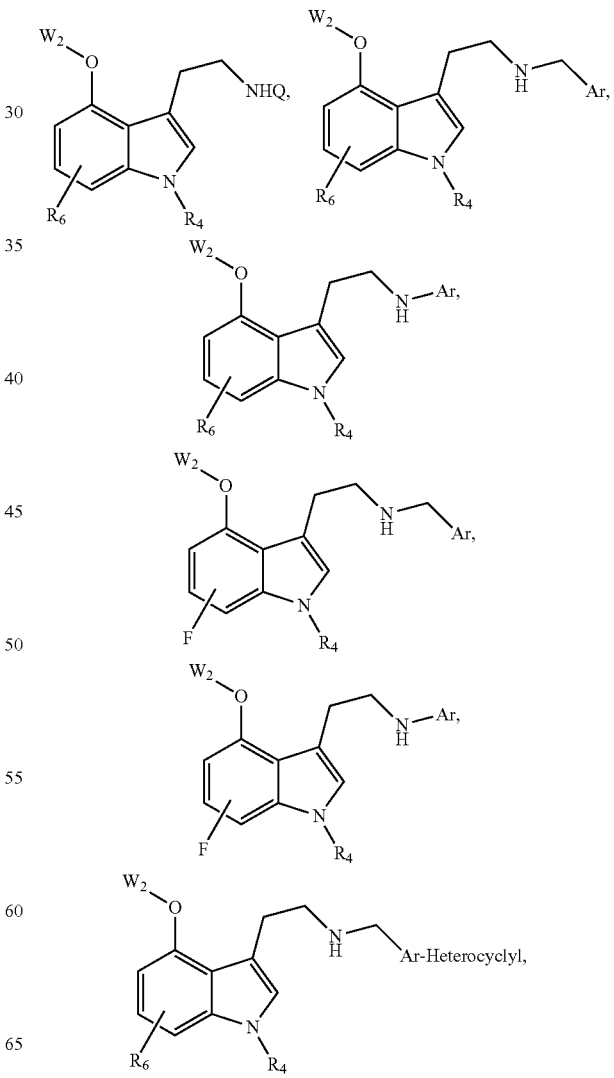

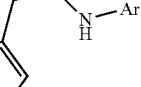

wherein Ar is optionally substituted aryl or optionally substituted heteroaryl, and heterocyclyl is optionally substituted 4-8-membered heterocycle.

15. The compound of claim 14 wherein the Ar or the heterocyclyl is substituted with 1-3 substituents, each of which is independently selected from the group consisting of halogen, $C_{3-8}$ cycloalkyl, —$OR^d$, $C_{1-8}$ haloalkoxy, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl), —$S(O)_{0-2}$ cycloalkyl, —$S(O)_{0-2}$ heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^b$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$-arylalkyl, —$NR^dS(O)_2$-heteroarylalkyl, —$NR^dS(O)_2$-cycloalkylalkyl, —$NR^dS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, optionally substituted —$C_{1-6}$ alkyl, —$NR^dC(O)R^a$, —$C(O)NR^dR^{d'}$, and —$C(O)$.

16. A compound selected from:
N-(2-(1-ethyl-7-fluoro-4-methoxy-1H-indol-3-yl)ethyl)aniline,
1-ethyl-7-fluoro-3-(2-(phenylamino)ethyl)-1H-indol-4-ol,
N-benzyl-2-(1-ethyl-7-fluoro-4-methoxy-1H-indol-3-yl)ethanamine,
3-(2-(benzylamino)ethyl)-1-ethyl-6-fluoro-1H-indol-4-ol,
2-(4-(benzyloxy)-1-ethyl-6-fluoro-1H-indol-3-yl)-N-(3-(trifluoromethyl)phenethyl)ethanamine,
1-ethyl-6-fluoro-3-(2-(3-(trifluoromethyl)phenethylamino)ethyl)-1H-indol-4-ol,
1-ethyl-6-fluoro-3-(2-(2-phenylpropylamino)ethyl)-1H-indol-4-ol,
N-benzyl-2-(4-(benzyloxy)-1-ethyl-6-fluoro-1H-indol-3-yl)ethanamine,
N-benzyl-2-(4-ethoxy-5-fluoro-1-methyl-1H-indol-3-yl)ethanamine,
N-(2-(4-ethoxy-5-fluoro-1-methyl-1H-indol-3-yl)ethyl)-2,3-dihydro-1H-inden-2-amine,
2-(4-(benzyloxy)-1-ethyl-6-fluoro-1H-indol-3-yl)-N-phenethylethanamine,
N-(2-chlorobenzyl)-2-(4-ethoxy-5-fluoro-1-methyl-1H-indol-3-yl)ethanamine,
N-(benzo[d][1,3]dioxol-5-ylmethyl)-2-(4-ethoxy-5-fluoro-1-methyl-1H-indol-3-yl)ethanamine,
N-(2-(4-ethoxy-5-fluoro-1-methyl-1H-indol-3-yl)ethyl)-2,3-dihydro-1H-inden-1-amine
1-ethyl-6-fluoro-3-(2-(phenethylamino)ethyl)-1H-indol-4-ol,
2-(4-ethoxy-5-fluoro-1-methyl-1H-indol-3-yl)-N-(3-methylbenzyl)ethanamine,
N-benzyl-2-(4-(benzyloxy)-1-ethyl-6-fluoro-1H-indol-3-yl)-N-methylethanamine,
2-(4-ethoxy-5-fluoro-1-methyl-1H-indol-3-yl)-N-(2-(trifluoromethyl)benzyl)ethanamine,
2-(4-ethoxy-5-fluoro-1-methyl-1H-indol-3-yl)-N-(3-(trifluoromethyl)benzyl)ethanamine,
2-(4-ethoxy-5-fluoro-1-methyl-1H-indol-3-yl)-N-phenethylethanamine,
2-(1-ethyl-7-fluoro-4-methoxy-1H-indol-3-yl)-N-phenethylethanamine,
2-(benzo[d][1,3]dioxol-5-yl)-N-(2-(4-ethoxy-5-fluoro-1-methyl-1H-indol-3-yl)ethyl)ethanamine,
N-benzyl-2-(1-ethyl-6-fluoro-4-methoxy-1H-indol-3-yl)ethanamine,
2-(4-ethoxy-5-fluoro-1-methyl-1H-indol-3-yl)-N-(2-(pyridin-2-yl)ethyl)ethanamine,
2-(4-ethoxy-5-fluoro-1-methyl-1H-indol-3-yl)-N-(thiophen-2-ylmethyl)ethanamine,
2-(5-fluoro-4-methoxy-1-methyl-1H-indol-3-yl)-N-(thiophen-2-ylmethyl)ethanamine,
N-benzyl-2-(5-fluoro-4-methoxy-1-methyl-1H-indol-3-yl)ethanamine,
2-(1-ethyl-6-fluoro-4-methoxy-1H-indol-3-yl)-N-(2-(1-ethyl-6-fluoro-4-methoxy-1H-indol-3-yl)ethyl)-N-methylethanamine,
2-(4-(benzyloxy)-1-ethyl-6-fluoro-1H-indol-3-yl)-N-(3-(trifluoromethyl)benzyl)ethanamine,
2-(4-(benzyloxy)-1-ethyl-6-fluoro-1H-indol-3-yl)-N-(3-chlorobenzyl)ethanamine,
2-(1-ethyl-7-fluoro-4-methoxy-1H-indol-3-yl)-N-(1-phenylethyl)ethanamine,
2-(1-ethyl-7-fluoro-4-methoxy-1H-indol-3-yl)-N-(2-methylbenzyl)ethanamine,
N-(2-chlorobenzyl)-2-(1-ethyl-7-fluoro-4-methoxy-1H-indol-3-yl)ethanamine,
N-(3,4-dimethoxybenzyl)-2-(5-fluoro-4-methoxy-1-methyl-1H-indol-3-yl)ethanamine,
3-(2-(benzhydrylamino)ethyl)-1-ethyl-6-fluoro-1H-indol-4-ol,
2-(2-(5-fluoro-4-methoxy-1-methyl-1H-indol-3-yl)ethylamino)-2-phenylethanol,
2-(5-fluoro-4-methoxy-1-methyl-1H-indol-3-yl)-N-(1-phenylethyl)ethanamine,
3-(2-(3-chlorobenzylamino)ethyl)-1-ethyl-6-fluoro-1H-indol-4-ol,
1-ethyl-6-fluoro-3-(2-(3-(trifluoromethyl)benzylamino)ethyl)-1H-indol-4-ol,
N-(2-(5-fluoro-4-methoxy-1-methyl-1H-indol-3-yl)ethyl)-4-phenylbutan-1-amine,
3-(2-(benzylamino)ethyl)-5-fluoro-1-methyl-1H-indol-4-ol,
(S)—N-(2-(5-fluoro-4-methoxy-1-methyl-1H-indol-3-yl)ethyl)-1,2,3,4-tetrahydronaphthalen-1-amine,
(S)—N-(2-(5-fluoro-4-methoxy-1-methyl-1H-indol-3-yl)ethyl)-1,2,3,4-tetrahydronaphthalen-1-amine, N-(2-(5-fluoro-4-methoxy-1-methyl-1H-indol-3-yl)ethyl)-3-(4-methylpiperazin-1-yl)aniline,
5-fluoro-3-(2-((6-methylpyridin-2-yl)methylamino)ethyl)-1-propyl-1H-indol-4-ol, and
5-fluoro-1-methyl-3-(2-((6-methylpyridin-2-yl)methylamino)ethyl)-1H-indol-4-ol.

17. A pharmaceutical composition comprising a compound of formulae (I) of claim 1 or (VIII) of claim 6.

18. The compound of claim 1, wherein phenyl is substituted.

19. The compound of claim 4, wherein g is 1 and $R^6$ is halogen.

20. A compound of formula (I):

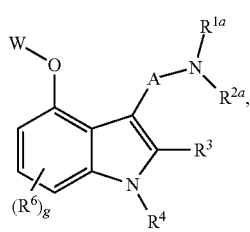

wherein
$R^{1a}$ and $R^{2a}$ are each independently selected from H and optionally substituted $C_{1-8}$ alkyl;
$R^3$ is selected from H and optionally substituted $C_{1-8}$ alkyl;
W is

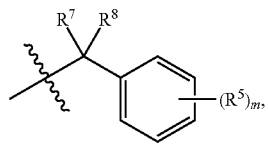

wherein:
when m is 1, then $R^5$ is from F, Cl, Br, $CF_3$, OH, —$OCH_3$, —$OCF_3$, and —$S(O)_{0-2}R^a$; and
when m is 2 or 3, then each $R^5$ is independently selected from F, Cl, Br, $CF_3$, methyl, OH, —$OCH_3$, —$OCF_3$, and —$S(O)_{0-2}R^a$;

A is optionally substituted $C_{1-4}$ alkylene, wherein alkylene is optionally substituted with 1-3 substituents, each of which is independently selected from the group consisting of halogen, oxo, optionally substituted $C_{1-6}$ alkyl, —$S(O)_{0-2}$alkyl, —$OR^d$—$NR^dR^{d'}$, aryl, heteroaryl, $C_3$-$C_8$ cycloalkyl and 4-8 membered heterocycle;

$R^4$ is selected from optionally substituted $C_{1-8}$ alkyl, optionally substituted $C_{1-8}$ heteroalkyl, $C_{3-8}$ cycloalkyl, and cycloalkylalkyl, wherein the alkyl and cycloalkyl are optionally substituted with 1-3 substituents, halo, alkyl, haloalkyl, heteroalkyl, —$OR^d$, —$NR^dR^{d'}$;

each $R^6$ is independently selected from halo, $C_{1-8}$ alkyl, aryl, heteroaryl, heteroalkyl, $C_{3-8}$ cycloalkyl, heterocyclyl, arylalkyl, heteroarylalkyl, cycloalkylalkyl, heterocycloalkyl, —SH, —$OR^d$, $C_{1-8}$ haloalkoxy, $C_{1-8}$ haloalkyl, —$S(O)_{0-2}$ $C_{1-8}$ alkyl, —$S(O)_{0-2}$ aryl, —$S(O)_{0-2}$ heteroaryl, —$S(O)_{0-2}$ arylalkyl, —$S(O)_{0-2}$ heteroarylalkyl, —$S(O)_{0-2}$cycloalkyl, —$S(O)_{0-2}$heterocycloalkyl, —$S(O)_{0-2}$ heterocycloalkylalkyl, —$S(O)_{0-2}$ cycloalkylalkyl, —$OC(O)NR^dR^{d'}$, —$NR^dC(O)NR^{d'}R^{d''}$, —$NR^dC(O)OR^a$, —$NR^dS(O)_2$alkyl, —$NR^dS(O)_2$aryl, —$NR^dS(O)_2$heteroaryl, —$NR^dS(O)_2$cycloalkyl, —$NR^dS(O)_2$heterocycloalkyl, —$NR^dS(O)_2$—$C_{1-4}$alkyl-aryl, —$NR^dS(O)_2$-heteroarylalkyl, —$NR^dS(O)_2$-cycloalkylalkyl, —$NR^aS(O)_2$-heterocycloalkyl, —$SO_2NR^dR^{d'}$, cyano, nitro, $C_{1-6}$ haloalkyl, $C_{1-6}$ haloalkoxy, —$NR^dR^{d'}$, —$C_{1-4}$alkyl-$NR^dR^{d'}$, optionally substituted $C_{1-6}$ alkyl, —$NR^dC(O)R^a$, —$C(O)NR^dR^{d'}$, and —$C(O)OR^d$; wherein alkyl, aryl, heteroaryl, cycloalkyl and heterocyclyl are optionally substituted;

each of $R^7$ and $R^8$ is independently H;

each $R^a$ is independently selected from optionally substituted $C_{1-8}$ alkyl, optionally substituted aryl, optionally substituted heteroaryl, optionally substituted $C_{3-8}$ cycloalkyl, optionally substituted arylalkyl, optionally substituted heteroarylalkyl, optionally substituted cycloalkylalkyl and optionally substituted heterocyclo alkyl;

$R^d$, $R^{d'}$, and $R^{d''}$ are each independently selected from H and $R^a$, or when taken together with the atom to which they are attached, two of $R^d$, $R^{d'}$ and $R^{d''}$ form a 4-8 membered heterocyclic moiety; and g is 1, 2 or 3.

* * * * *